US012702691B2

(12) United States Patent
Mayer

(10) Patent No.: US 12,702,691 B2
(45) Date of Patent: Aug. 11, 2026

(54) EXTRACT OF AN HERBAL COMPOSITION AS ANTIMICROBIAL AND/OR ANTIBIOFILM AGENT

(71) Applicant: ALPHANOSOS S.A.S., Riom (FR)

(72) Inventor: Pascal Mayer, Riom (FR)

(73) Assignee: ALPHANOSOS S.A.S., Riom (FR)

( * ) Notice: Subject to any disclaimer, the term of this patent is extended or adjusted under 35 U.S.C. 154(b) by 832 days.

(21) Appl. No.: 17/858,093

(22) Filed: Jul. 6, 2022

(65) Prior Publication Data

US 2022/0354919 A1 Nov. 10, 2022

Related U.S. Application Data

(63) Continuation-in-part of application No. 16/345,844, filed as application No. PCT/EP2017/077956 on Nov. 1, 2017, now Pat. No. 11,717,552.

(30) Foreign Application Priority Data

Nov. 2, 2016 (FR) ....................................... 1660588
Nov. 4, 2016 (EP) ..................................... 16197217

(51) Int. Cl.

| | |
|---|---|
| ***A61K 36/73*** | (2006.01) |
| ***A61K 36/185*** | (2006.01) |
| ***A61K 36/232*** | (2006.01) |
| ***A61K 36/258*** | (2006.01) |
| ***A61K 36/28*** | (2006.01) |
| ***A61K 36/288*** | (2006.01) |
| ***A61K 36/35*** | (2006.01) |
| ***A61K 36/45*** | (2006.01) |
| ***A61K 36/484*** | (2006.01) |
| ***A61K 36/53*** | (2006.01) |
| ***A61K 36/537*** | (2006.01) |
| ***A61K 36/61*** | (2006.01) |
| ***A61K 36/708*** | (2006.01) |
| ***A61K 36/74*** | (2006.01) |
| ***A61K 36/82*** | (2006.01) |
| ***A61K 36/87*** | (2006.01) |
| ***A61K 36/8965*** | (2006.01) |
| ***A61P 31/04*** | (2006.01) |

(52) U.S. Cl.

CPC ............ *A61K 36/73* (2013.01); *A61K 36/185* (2013.01); *A61K 36/232* (2013.01); *A61K 36/258* (2013.01); *A61K 36/28* (2013.01); *A61K 36/288* (2013.01); *A61K 36/3486* (2024.05); *A61K 36/35* (2013.01); *A61K 36/45* (2013.01); *A61K 36/484* (2013.01); *A61K 36/53* (2013.01); *A61K 36/537* (2013.01); *A61K 36/577* (2024.05); *A61K 36/61* (2013.01); *A61K 36/708* (2013.01); *A61K 36/74* (2013.01); *A61K 36/82* (2013.01); *A61K 36/87* (2013.01); *A61K 36/8965* (2013.01); *A61P 31/04* (2018.01); *A61K 2236/17* (2013.01); *A61K 2236/331* (2013.01); *A61K 2236/37* (2013.01); *A61K 2236/53* (2013.01)

(58) Field of Classification Search

None

See application file for complete search history.

(56) References Cited

U.S. PATENT DOCUMENTS

| | | | |
|---|---|---|---|
| 2004/0146539 | A1 | 7/2004 | Gupta |
| 2004/0208902 | A1 | 10/2004 | Gupta |
| 2004/0219124 | A1 | 11/2004 | Gupta |
| 2015/0056255 | A1 | 2/2015 | Ragot et al. |

FOREIGN PATENT DOCUMENTS

| | | | |
|---|---|---|---|
| FR | 2827774 | A1 | 1/2003 |
| JP | H10265358 | A | 10/1998 |
| JP | 2004035425 | A | 2/2004 |
| WO | 1999020289 | A1 | 4/1999 |
| WO | 2009031041 | A2 | 3/2009 |

OTHER PUBLICATIONS

Che C-T et al., "Herb-Herb combination for therapeutic enhancement and advancement; theory, practice and future perspective" Molecules 2013, 18, 5125-5141.

Glyn J et al."Combining hers synergy in action", Tibb institute, The art of Care, Jan. 2012.

Letter reporting office action issued Oct. 27, 2024 in connection with Egyptian application no. 641/2019.

Office Action a issued in counterpart Egyptian Application No. 641/2019 on Oct. 27, 2024.

Azwanida NN: "A review on the extraction methods use in medicinal plants, principle, strength and limitation", Medicinal & Aromatic Plants, vol. 04, No. 03, Jan. 1, 2015, pp. 1-6.

Bonnet D. et al., "Acute hepatitis probably imputable to phytothepie products such as extracts of Fumaria Officinalis and Vitis Vinifera" Gastroeterol Clin Biol 2007, vol. 31, pp. 1041-1042.

Communication received from EPO on Sep. 5, 2019 for PCT/EP2017/077956.

Denev P., et al., "Antioxidant, antimicrobial and neutrophil-modulating activities of herb extracts," Acta Biochimica Polonica, vol. 61, No. 2/, Jan. 1, 2014 pp. 359-367.

(Continued)

*Primary Examiner* — Michael V Meller

(74) *Attorney, Agent, or Firm* — Silvia Salvadori, P.C.; Silvia Salvadori

(57) ABSTRACT

An extract of an herbal composition comprising at least two different dried plants useful as antimicrobial and/or antibiofilm agent in the treatment or prevention of microbial infections caused by bacteria, such as for example *Escherichia, Klebsiella, Listeria, Pseudomonas, Salmonella, Streptococcus* or *Staphylococcus*, or by fungi, such as for example is herein described. It has been found that in such extract, the active ingredients exert their biological effects in a synergistic manner. The extract may constitute the active ingredient of a food supplement, a nutraceutical, pharmaceutical or cosmetic composition or a functional food or a food additive. A process for preparing said extract is also described here.

2 Claims, 4 Drawing Sheets

(56) References Cited

OTHER PUBLICATIONS

English translation of document cited in Chinese Office Action issued Mar. 2, 2021 in corresponding chinese application No. 201780067636.X.
English Translation of reporting letter and office action dated Mar. 2, 2021 issued in corresponding Chinese application No. 201780067636.x.
Horowitz N.H., et al., Bacteriology: Waksman et al., Biol. Symposia Quart. Rev. Biol. Biol.-Rev. Am. Nat. Physiol. Rev. Jour. Biol. Chem, Jan. 1, 1923, pp. 337-355.
Jain D.P. et al., "Synergistic antioxidant activity of green tea with some herbs" Journal of Advanced Pharmaceutical Technology & Research Jul.-Sep. 2011; 2(3): 177-183.
Liu Chao et al., "Advances in Studies on Chemical Constituents and Biological Activities of Desmodium Adscendens", China Journal of Chinese Traditional Medicine, vol. 38, No. 23, Dec. 31, 2013.
Office Action issued in counterpart Japanese Patent Application 2019545855 on Oct. 19, 2021.
Search Report and Written Opinion of PCT/EP2017/077956 of Jan. 17, 2018.
Shimizu M., et al., "Marked potentiation of activity of beta-lactams against methicillin-resistant *Staphylococcus aureus* by corilagin", Antimicrobial Agents and Chemotherapy, vol. 45, No. 11, Nov. 1, 2001, pp. 3198-3201.
Updated Search Report for PCT/EP2017/077956 mailed Sep. 2, 2019.
Wu Tong et al., "Medicine research on Aloe", Henan People's Publishing House, the 1st edition in Nov. 2010, Nov. 30, 2010.
Yam T. S., et al., "Microbiological activity of whole and fractionated crude extracts of tea (*Camellia sinensis*), and of tea components", FEMS Microbiology Letters, , vol. 152, Jan. 1, 1997 pp. 169-174.
Database: Paid Version of TKDL, Abstract ID: NA4/3925, "Hab-e-chai-Deegar Qawi Tar".
Letter issued Nov. 3, 2025 reporting an Office Action issued Nov. 3, 2025 in counterpart Indian Patent Application No. 201917015387.
Aly M. M. et al., "Antimicrobial efficacy of Rheum palmatum, Curcuma longa and Alpinia officinarum extracts against some pathogenic microorganisms", African Journal of Biotechnology, vol. 10(56) p. 12058-12063, Sep. 26, 2011.
Communication from Korean associate reporting office action issued Apr. 28, 2023 in connection with counterpart Korean application No. 10?2019?7012564.
European Medicine Agency "Assessment report on artcostaphylos uva-ursi (L.) Spreng, folium", Jul. 15, 2010 pp. 1-32.
Farooqui A. et al., "Synergistic antimicrobial activity of Camellia sinensis and Juglans regia against multidrug-resistant bacteria", PLOS One 10(2): e0118431, Feb. 26, 2015, pp. 1-14.
Office Action issued in counterpart Korean Application No. 10?2019?7012564 on Apr. 28, 2023.
Oskay M. et al., "Antimicrobial screening of some turkish medicinal plants", Pharmaceutical Biology, vol. 45, No. 3, p. 176-181, 2007.
Rauha J-P. et al., "Antimicrobial effects of Finnish plant extracts containing flavonoids and other phenolic compounds", International Journal of Food Microbiology 56 (2000), 3-12.

Growth kinetic of *Pseudomonas aeruginosa* ATCC® 27853™ at 37°C in TS broth, OD measured in 96 well plate, with the following final dilution of processed samples : 1:10

Close-up of the growth kinetic of *Pseudomonas aeruginosa* ATCC® 27853™ at 37°C in TS broth, OD measured in 96 well plate, with the following final dilution of processed samples : 1:10

Growth kinetic of *Staphylococcus aureus subsp. aureus* ATCC® 29213™ at 37°C in TS broth, OD measured in 96 well plate, with the following final dilution of processed samples : 1:40

Close-up of the growth kinetic of *Staphylococcus aureus subsp. aureus* ATCC® 29213™ at 37°C in TS broth, OD measured in 96 well plate, with the following final dilution of processed samples : 1:40

EXTRACT OF AN HERBAL COMPOSITION AS ANTIMICROBIAL AND/OR ANTIBIOFILM AGENT

This application is a Continuation-in-Part of U.S. Ser. No. 16/345,844 filed Apr. 29, 2019, which is a National Stage of PCT/EP2017/077956 filed on 1 Nov. 2017, which claims priority to and the benefit of European Application No. 16197217.9 filed on 4 Nov. 2016, and which claims priority to and the benefit of French Application no. 1660588 filed on 2 Nov. 2016, the contents of which are all incorporated herein by reference in their entireties.

FIELD OF THE INVENTION

The invention relates to an extract of an herbal composition comprising at least two different dried plants useful as antimicrobial and/or antibiofilm agent. It has also been found that in such extract, the active ingredients exert their biological effects in a synergistic manner.

BACKGROUND OF THE INVENTION

Like any living organism, plants contain numerous chemical entities, comprising low molecular weight chemicals, polypeptides, polysaccharides, enzymes. A plant extract is thus a trivial example of naturally occurring mix of chemical entities.

The biological and therapeutic activities of many chemical entities mixes obtained from plants is of secular knowledge and is compiled in numerous manuscripts (see for example, Encyclopedia of Herbal Medicine: The Definitive Home Reference Guide to 550 Key Herbs with all their Uses as Remedies for Common Ailments Hardcover—Nov. 15, 2000, by Andrew Chevallier).

Modern science allows to observe biological and therapeutic effects of chemical entities combinations obtained from plants on a large number of organisms.

For instance, it is described in Scheggi (Scheggi S. et al, Pharm. Biol. 2016 Jan. 5:1-11. [Epub ahead of print]) how a rat model allows to test the effect against depression of chemical entities combinations obtained from plants.

In Zhipeng Q U (Oncotarget. 2016 Sep. 1 Epub) it is shown how it is possible to identify candidate anti-cancer molecular mechanisms of Compound Kushen Injection using functional genomics. Compound Kushen Injection (CKI) has been clinically used in China for over 15 years to treat various types of solid tumours. However, because such Traditional Chinese Medicine (TCM) preparations are complex mixtures of plant secondary metabolites, it is essential to explore their underlying molecular mechanisms in a systematic fashion. This study shows that CKI inhibited MCF-7 cell proliferation and induced apoptosis in a dose-dependent fashion. Multiple pathways were found to be perturbed and the cell cycle was identified as the potential primary target pathway of CKI in MCF-7 cells. CKI may also induce apoptosis in MCF-7 cells via a p53 independent mechanism. In addition, they identified novel lncRNAs and showed that many of them might be expressed as a response to CKI treatment.

The effect of chemical entities mixtures obtained for instance from plants, fungi or bacteria on the growth of microorganisms such as bacteria and fungi has been described many times, for instance in Venkatadri (Venkatadri B. et al., Indian J. Pharm. Sci. 2015 November-December; 77(6):788-91).

The effect of chemical entities combinations obtained for instance from plants, fungi or bacteria on the formation of biofilms (communities of microorganisms embedded in a polymeric matrix attached to a surface) has also been described many times, for instance in Suntar (Suntar I. et al., Pharm. Biol. 2016 June; 54(6):1065-70Epub 2015 Oct. 29).

Shimizu M. et al. (Antimicrob Agents Chemother. 2001 November; 45(11):3198-201) found that an extract of *Arctostaphylos uva-ursi* markedly reduced the MICs (Minimum Inhibitory Concentrations) of beta-lactam antibiotics, such as oxacillin and cefmetazole, against methicillin-resistant *Staphylococcus aureus*. The same group also isolated the effective compound and identified it as corilagin.

Another group (Denev P. et al., Acta Biochim. Pol. 2014; 61(2):359-67. Epub 2014 Jun. 18) studied the antioxidant, antimicrobial and neutrophil-modulating activities of extracts from six medicinal plants—blackberry (*Rubus fruticosus*) leaves, chokeberry (*Aronia melanocarpa*) leaves, hawthorn (*Crataegus monogyna*) leaves, lady's mantle (*Alchemilla glabra*) aerial parts, meadowsweet (*Filipendula ulmaria*) aerial parts and raspberry (*Rubus idaeus*) leaves. The antimicrobial activity of the investigated extracts against 11 human pathogens was investigated using three different methods and the results of this study allowed concluding that meadowsweet and blackberry leaves extracts had the highest antimicrobial effect and the lowest minimal inhibiting concentrations (MICs) against the microorganisms tested.

Yam T. et al. (FEMS Microbiol Lett. 1997 Jul. 1; 152(1): 169-74) focused their study on the microbiological activity of whole and fractionated crude extracts of tea (*Camellia sinensis*), and of tea components. Aqueous extracts of teas (*Camellia sinensis*) of different types and from various sources were tested and found to inhibit a wide range of pathogenic bacteria, including methicillin-resistant *Staphylococcus aureus*. Tea extracts were bactericidal to staphylococci and *Yersinia enterocolitica* at well below 'cup of tea' concentrations. Activity was confined to one of four fractions obtained from a green tea extract by partition chromatography. Testing of pure tea compounds and closely related chemicals suggested that the antibacterial activity of extracts of green tea can be explained by its content of epigallocatechin, epigallocatechin gallate and epicatechin gallate. In black tea extracts, theaflavin and its gallates are additional antibacterially active components.

WO 2009/031041 reports a composition comprising (a) an antimicrobial compound having a given chemical structural formula, (b) an antimicrobial material selected from lanthionine bacteriocins, tea [*Camellia sinensis*] extract, hop [*Humulus lupulus* L] extract, grape skin extract, grape seed extract, Uva *Ursi* [*Arctostaphylos uva-ursi*] extract and combinations thereof.

WO 99/20289 reports a clear herbal extract solution comprising a concentrated herbal extract and a fill liquid. The concentrated herbal extract is reported to be selected from a long list of plants extracts, where such list includes *Filipendula ulmaria, Camellia sinensis* and *Arctostaphylos uva-ursi*. However, WO 99/20289 does not mention any specific therapeutic or medical use of the claimed herbal solution.

US 2015/0056255 reports a product for medicinal, cosmetic, coloring, or dermatologic use, the product comprising a layer of a fibrous plant product and a plant extract applied to the layer of the fibrous plant product. The plant extract is said to comprise substances from one or more specific parts of one or more plants, wherein the plants are selected from at least one of a long list of plants.

Azanida N N (Med. Aromat. Plants, 4:3, p. 1-6, 2015) published a review, which reports a description and a comparison of the most commonly used methods for preparing medicinal plant extracts. The authors conclude their article by stating that "no universal extraction method is the ideal method and each extraction procedure is unique to the plants" (see "Conclusions", lines 5-7).

Selman A. Wachsman et al. (Bacteriology, 31, p. 157-164, 1945) reports that different strains of the same bacterial species may vary greatly in their resistance to streptomycin. Different *Staphylococcus aureus* bacterial strains are used in such paper to test the activity of streptomycin. However, no plant extract is tested on the same strains and therefore no clear guidance can be drawn from such paper.

Biological effects such as contemplated in the previous examples can be induced either by a single chemical entity, such as in standard drugs, or by a synergistic effects of different chemical entities, such as in extracts. In some cases, the biological effect is nearly fully attributable to a single chemical entity contained in the extract. In this case, the extract can be replaced by the purified active chemical entity.

Biological effects of a chemical entity can be either due to chemical reactions (transformations) with the chemical entities constituting the organism or be due to the transient or permanent binding to the chemical entities, in particular the macromolecules, constituting the organism. Such binding will modulate the activity of the organism's chemical entities, in particular the macromolecules, e.g., increase or decrease the activity of an enzyme.

Unfortunately, chemical entities have never a single effect on an organism. In particular, the interactions with the macromolecular constituents are numerous. As a matter of fact, it is well established that any chemical entity, whether natural or resulting from chemical synthesis, will have deleterious effects on organisms (humans, animals, plants, micro-flora, etc.) in a dose related fashion. Eventually, a dose related positive or therapeutic effect can be observed also. It is obvious that for the chemical entity to be of industrial interest, the dose required to observe the positive or therapeutic effect needs to be lower than the dose for which the deleterious effects become unacceptable.

Chemical entities differing in their chemical composition or structure will have different affinities (or binding constants) with the different macromolecules constituting the organism, and thus different modes of actions resulting in the observed deleterious, positive and therapeutic effects.

The macromolecules involved in deleterious effects and those involved in positive or therapeutic effects are different in many cases. Chemical entities differing in their chemical composition will in most of the cases have very different affinities (or binding constants) with the numerous different macromolecules constituting the organism.

In most cases, different chemical entities will have different affinities (or binding constants) with a given macromolecule. In rare cases, different chemical entities will have similar affinities (or binding constants) with the same macromolecule or sets of macromolecules involved in a positive or therapeutic effect. Among these cases, it will be rare that these different chemical entities will have comparable affinities (or binding constants) with the macromolecules involved in given deleterious effect.

Mixes of different chemical entities may thus have a synergistic positive or therapeutic effect without a cumulative given deleterious effect. Thus, for a given positive or therapeutic effect, the dose required for each individual different chemical entity in a mix will be lower than the dose required by each of the chemical entity considered individually to obtain that given positive or therapeutic effect. In those cases where the deleterious effects induced by each different chemical compound is different or has a different macromolecular aetiology, each deleterious effect of the mix will be lower than the deleterious effect of the chemical entity considered individually because it is used at a lower dose in the mix.

Note that the synergistic situation of the simultaneous administration of reduced doses of different chemical entities is different from the co-administration of different drugs (chemical entities) having different therapeutic effects administered at their standard doses. In the latter situation, increased side effects due to drug-interactions are well known. One of the causes of side effects is the possible chemical interaction of the different drugs (chemical entities). In the synergistic situation, each chemical entity is present at a reduced concentration and thus with much lower rates of chemical interactions. For illustration purposes, a synergistic mix of 10 different chemical entities (drugs) administrated each at $1/10^{th}$ of the concentration (dose) required for a chemical entity (drug) administrated individually, the rate of inter-drug chemical reactions will be reduced by a factor of 100 as implied by the universal law of action of mass.

It is therefore of interest to use synergistic mixes of different chemical entities in order to obtain a given positive or therapeutic effect with reduced deleterious effects, or to obtain an increased positive or therapeutic effect with a given level of different deleterious effects. Indeed, several extracts are known have synergistic activities relative to isolated chemical entities (see for instance, Deharo E. et al., Malar. J. 2011 Mar. 15; 10 Suppl 1:55).

Natural extracts composed of a mix of synergistic chemical entities can be discovered for example by means of systematic testing numerous natural extracts of single plant powders or herbal compositions containing at least two or more different plant powders.

DESCRIPTION OF THE INVENTION

It has now been found that an extract of an herbal composition comprising at least two dried plants selected among *Filipendula ulmaria, Camellia sinensis* and *Arctostaphylos uva-ursi* is useful as antimicrobial and/or antibiofilm agent in the treatment or prevention of microbial infections caused by bacteria, such as for example *Escherichia, Klebsiella, Listeria, Pseudomonas, Salmonella, Streptococcus* or *Staphylococcus*, or by fungi, such as for example *Candida*. It has also been found that in such extract, the active ingredients exert their biological effects in a synergistic manner.

Therefore, one object of the present invention is a method for the treatment or prevention of the above mentioned microbial infections comprising administering an effective amount of an extract of an herbal composition comprising at least two dried plants selected among *Filipendula ulmaria, Camellia sinensis* and *Arctostaphylos uva-ursi*, a lyophilisate of said extract, or a pharmaceutical or veterinary composition comprising said extract or said lyophilisate, to a subject in the need thereof.

Another object of the present invention is an extract of an herbal composition, comprising at least two dried plants selected among *Filipendula ulmaria, Camellia sinensis* and *Arctostaphylos uva-ursi* and at least one plant selected among *Vitis vinifera* var. *tinctoria, Eugenia caryophyllus* and *Desmodium adscendens.*

Another object of the present invention is an extract of an herbal composition comprising the following dried plants: *Filipendula ulmaria, Camellia sinensis* and *Vitis vinifera* var. *tinctoria*, wherein the w/w weight ratio between *Filipendula ulmaria* and each of the dried *Camellia sinensis* and *Vitis vinifera* var. *tinctoria* is between 0.2 and 5, optionally between 0.3 and 3, more optionally between 0.5 and 2.5.

Said herbal composition may further comprise one or more additional dried plants selected among:

*Achillea millefolium, Acorus calamus, Agrimonia eupatoria, Agropyrum repens, Agropyrum repens, Alchemilla vulgaris, Alkanna tinctoria, Althaea officinalis, Anethum graveolens, Angelica archangelica, Arbutus unedo, Arnica montana, Artemisia pontica, Artemisia vulgaris, Asparagus officinalis, Asparagus officinalis, Asperula odorata, Betula pendula, Borrago officinalis, Buxus sempervirens, Calamintha officinalis, Calendula officinalis, Calluna vulgaris, Carum carvi, Cassia angustifolia, Centaurea cyanus, Centaurium erythraea, Centella asiatica, Cetraria islandica, Chamaemelum nobile, Chamomilla recutita, Chrysanthellum americanum, Cichorium endivia, Cichorium intybus, Cinnamomum zeylanicum, Citrus aurantium, Combretum micranthum, Crataegus oxyacantha, Cuminum cyminum, Cupressus sempervirens, Curcuma zedoaria, Cynara scolymus, Cytisus scoparius, Elettaria cardamomum, Eleutherococcus senticosus, Epilobium parviflorum, Erysimum officinale, Eucalyptus globulus, Eupatorium cannabinum, Foeniculum vulgare, Fraxinus excelsior, Fucus vesiculosus, Fumaria officinalis, Galium odoratum, Gentiana lutea, Geranium robertianum, Ginkgo biloba, Glechoma hederacea, Glycyrrhiza glabra, Handroanthus impetiginosus, Harpagophytum procumbens, Hieracium pilosella, Humulus lupulus, Hypericum perforatum, Hyssopus officinalis, Illicium verum, Inula helenium, Juglans regia, Juniperus communis, Lamium album, Lavandula angustifolia, Levisticum officinale, Lippia citriodora, Lotus corniculatus, Lythrum salicaria, Malva sylvestris, Marrubium vulgare, Medicago sativa, Melissa officinalis, Mentha×piperita, Morus nigra, Myrtus communis, Olea europaea, Origanum majorana, Panax ginseng, Papaver rhoeas, Parietaria officinalis, Passiflora incarnata, Petroselinum crispum, Peumus boldus, Phaseolus vulgaris, Pimpinella anisum, Plantago lanceolata, Plantago ovata, Potentilla anserina, Quercus robur, Rhamnus frangula, Rheum palmatum, Rosa centifolia, Rosmarinus officinalis, Rubia tinctorum, Rubus idaeus, Salix alba, Salvia officinalis, Sambucus nigra, Satureja montana, Silybum marianum, Solanum dulcamara, Tabebuia impetiginosa, Tanacetum vulgare, Taraxacum officinalis, Thymus serpyllum, Thymus vulgaris, Tilia tomentosa, Tilia cordata, Trigonella foenum-graecum, Tussilago farfara, Vaccinium myrtillus, Valeriana officinalis, Verbascum thapsus, Verbena officinalis, Viscum album, Zea mays and Zingiber officinale.*

A further object of the invention is an extract of an herbal composition comprising from three to seven dried plants selected among *Filipendula ulmaria, Camellia sinensis, Arctostaphylos uva-ursi, Rheum palmatum, Rosmarinus officinalis, Vitis vinifera tinctoria, Desmodium adscendes, Eugenia caryophyllus* and *Eucalyptus globulus*, wherein at least two of such plants are selected among *Filipendula ulmaria, Camellia sinensis* and *Arctostaphylos uva-ursi* and at least one of such plants is selected among *Vitis vinifera tinctoria, Desmodium adscendes* and *Eugenia caryophyllus*.

Another object of the invention is an extract of an herbal composition comprising the following dried plants: *Rosmarinus officinalis, Filipendula ulmaria, Camellia sinensis, Vitis vinifera tinctoria* and *Arctostaphylos uva-ursi*.

Another object of the invention is an extract of an herbal composition comprising the following dried plants: *Rheum palmatum, Filipendula ulmaria, Camellia sinensis, Vitis vinifera tinctoria* and *Arctostaphylos uva-ursi*.

Another object of the invention is an extract of an herbal composition comprising the following dried plants: *Rheum palmatum, Rosmarinus officinalis, Filipendula ulmaria, Camellia sinensis, Vitis vinifera tinctoria, Eugenia caryophyllus* and *Arctostaphylos uva-ursi*.

A further object of the invention is an extract of an herbal composition comprising the following dried plants: *Rheum palmatum, Rosmarinus officinalis, Filipendula ulmaria, Camellia sinensis, Vitis vinifera tinctoria, Eucalyptus globulus, Arctostaphylos uva-ursi, Mentha spicata* and *Rubia tinctorium*.

Another object of the invention is an extract of an herbal composition comprising at least fourteen or fifteen dried plants selected among the following sixteen: *Rheum palmatum, Rosmarinus officinalis, Filipendula ulmaria, Satureja montana, Valeriana officinalis, Camellia sinensis, Vitis vinifera tinctoria, Fucus vesiculosus, Foeniculum vulgare, Arctostaphylos uva-ursi, Arbutus unedo, Eugenia caryophyllus, Juniperus communis, Combretum micranthum, Lippia citrodora* and *Tanacetum vulgare*

Another object of the invention is an extract of an herbal composition comprising the following dried plants: *Rheum palmatum, Rosmarinus officinalis, Filipendula ulmaria, Satureja montana, Valeriana officinalis, Camellia sinensis, Vitis vinifera tinctoria, Fucus vesiculosus, Foeniculum vulgare, Arctostaphylos uva-ursi, Arbutus unedo, Eugenia caryophyllus, Juniperus communis, Combretum micranthum* and *Lippia citrodora*.

Another object of the invention is an extract of an herbal composition comprising the following dried plants: *Rheum palmatum, Rosmarinus officinalis, Filipendula ulmaria, Satureja montana, Valeriana officinalis, Camellia sinensis, Vitis vinifera tinctoria, Fucus vesiculosus, Foeniculum vulgare, Arctostaphylos uva-ursi, Arbutus unedo, Eugenia caryophyllus, Juniperus communis, Combretum micranthum, Lippia citrodora* and *Tanacetum vulgare*.

All the above-mentioned herbal compositions are also an object of the invention, as intermediates in the preparation of the corresponding extracts.

The extract may constitute the active ingredient of a food supplement, a nutraceutical, pharmaceutical or cosmetic composition or a functional food or a food additive.

The extract of the invention may be used as such or in a dried or lyophilized form.

A food supplement, a nutraceutical, pharmaceutical, veterinary or cosmetic composition or a functional food or a food additive containing the extract defined above together with suitable excipients are further objects of the invention.

Such food supplement, a nutraceutical, pharmaceutical, veterinary or cosmetic composition or a functional food or a food additive may be formulated in any form suitable, for example, for oral administration, including solid forms such as powders, granules, capsules, pills, tablets (normal or controlled release), chewing gums, or liquid forms such as syrups, drops, elixirs, solutions and suspensions in general.

Furthermore, the extract according to the invention can be incorporated into other formulations, such as creams, ointments, gels, milks, pastes, creams based on water, emulsions, serums, masks, balms, fluids, sprays, suppositories, vaginal suppositories, transdermal patches and toothpastes, periodontal gels, mouthwashes.

According to the present invention, the expression "herbal composition" refers to a powder containing one or more different grinded dried plants. The powder of a single dried plant may have been obtained from the whole plant or form a specific part of it, for example, flowers, buds, fruits, stems, leaves, seeds, roots or other.

According to the invention, an extract may be obtainable by simple incubation of an herbal composition with an extraction solvent (with or without the addition of a sugar) at room temperature.

Suitable extraction solvents according to the invention are water and all non-aqueous solvents authorized for use in the production of foodstuffs and food ingredients. For example, according to Directive 2009/32/EC a list of such non-aqueous solvents includes propane, butane, ethyl acetate, ethanol, carbon dioxide, acetone, nitrous oxide. According to specific embodiments of the invention, the extraction solvent is selected among water, ethanol, ethyl acetate and any mixture thereof.

According to another alternative embodiment, an extract may be obtainable by incubation of an herbal composition with an extraction solvent (with or without the addition of a sugar) and subsequent heating, with or without centrifugation and filtration.

According to an alternative embodiment, a water extract may be obtainable by incubation of an herbal composition with water (with or without the addition of a sugar) and subsequent heating (for example by heating the resulting liquid preparation at a temperature ranging from 60° C. to 134° C., preferably from 119° to 121° C., for a time ranging from 5 to 60 minutes, preferably from 20 to 30 minutes).

With the term "sugar", we herein intend to mean a pharmaceutical or alimentary grade sugar, such as for example dextrose, lactose, anhydrous lactose, mannitol, sorbitol, maltose, galactose or sucrose.

According to a particular embodiment of the invention, such sugar is sucrose.

Said sugar may be used at concentrations varying from 1 to 100 g/l, optionally from 50 to 75 g/l.

With the term "food supplement" it is here meant a food product intended to supplement the common diet and which is a concentrated source of nutrients, such as vitamins and minerals, or other substances with a nutritional or physiological effect, in unit dose form (see also Directive 2002/46/EC of 10 Jun. 2002.

The expression "functional food" means to include foods characterized by additional effects due to the presence of components (generally non-nutrients) naturally present or added, which interact more or less selectively with one or more physiological functions of the organism (biomodulation) leading to a positive effect on maintaining health and/or disease prevention. A food can be considered 'functional', if it is sufficiently demonstrated its beneficial influence on one or more functions of the body, in addition to adequate nutritional effects, so as to be relevant to a state of well-being and health, or for risk reduction of an illness. The beneficial effects could include both in maintaining that in promoting a state of well-being or health and/or a reduction in the risk of a disease process or disease (see A T Diplock et al: Scientific concepts of functional foods in Europe: Consensus Document, British Journal of Nutrition 1999, 81 (Suppl. 1), S1-S27).

According to the present invention with the expression, "nutraceutical composition" it is intended to mean a product, which not only supplement the diet, but should also aid in the prevention and/or treatment of disease and/or disorder. This expression was coined in 1989 by Stephen L. DeFelice (MD, founder and chairperson of the Foundation for Innovation in Medicine (FIM)) joining the concepts of "nutrition" and "pharmaceutical".

With the term "excipient", it is intended here to refer to conventional excipients, i.e., inert compounds towards the active ingredient of a composition.

Excipients may be divided into various functional classifications, depending on the role that they are intended to play in the resultant formulation, e.g., in solid dosage forms they may act as diluents (e.g. lactose, microcrystalline cellulose), disintegrants (e.g. sodium starch glycolate, croscarmellose sodium), binders (e.g. PVP, HPMC), lubricants (e.g. magnesium stearate), glidants (e.g. colloidal $SiO_2$) or flavoring agents (e.g. peppermint, lemon oils). In liquid dosage forms they may act as solvents, co-solvents or solubilizers (e.g., propylene glycol, glycerol, ethanol, sorbitol, dextrose), buffering agents (e.g. sodium phosphate), antimicrobial agents (e.g. potassium sorbate), wetting agents (e.g. polysorbates or Tweens), anti-foaming agents (e.g. polydimethylsiloxane-silicon dioxide), thickening agents (e.g. methylcellulose or hydroxyethylcellulose) or sweetening agents (e.g. sorbitol, acesulfame-K).

As already said, the extract of the invention is an antimicrobial and/or antibiofilm agent and it is advantageously used in the treatment, the prevention and/or the diagnosis of microbial infections in humans and animals.

Another object of the invention is therefore the use of the extract of the invention in the manufacture of a medicament for the treatment, prevention or diagnosis of microbial infections. Such medicament may be useful for humans of animals.

According to the present invention, the expressions "treatment" or "treating" are intended to activities designed to cure, mitigate the symptoms or delay the progression of a disease or a pathological condition.

The expressions "prevention" or "preventing" are intended to refer to activities designed to minimize the incidence or effects of a disease or a pathological condition. For example, in the case of microbial infections, prevention specifically herein means to prevent the adhesion and colonization of pathogenic microbes to cells, tissues and organs.

The expressions "diagnosis" or "diagnosing" are intended to refer to activities designed to identify a series of physiological parameters in order to assess the presence and the extent of a determined disease or pathological condition.

The expression "antimicrobial agent" will here be used to mean an agent that is able to inhibit the growth of microbial cells. If the microbial cells are pathogenic microbial cells, the antimicrobial agent can be used as active ingredient of a pharmaceutical or veterinary composition for the treatment of microbial infections in humans or animals.

The expression "antibiofilm agent" will here be used to mean an agent that is able to inhibit the formation of biofilm by microbial cells and/or to facilitate the dispersion of preformed biofilms. In contrast to conventional antimicrobial agents, an antibiofilm agent does not directly affect microbial survival and thus the expectation is that resistance to these agents will not readily occur.

According to the present invention, the term "synergistic" is intended as referred to a biological effect or activity (herein antimicrobial or antibiofilm), presented by the extract of an herbal composition of the invention (i.e. comprising at least two dried plants selected among *Filipendula ulmaria, Camellia sinensis* and *Arctostaphylos uva-ursi*), which is greater than the sum of the effects or activities of the extracts of the corresponding single dried plants.

Such greater biological effect or activity may be illustrated, for example, in terms of inhibition of planktonic growth (antimicrobial activity), in terms of biofilm formation inhibition (antibiofilm activity) or in terms of number of strains, in which one or both these activities can be identified.

According to a particular embodiment of the invention, the microbial infections are caused by bacteria, such as for example *Escherichia coli, Klebsiella pneumoniae, Listeria innocua, Listeria monocytogenes, Pseudomonas aeruginosa, Salmonella enterica* subsp. *Enterica serovar Enteritidis, Salmonella enterica* subsp. *Enterica serovar Typhimurium, Streptococcus pneumoniae, Streptococcus equi* subsp. *zooepidemicus, Streptococcus pyogenes*, or by fungi, such as for example *Candida albicans*.

According to another particular embodiment of the invention, the microbial infections are caused by *Staphylococcus aureus, Staphylococcus epidermidis* or *Staphylococcus pseudintermedius*.

*Staphylococcus aureus*, a commensal Gram-positive bacterium is a leading pathogen that may cause a wide variety of diseases in human ranging from skin and soft tissue infections to severe septicemia, toxic choc or pneumonia. *Staphylococcus aureus* is an important cause of hospital-associated infections, and many hospital strains of *Staphylococcus aureus* have acquired resistant to antibiotics, most particularly to methicillin. There is no vaccine available yet, but important efforts are conducted to develop active and passive immunotherapy against various targets of *Staphylococcus aureus*.

In order to evaluate such biological activities for the extract of the invention and for comparative samples, many different strains have been used and will be mentioned in the Examples' section.

In particular, the following bacterial strains have been used to test both the antimicrobial and antibiofilm activity of the extracts of the invention.

ATCC 25923, also known as Seatle 1945, is a *Staphylococcus aureus* strain widely used in academic research (it is cited in 627 publications as of October 2016 (see NIH-NCBI-Pubmed)). Its antibiotic resistance behavior has been thoroughly characterized (see, for instance, Reimer L. G. et al., Antimicrob. Agents Chemother. 1981 June; 19(6):1050-5).

ATCC 29213 is also a *Staphylococcus aureus* strain widely used in academic research (cited in 327 publications as of October 2016 (see NIH-NCBI-Pubmed)). It has been used in biofilm research (see, for instance, Ceri H. et al., J. Clin. Microbiol. 1999 June; 37(6):1771-6).

ATCC 1228 is a *Staphylococcus epidermidis* strain (cited in 101 publications as of October 2016 (see NIH-NCBI-Pubmed)). The Code of Federal Regulations (FDA) lists such strain as the preferred assay organism for neomycin (see also Robertson J. H. et al., Appl. Microbiol. 1971 December; 22(6):1164-5).

ATCC 43300 is a *Staphylococcus aureus* strain isolated from a clinical study (cited in 81 publications as of October 2016 (see NIH-NCBI-Pubmed), including Lubenko et al., J. Antimicrob. Chemother. 2008 November; 62(5):1065-9).

*Staphylococcus aureus* strain Newman was isolated in 1952 from a human infection and has been used extensively in animal models of staphylococcal infections due to its robust virulence phenotype (see Baba T. et al., Journal of bacteriology, 190:300-310 (2008)). In contrast to hospital-acquired MRSA (Methicillin-resistant *Staphylococcus aureus*), *Staphylococcus aureus* Newman carries a harbors only small a small number of insertion sequences (IS) and lacks known antibiotic resistance determinants.

Other strains used in the examples are also commonly used in academic research or in industry for quality control (QC). Most of them are also methicillin resistant.

For reference to ATCC 33591, see Reyes N. et al., J. Antimicrob. Chemother. 2006 August; 58(2):462-5, Epub 2006 May 30. For reference to ATCC 33592, see Teka A. et al., BMC Complement Altern Med. 2015 Aug. 18; 15:286. For reference to NCTC 12493, see Carey B. E. et al., J. Antimicrob. Chemother. 2006 August; 58(2):455-7, Epub 2006 Jun. 20. For reference to ATCC 700698, see Kirker K. R. et al., Int. J. Antimicrob Agents, 2015 October; 46(4): 451-5, Epub 2015 Jul. 9. For reference to ATCC 700699, see Sy C. L. et al., J. Clin. Microbiol. 2016 March; 54(3):565-8, Epub 2015 Dec. 16. For reference to ATCC 9144, see Carson C. F. et al., Antimicrob. Agents Chemother. 2002 June; 46(6):1914-20. For reference to ATCC BAA-44, see Monecke S. et al., PLoS One. 2011 Apr. 6; 6(4): e17936. For reference to ATCC 14990, see Bernardo T. H. et al., Scientific World Journal. 2015; 751791, Epub 2015 Jun. 3). For reference to ATCC 49444, see Ramsey K J et al., J Food Prot. (2010). For reference to ATCC 60193, see Petrikaite V et al., Medicina (Kaunas). 2007; 43(8):657-63. For reference to ATCC 11775, see Usman H et al., Afr J Tradit Complement Altern Med. 2007 Jun. 10; 4(4):488-94. For reference to ATCC 13883, see Supardy N A et al., J Microbiol Biotechnol. 2012 June; 22(6):872-81. For reference to ATCC 33090, see Le Marc Y et al., Int J Food Microbiol. 2002 March; 73(2-3):219-37. For reference to ATCC 19115, see Vodnar D C., Chem Cent J. 2012 Jul. 28; 6(1):74. doi: 10.1186/1752-153X-6-74. For reference to ATCC 27853, see Reimer L G et al., Antimicrob Agents Chemother. 1981 June; 19(6):1050-5. For reference to ATCC 13076, see Fioretto F et al., Braz J Med Biol Res. 2005 August; 38(8):1259-65. Epub 2005 Jul. 30. For reference to ATCC 13311, see Leguérinel I et al., Int J Food Microbiol. 2007 May 1; 116(1):88-95. Epub 2007 Jan. 13. For reference to ATCC 27336, see Chen S et al., Appl Environ Microbiol. 2013 July; 79(13):4015-23. doi: 10.1128/AEM.00704-13. Epub 2013 Apr. 19. For reference to ATCC 43079, see Farrow J A and Collins M D., Syst. Appl. Microbiol. 5: 483-493, 1984. For reference to ATCC BAA-1323, see Svensson Mikael D et al., Microbiology 148: 3933-3945, 2002.

The food supplement, the nutraceutical, pharmaceutical or cosmetic composition of the invention may be suitably formulated for different routes of administration. Such routes of administrations include auricular, buccal, cutaneous, dental, nasal, ophthalmic, oral, oropharyngeal, rectal, respiratory (inhalation), sublingual, topical or vaginal.

Generally, the compositions comprising the extracts of the invention are administered in a "therapeutically effective amount".

For the aim of the present description and of the following claims, the term "comprising" also includes the terms "which essentially consists of" or "which consists of".

The amount of the composition actually administered will typically be determined by a physician, in the light of the relevant circumstances, including the condition to be treated, the chosen route of administration, the actual composition administered, the age, body weight, and response of the individual subject, the severity of the subject's symptoms and the like. For any composition, the therapeutically effective dose can be estimated initially either in cell culture assays or in animal models, usually mice, rats, guinea pigs, rabbits, dogs, or pigs.

The animal model may also be used to determine the appropriate concentration range and route of administration. Such information can then be used to determine useful doses and routes for administration in humans. In calculating the Human Equivalent Dose (HED) it is recommended to use the conversion table provided in Guidance for Industry and Reviewers document (2005, U.S. Food and Drug Administration, Rockville, Maryland, USA).

According to the invention, the dose of the extract to be administered to humans may be regulated referring to the herbal composition used to prepare it and, consequently, the amount of grinded single dried plants present in the herbal composition. Usually, from 0.001 to 500 g of each grinded dried plant is used to prepare the final extract, optionally from 0.01 to 100 g. Preferably, from 1 to 100 g of each grinded dried plant is used per 1 kg of final extract. Such extract may be used as such or in a lyophilized, dried or freeze dried form in the final composition for human or animal use or it may be further diluted.

Preferably, from 0.001 to 5 g of each grinded dried plant is used per 1 kg of final product on sale.

The precise effective dose for a human subject will depend upon the severity of the disease or condition, general health of the subject, age, weight and gender of the subject, diet, time and frequency of administration, other simultaneous therapies, reaction sensitivities, and tolerance/response to therapy. This amount can be determined by routine experimentation and is within the judgement of the clinician.

Dosage treatment may be a single dose schedule or a multiple dose schedule.

Another object of the invention is the process for preparing the extract of the invention. Such process schematically comprises the following steps:

a) chopping or grinding separately or in a mixture at least two single dried plants to obtain corresponding plant powders;
b) mixing at least two different plant powders to obtain an herbal composition;
c) adding an extraction solvent to said herbal composition to obtain a corresponding liquid preparation (or extract);
d) incubating said liquid preparation at room temperature for a time ranging between 5 and 15 minutes; optionally,
e) heating said liquid preparation at a temperature ranging from 60° C. to 134° C. for a time ranging from 5 to 60 minutes; optionally,
f) centrifuging, collecting the supernatant and filtering the collected supernatant; and, optionally,
g) concentrating and/or drying or freeze drying the liquid preparation obtained from step e) or f).

According to the present application the word “lyophilisate” will refer to both freeze-dried (de-dehydrated) and dried extracts according to the invention.

The single dried plants are commercial products that may be purchased as part of the dried plants collections of pharmacies or herbal shops. Lists of dried plants collections are available at each pharmacy of herbal shop of choice and the dried plants available in such collections may vary from country to country.

For example, Belgium, France and Italy, decided in 2012 to join forces to develop a common list of plants, whose use could be allowed, provided that manufacturers meet the quality requirements of European law (EC Regulation 852/2004). Thanks to the hard work of three recognized experts (Robert Anton, Luke Delmulle and Mauro Serafini) the project resulted in the establishment of a list of 1,029 plants and 11 mushrooms (see list BelFrit at http://www.economie.gouv.fr/fils/fils/directions_services/dgccrf/imgs/breve/2014/documents/ha rmonized_list_Section_A.pdf)

The invention will now be described by making reference to the following non-limiting Examples.

EXAMPLES

Figure 1:
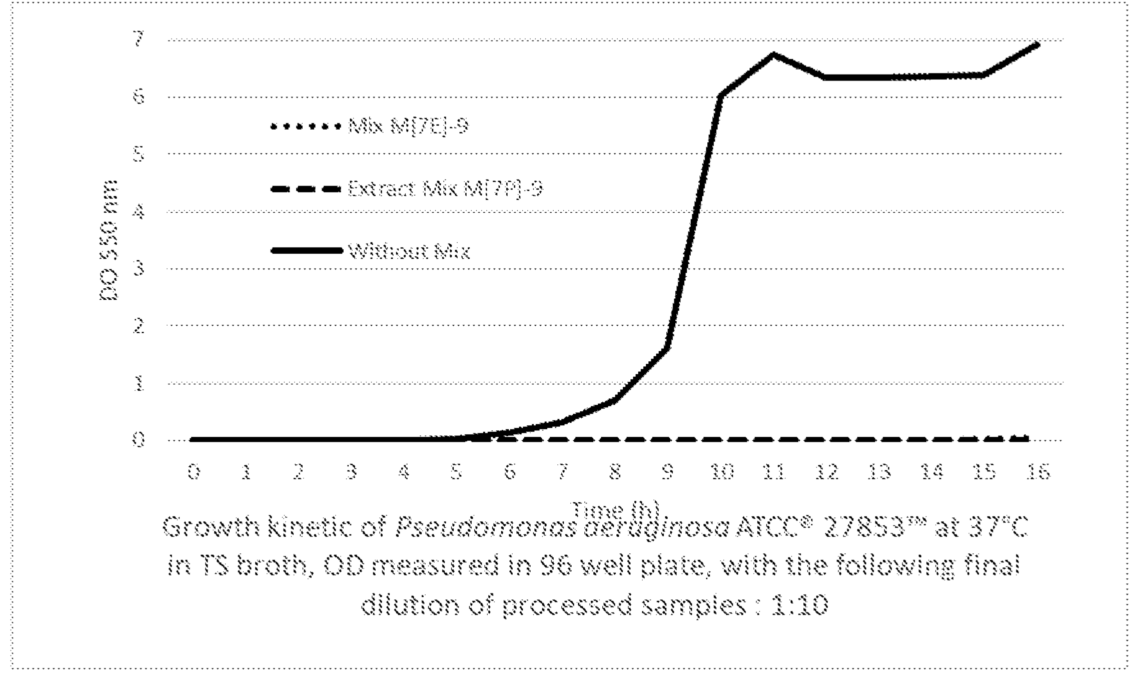
FIG. 1 shows the growth kinetics of *Pseudomonas aeruginosa* ATCC®27853™ at 37° C. in TS broth, OD measured in 96 well plate, with the following final dilution of processed sample: 1:10.

List of Plants Used in the Examples

The plants and parts of plants in the following list have been used in the different Examples. For the sake of conciseness, each plant is identified by a code used throughout the Examples. The weight corresponding to 200 μl (volume of the calibrated spoon) of plant powder is also indicated (Table 0-1). The dried plants of pharmaceutical grade PA00 to PB12 were obtained from “Pharmacie Fontgiève” (Clermont-Ferrand, France) and the dried plants of pharmaceutical grade PB13 to PD08 were obtained from “Pharmacie St Herem” (Clermont-Ferrand, France). When indicated in the Example, plants were also obtained from “Herboristerie Cailleau” (Chemillé. France) or from Siccarapam (Aubiat, France).

TABLE 0-1

List of plants with associated codes and weights of dried powders for one calibrated spoon

| Plant Code | Botanic Name | Part used | Weight (g) |
|---|---|---|---|
| PA00 | *Sambucus nigra* | flower | 0.0684 |
| PA01 | *Plantaga afra* | seed | 0.1357 |
| PA02 | *Eguisetum arvense* | aerial part | 0.0578 |
| PA05 | *Aloysio citrodora* | leaf | 0.0712 |
| PA06 | *Glycyrrhiza glabra* | root | 0.0774 |
| PA07 | *Camellia sinensis* | leaf | 0.07 |
| PA08 | *Solidago virg aurea* | aerial part | 0.0394 |
| PA10 | *Taraxacum officinale* | root | 0.0585 |
| PA11 | *Rheum palmatum* | root and rhizome | 0.1016 |
| PA12 | *Rosmarinus officinalis* | leaf | 0.0545 |
| PA13 | *Filipendula ulmaria* | flower | 0.095 |
| PA14 | *Satureja montana* | leaf | 0.0619 |
| PA15 | *Calendula officinalis* | petal | 0.0383 |
| PA16 | *Salvia officinalis* | leaf | 0.0415 |
| PA17 | *Passiflora incarnata* | aerial part | 0.0423 |
| PA18 | *Plantago lanceolata* | leaf | 0.0626 |

TABLE 0-1-continued

List of plants with associated codes and weights of dried powders for one calibrated spoon

| Plant Code | Botanic Name | Part used | Weight (g) |
|---|---|---|---|
| PA19 | *Tussilago farfara* | inflorescence | 0.0494 |
| PA20 | *Valeriana officinalis* | root | 0.1142 |
| PA21 | *Camellia sinensis* | leaf | 0.135 |
| PA22 | *Vitis vinifera* var. *tinctoria* | leaf | 0.0762 |
| PA23 | *Thymus vulgaris* | leaf | 0.0373 |
| PA24 | *Cassia angustifolia* | leaflet | 0.0648 |
| PA25 | *Tilia cordata* | sapwood | 0.0391 |
| PA26 | *Thymus serpyllum* | aerial part | 0.0442 |
| PA27 | *Tilia tomentosa* | bract | 0.0775 |
| PA28 | *Rubus idaeus* | leaf | 0.0463 |
| PA29 | *Fucus vesiculosus* | lamina | 0.1702 |
| PA30 | *Lavandula angustifolia* | flower | 0.0216 |
| PA31 | *Trigonella foenum-graecum* | seed | 0.1043 |
| PA32 | *Lotus corniculatus* | aerial part | 0.0497 |
| PA33 | *Handroanthus impetiginosus* | bark | 0.0814 |
| PA34 | *Viscum album* | leaf | 0.0783 |
| PA35 | *Fumaria officinalis* | flowering top | 0.0661 |
| PA36 | *Humulus lupulus* | fruit | 0.0307 |
| PA37 | *Fraxinus excelsior* | leaf | 0.0647 |
| PA38 | *Cytisus scoparius* | flower | 0.0253 |
| PA39 | *Foeniculum vulgare* | fruit | 0.081 |
| PA40 | *Origanum majorana* | leaf | 0.0345 |
| PA41 | *Citrus aurantium* var. *dulcis* | leaf | 0.0574 |
| PA44 | *Hyssopus officinalis* | flowering top | 0.0677 |
| PA45 | *Mentha x piperita* | leaf | 0.07 |
| PA46 | *Melissa officinalis* | leaf | 0.0747 |
| PA47 | *Fragaria vesca* | whole plant | 0.0692 |
| PA48 | *Phaseolus vulgaris* | fruit | 0.0608 |
| PA51 | *Marrubium vulgare* | aerial part | 0.0457 |
| PA52 | *Malva sylvestris* | flower | 0.0355 |
| PA53 | *Citrus aurantium var. dulcis* | petal | 0.0851 |
| PA55 | *Ginkgo biloba* | leaf | 0.0701 |
| PA57 | *Lamium album* | flower | 0.0591 |
| PA60 | *Olea europaea* | leaf | 0.0572 |
| PA61 | *Ilex paraguariensis* | leaf | 0.0598 |
| PA62 | *Artemisia vulgaris* | leaf | 0.0447 |
| PA67 | *Epilobium parviflorum* | aerial part | 0.0549 |
| PA69 | *Chamomilla recutita* | inflorescence | 0.0399 |
| PA70 | *Sisymbrium officinale* | aerial part | 0.0334 |
| PA72 | *Asparagus officinalis* | root | 0.0523 |
| PA73 | *Pimpinella anisum* | fruit | 0.0993 |
| PA74 | *Ribes nigrum* | fruit | 0.0769 |
| PA75 | *Crataegus oxyacantha* | flowering top | 0.0656 |
| PA76 | *Chamaemelum nobile* | inflorescence | 0.0193 |
| PA79 | *Eucalyptus globulus* | leaf | 0.0703 |
| PA80 | *Prunus cerasus* | peduncle | 0.0141 |
| PA81 | *Acorus calamus* | rhizome | 0.0631 |
| PA82 | *Calluna vulgaris* | flower | 0.0493 |
| PA83 | *Papaver rhoeas* | petal | 0.0278 |
| PA85 | *Cumimum cymimum* | fruit | 0.102 |
| PA86 | *Centaurium erythraea* | aerial part | 0.0591 |
| PA88 | *Vaccinium myrtillus* | fruit | 0.0939 |
| PA89 | *Vaccinium myrtillus* | leaf | 0.0711 |
| PA90 | *Angelica archangelica* | fruit | 0.0388 |
| PA92 | *Borago officinalis* | flower | 0.067 |
| PA93 | *Alchemilla vulgaris* | aerial part | 0.0588 |
| PA94 | *Artemisia pontica* | flowering top | 0.431 |
| PA95 | *Illicium verum* | fruit | 0.0793 |
| PA96 | *Chrysanthellum americanum* | aerial part | 0.0768 |
| PA97 | *Harpagophytum procumbens* | root | 0.0853 |

TABLE 0-1-continued

List of plants with associated codes and weights of dried powders for one calibrated spoon

| Plant Code | Botanic Name | Part used | Weight (g) |
|---|---|---|---|
| PA98 | *Betula pendula* | leaf | 0.0633 |
| PA99 | *Plantago lanceolata* | aerial part | 0.0718 |
| PB00 | *Agropyrum repens* | rhizome | 0.0646 |
| PB01 | *Carum carvi* | fruit | 0.1089 |
| PB02 | *Buxus sempervirens* | leaf | 0.0631 |
| PB03 | *Cichorium endivia* | root | 0.1513 |
| PB04 | *Rosa canina* | fruit | 0.1227 |
| PB05 | *Silybum marianum* | aerial part | 0.0502 |
| PB06 | *Asperula odorata* | aerial part | 0.062 |
| PB07 | *Desmodium adscendens* | leaf | 0.0493 |
| PB08 | *Combretum micranthum* | leaf | 0.0709 |
| PB09 | *Peumus boldus* | foliole | 0.0574 |
| PB10 | *Rhamnusfrangula* | bark | 0.0682 |
| PB11 | *Arctium lappa* | root | 0.1166 |
| PB12 | *Arctostaphylos uva-ursi* | leaf | 0.122 |
| PB13 | *Cichorium intybus* | root | 0.0924 |
| PB14 | *Fragaria vesca* | rhizome | 0.0529 |
| PB15 | *Citrus aurantium* var. *dulcis.* | peel | 0.0817 |
| PB16 | *Elettaria cardamomum* | fruit | 0.0606 |
| PB17 | *Althaea officinalis* | leaf | 0.0302 |
| PB18 | *Malva sylvestris* | leaf | 0.0809 |
| PB19 | *Althaea officinalis* | leaf | 0.0322 |
| PB20 | *Tilia cordata* | flowering top | 0.0596 |
| PB22 | *Betula pendula* | leaf | 0.0609 |
| PB24 | *Tilia cordata* | sapwood | 0.0368 |
| PB25 | *Fucus vesiculosus* | lamina | 0.1119 |
| PB26 | *Borago officinalis* | flower | 0.0342 |
| PB27 | *Vaccinium myrtillus* | fruit | 0.1553 |
| PB28 | *Verbascum thapsus* | flower | 0.045 |
| PB29 | *Citrus aurantium* | petal | 0.0477 |
| PB31 | *Galega officinalis* | aerial part | 0.0678 |
| PB32 | *Tabebuia impetiginosa* | bark | 0.0775 |
| PB33 | *Giechoma hederacea* | aerial part | 0.0601 |
| PB35 | *Cetraria islandica* | aerial part | 0.0776 |
| PB36 | *Rubus idaeus* | leaf | 0.0553 |
| PB38 | *Fraxinus excelsior* | leaf | 0.1241 |
| PB39 | *Lavandula angustifolia* | flower | 0.0207 |
| PB41 | *Cassia angustifolia* | fruit | 0.0568 |
| PB42 | *Fragaria vesca* | leaf | 0.0692 |
| PB45 | *Aspalathus linearis* | leaf | 0.0684 |
| PB46 | *Trigonella foenum-graecum* | seed | 0.1342 |
| PB47 | *Foeniculum vulgare* | fruit | 0.0818 |
| PB48 | *Alkanna tinctoria* | root | 0.0606 |
| PB49 | *Mentha spicata* | leaf | 0.0694 |
| PB50 | *Eupatorium cannabinum* | aerial part | 0.0529 |
| PB51 | *Echinacea purpurea* | root | 0.0915 |
| PB55 | *Eucalyptus globulus* | leaf | 0.0666 |
| PB57 | *Rosaxcentifolia* | bud | 0.0819 |
| PB58 | *Solanum dulcamara* | stem | 0.0709 |
| PB60 | *Arbutus unedo* | leaf | 0.0891 |
| PB61 | *Borrago officinalis* | aerial part | 0.0754 |
| PB76 | *Eleutherococcus senticosus* | root | 0.0571 |
| PB77 | *Cupressus sempervirens* | nut | 0.0862 |
| PB78 | *Curcuma longa* | root | 0.0946 |
| PB79 | *Cuminum cyminum* | fruit | 0.1109 |
| PB81 | *Salvia officinalis* | leaf | 0.0536 |
| PB82 | *Salix alba* | bark | 0.0522 |
| PB83 | *Saponaria officinalis* | aerial part | 0.0602 |
| PB85 | *Lythrum salicaria* | aerial part | 0.0581 |
| PB86 | *Citrus limon* (L) *Bumf.* | peel | 0.098 |
| PB88 | *Centella asiatica* | aerial part | 0.0685 |

TABLE 0-1-continued

List of plants with associated codes and weights of dried powders for one calibrated spoon

| Plant Code | Botanic Name | Part used | Weight (g) |
|---|---|---|---|
| PB92 | *Plantago ovata* | seed | 0.1266 |
| PB97 | *Agropyrum repens* | rhizome | 0.0555 |
| PB98 | *Cichorium intybus* | leaf | 0.0715 |
| PB99 | *Potentilla anserina* | leaf | 0.0298 |
| PC01 | *Ouercus robur* | bark | 0.06 |
| PC02 | *Chelidonium majus* | aerial part | 0.0608 |
| PC04 | *Prunus cerasus* | peduncle | 0.0199 |
| PC06 | *Asparagus officinalis* | root | 0.0812 |
| PC08 | *Medicago sativa* | seed | 0.113 |
| PC11 | *Juglans regia* | leaf | 0.0641 |
| PC12 | *Olea europaea* | leaf | 0.0561 |
| PC14 | *Myrtus communis* | leaf | 0.0716 |
| PC15 | *Trifolium rubens* | flower | 0.0484 |
| PC17 | *Curcuma zedoaria* | rhizome | 0.077 |
| PC19 | *Vitis vinifera* var. *tinctoria* | leaf | 0.0695 |
| PC20 | *Eugenia caryophyllus* | clove | 0.0852 |
| PC21 | *Althaea officinalis* | root | 0.0642 |
| PC22 | *Alpinia officinarum* | rhizome | 0.0658 |
| PC23 | *Ginkgo biloba* | leaf | 0.0775 |
| PC24 | *Panax ginseng* | lateral root | 0.1782 |
| PC25 | *Zingiber officinale* | rhizome | 0.078 |
| PC26 | *Juniperus communis* | fruit | 0.0505 |
| PC27 | *Geranium robertianum* | aerial part | 0.0639 |
| PC28 | *Gentiana lutea* | root | 0.0992 |
| PC29 | *Rubia tinctorium* | root | 0.0868 |
| PC32 | *Jasminum officinale* | flower | 0.0616 |
| PC33 | *Combretum micranthum* | leaf | 0.0769 |
| PC34 | *Satureja montana* | leaf | 0.0715 |
| PC35 | *Cassia angustifolia* | leaflet | 0.0881 |
| PC36 | *Verbena officinalis* | aerial part | 0.0603 |
| PC37 | *Lippia citrodora* | leaf | 0.0813 |
| PC38 | *Veronica officinalis* | complete | 0.0781 |
| PC41 | *Calendula officinalis* | petal | 0.0523 |
| PC42 | *Sambucus nigra* | bark | 0.0593 |
| PC45 | *Solidago gigantea* | aerial part | 0.0612 |
| PC49 | *Tanacetum vulgare* | aerial part | 0.0577 |
| PC50 | *Galium odoratum* | aerial part | 0.041 |
| PC51 | *Rhamnusfrangula* | bark | 0.0726 |
| PC52 | *Betula alba* | bark | 0.0806 |
| PC53 | *Verbascum thapsus* | bark | 0.0435 |
| PC54 | *Peumus boldus* | leaf | 0.0695 |
| PC55 | *Centaurea cyanus* | petal | 0.0456 |
| PC57 | *Illicum verum* | fruit | 0.1027 |
| PC58 | *Inula helenium* | root | 0.0904 |
| PC60 | *Cinnamomum zeylanicum* | bark | 0.1374 |
| PC61 | *Chamaemelum nobile* | flower | 0.0316 |
| PC62 | *Calamintha officinalis* | aerial part | 0.0726 |
| PC63 | *Arctostaphylosu vaursi* | leaf | 0.088 |
| PC64 | *Ononis spinosa* | root | 0.0832 |
| PC65 | *Calluna vulgaris* | flower | 0.0446 |
| PC66 | *Morus nigra* | leaf | 0.1032 |
| PC67 | *Hypericum perforatum* | flowering top | 0.0829 |
| PC68 | *Achillea millefolium* | flowering top | 0.0332 |
| PC70 | *Mentha × piperita* | leaf | 0.071 |
| PC71 | *Melissa officinalis* | leaf | 0.0847 |
| PC72 | *Cochlearia officinalis* | flowers | 0.0497 |
| PC73 | *Malva sylvestris* | flower | 0.0615 |
| PC74 | *Cynara scolymus* | leaf | 0.0458 |
| PC75 | *Arnica montana* | flower | 0.0254 |
| PC76 | *Artemisia vulgaris* | aerial part | 0.0289 |
| PC78 | *Angelica archangelica* | complete | 0.0909 |
| PC79 | *Anethum graveolens* | fruit | 0.1335 |
| PC82 | *Ballota nigra* | aerial part | 0.0368 |
| PC83 | *Origanum majorana* | leaf | 0.0539 |
| PC84 | *Zea mays* | stigma | 0.0632 |
| PC86 | *Agrimonia eupatoria* | aerial part | 0.0721 |
| PC88 | *Levisticum officinale* | aerial part | 0.0848 |
| PC94 | *Phaseolus vulgaris* | fruit | 0.0686 |
| PC97 | *Hieracium pilosella* | aerial part | 0.0406 |
| PC98 | *Parietaria officinalis* | aerial part | 0.0349 |
| PC99 | *Passiflora incarnata* | aerial part | 0.0817 |
| PD00 | *Rumex patientia* | root | 0.1208 |
| PD02 | *Petroseiinum crispum* | fruit | 0.1084 |
| PD05 | *Urtica dioica* | aerial part | 0.0584 |
| PD06 | *Cola acuminata* | nut | 0.1556 |
| PD07 | *Capsellabursapastoris* | aerial part | 0.0535 |
| PD08 | *Centaurea erythraea* | aerial part | 0.058 |

Method for Preparing the Herbal Compositions (Method A)

Each dried plant was grinded using a coffee bean grinder (Type 8100, SEB, France). The obtained powder (plant powder) was sieved using a 2 mm mesh sieve, and conserved in 60 ml containers (Labbox, France).

Mixtures of different grinded dried plants (or plant powders) were prepared by collecting a fixed volume of plant powder with a calibrated spoon allowing to collect 200 μL of powder. The weight of the collected volume is dependent on the specific plant powder (see Table 0-1).

Such mixes or mixtures of different grinded dried plants (or plant powders) as well as single dried plants will herein be called also as “herbal compositions”.

Method for Preparing the Water Extracts (Also Called in this Examples Section as “Processed Samples”, “Extracts” or “Mixes Extracts”) (Method B)

Such herbal compositions were placed into 50 ml falcon tubes (Falcon, USA) and 20 ml or 40 ml (as indicated in Examples) of alimentary grade spring water (Volvic, France) solution containing 100 g/l of alimentary grade sucrose (Daddy, France) were added. The choice of alimentary grade sucrose and water rather than their scientific grade counterparts was dictated by the objective of obtaining an edible composition entering the class of “flavourings” that may be directly consumed under the Regulation (EC) No 1334/2008 of 16 Dec. 2008 on flavourings and certain food ingredients with flavouring properties for use in and on foods.

Each falcon tube containing such liquid preparations was agitated using a vortex mixer (ThermoFisher, USA) for 10 seconds, incubated at room temperature for 10 min and placed in an autoclave (MED 12, JP Selecta, Spain) and underwent a 20 minute sterilization cycle at 119° or 121° C., as indicated. After cooling down, the sterilized preparation was kept at −20° C. until use.

The day of manipulation, the preparation was defrosted at 37° C. The preparation was centrifuged at 4000 rpm during 10 min (Multifuge 35-R, Heraeus, Germany) or incubated at room temperature for decantation (as indicated in Examples). 2 mL of the supernatant was collected with a 10 mL syringe and filtered using 0.2 μM filters (Minisart Syringe Filters, Sartorius, Germany) and collected onto a 2 mL Eppendorf tube. The remaining sterilized preparation is kept at −20° C. for further use.

The samples so obtained will herein be called also as “processed samples” and will be identified by the same name or code given to the corresponding herbal composition (for example the name “Mix[2P]-1” will be used to identify an herbal composition and the corresponding extract (or processed sample), for which a biological activity is determined).

Method for Determining the Antimicrobial and Antibiofilm Activity (Method C)

The biological activity of each processed sample was determined by using the strains indicated in each experiment (or Example). For each measurement, each bacterium stored at −80° C. on cryobeads (Technical Service, UK) is plated on a TS agar plate (Tryptic Soy Broth, Sigma, USA; Agar, Fisherbrand, USA) and incubated at 37° C. overnight. Several colonies are collected using an inoculation loop and suspended in saline solution. The optical density is measured, and a dilution is performed in TS broth to obtain a concentration of $2.10^{5.5}$ bacteria/mL for *Staphylococcus aureus* and *Staphylococcus pseudintermedius* strains, $2.10^{5}$ bacteria/mL for *Staphylococcus epidermidis*.

The biological activity of each processed sample was measured on 96 wells plates, using the strains indicated in each experiment (or Example) and a control without bacteria. Each well contains 190 μL of TS broth inoculated with $10^{5.5}$ bacteria/mL for *Staphylococcus aureus* and *Staphylococcus pseudintermedius* strains, $10^{5}$ bacteria/mL for *Staphylococcus epidermidis* (or at the concentration indicated in the Examples for all other species) or no bacteria for the control and diluted processed sample or negative control (sucrose solution at 100 g/l without any plants) at 1:10, 1:20, 1:40 and 1:80 final concentration or at 1:20, 1:63 and 1:200 (as indicated in Examples).

Each plate was incubated for 17 hours at 37° C. in an incubator (HettCube 400, Hettich, Germany).

The measurements were performed based on analyzing with the ImageJ software (NIH, USA) (but any other equivalent software may be used) images of the plates obtained using a commercial document scanner (V 220, Epson, Japan). Images of the plate positioned on the scanning area are acquired at 600 dpi using the software provided with the scanner. For each plate, 3 images were acquired: the first, before incubation (T0), the second after 17 h incubation (Tf), and the third after Crystal Violet (CV) staining as described in Optimization of microtitre plate assay for the testing of biofilm formation ability in different *Salmonella* serotypes (Agarwal, R. K. et al., International Food Research Journal 18(4):1493-1498, 2011).

For each well of interest, from respectively the first, second and the third image, circular regions of diameter, respectively, 14, 14 and 76 pixels, centered relative to the well, were characterized using an ImageJ macro to calculate, respectively, the mean M1 and M2 of the 1% less intense pixels of the region and the mean M3 of all the pixels of the region. The turbidity of the bacterial solution in the well was deduced from M1 and M2 using a reference curve obtained in an independent experiment where the mean of the 1% less intense pixels of the region 14 pixels diameter region was measured from wells containing bacterial solutions of known turbidity. The optical density of the Crystal Violet solution in the well was deduced from M3 using a reference curve obtained in an independent experiment where the mean of the pixels of the region 76 pixels diameter region was measured from wells containing Crystal Violet solutions of known optical density.

For each processed sample and a given bacterium, the MIC was determined from the highest inhibitory dilution (HID) among the 4 tested (1:10, 1:20, 1:40, 1:80) of processed sample which prevents the appearance of visible growth within 17 h. "0" was assigned when none of the tested dilutions was preventing bacterial growth.

For each well containing processed sample and a given bacterium, the inhibition percentage of bacteria planktonic growth was established according to the formula below:

$$\text{Planktonic growth inhibition (\%)} = \left(1 - \frac{Tf(\text{processed sample}) - T0(\text{processed sample})}{Tf(\text{negative control}) - T0(\text{negative control})}\right) * 100$$

where Tf(processed sample) is the turbidity from the second image of the sample well, T0(processed sample) is the turbidity of the first image of the same well, Tf(negative control) is the turbidity from the second image of a well containing the same bacteria without processed sample, T0(negative control) is the turbidity of the first image of the same well.

For each well containing processed sample and a given bacterium, the percentage of inhibition of biofilm formation (IBF) was established according to the following formula:

$$\text{Biofilm formation inhibition (\%)} = \left(1 - \frac{CV(\text{processed sample}) - CV(\text{processed sample})}{CV(\text{negative control}) - CV(\text{negative control})}\right) * 100$$

where CV(processed sample) is the OD from the third image of the sample well, CV(negative control) is the OD from the third image of a well containing the same bacteria without processed sample, CV(control sample) is the OD of the third image of a well containing the same sample or the negative control at the same dilution without any bacteria. A negative value of IBF means that the tested mixture is promoting the formation of biofilm.

Example 1

In this Example we illustrate simultaneous antimicrobial and antibiofilm activities against *Staphylococcus aureus* of the disclosed composition of 2 plants among 3: *Filipendula ulmaria, Camellia sinensis, Arctostaphylos uva-ursi*. The dried plants of pharmaceutical grade were obtained from "Herboristerie Cailleau" (Chemillé, France).

Starting from such three different plant powders six herbal compositions were prepared according to the Method A reported before, whose content is reported in Table 1-1.

TABLE 1-1

| herbal compositions of processed samples | | | |
|---|---|---|---|
| Herbal compositions | PA13 (nb spoon) | PA21 (nb spoon) | PB12 (nb spoon) |
| PA13 | 1 | | |
| PA21 | | 1 | |
| PB12 | | | 1 |
| Mix[2P]-1 | 1 | 1 | |
| Mix[2P]-2 | | 1 | 1 |
| Mix[2P]-3 | 1 | | 1 |

As shown in Table 1-1 the first three herbal compositions only contain a single plant powder, while the last three compositions contain two of the three different plant powders.

Starting from each herbal composition reported in Table 1-1 corresponding processed samples were prepared according to the Method B reported before using 20 mL of water containing 100 g/l of sucrose for water extraction and including the centrifugation step before filtration.

The bacteria planktonic growth and antibiofilm formation inhibition percentage of the processed samples of the 2 plant mixes and the associated separated plants of this Example 1 at 1:10 dilution was determined by using the following *Staphylococcus aureus* strains: ATCC 25923 and ATCC 29213, according to the Method C reported before and are given in Table 1-2.

TABLE 1-2 planktonic growth and biofilm formation inhibition (IBF) of 2 plants mixture processed sample and single plants processed sample at 1:10 dilution

| | | PA13 | PA21 | Mix[2P]-1 |
|---|---|---|---|---|
| ATCC 25923 | Planktonic growth inhibition | 20% | 26% | 82% |
| | Biofilm formation inhibition | 32% | 44% | 78% |
| ATCC 29213 | Planktonic growth inhibition | 16% | 27% | 100% |
| | Biofilm formation inhibition | 33% | 17% | 85% |
| | | **PA21** | **PB12** | **Mix[2P]-2** |
| ATCC 25923 | Planktonic growth inhibition | 26% | 17% | 104% |
| | Biofilm formation inhibition | 44% | 51% | 88% |
| ATCC 29213 | Planktonic growth inhibition | 27% | 8% | 100% |
| | Biofilm formation inhibition | 17% | 28% | 83% |
| | | **PA13** | **PB12** | **Mix[2P]-3** |
| ATCC 25923 | Planktonic growth inhibition | 20% | 17% | 82% |
| | Biofilm formation inhibition | 32% | 51% | 93% |
| ATCC 29213 | Planktonic growth inhibition | 16% | 8% | 66% |
| | Biofilm formation inhibition | 33% | 28% | 78% |

PA13, PA21 and PB12 have a known antibiotic effect. Limited inhibition of planktonic growth (<27%) and biofilm formation (<51%) were measured at 1:10 dilution, whereas the 3 aromatic preparations of 2 plant mix extract show antimicrobial effects (>66%) and antibiofilm effects (>78%) on both tested strains, ATCC 25923 and ATCC 29213.

For all Mixes (Mix[2P]-1, Mix[2P]-2, Mix[2P]-3), a synergistic effect of the 2 plants is observed for antimicrobial effects on the 2 strains tested.

Comparative Example 1

As a comparative Example, we illustrate the activity of some processed samples, which have been found to have none or poor antimicrobial and antibiofilm activities against *Staphylococcus aureus* and which were obtained from corresponding herbal compositions containing 2 different plant powders.

Five processed samples were prepared using 2 additional plants powders: PA74 (*Ribes nigrum* fruit powder) and PC72 (*Cochlearia officinalis* flowers powder).

The single dried plant powders were treated as described in Example 1 and five herbal compositions were prepared following the protocol reported in Method A described before. Such five herbal compositions had the content reported in Table 1-3.

TABLE 1-3 herbal compositions of processed samples

| Herbal Compositions | PA74 (nb spoon) | PC72 (nb spoon) | PA13 (nb spoon) | PA21 (nb spoon) |
|---|---|---|---|---|
| PA74 | 1 | | | |
| PC72 | | 1 | | |
| Mix 1 | 1 | 1 | | |
| Mix 2 | 1 | | 1 | |
| Mix 3 | | 1 | | 1 |

Each herbal composition was treated following the protocol reported in Method B to arrive at the corresponding processed sample using 20 mL of water containing 100 g/l of sucrose for water extraction and including the centrifugation step before filtration.

The biological activity of each processed sample was determined by using the following *Staphylococcus aureus* strains: ATCC 25923 and ATCC 29213, according to Method C described before.

The bacteria planktonic growth and antibiofilm formation inhibition percentage of the processed samples of the 2 plant mixes and the associated separated plants at 1:10 dilution are given in Table 1-4.

TABLE 1-4 planktonic growth and biofilm formation inhibition (IBF) of 2 plants mixture processed sample and single plants processed sample at 1:10 dilution

| | | PC72 | PA74 | Mix 1 |
|---|---|---|---|---|
| ATCC 25923 | Planktonic growth inhibition | −9% | 0% | −3% |
| | Biofilm formation inhibition | 12% | 36% | 24% |
| ATCC 29213 | Planktonic growth inhibition | −10% | −7% | −6% |
| | Biofilm formation inhibition | 13% | 5% | −2% |
| | | **PA13** | **PA74** | **Mix 2** |
| ATCC 25923 | Planktonic growth inhibition | 20% | 0% | 19% |
| | Biofilm formation inhibition | 32% | 36% | 48% |
| ATCC 29213 | Planktonic growth inhibition | 16% | −7% | 13% |
| | Biofilm formation inhibition | 33% | 5% | 37% |
| | | **PA21** | **PC72** | **Mix 3** |
| ATCC 25923 | Planktonic growth inhibition | 26% | −9% | 25% |
| | Biofilm formation inhibition | 44% | 12% | 51% |
| ATCC 29213 | Planktonic growth inhibition | 27% | −10% | 18% |
| | Biofilm formation inhibition | 17% | 13% | 29% |

PC72 and PA74 and the associated Mix 1 showed no antimicrobial activity and limited antibiofilm activity on both tested strains at 1:10 dilution. In each case, no synergistic effect was observed.

For all mixes containing PA13 and PA21 (Mix 2 and 3), no synergistic effect was observed for antimicrobial effects on the 2 strains tested at 1:10 dilution, when such mixes contained also PC72 or PA74.

It is interesting to note that both *Ribes nigrum* and *Cochlearia officinalis* were known to have antimicrobial effect.

This comparative Example illustrates that not any random combination between single dried plants having known antimicrobial and/or antibiofilm activity allows to obtain a water extract, in which a synergistic activity is observed.

Example 2

In this Example we illustrate simultaneous antimicrobial and antibiofilm activities against *Staphylococcus aureus* of different water extracts obtained from the herbal compositions containing 2 plants among the 3 reported in Example 1, when such water extracts are prepared according to different methods.

The dried plants of pharmaceutical grade were obtained from "Herboristerie Cailleau" (Chemillé, France).

Twenty herbal compositions, whose content is reported in Table 2-1 were prepared according to the Method A reported before.

TABLE 2-1 herbal compositions of processed samples

| Herbal compositions | PA13 (nb spoon) | PA21 (nb spoon) | PB12 (nb spoon) |
|---|---|---|---|
| Mix 1 | | 1 | 1 |
| Mix 2 | 1 | | 1 |

For each herbal composition, 20 liquid (water) preparations were prepared as follow:

The collected powders were placed into twenty 50 ml falcon tubes (Falcon, USA). 20 ml of alimentary grade spring water (Volvic, France) solution containing 0, 25, 50, 75 or 100 g/l of alimentary grade sucrose (Daddy, France) were added to 4 flacon tubes per condition. Each falcon tube containing such liquid preparations was agitated using a vortex mixer (ThermoFisher, USA) for 10 seconds, incubated at room temperature for 10 minutes, then 4 different heating treatments were applied to each condition:

Cold Infusion (No Heating Before Centrifugation and Filtration):

after incubation at room temperature, the preparations were centrifuged at 4,000 rpm during 10 minutes (Multifuge 35-R, Heraeus, Germany), 2 mL of the supernatant was collected with a 10 mL syringe and filtered using 0.2 μM filters (Minisart Syringe Filters, Sartorius, Germany) and collected onto a 2 mL Eppendorf tube and kept at −20° C. until use. The day of manipulation, the preparation was defrosted at 37° C.

Heating at 60° C. for 30 minutes:

after incubation at room temperature, the preparations were placed in an autoclave (VWR, USA) and underwent a 20 minutes cycle at 60° C. After cooling down, the treated preparations were centrifuged at 4000 rpm during 10 min (Multifuge 35-R, Heraeus, Germany), 2 mL of the supernatant was collected with a 10 mL syringe and filtered using 0.2 μM filters (Minisart Syringe Filters, Sartorius, Germany) and collected onto a 2 mL Eppendorf tube and kept at −20° C. until use. The day of manipulation, the preparation was defrosted at 37° C.

Heating at 119° C. for 20 minutes:

after incubation at room temperature, the preparations were placed in an autoclave (VWR, USA) and underwent a 20 minutes sterilization cycle at 119° C. After cooling down, the treated preparations were kept at −20° C. until use. The day of manipulation, the preparation was defrosted at 37° C., centrifuged at 4000 rpm during 10 min (Multifuge 35-R, Heraeus, Germany), 1 mL of the supernatant was collected with a 10 mL syringe and filtered using 0.2 μM filters (Minisart Syringe Filters, Sartorius, Germany) and collected onto a 2 mL Eppendorf tube.

These samples will herein called "processed sample".

The biological activity of each processed sample was determined by using *Staphylococcus aureus* strain ATCC 25923, according to the previously described Method C.

The bacteria planktonic growth percentage of 20 processed samples, prepared starting from the herbal compositions after each of the different heating treatment presented before, at 1:10 dilution are given in Table 2-2.

TABLE 2-2 planktonic growth of ATCC 25923 with 20 processed samples at 1:10 dilution prepared starting from the herbal compositions (Mix 1 and Mix 2 of Table 2-1)

| Temperature treatment | Sucrose concentration (g/l) | Mix 1 Processed samples | Mix 2 Processed samples |
|---|---|---|---|
| Cold infusion | 100 | −4% | 48% |
| | 75 | −3% | 52% |
| | 50 | −4% | 31% |
| | 25 | −4% | 31% |
| | 0 | 1% | 0% |
| 60° C. 30 min | 100 | 0% | 82% |
| | 75 | 4% | 83% |
| | 50 | 1% | 83% |
| | 25 | 1% | 86% |
| | 0 | −4% | 16% |
| 119° C. 20 min | 100 | 103% | 92% |
| | 75 | 103% | 91% |
| | 50 | 70% | 94% |
| | 25 | 103% | 99% |
| | 0 | 96% | 99% |

All processed samples prepared from Mix 1 showed antimicrobial effects on ATCC 25923, only after temperature treatment at 1190, whereas Mix 2 showed limited antimicrobial effects (31 to 52% of inhibition) after cold infusion for all concentration of sucrose except for the condition without sucrose and after all tested temperature treatments (>82% of inhibition) except for the condition with no sucrose addition treated at 60° C., for which the processed sample showed only 16% of planktonic growth inhibition. The temperature treatments enhanced the antimicrobial effects of Mix 2. The optimal temperature treatment among tested treatments for Mix 1 and Mix 2 was 119° C. for 20 minutes.

Sucrose concentration influence on antimicrobial effect depends on the temperature treatment applied. For Mix 1 treated at 119° C. during 20 min, the same antimicrobial effect was obtained with 100, 75, 25 and 0 g/l of sucrose, lower activity was observed with 50 g/l. For Mix 2, the same antimicrobial effect was obtained regardless of sucrose concentration for 119° C. temperature treatment.

The biofilm formation inhibition (IBF) percentage of 20 processed samples, prepared starting from the herbal compositions after each of the different heating treatment presented before, at 1:10 dilution are given in Table 2-3.

TABLE 2-3 biofilm formation inhibition (IBF) of ATCC 25923 with 20 processed samples at 1:10 dilution prepared starting from the herbal compositions (Mix 1 and Mix 2 of Table 2-1)

| Temperature treatment | Sucrose concentration (g/l) | Mix1 Processed samples | Mix 2 Processed samples |
|---|---|---|---|
| Cold infusion | 100 | 34% | 74% |
| | 75 | 29% | 72% |
| | 50 | 22% | 60% |
| | 25 | 30% | 55% |
| | 0 | 54% | 50% |

TABLE 2-3-continued biofilm formation inhibition (IBF) of ATCC 25923 with 20 processed samples at 1:10 dilution prepared starting from the herbal compositions (Mix 1 and Mix 2 of Table 2-1)

| Temperature treatment | Sucrose concentration (g/l) | Mix1 Processed samples | Mix 2 Processed samples |
|---|---|---|---|
| 60° C. 30 min | 100 | 48% | 91% |
| | 75 | 34% | 94% |
| | 50 | 26% | 91% |
| | 25 | 26% | 88% |
| | 0 | 48% | 78% |
| 119° C. 20 min | 100 | 91% | 89% |
| | 75 | 91% | 88% |
| | 50 | 75% | 89% |
| | 25 | 92% | 87% |
| | 0 | 90% | 89% |

In all tested conditions, processed samples showed some antibiofilm effect.

For Mix 1, limited antibiofilm activity was observed for all concentration of sucrose with cold infusion and with 60° C. temperature treatment (22 to 55% of inhibition). High antibiofilm activity (>90% of inhibition) was observed with 119° C. temperature treatment for all concentrations of sucrose except for 50 g/l which showed 75% of inhibition.

For Mix 2, equivalent antibiofilm activities were obtained regardless of sucrose concentrations for 60° C. and 119° C. temperature treatments (>77% of inhibition). After cold infusion, Mix 2 showed medium to good antibiofilm effect (from 50% to 74% of inhibition) depending on the sucrose concentrations: the more the sucrose concentration was high, the more the preparation was active.

Example 3

In this Example we illustrate simultaneous antimicrobial and antibiofilm activities against *Staphylococcus aureus* and *Staphylococcus epidermidis* of 12 mixtures containing 2 to 7 plants.

The dried plants of pharmaceutical grade were obtained from "Herboristerie Cailleau" (Chemillé, France).

Herbal compositions comprising from 2 to 7 plant powders were prepared by collecting a fixed volume of plant powder with a calibrated spoon allowing to collect 200 μL of powder Twelve herbal composition were prepared as below (Table 3-1) according to the previously described Method A.

TABLE 3-1 herbal compositions of processed samples

| Herbal compositions | PA13 (nb spoon) | PA21 (nb spoon) | PB12 (nb spoon) | PA11 (nb spoon) | PA12 (nb spoon) | PA22 (nb spoon) | PA79 (nb spoon) |
|---|---|---|---|---|---|---|---|
| Mix[2P]-1 | 1 | 1 | | | | | |
| Mix[2P]-2 | | 1 | 1 | | | | |
| Mix[2P]-3 | 1 | | 1 | | | | |
| Mix[3P]-1 | 1 | 1 | 1 | | | | |
| Mix[4P]-1 | 1 | 1 | 1 | 1 | | | |
| Mix[4P]-2 | 1 | 1 | 1 | | 1 | | |
| Mix[4P]-3 | 1 | 1 | 1 | | | 1 | |
| Mix[5P]-1 | 1 | 1 | 1 | | 1 | 1 | |
| Mix[5P]-2 | 1 | 1 | 1 | 1 | | 1 | |
| Mix[5P]-3 | 1 | 1 | 1 | 1 | 1 | | |
| Mix[6P]-1 | 1 | 1 | 1 | 1 | 1 | 1 | |
| Mix[7P]-1 | 1 | 1 | 1 | 1 | 1 | 1 | 1 |

Twelve corresponding processed samples were prepared starting from each herbal composition according to the previously described Method B using 20 mL of water containing 100 g/l of sucrose for water extraction and including the centrifugation step before filtration.

The biological activity of the processed sample was determined by using the following *Staphylococcus aureus* strains: ATCC 25923, ATCC 29213, NCTC 12493, ATCC 33591, ATCC 33592, ATCC 43300, ATCC 700698, ATCC 700699, ATCC 9144 and ATCC BAA-44 and the following *Staphylococcus epidermidis* strains: ATCC 12228, ATCC 700296, ATCC 49461 and ATCC 14990, according to the previously described Method C.

The minimum inhibitory concentration (MIC) observed with the 12 processed samples is given in Table 3-2 in the form of HID, as well as the average efficacy over all the strains of *Staphylococcus aureus* and *Staphylococcus epidermidis*.

TABLE 3-2

HID of the 12 processed samples on 10 strains of *Staphylococcus aureus* and 4 strains of *Staphylococcus epidermidis*

| | | Mix[2P]-1 | Mix[2P]-2 | Mix[2P]-3 | Mix[3P]-1 | Mix[4P]-1 | Mix[4P]-2 |
|---|---|---|---|---|---|---|---|
| *S. aureus* | ATCC 25923 | 10 | 10 | 10 | 10 | 10 | 10 |
| | ATCC 29213 | 10 | 10 | 0 | 10 | 10 | 10 |

TABLE 3-2-continued

HID of the 12 processed samples on 10 strains of *Staphylococcus aureus* and 4 strains of *Staphylococcus epidermidis*

| | | | | | | | |
|---|---|---|---|---|---|---|---|
| | NCTC 12493 | 10 | 10 | 10 | 10 | 10 | 20 |
| | ATCC 33591 | 10 | 10 | 10 | 10 | 10 | 10 |
| | ATCC 33592 | 10 | 10 | 10 | 10 | 10 | 10 |
| | ATCC 43300 | 10 | 10 | 0 | 10 | 10 | 10 |
| | ATCC 700698 | 10 | 10 | 10 | 10 | 10 | 10 |
| | ATCC 700699 | 10 | 10 | 10 | 20 | 20 | 20 |
| | ATCC 9144 | 10 | 10 | 10 | 10 | 10 | 10 |
| | ATCC BAA-44 | 10 | 10 | 10 | 10 | 10 | 20 |
| | Average | 10.0 | 10.0 | 8.0 | 11.0 | 11.0 | 13.0 |
| *S. epidermidis* | ATCC 12228 | 10 | 10 | 10 | 20 | 20 | 20 |
| | ATCC 700296 | 20 | 20 | 20 | 20 | 20 | 20 |
| | ATCC 49461 | 10 | 10 | 20 | 20 | 20 | 20 |
| | ATCC 14990 | 10 | 20 | 10 | 20 | 20 | 20 |
| | Average | 12.5 | 15 | 15 | 20 | 20 | 20 |
| | Total average | 10.7 | 11.4 | 10.0 | 13.6 | 13.6 | 15.0 |
| | | Mix[4P]-3 | Mix[5P]-1 | Mix[5P]-2 | Mix[5P]-3 | Mix[6P]-1 | Mix[7P]-1 |
| *S. aureus* | ATCC 25923 | 10 | 10 | 10 | 20 | 10 | 20 |
| | ATCC 29213 | 10 | 10 | 10 | 10 | 10 | 10 |
| | NCTC 12493 | 20 | 20 | 20 | 20 | 20 | 20 |
| | ATCC 33591 | 10 | 20 | 20 | 20 | 20 | 20 |
| | ATCC 33592 | 10 | 20 | 20 | 20 | 10 | 20 |
| | ATCC 43300 | 10 | 10 | 10 | 10 | 10 | 20 |
| | ATCC 700698 | 10 | 20 | 20 | 20 | 10 | 20 |
| | ATCC 700699 | 20 | 20 | 20 | 20 | 20 | 20 |
| | ATCC 9144 | 10 | 20 | 20 | 20 | 10 | 20 |
| | ATCC BAA-44 | 20 | 20 | 20 | 20 | 20 | 20 |
| | Average | 13.0 | 17.0 | 17.0 | 18.0 | 14.0 | 19.0 |
| *S. epidermidis* | ATCC 12228 | 20 | 20 | 20 | 20 | 20 | 40 |
| | ATCC 700296 | 20 | 20 | 20 | 20 | 20 | 40 |
| | ATCC 49461 | 20 | 20 | 20 | 20 | 20 | 20 |
| | ATCC 14990 | 20 | 20 | 20 | 20 | 20 | 20 |
| | Average | 20 | 20 | 20 | 20 | 20 | 30 |
| | Total average | 15.0 | 17.9 | 17.9 | 18.6 | 15.7 | 22.1 |

Since in this Example observed HID are in most case between 1:10 and 1:20, 1:20 dilution was chosen as the dilution of reference for the calculation of bacteria planktonic growth inhibition percentage and bioflim formation inhibition percentage. The bacteria planktonic growth inhibition percentage of the 12 processed samples at 1:20 dilution is given in Table 3-3, as well as the average efficacy over all the strains of *Staphylococcus aureus* and *Staphylococcus epidermidis*.

TABLE 3-3 planktonic growth inhibition of the 12 processed samples on 10 strains of *Staphylococcus aureus* and 4 strains of *Staphylococcus epidermidis* at 1:20 dilution

| | | Mix [2P]-1 | Mix [2P]-2 | Mix [2P]-3 | Mix [3P]-1 | Mix [4P]-1 | Mix [4P]-2 | Mix [4P]-3 | Mix [5P]-1 | Mix [5P]-2 | Mix [5P]-3 | Mix [6P]-1 | Mix [7P]-1 |
|---|---|---|---|---|---|---|---|---|---|---|---|---|---|
| *S. aureus* | ATCC 25923 | 12% | 12% | 9% | 11% | 20% | 11% | 20% | 34% | 41% | 35% | 21% | 96% |
| | ATCC 29213 | 11% | 11% | 7% | 11% | 19% | 11% | 11% | 33% | 33% | 33% | 29% | 45% |
| | NCTC 12493 | 19% | 8% | 5% | 25% | 21% | 101% | 97% | 98% | 108% | 108% | 96% | 100% |
| | ATCC 33591 | 12% | 8% | 8% | 12% | 19% | 16% | 34% | 104% | 107% | 111% | 83% | 98% |
| | ATCC 33592 | 19% | 15% | 12% | 18% | 26% | 23% | 26% | 86% | 105% | 98% | 38% | 100% |
| | ATCC 43300 | 18% | 11% | 11% | 15% | 18% | 18% | 18% | 33% | 34% | 37% | 16% | 97% |
| | ATCC 700698 | 11% | 8% | 8% | 11% | 11% | 11% | 16% | 107% | 97% | 73% | 40% | 98% |
| | ATCC 700699 | 43% | 36% | 38% | 87% | 98% | 99% | 99% | 100% | 108% | 112% | 116% | 98% |
| | ATCC 9144 | 12% | 7% | 8% | 12% | 24% | 17% | 24% | 80% | 97% | 73% | 43% | 94% |
| | ATCC BAA-44 | 30% | 11% | 12% | 32% | 28% | 83% | 102% | 100% | 107% | 110% | 114% | 103% |
| | Average | 19% | 13% | 12% | 23% | 28% | 39% | 45% | 78% | 84% | 79% | 60% | 93% |
| *S. epidermidis* | ATCC 12228 | 49% | 49% | 66% | 94% | 99% | 99% | 98% | 99% | 99% | 104% | 114% | 97% |
| | ATCC 700296 | 87% | 83% | 78% | 94% | 99% | 99% | 95% | 101% | 98% | 102% | 105% | 92% |
| | ATCC 49461 | 68% | 68% | 70% | 93% | 101% | 101% | 97% | 102% | 102% | 106% | 112% | 93% |
| | ATCC 14990 | 38% | 71% | 61% | 92% | 103% | 100% | 95% | 102% | 102% | 106% | 107% | 93% |
| | Average | 61% | 68% | 69% | 94% | 100% | 100% | 96% | 101% | 100% | 104% | 109% | 94% |
| | Total average | 31% | 28% | 28% | 43% | 49% | 56% | 59% | 84% | 88% | 86% | 74% | 93% |

The biofilm formation inhibition (IBF) percentage of the 12 processed samples at 1:20 dilution is given in Table 3-4, as well as the average efficacy over all the strains of *Staphylococcus aureus* and *Staphylococcus epidermidis*. The average efficacy of bacteria planktonic growth inhibition and biofilm formation inhibition percentage over all the tested strains is a good indicator of antimicrobial and antibiofilm efficacy on different bacterial strains.

TABLE 3-4 biofilm formation inhibition (IBF) of the 12 processed samples on 10 strains of *Staphylococcus aureus* and 4 strains of *Staphylococcus epidermidis* at 1:20 dilution

| | | Mix [2P]-1 | Mix [2P]-2 | Mix [2P]-3 | Mix [3P]-1 | Mix [4P]-1 | Mix [4P]-2 | Mix [4P]-3 | Mix [5P]-1 | Mix [5P]-2 | Mix [5P]-3 | Mix [6P]-1 | Mix [7P]-1 |
|---|---|---|---|---|---|---|---|---|---|---|---|---|---|
| *S. aureus* | ATCC 25923 | 37% | 14% | 22% | 18% | 29% | 36% | 35% | 51% | 41% | 40% | 38% | 90% |
| | ATCC 29213 | 49% | 12% | 38% | 27% | 33% | 38% | 25% | 35% | 38% | 34% | 38% | 41% |
| | NCTC 12493 | 49% | −6% | 47% | 36% | 35% | 88% | 87% | 92% | 92% | 89% | 47% | 93% |
| | ATCC 33591 | 38% | −21% | 30% | 16% | 20% | 25% | 19% | 92% | 91% | 89% | 57% | 93% |
| | ATCC 33592 | 51% | −10% | 26% | 25% | 43% | 47% | 31% | 60% | 78% | 70% | 43% | 91% |
| | ATCC 43300 | 33% | −19% | 24% | 2% | 18% | 26% | 2% | −15% | −22% | −18% | −19% | 68% |
| | ATCC 700698 | 27% | −8% | 20% | 10% | 25% | 23% | 13% | 62% | 61% | 39% | 24% | 88% |
| | ATCC 700699 | 61% | 34% | 63% | 64% | 79% | 78% | 86% | 89% | 87% | 86% | 87% | 90% |
| | ATCC 9144 | 33% | −10% | 22% | 16% | 21% | 10% | 16% | 37% | 59% | 28% | 0% | 81% |
| | ATCC BAA-44 | 50% | 22% | 47% | 40% | 39% | 48% | 89% | 92% | 90% | 87% | 91% | 93% |
| | Average | 43% | 1% | 34% | 25% | 34% | 42% | 40% | 59% | 62% | 54% | 41% | 83% |
| *S. epidermidis* | ATCC 12228 | 62% | −32% | 78% | 84% | 95% | 92% | 92% | 92% | 91% | 93% | 96% | 96% |
| | ATCC 700296 | 61% | 39% | 78% | 73% | 85% | 86% | 84% | 80% | 75% | 76% | 79% | 87% |
| | ATCC 49461 | 18% | 15% | 72% | 84% | 90% | 90% | 90% | 88% | 88% | 86% | 90% | 94% |
| | ATCC 14990 | 68% | 39% | 68% | 88% | 94% | 91% | 92% | 90% | 90% | 89% | 91% | 90% |
| | Average | 52% | 15% | 74% | 82% | 91% | 90% | 89% | 87% | 86% | 86% | 89% | 92% |
| | Total average | 45% | 5% | 45% | 42% | 50% | 56% | 54% | 67% | 69% | 63% | 54% | 85% |

2-plants mixes extracts showed full antimicrobial activity at 1:10 dilution on the 10 *Staphylococcus aureus* strains tested except for the Mix[2P]-3 which had no antimicrobial at the tested dilution on 2 of the 10 *Staphylococcus aureus* strains tested (ATCC 29213 and ATCC 43300) (see Table 3-2).

The three 2-plant mixes extracts showed different antimicrobial activity on the 4 *Staphylococcus epidermidis* strains tested. Mix[2P]-1 had an HID of 1:10 on 3 strains (ATCC 12228, ATCC 49461 and ATCC 14990) and an HID of 1:20 on ATCC 700296 strain. Mix[2P]-2 had an HID of 1:10 on 2 strains (ATCC 12228 and ATCC 49461) and an HID of 1:20 on the 2 other strains (ATCC 700296 and ATCC 14990). Whereas Mix[2P]-3 had an HID of 1:10 on 2 strains (ATCC 12228 and ATCC 14990) and an HID of 1:20 on the 2 other strains (ATCC 700296 and ATCC 49461) (see Table 3-2).

Mix[3P]-1 obtained from the 3 plants which are included in Mix[2P]-1, Mix[2P]-2 and Mix[2P]-3, showed a wider antimicrobial activity than the 3 two-plant mixes (HID of 1:10 on 9 *Staphylococcus aureus* strains and HID of 1:20 on ATCC 700699, HID of 1:20 on the 4 *Staphylococcus epidermidis* tested) (see Table 3-2). The gain of antimicrobial activity is confirmed by the calculation of the planktonic growth inhibition percentage of each plant mixes (see Table 3-3).

3 different plants, PA11, PA12 and PA22, were added to the 3-plant mix Mix[3P]-1 to obtain three 4 plant-mixes extracts, Mix[4P]-1, Mix[4P]-2 and Mix[4P]-3 respectively. These 4-plant mixes extracts showed same HID or better HID than the 3-plant mix extract Mix[3P]-1 (see Table 3-2), and higher planktonic growth inhibition percentage: an average of 28% to 45% is obtained with 4-plant mixes extracts on the 10 *Staphylococcus aureus* strains compare to 23% with the 3-plant mix extract (see Table 3-3). They also showed higher biofilm formation inhibition percentage: an average of 34% to 42% is obtained with 4-plant mixes extracts on the 10 *Staphylococcus aureus* strains compare to 25% with the 3-plant mix extract (see Table 3-4).

5-plant mixes were prepared by adding 2 plants among the 3 selected additional plants. All the three 5-plant mixes extracts showed higher antimicrobial and antibiofilm activity than the 4-plant mixes extracts (see Tables 3-2, 3-3 and 3-4).

Mix[6P]-1 consists in the 6 plants which were used for the preparation of the previously tested processed samples. Interestingly, the 6-plant mix extract showed less antimicrobial and antibiofilm activity than 5-plant mixes extracts but higher antimicrobial effect and higher to equivalent antibiofilm effects than 4-plant mixes extracts. Antimicrobial and antibiofilm activity was recovered and enhanced by the addition of a new plant (PA79) (see Tables 3-2, 3-3 and 3-4).

Increasing the number of plants in the mixes allowed to prepare corresponding water extracts having enhanced antimicrobial and antibiofilm activity and increased the number of strains, in which one or both these activities can be identified.

Example 4

In this Example we illustrate simultaneous antimicrobial and antibiofilm activities against *Staphylococcus aureus* of 196 water extract obtained from herbal compositions including at least 2 plants among the 3 plants described in Example 1 and additional plants to form mixtures of 3 to 10 plants.

The dried plants of pharmaceutical grade were obtained from “Pharmacie Fontgiève” (Clermont-Ferrand, France, plants PA00 to PB12) and “Pharmacie St Herem” (Clermont-Ferrand, France, plants PB13 to PD08).

The 4 reference herbal compositions Mix[2P]-1, Mix[2P]-2, Mix[2P]-3, Mix[3P]-1 and the 196 new herbal compositions were prepared according to the previously described Method A and had the content reported in List 4-1.

List 4-1: Herbal Compositions of Processed Samples

Mix[2P]-1: PA13; PA21;

Mix[2P]-2: PA21; PB12;

Mix[2P]-3: PA13; PB12;
Mix[3P]-1: PA13; PA21; PB12;
Mix[3P]-2: PA11; PA13; PA21;
Mix[3P]-3: PA21; PB12; PC63;
Mix[3P]-4: PA13; PB12; PC63;
Mix[3P]-5: PA13; PA21; PC63;
Mix[3P]-6: PA13; PA21; PB12;
Mix[3P]-7: PA21; PB12; PC29;
Mix[3P]-8: PA13; PB12; PC29;
Mix[3P]-9: PA13; PA21; PB12;
Mix[4P]-1: PA11; PA13; PA21; PB12;
Mix[4P]-2: PA12; PA13; PA21; PB12;
Mix[4P]-3: PA13; PA21; PA22; PB12;
Mix[4P]-4: PA11; PA13; PA21; PA22;
Mix[4P]-5: PA13; PA21; PB12; PC63;
Mix[4P]-6: PA11; PA12; PA21; PB12;
Mix[4P]-7: PA11; PA12; PA13; PB12;
Mix[4P]-8: PA11; PA13; PA21; PB12;
Mix[4P]-9: PA12; PA13; PA21; PB12;
Mix[4P]-10: PA13; PA21; PB12; PC29;
Mix[5P]-1: PA12; PA13; PA21; PA22; PB12;
Mix[5P]-2: PA11; PA13; PA21; PA22; PB12;
Mix[5P]-3: PA11; PA12; PA13; PA21; PB12;
Mix[5P]-4: PA11; PA12; PA21; PA22; PB12;
Mix[5P]-5: PA11; PA12; PA13; PA22; PB12;
Mix[5P]-6: PA11; PA12; PA13; PA21; PA22;
Mix[5P]-7: PA13; PA21; PA22; PB12; PC63;
Mix[5P]-8: PA13; PA21; PB12; PC29; PC63;
Mix[6P]-1: PA11; PA12; PA13; PA21; PA22; PB12;
Mix[6P]-2: PA12; PA13; PA21; PA22; PB12; PC63;
Mix[6P]-3: PA11; PA13; PA21; PA22; PB12; PC63;
Mix[6P]-4: PA11; PA12; PA13; PA21; PB12; PC63;
Mix[6P]-5: PA12; PA13; PA21; PA22; PB12; PC63;
Mix[6P]-6: PA11; PA13; PA21; PA22; PB12; PC63;
Mix[6P]-7: PA11; PA12; PA21; PA22; PB12; PC63;
Mix[6P]-8: PA11; PA12; PA13; PA22; PB12; PC63;
Mix[6P]-9: PA11; PA12; PA13; PA21; PB12; PC63;
Mix[6P]-10: PA11; PA12; PA13; PA21; PA22; PC63;
Mix[6P]-11: PA11; PA12; PA13; PA21; PA22; PB12;
Mix[7P]-1: PA11; PA12; PA13; PA21; PA22; PB12; PA79;
M[7P]-2: PA11; PA12; PA13; PA21; PA22; PB12; PB49;
M[7P]-3: PA11; PA12; PA13; PA21; PA22; PB12; PC29;
M[7P]-4: PA11; PA12; PA13; PA21; PA22; PB12; PC63;
M[9P]-11: PA12; PA13; PA21; PA22; PA79; PB12; PB49; PC29; PC63;
M[9P]-12: PA11; PA13; PA21; PA22; PA79; PB12; PB49; PC29; PC63;
M[9P]-13: PA11; PA12; PA21; PA22; PA79; PB12; PB49; PC29; PC63;
M[9P]-14: PA11; PA12; PA13; PA22; PA79; PB12; PB49; PC29; PC63;
M[9P]-15: PA11; PA12; PA13; PA21; PA79; PB12; PB49; PC29; PC63;
M[9P]-16: PA11; PA12; PA13; PA21; PA22; PB12; PB49; PC29; PC63;
M[9P]-17: PA11; PA12; PA13; PA21; PA22; PA79; PB49; PC29; PC63;
M[9P]-18: PA11; PA12; PA13; PA21; PA22; PA79; PB12; PC29; PC63;
M[9P]-19: PA11; PA12; PA13; PA21; PA22; PA79; PB12; PB49; PC63;
M[9P]-20: PA11; PA12; PA13; PA21; PA22; PA79; PB12; PB49; PC29;
M[10P]-40: PA11; PA13; PA14; PA20; PA21; PA23; PA67; PB12; PC27; PC60;
M[10P]-44: PA13; PA40; PA41; PA62; PA75; PB18; PC22; PC63; PC64; PD05;
M[10P]-71: PA21; PA85; PB14; PB18; PB85; PC19; PC61; PC63; PD05; PD08;
M[10P]-75: PA02; PA10; PA12; PA13; PA18; PA21; PA27; PA79; PB86; PC26;
M[10P]-84: PA10; PA21; PA27; PB12; PB15; PC26; PC68; PD05; PD06; PD08;
M[10P]-98: PA11; PA12; PA13; PA14; PA20; PA21; PA27; PB16; PB18; PD06;
M[10P]-102: PA12; PA13; PA19; PA21; PA41; PA79; PB10; PC26; PC61; PC64;
M[10P]-103: PA13; PA17; PA21; PA24; PB08; PB49; PB85; PC15; PC29; PD05;
M[10P]-105: PA10; PA11; PA12; PA18; PA19; PA21; PA22; PB12; PC63; PD08;
M[10P]-109: PA10; PA12; PA13; PA21; PA27; PA75; PB14; PB16; PC45; PC63;
M[10P]-112: PA08; PA13; PA15; PA17; PA18; PA21; PA27; PB18; PB41; PB81;
M[10P]-115: PA13; PA20; PA21; PA22; PA62; PA79; PB08; PB19; PC15; PC61;
M[10P]-119: PA11; PA13; PA14; PA24; PB12; PB41; PB49; PC51; PD06; PD08;
M[10P]-123: PA10; PA13; PA15; PA20; PA21; PA75; PB12; PB18; PB49; PC63;
M[10P]-124: PA08; PA13; PA21; PA24; PA27; PB08; PB41; PB49; PC64; PD05;
M[10P]-125: PA13; PA14; PA19; PA21; PA75; PB12; PC15; PC26; PC61; PC63;
M[10P]-129: PA08; PA12; PA18; PA21; PA41; PB08; PB85; PC63; PC64; PD08;
M[10P]-130: PA12; PA13; PA21; PA24; PA27; PB10; PB41; PB49; PC15; PC61;
M[10P]-132: PA12; PA20; PA21; PA24; PC15; PC26; PC61; PC63; PC64; PD08;
M[10P]-134: PA21; PA22; PA24; PA27; PB10; PB12; PB49; PC15; PC29; PD05;
M[10P]-136: PA10; PA11; PA12; PA13; PA18; PA21; PB16; PB18; PC26; PC29;
M[10P]-140: PA13; PA15; PA21; PA24; PA62; PA79; PB10; PB12; PC63; PC64;
M[10P]-142: PA11; PA12; PA13; PA19; PA21; PB12; PB85; PC15; PC26; PC64;
M[10P]-144: PA13; PA15; PA21; PA24; PA75; PB49; PC51; PC61; PC64; PD05;
M[10P]-145: PA12; PA13; PA17; PA20; PA21; PA79; PB08; PB16; PB85; PC63;
M[10P]-148: PA10; PA13; PA20; PA24; PB08; PB12; PB49; PC26; PC51; PC64;
M[10P]-149: PA13; PA14; PA15; PA19; PA21; PB08; PB10; PB41; PC15; PC61;
M[10P]-150: PA10; PA12; PA13; PA14; PA21; PA62; PB10; PC26; PC64; PD06;
M[10P]-151: PA10; PA13; PA21; PA22; PA24; PA41; PB49; PC15; PC61; PC63;
M[10P]-152: PA11; PA12; PA13; PA15; PA21; PA27; PA75; PB12; PB49; PB85;
M[10P]-154: PA11; PA12; PA13; PA21; PA22; PA79; PB12; PB49; PC29; PC63;
M[10P]-156: PA15; PA21; PA22; PB10; PB85; PC26; PC29; PC61; PC63; PC64;
M[10P]-157: PA11; PA13; PA15; PA19; PA21; PB18; PB41; PC15; PC51; PD08;
M[10P]-158: PA10; PA17; PA21; PA24; PA27; PA41; PB49; PC26; PC61; PC63;

M[10P]-160: PA10; PA12; PA13; PA15; PA18; PA20; PA21; PA24; PB12; PC26;

M[10P]-162: PA12; PA13; PA21; PA27; PA79; PB12; PB16; PB18; PC63; PC64;

M[10P]-164: PA12; PA13; PA15; PA19; PA21; PA27; PB08; PB12; PB49; PD05;

M[10P]-165: PA13; PA15; PA22; PA75; PA79; PB12; PB18; PC15; PC26; PC29;

M[10P]-167: PA12; PA13; PA75; PB08; PB12; PB85; PC15; PC51; PC61; PC63;

M[10P]-168: PA11; PA13; PA17; PA21; PA27; PA62; PA79; PB16; PB49; PC64;

M[10P]-169: PA12; PA17; PA21; PA24; PA75; PA79; PB10; PB12; PB85; PC15;

M[10P]-170: PA11; PA13; PA15; PA20; PA21; PA22; PC26; PC29; PC63; PC64;

M[10P]-172: PA13; PA20; PA21; PA75; PB10; PB12; PB18; PB49; PC29; PC61;

M[10P]-173: PA10; PA12; PA13; PA14; PA19; PA20; PA21; PA79; PC15; PC63;

M[10P]-174: PA11; PA12; PA13; PA27; PA62; PB12; PB16; PB49; PB85; PC26;

M[10P]-175: PA11; PA12; PA13; PA21; PA22; PA75; PB10; PB49; PC15; PC63;

M[10P]-176: PA11; PA13; PA21; PA24; PA62; PB12; PC15; PC26; PC61; PC64;

M[10P]-178: PA11; PA14; PA15; PA18; PA19; PA21; PA22; PB16; PC15; PC63;

M[10P]-180: PA08; PA11; PA12; PA13; PA15; PA17; PA21; PA62; PB12; PC63;

M[10P]-181: PA13; PA19; PA21; PA22; PA79; PB08; PB10; PB18; PC15; PC29;

M[10P]-182: PA11; PA15; PA20; PA21; PA22; PA75; PB12; PC29; PC63; PC64;

M[10P]-183: PA11; PA12; PA13; PA27; PA79; PB16; PB18; PB49; PC15; PC63;

M[10P]-184: PA11; PA13; PA15; PA20; PA21; PA22; PA27; PA75; PB12; PC29;

M[10P]-186: PA11; PA15; PA19; PA20; PA21; PA22; PA27; PB10; PB12; PB85;

M[10P]-188: PA11; PA12; PA13; PA19; PA21; PA75; PA79; PB49; PC15; PC63;

M[10P]-190: PA11; PA13; PA21; PA22; PA27; PA75; PB10; PB12; PB49; PC63;

M[10P]-191: PA13; PA19; PA20; PA21; PA79; PB10; PB18; PB85; PC29; PC61;

M[10P]-192: PA12; PA13; PA19; PA21; PA27; PA75; PB12; PB49; PC63; PC64;

M[10P]-193: PA13; PA15; PA20; PA21; PA79; PB16; PC15; PC26; PC29; PC61;

M[10P]-194: PA11; PA17; PA21; PA22; PA27; PB12; PB49; PC15; PC63; PC64;

M[10P]-196: PA11; PA12; PA13; PA15; PA21; PA75; PB10; PB18; PC51; PC63;

M[10P]-197: PA11; PA12; PA13; PA15; PA21; PA24; PA79; PB49; PC61; PC64;

M[10P]-198: PA12; PA15; PA21; PA22; PB12; PB16; PB85; PC15; PC26; PC29;

M[10P]-199: PA11; PA12; PA13; PA15; PA21; PA75; PB12; PC15; PC63; PC64;

M[10P]-201: PA11; PA13; PA20; PA21; PA22; PA27; PA75; PB12; PB49; PC64;

M[10P]-202: PA11; PA21; PA75; PB10; PB12; PB61; PC26; PC29; PC42; PC63;

M[10P]-205: PA11; PA13; PA19; PA21; PA22; PA27; PA75; PB12; PB41; PC63;

M[10P]-207: PA11; PA13; PA21; PA75; PB10; PB12; PB41; PB51; PC45; PC63;

M[10P]-209: PA12; PA13; PA21; PA24; PA75; PB12; PB16; PB49; PB60; PC15;

M[10P]-210: PA13; PA15; PA20; PA22; PA27; PB08; PB10; PB12; PB18; PC63;

M[10P]-212: PA11; PA13; PA21; PA22; PA27; PA75; PB12; PB16; PC15; PC63;

M[10P]-214: PA11; PA12; PA15; PA21; PA22; PA75; PB12; PB49; PC15; PC61;

M[10P]-215: PA11; PA12; PA13; PA21; PA25; PB12; PC02; PC29; PC51; PC64;

M[10P]-216: PA11; PA12; PA13; PA21; PA27; PA75; PA85; PB18; PB49; PC49;

M[10P]-217: PA18; PA20; PA21; PA22; PA75; PB10; PB12; PB16; PB85; PC64;

M[10P]-218: PA10; PA13; PA15; PA20; PA22; PA27; PB18; PB49; PC51; PC63;

M[10P]-219: PA12; PA13; PA15; PA19; PA21; PA22; PA75; PB10; PB12; PC26;

M[10P]-220: PA11; PA12; PA13; PA19; PA21; PA22; PA27; PB12; PB49; PC63;

M[10P]-221: PA13; PA15; PA19; PA20; PA21; PA41; PA75; PB12; PC15; PC60;

M[10P]-222: PA05; PA13; PA21; PA22; PA75; PA79; PB49; PC26; PC29; PC63;

M[10P]-223: PA11; PA12; PA13; PA22; PA25; PA75; PB12; PB49; PC61; PC64;

M[10P]-225: PA12; PA13; PA21; PA27; PB10; PB12; PC29; PC63; PC64; PD08;

M[10P]-226: PA11; PA12; PA21; PA39; PA79; PB18; PB49; PB85; PC61; PC63;

M[10P]-227: PA11; PA12; PA15; PA20; PA21; PA22; PB12; PB42; PC15; PC26;

M[10P]-229: PA13; PA20; PA62; PA79; PB12; PB46; PB85; PC29; PC64; PD08;

M[10P]-230: PA11; PA12; PA13; PA21; PA22; PA75; PB10; PB12; PB58; PC61;

M[10P]-232: PA12; PA13; PA15; PA22; PA27; PA83; PB12; PB49; PC26; PC63;

M[10P]-235: PA12; PA13; PA15; PA20; PA21; PA22; PC29; PC51; PC63; PC65;

M[10P]-236: PA12; PA13; PA20; PA21; PA27; PA75; PB50; PB85; PC29; PC64;

M[10P]-237: PA11; PA13; PA15; PA21; PA27; PA75; PB10; PB12; PC63; PC70;

M[10P]-239: PA10; PA11; PA12; PA20; PA21; PB10; PB41; PB49; PC63; PD08;

M[10P]-240: PA11; PA12; PA15; PA21; PA27; PA79; PB46; PC29; PC51; PC63;

M[10P]-241: PA11; PA14; PA20; PA21; PA22; PA75; PB12; PB18; PC15; PC29;

M[10P]-242: PA11; PA12; PA13; PA21; PA22; PA79; PB18; PB49; PC51; PC63;

M[10P]-244: PA11; PA12; PA13; PA20; PA22; PA27; PB10; PB12; PC63; PC64;

M[10P]-246: PA11; PA12; PA13; PA21; PA61; PA79; PB10; PB12; PB18; PB85;

M[10P]-247: PA11; PA12; PA21; PA27; PB16; PB49; PC21; PC51; PC61; PC63;

M[10P]-248: PA11; PA13; PA14; PA19; PA21; PA75; PA79; PB14; PB49; PC15;

M[10P]-250: PA11; PA12; PA15; PA20; PA21; PA41; PA75; PB49; PC26; PC63;

M[10P]-251: PA12; PA13; PA21; PA22; PA27; PA79; PB10; PB12; PB13; PB16;

M[10P]-252: PA11; PA13; PA20; PA21; PA44; PB08; PB12; PB18; PB88; PD06;
M[10P]-253: PA10; PA11; PA12; PA13; PA15; PA21; PA22; PA27; PA79; PC63;
M[10P]-255: PA11; PA13; PA21; PA75; PB12; PB18; PB49; PC15; PC26; PC63;
M[10P]-256: PA11; PA12; PA13; PA21; PA22; PA23; PA75; PA79; PC29; PC64;
M[10P]-257: PA13; PA20; PA21; PA27; PB12; PB49; PB83; PC29; PC63; PD00;
M[10P]-258: PA12; PA13; PA20; PA21; PA22; PA75; PB10; PB12; PC15; PC63;
M[10P]-262: PA11; PA12; PA21; PA31; PA75; PB49; PB85; PC61; PC63; PC64;
M[10P]-264: PA21; PA24; PA27; PA31; PA79; PB10; PB18; PB49; PC15; PC63;
M[10P]-267: PA11; PA12; PA21; PA22; PA75; PC29; PC51; PC52; PC61; PC63;
M[10P]-268: PA11; PA12; PA13; PA15; PA27; PA75; PB10; PB12; PB45; PC64;
M[10P]-269: PA13; PA20; PA21; PA22; PA79; PB10; PB11; PB49; PC61; PC63;
M[10P]-270: PA11; PA12; PA13; PA15; PA21; PA75; PB12; PB14; PB18; PC49;
M[10P]-271: PA11; PA13; PA20; PA22; PA27; PA45; PB08; PB12; PB49; PC64;
M[10P]-272: PA13; PA21; PA24; PA79; PB10; PB12; PB41; PC15; PC29; PC63;
M[10P]-273: PA11; PA15; PA21; PA22; PA27; PA75; PB12; PB14; PC64; PD00;
M[10P]-274: PA12; PA13; PA21; PA22; PB12; PB49; PC26; PC51; PC63; PC64;
M[10P]-278: PA13; PA15; PA21; PA22; PA75; PA79; PB10; PB12; PB49; PC63;
M[10P]-280: PA11; PA12; PA15; PA21; PB08; PB12; PB18; PB49; PB58; PC51;
M[10P]-281: PA11; PA12; PA20; PA21; PA22; PA27; PA29; PA75; PB16; PC63;
M[10P]-282: PA10; PA13; PA21; PA22; PA27; PA79; PB12; PC15; PC29; PC61;
M[10P]-284: PA11; PA13; PA20; PA21; PA22; PA27; PA95; PC15; PC29; PC63;
M[10P]-285: PA11; PA13; PA14; PA21; PA79; PB10; PB12; PB18; PB49; PB82;
M[10P]-286: PA11; PA12; PA13; PA14; PA20; PA21; PA79; PC51; PC64; PC82;
M[10P]-287: PA12; PA13; PA19; PA20; PA75; PB10; PB12; PC26; PC63; PD08;
M[10P]-289: PA12; PA13; PA15; PA19; PA20; PA21; PB10; PB12; PC29; PC51;
M[10P]-290: PA11; PA12; PA13; PA22; PA27; PA75; PB85; PC29; PC63; PDO7;
M[10P]-292: PA12; PA13; PA15; PA75; PA79; PB10; PB12; PC29; PC45; PC63;
M[10P]-293: PA00; PA11; PA12; PA13; PA21; PA27; PA75; PB18; PB85; PC26;
M[10P]-294: PA12; PA13; PA15; PA21; PA22; PA79; PB12; PB49; PC51; PC63;
M[10P]-296: PA11; PA13; PA15; PA17; PA21; PA62; PA79; PB10; PB12; PC63;
M[10P]-300: PA12; PA13; PA17; PA48; PB10; PB12; PB16; PC26; PC29; PC63;
M[10P]-301: PA11; PA12; PA13; PA20; PA21; PA75; PB08; PC15; PC35; PC51;
M[10P]-302: PA11; PA12; PA13; PA21; PA70; PB12; PB16; PB18; PC26; PC63;
M[10P]-303: PA11; PA12; PA15; PA21; PA75; PA79; PB10; PB12; PC29; PC64;
M[10P]-307: PA12; PA13; PA21; PB10; PB12; PB18; PB78; PC51; PC63; PD08;
M[10P]-308: PA17; PA21; PA22; PA27; PB12; PB49; PB85; PC15; PC26; PC29;
M[10P]-309: PA13; PA22; PA27; PA53; PA62; PA75; PB10; PC51; PC63; PDO6;
M[10P]-311: PA12; PA15; PA19; PA21; PA79; PB12; PB49; PC26; PC63; PC83;
M[10P]-312: PA00; PA11; PA13; PA21; PA22; PA29; PA75; PB10; PB85; PC29;
M[10P]-313: PA13; PA15; PA21; PA22; PA27; PA75; PB49; PC51; PC61; PC63;
M[10P]-314: PA08; PA12; PA13; PA21; PB10; PB12; PB49; PC15; PC32; PC64;
M[10P]-315: PA11; PA13; PA21; PA47; PA75; PB16; PB83; PC15; PC51; PC63;
M[10P]-317: PA11; PA12; PA19; PA21; PA22; PA79; PB10; PB16; PC29; PC63;
M[10P]-319: PA12; PA13; PA22; PA75; PA79; PA98; PB08; PB10; PB85; PC63;
M[10P]-321: PA11; PA12; PA13; PA20; PA21; PA22; PB49; PB85; PC55; PC63.

The corresponding water extracts (or processed samples) of such herbal compositions were prepared according to the previously described Method B using 20 mL of water containing 100 g/l of sucrose for water extraction and including centrifugation step before filtration.

The biological activity of the processed sample was determined by using the following *Staphylococcus aureus* strains: ATCC 25923, ATCC 49476, ATCC 6538, ATCC 51740, ATCC 29213 and ATCC 14775, with the following final dilutions of processed samples: 1:10, 1:20, 1:40 and 1:80 for processed samples containing less than 10 spoons of plant powder (M[2P] to M[9P]) or 1:20, 1:63 and 1:200 for processed samples containing 10 spoons of plant powder (M[10P]), according to the previously described Method C.

The bacteria planktonic growth inhibition percentage average and biofilm formation inhibition percentage average over all the tested strains of the processed samples obtained from the 2 plants of Mix[2P]-1 at 1:20 dilution is given in Table 4-1.

TABLE 4-1 average of planktonic growth inhibition percentage and biofilm formation inhibition percentage efficacy on the 6 tested *Staphylococcus aureus* strains of the processed sample based on Mix[2P]-1 at 1:20 dilution

| | Planktonic growth inhibition | Biofilm formation inhibition |
|---|---|---|
| (A) | | |
| Mix[2P]-1 | 22% | 36% |
| M[10P]-124 | 28% | 47% |
| M[10P]-236 | 24% | 50% |
| M[10P]-193 | 27% | 54% |
| M[10P]-286 | 45% | 38% |
| Mix[5P]-6 | 39% | 45% |
| M[10P]-197 | 32% | 55% |
| M[10P]-112 | 40% | 49% |
| M[10P]-157 | 41% | 52% |
| M[10P]-136 | 39% | 55% |
| M[10P]-144 | 45% | 52% |
| M[10P]-191 | 39% | 57% |
| M[10P]-168 | 44% | 53% |
| M[10P]-115 | 44% | 54% |

TABLE 4-1-continued average of planktonic growth inhibition percentage and biofilm formation inhibition percentage efficacy on the 6 tested *Staphylococcus aureus* strains of the processed sample based on Mix[2P]-1 at 1:20 dilution

| | Planktonic growth inhibition | Biofilm formation inhibition |
|---|---|---|
| M[10P]-98 | 48% | 51% |
| M[10P]-102 | 51% | 54% |
| M[10P]-150 | 49% | 59% |
| M[10P]-103 | 51% | 58% |
| M[10P]-130 | 57% | 61% |
| M[10P]-149 | 56% | 63% |
| M[10P]-181 | 65% | 70% |
| (B) | | |
| Mix[2P]-1 | 22% | 36% |
| M[10P]-75 | 23% | 40% |
| M[10P]-216 | 22% | 41% |
| M[10P]-256 | 19% | 47% |
| M[10P]-248 | 14% | 48% |
| (C) | | |
| Mix[2P]-1 | 22% | 36% |
| Mix[3P]-2 | 27% | 26% |
| Mix[4P]-4 | 27% | 29% |
| M[10P]-293 | 28% | 32% |
| M[10P]-301 | 28% | 28% |
| M[10P]-312 | 40% | 37% |

20 processed samples obtained from herbal compositions containing 5 or 10 plants were found to have higher anti-biofilm and antimicrobial activity than the reference mix extract Mix[2P]-1 (Table 4-1 A). Four 10 plant mixes extracts were found to have higher antibiofilm activity and equivalent or lower antimicrobial activity (Table 4-1 B). Five processed samples containing 3, 4 or 10 plants were found to have higher antimicrobial activity and equivalent or lower antibiofilm activity (Table 4-1 C).

The bacteria planktonic growth inhibition percentage average and biofilm formation inhibition percentage average over all the tested strains of the processed samples obtained from herbal compositions containing the 2 plants of Mix [2P]-2 at 1:20 dilution is given in Table 4-2.

TABLE 4-2 average of planktonic growth inhibition percentage and biofilm formation inhibition percentage efficacy on the 6 tested *Staphylococcus aureus* strains of the processed sample based on Mix[2P]-2 at 1:20 dilution. (A) Mixes extracts showing higher antimicrobial and antibiofilm activity. (B) Mixes extracts showing antibiofilm activity and equivalent or lower antimicrobial activity. (C) Mixes extracts showing antimicrobial activity and equivalent or lower antibiofilm activity.

| | Planktonic growth inhibition | Biofilm formation inhibition |
|---|---|---|
| (A) | | |
| Mix[2P]-2 | 12% | −3% |
| M[10P]-308 | 16% | 13% |
| Mix[3P]-7 | 23% | 9% |
| M[10P]-264 | 15% | 29% |
| M[10P]-317 | 36% | 9% |
| M[10P]-217 | 17% | 28% |
| M[10P]-280 | 21% | 27% |
| Mix[6P]-7 | 36% | 16% |
| M[10P]-267 | 17% | 36% |
| Mix[3P]-3 | 27% | 28% |
| M[10P]-247 | 16% | 40% |
| M[10P]-214 | 23% | 33% |
| M[10P]-303 | 35% | 22% |
| M[10P]-281 | 17% | 42% |
| M[10P]-273 | 19% | 41% |
| Mix[5P]-4 | 34% | 27% |
| M[10P]-198 | 16% | 46% |
| M[10P]-241 | 26% | 38% |
| M[10P]-132 | 23% | 41% |
| M[10P]-239 | 28% | 44% |
| M[10P]-262 | 25% | 48% |
| M[10P]-129 | 28% | 46% |
| M[10P]-186 | 31% | 44% |
| M[10P]-311 | 40% | 38% |
| M[10P]-134 | 32% | 48% |
| M[10P]-182 | 40% | 44% |
| M[10P]-178 | 39% | 45% |
| M[10P]-202 | 37% | 50% |
| M[10P]-156 | 40% | 48% |
| M[10P]-194 | 41% | 49% |
| M[10P]-105 | 47% | 44% |
| M[10P]-240 | 42% | 61% |
| M[10P]-169 | 53% | 57% |
| M[9P]-13 | 100% | 86% |
| (B) | | |
| Mix[2P]-2 | 12% | −3% |
| M[10P]-84 | 9% | 27% |
| M[10P]-158 | 12% | 30% |
| M[10P]-071 | 11% | 35% |
| M[10P]-227 | 12% | 42% |
| M[10P]-250 | 11% | 44% |
| M[10P]-226 | 13% | 51% |
| (C) | | |
| Mix[2P]-2 | 12% | −3% |
| Mix[4P]-6 | 19% | −5% |

33 processed samples obtained from herbal compositions containing 3, 5, 9 or 10 plants were found to have higher antibiofilm and antimicrobial activity than the reference mix extract Mix[2P]-2 (Table 4-2 A). Six 10 plant mixes extracts were found to have higher antibiofilm activity and equivalent or lower antimicrobial activity (Table 4-2 B). One 4 plant mix extract was found to have higher antimicrobial activity and equivalent antibiofilm activity (Table 4-2 C).

The bacteria planktonic growth inhibition percentage average and biofilm formation inhibition percentage average over all the tested strains of the processed samples obtained from herbal compositions containing the 2 plants of Mix [2P]-3 at 1:20 dilution is given in Table 4-3.

TABLE 4-3 average of planktonic growth inhibition percentage and biofilm formation inhibition percentage efficacy on the 6 tested *Staphylococcus aureus* strains of the processed sample based on Mix[2P]-3 at 1:20 dilution. (A) Mixes extracts showing higher antimicrobial and antibiofilm activity. (B) Mixes extracts showing antimicrobial activity and equivalent or lower antibiofilm activity.

| | Planktonic growth inhibition | Biofilm formation inhibition |
|---|---|---|
| (A) | | |
| Mix[2P]-3 | 12% | 28% |
| M[10P]-44 | 15% | 35% |
| M[10P]-271 | 13% | 47% |
| M[10P]-218 | 19% | 42% |
| M[10P]-268 | 16% | 46% |
| Mix[3P]-4 | 17% | 47% |
| M[10P]-210 | 22% | 42% |
| M[10P]-165 | 22% | 42% |
| Mix[5P]-5 | 29% | 36% |
| M[10P]-287 | 34% | 31% |
| M[10P]-148 | 28% | 41% |
| M[10P]-290 | 31% | 39% |
| M[10P]-229 | 15% | 56% |
| M[6P]-8 | 34% | 40% |
| M[10P]-319 | 38% | 37% |
| M[10P]-244 | 21% | 56% |
| M[10P]-223 | 23% | 55% |
| M[10P]-232 | 25% | 61% |
| M[10P]-119 | 42% | 48% |
| M[10P]-183 | 39% | 51% |
| M[10P]-292 | 47% | 48% |
| M[10P]-174 | 47% | 59% |
| M[10P]-167 | 80% | 71% |
| M[9P]-14 | 90% | 83% |
| (B) | | |
| Mix[2P]-3 | 12% | 28% |
| Mix[4P]-7 | 17% | 5% |
| Mix[3P]-8 | 19% | 14% |
| M[10P]-300 | 20% | 15% |
| M[10P]-309 | 33% | 2% |

23 processed samples obtained from herbal compositions containing 3, 5, 9 or 10 plants were found to have higher antibiofilm and antimicrobial activity than the reference mix extract Mix[2P]-3 (Table 4-3 A). Four processed samples obtained from herbal compositions containing 3, 4 or 10 plants were found to have higher antibiofilm activity and equivalent or lower antimicrobial activity (Table 4-3 B).

The bacteria planktonic growth inhibition percentage average and biofilm formation inhibition percentage average over all the tested strains of the processed samples obtained from herbal compositions containing the 3 plants of Mix [3P]-1 at 1:20 dilution is given in Table 4-4.

TABLE 4-4 average of planktonic growth inhibition percentage and biofilm formation inhibition percentage efficacy on the 6 tested *Staphylococcus aureus* strains of the processed sample based on Mix[3P]-1 at 1:20 dilution. (A) Mixes extracts showing higher antimicrobial and antibiofilm activity. (B) Mixes extracts showing antibiofilm activity and equivalent or lower antimicrobial activity. (C) Mixes extracts showing antimicrobial activity and equivalent or lower antibiofilm activity.

| | Planktonic growth inhibition | Biofilm formation inhibition |
|---|---|---|
| (A) | | |
| Mix[3P]-1 | 31% | 15% |
| Mix[4P]-8 | 37% | 20% |
| Mix[6P]-10 | 33% | 25% |
| M[10P]-314 | 34% | 24% |
| Mix[4P]-2 | 37% | 22% |
| Mix[6P]-11 | 35% | 27% |
| Mix[4P]-3 | 41% | 24% |
| M[10P]-315 | 39% | 27% |
| M[10P]-284 | 41% | 31% |
| M[10P]-321 | 37% | 39% |
| M[10P]-109 | 36% | 43% |
| M[10P]-302 | 44% | 35% |
| Mix[5P]-8 | 43% | 40% |
| M[6P]-9 | 51% | 35% |
| M[10P]-160 | 35% | 52% |
| M[10P]-212 | 43% | 45% |
| M[10P]-274 | 38% | 51% |
| M[10P]-246 | 34% | 56% |
| M[10P]-205 | 42% | 48% |
| M[10P]-285 | 52% | 39% |
| M[10P]-201 | 37% | 54% |
| M[10P]-222 | 32% | 59% |
| Mix[4P]-10 | 52% | 40% |
| M[10P]-230 | 38% | 54% |
| M[10P]-220 | 43% | 50% |
| Mix[5P]-2 | 51% | 42% |
| Mix[5P]-1 | 50% | 44% |
| M[10P]-215 | 38% | 55% |
| Mix[6P]-6 | 56% | 38% |
| M[10P]-235 | 40% | 54% |
| M[10P]-207 | 43% | 53% |
| Mix[5P]-3 | 51% | 48% |
| M[10P]-307 | 58% | 43% |
| M[10P]-289 | 60% | 41% |
| M[10P]-272 | 40% | 62% |
| M[10P]-184 | 48% | 55% |
| M[10P]-151 | 48% | 57% |
| M[10P]-123 | 51% | 55% |
| M[6P]-1 | 60% | 50% |
| M[6P]-5 | 61% | 51% |
| M[7P]-3 | 61% | 54% |
| M[10P]-192 | 57% | 60% |
| M[10P]-164 | 58% | 59% |
| M[7P]-1 | 62% | 57% |
| M[10P]-296 | 63% | 60% |
| M[6P]-4 | 73% | 51% |
| Mix[5P]-7 | 64% | 60% |
| M[6P]-2 | 68% | 57% |
| M[10P]-225 | 60% | 66% |
| M[10P]-188 | 65% | 61% |
| Mix[4P]-5 | 61% | 66% |
| M[10P]-125 | 66% | 62% |
| M[10P]-173 | 65% | 67% |
| M[10P]-237 | 69% | 63% |
| M[7P]-3 | 71% | 64% |
| M[10P]-294 | 71% | 65% |
| M[10P]-199 | 70% | 69% |
| M[10P]-142 | 71% | 69% |
| Mix[6P]-3 | 72% | 68% |
| M[10P]-145 | 72% | 69% |
| M[10P]-180 | 72% | 70% |
| M[10P]-140 | 72% | 71% |
| M[10P]-162 | 73% | 70% |
| M[10P]-176 | 74% | 70% |
| M[10P]-172 | 72% | 73% |
| M[10P]-152 | 71% | 74% |
| M[10P]-40 | 77% | 68% |
| M[7P]-4 | 72% | 76% |
| M[10P]-170 | 80% | 74% |
| M[10P]-196 | 78% | 77% |

TABLE 4-4-continued average of planktonic growth inhibition percentage and biofilm formation inhibition percentage efficacy on the 6 tested *Staphylococcus aureus* strains of the processed sample based on Mix[3P]-1 at 1:20 dilution. (A) Mixes extracts showing higher antimicrobial and antibiofilm activity. (B) Mixes extracts showing antibiofilm activity and equivalent or lower antimicrobial activity. (C) Mixes extracts showing antimicrobial activity and equivalent or lower antibiofilm activity.

| | Planktonic growth inhibition | Biofilm formation inhibition |
|---|---|---|
| M[10P]-190 | 82% | 76% |
| M[10P]-154 | 80% | 79% |
| M[10P]-175 | 84% | 77% |
| M[9P]-20 | 93% | 81% |
| M[9P]-17 | 95% | 84% |
| M[9P]-19 | 95% | 86% |
| M[9P]-11 | 96% | 91% |
| M[9P]-18 | 98% | 89% |
| M[9P]-12 | 103% | 91% |
| M[9P]-15 | 106% | 88% |
| M[9P]-16 | 106% | 91% |
| (B) | | |
| Mix[3P]-1 | 31% | 15% |
| Mix[3P]-6 | 16% | 20% |
| Mix[4P]-9 | 30% | 21% |
| Mix[3P]-9 | 19% | 23% |
| M[10P]-282 | 24% | 26% |
| Mix[3P]-5 | 29% | 36% |
| M[10P]-269 | 14% | 37% |
| M[10P]-278 | 18% | 40% |
| M[10P]-219 | 30% | 42% |
| M[10P]-255 | 20% | 43% |
| M[10P]-270 | 15% | 43% |
| M[10P]-251 | 13% | 44% |
| M[10P]-258 | 20% | 44% |
| M[10P]-209 | 21% | 45% |
| M[10P]-221 | 17% | 49% |
| M[10P]-253 | 21% | 49% |
| M[10P]-252 | 18% | 50% |
| M[10P]-257 | 18% | 51% |
| M[10P]-242 | 29% | 54% |
| (C) | | |
| Mix[3P]-1 | 31% | 15% |
| Mix[4P]-1 | 37% | 15% |
| M[10P]-313 | 38% | 12% |

80 processed samples obtained from herbal compositions containing 4, 5, 6, 7, 9 or 10 plants were found to have higher antibiofilm and antimicrobial activity than the reference mix extract Mix[3P]-1 (Table 4-4 A). 18 processed samples obtained from herbal compositions containing 3, 4, or 10 plants were found to have higher antibiofilm activity and equivalent or lower antimicrobial activity (Table 4-4 B). Two processed samples obtained from herbal compositions 4 and 10 plants were found to have higher antimicrobial activity and equivalent antibiofilm activity (Table 4-4 C).

Comparative Example 2

As a comparative Example, we illustrate several 3 or 10 plants mixes extracts obtained from herbal compositions containing only one plant among the 3 plants of Example 1 (PA13, PA21, PB12), which have been found to have none or poor antimicrobial and antibiofilm activities against *Staphylococcus aureus.*

Ten herbal compositions, whose content is reported in List 4-8, were prepared according to the previously described Method A.

List 4-8: Herbal Compositions of Processed Samples

- M[3P]-31: PA21; PA05; PB06;
- M[3P]-35: PA21; PA76; PB50;
- M[3P]-37: PA21; PB06; PB50;
- M[3P]-43: PB12; PA05; PC34;
- M[3P]-45: PB12; PA76; PB50;
- M[10P]-65: PA01; PA08; PA25; PA29; PA37; PB12; PB50; PC15; PC37; PD05;
- M[10P]-70: PA10; PA16; PA21; PA25; PA37; PA75; PB18; PB45; PC04; PC57;
- M[10P]-72: PA08; PA21; PA62; PA70; PA85; PB19; PB31; PB45; PB49; PC26;
- M[10P]-89: PA10; PA13; PA18; PA19; PA37; PA41; PA75; PB49; PC21; PC67;
- M[10P]-306: PA15; PA21; PA22; PA62; PA75; PB18; PB49; PB85; PC49; PC61;

Ten water extracts (or processed samples) were prepared starting from the corresponding herbal compositions.

The bacteria planktonic growth inhibition percentage average and biofilm formation inhibition percentage average over all the tested strains for such processed samples at 1:20 dilution were determined according to the previously reported Method C and are given in Table 4-5.

TABLE 4-5 average of planktonic growth inhibition percentage and biofilm formation inhibition percentage efficacy on the 6 tested *Staphylococcus aureus* strains of the processed samples at 1:20 dilution.

| | Planktonic growth inhibition | Biofilm formation inhibition |
|---|---|---|
| Mix[2P]-1 | 22% | 36% |
| Mix[2P]-2 | 12% | −3% |
| Mix[2P]-3 | 12% | 28% |
| M[3P]-45 | −4% | −5% |
| M[3P]-35 | 0% | −8% |
| M[3P]-37 | 2% | −9% |
| M[3P]-31 | 2% | −9% |
| M[3P]-43 | 1% | −1% |
| M[10P]-72 | 3% | 1% |
| M[10P]-70 | 1% | 15% |
| M[10P]-306 | 10% | 6% |
| M[10P]-65 | 3% | 17% |
| M[10P]-89 | 10% | 27% |

All tested processed samples, obtained from herbal compositions composed of 3 or 10 plants, which included one plant among the 3 plants of Example 1 (PA13, PA21, PB12), showed lower antimicrobial activity than the three 2 plant mixes extracts of reference Mix[2P]-1 (obtained from PA13 and PA21), Mix[2P]-2 (obtained from PA21 and PB12) and Mix[2P]-3 (obtained from PA13 and PB12) and lower antibiofilm activity than Mix[2P]-1 and Mix[2P]-3.

Example 5

In this Example, we illustrate simultaneous antimicrobial and antibiofilm activities against *Staphylococcus aureus* of 390 mixtures extracts obtained from herbal compositions including at least 2 plants among the 3 plants described in Example 1 (cf Table 1-1) and additional plants to assemble mixtures of 9 to 20 plants.

The dried plants of pharmaceutical grade were obtained from "Pharmacie Fontgiève" (Clermont-Ferrand, France, plants PA00 to PB12) and "Pharmacie St Herem" (Clermont-Ferrand, France, plants PB13 to PD02).

Herbal compositions containing from 9 to 20 plant powders were prepared according to the previously described Method A.

The 4 reference herbal compositions Mix[2P]-1, Mix[2P]-2, Mix[2P]-3, Mix[3P]-1 and 390 new herbal compositions were prepared having the content showed below (List 5-3).

List 5-3: Herbal Compositions of Processed Samples

Mix[2P]-1: PA13; PA21;

Mix[2P]-2: PA21; PB12;

Mix[2P]-3: PA13; PB12;

Mix[3P]-1: PA13; PA21; PB12;

M[09P]-1: PA13; PA14; PA20; PA21; PA23; PA67; PB12; PC27; PC60;

M[09P]-2: PA11; PA14; PA20; PA21; PA23; PA67; PB12; PC27; PC60;

M[09P]-3: PA11; PA13; PA20; PA21; PA23; PA67; PB12; PC27; PC60;

M[09P]-4: PA11; PA13; PA14; PA21; PA23; PA67; PB12; PC27; PC60;

M[09P]-6: PA11; PA13; PA14; PA20; PA23; PA67; PB12; PC27; PC60;

M[09P]-6: PA11; PA13; PA14; PA20; PA21; PA67; PB12; PC27; PC60;

M[09P]-7: PA11; PA13; PA14; PA20; PA21; PA23; PB12; PC27; PC60;

M[09P]-8: PA11; PA13; PA14; PA20; PA21; PA23; PA67; PC27; PC60;

M[09P]-9: PA11; PA13; PA14; PA20; PA21; PA23; PA67; PB12; PC60;

M[09P]-10: PA11; PA13; PA14; PA20; PA21; PA23; PA67; PB12; PC27;

M[09P]-21: PC49; PC37; PA13; PA13; PA13; PA11; PA29; PA21; PB12;

M[10P]-41: PA13; PA20; PA21; PB02; PB12; PB27; PB33; PB60; PB88; PC20;

M[10P]-303: PC49; PC37; PA13; PA13; PA13; PA11; PA29; PA21; PB12; PC33;

M[11P]-1: PA13; PA20; PA21; PB02; PB12; PB27; PB33; PB60; PB88; PC20; PA11;

M[11P]-2: PA13; PA20; PA21; PB02; PB12; PB27; PB33; PB60; PB88; PC20; PA14;

M[11P]-3: PA13; PA20; PA21; PB02; PB12; PB27; PB33; PB60; PB88; PC20; PA25;

M[11P]-4: PA13; PA20; PA21; PB02; PB12; PB27; PB33; PB60; PB88; PC20; PA26;

M[11P]-5: PA13; PA20; PA21; PB02; PB12; PB27; PB33; PB60; PB88; PC20; PA28;

M[11P]-6: PA13; PA20; PA21; PB02; PB12; PB27; PB33; PB60; PB88; PC20; PA29;

M[11P]-7: PA13; PA20; PA21; PB02; PB12; PB27; PB33; PB60; PB88; PC20; PA67;

M[11P]-8: PA13; PA20; PA21; PB02; PB12; PB27; PB33; PB60; PB88; PC20; PA75;

M[11P]-9: PA13; PA20; PA21; PB02; PB12; PB27; PB33; PB60; PB88; PC20; PC49;

M[11P]-10: PA13; PA20; PA21; PB02; PB12; PB27; PB33; PB60; PB88; PC20; PC60;

M[11P]-11: PC49; PC37; PA13; PA13; PA13; PA11; PA29; PA21; PB12; PC33; PA39;

M[11P]-12: PA11; PC37; PC33; PA39; PB60; PC26; PB12; PA13; PA13; PA13; PA21;

M[12P]-1: PC49; PC37; PA13; PA13; PA13; PA11; PA29; PA21; PB12; PC33; PA39; PA22;

M[12P]-2: PA11; PC37; PC33; PA39; PB60; PC26; PB12; PA13; PA13; PA13; PA21; PA29;

M[13P]-1: PC49; PC37; PA13; PA13; PA13; PA11; PA29; PA21; PB12; PC33; PA39; PA22; PA20;

M[13P]-2: PA11; PC37; PC33; PA39; PB60; PC26; PB12; PA13; PA13; PA13; PA21; PA29; PC20;

M[14P]-1: PC49; PC37; PA13; PA13; PA13; PA11; PA29; PA21; PB12; PC33; PA39; PA22; PA20; PC26;

M[14P]-2: PA11; PC37; PC33; PA39; PB60; PC26; PB12; PA13; PA13; PA13; PA21; PA29; PC20; PC49;

M[15P]-1: PA10; PA11; PA13; PA15; PA20; PA21; PA23; PA26; PA33; PB08; PB12; PB60; PB88; PC12; PC20;

M[15P]-5: PC49; PC37; PA13; PA13; PA13; PA11; PA29; PA21; PB12; PC33; PA39; PA22; PA20; PC26; PC20;

M[16P]-1: PA00; PA10; PA20; PA21; PA23; PA24; PA29; PA57; PB07; PB12; PC11; PC12; PC20; PC51; PC55; PC67;

M[16P]-2: PA11; PA12; PA13; PA14; PA20; PA21; PA22; PA29; PA39; PB12; PB60; PC20; PC26; PC33; PC37; PC49;

M[16P]-3: PA11; PA12; PA14; PA14; PA20; PA21; PA22; PA29; PA39; PB12; PB60; PC20; PC26; PC33; PC37; PC49;

M[16P]-5: PC49; PC37; PA13; PA13; PA13; PA11; PA29; PA21; PB12; PC33; PA39; PA22; PA20; PC26; PC20; PA12;

M[16P]-6: PA11; PC37; PC33; PA39; PB60; PC26; PB12; PA13; PA13; PA13; PA21; PA29; PC20; PC49; PA14; PA14;

M[17P]-1: PA00; PA10; PA20; PA21; PA23; PA24; PA29; PA57; PB07; PB12; PC11; PC11; PC12; PC20; PC51; PC55; PC67;

M[17P]-2: PA11; PA12; PA13; PA14; PA14; PA20; PA21; PA22; PA29; PA39; PB12; PB60; PC20; PC26; PC33; PC37; PC49;

M[17P]-3: PA11; PA12; PA13; PA13; PA13; PA20; PA21; PA22; PA29; PA39; PB12; PB60; PC20; PC26; PC33; PC37; PC49;

M[17P]-5: PA00; PA10; PA20; PA21; PA23; PA24; PA29; PA57; PB07; PB12; PC11; PC11; PC12; PC20; PC51; PC55; PC67;

M[17P]-4: PA10; PA10; PA11; PA13; PA15; PA20; PA20; PA21; PA23; PA33; PB08; PB12; PB12; PB60; PB88; PC12; PC20;

M[17P]-6: PA10; PA11; PA14; PA18; PA21; PA23; PA29; PA67; PB00; PB07; PB12; PB33; PB77; PC11; PC52; PC60; PC71;

M[17P]-8: PA11; PC37; PC33; PA39; PB60; PC26; PB12; PA13; PA13; PA13; PA21; PA29; PC20; PC49; PA14; PA14; PA22;

M[17P]-9: PA13; PA13; PA13; PC49; PC37; PA11; PA20; PA22; PA12; PC26; PB60; PA39; PC33; PC20; PA14; PA14; PA21;

M[18P]-1: PA10; PA11; PA13; PA14; PA18; PA21; PA23; PA29; PA67; PB00; PB07; PB12; PB33; PB77; PC11; PC52; PC60; PC71;

M[18P]-2: PA11; PA11; PA12; PA13; PA14; PA14; PA20; PA21; PA22; PA29; PA39; PB12; PB60; PC20; PC26; PC33; PC37; PC49;

M[18P]-3: PA12; PA13; PA13; PA13; PA14; PA14; PA20; PA21; PA22; PA29; PA39; PB12; PB60; PC20; PC26; PC33; PC37; PC49;

M[18P]-4: PA11; PA13; PA13; PA13; PA14; PA14; PA20; PA21; PA22; PA29; PA39; PB12; PB60; PC20; PC26; PC33; PC37; PC49;

M[18P]-5: PA11; PA12; PA13; PA13; PA14; PA14; PA20; PA21; PA22; PA29; PA39; PB12; PB60; PC20; PC26; PC33; PC37; PC49;

M[18P]-6: PA11; PA12; PA13; PA13; PA13; PA14; PA20; PA21; PA22; PA29; PA39; PB12; PB60; PC20; PC26; PC33; PC37; PC49;

M[18P]-7: PA11; PA12; PA13; PA13; PA13; PA14; PA14; PA21; PA22; PA29; PA39; PB12; PB60; PC20; PC26; PC33; PC37; PC49;

M[18P]-9: PA11; PA12; PA13; PA13; PA13; PA14; PA14; PA20; PA22; PA29; PA39; PB12; PB60; PC20; PC26; PC33; PC37; PC49;

M[18P]-9: PA11; PA12; PA13; PA13; PA13; PA14; PA14; PA20; PA21; PA29; PA39; PB12; PB60; PC20; PC26; PC33; PC37; PC49;

M[18P]-10: PA11; PA12; PA13; PA13; PA13; PA14; PA14; PA20; PA21; PA22; PA39; PB12; PB60; PC20; PC26; PC33; PC37; PC49;

M[18P]-11: PA11; PA12; PA13; PA13; PA13; PA14; PA14; PA20; PA21; PA22; PA29; PB12; PB60; PC20; PC26; PC33; PC37; PC49;

M[18P]-12: PA11; PA12; PA13; PA13; PA13; PA14; PA14; PA20; PA21; PA22; PA29; PA39; PB60; PC20; PC26; PC33; PC37; PC49;

M[18P]-13: PA11; PA12; PA13; PA13; PA13; PA14; PA14; PA20; PA21; PA22; PA29; PA39; PB12; PC20; PC26; PC33; PC37; PC49;

M[18P]-14: PA11; PA12; PA13; PA13; PA13; PA14; PA14; PA20; PA21; PA22; PA29; PA39; PB12; PB60; PC26; PC33; PC37; PC49;

M[18P]-15: PA11; PA12; PA13; PA13; PA13; PA14; PA14; PA20; PA21; PA22; PA29; PA39; PB12; PB60; PC20; PC33; PC37; PC49;

M[18P]-16: PA11; PA12; PA13; PA13; PA13; PA14; PA14; PA20; PA21; PA22; PA29; PA39; PB12; PB60; PC20; PC26; PC37; PC49;

M[18P]-17: PA11; PA12; PA13; PA13; PA13; PA14; PA14; PA20; PA21; PA22; PA29; PA39; PB12; PB60; PC20; PC26; PC33; PC49;

M[18P]-18: PA11; PA12; PA13; PA13; PA13; PA14; PA14; PA20; PA21; PA22; PA29; PA39; PB12; PB60; PC20; PC26; PC33; PC37;

M[18P]-23: PA00; PA10; PA20; PA21; PA23; PA24; PA29; PA57; PB07; PB12; PB12; PC11; PC11; PC12; PC20; PC51; PC55; PC67;

M[18P]-19: PA11; PA13; PA15; PA20; PA20; PA21; PA23; PA26; PA26; PA26; PA33; PB08; PB12; PB12; PB60; PB88; PC12; PC20;

M[18P]-20: PA10; PA10; PA11; PA13; PA15; PA21; PA23; PA26; PA26; PA26; PA33; PB08; PB12; PB12; PB60; PB88; PC12; PC20;

M[18P]-21: PA10; PA10; PA11; PA13; PA15; PA20; PA20; PA21; PA23; PA26; PA33; PB08; PB12; PB12; PB60; PB88; PC12; PC20;

M[18P]-22: PA10; PA10; PA11; PA13; PA15; PA20; PA20; PA21; PA23; PA26; PA26; PA26; PA33; PB08; PB60; PB88; PC12; PC20;

M[18P]-24: PA00; PA10; PA20; PA21; PA23; PA24; PA29; PA57; PB07; PB12; PB12; PB12; PB12; PC12; PC20; PC51; PC55; PC67;

M[18P]-25: PA10; PA11; PA13; PA14; PA18; PA21; PA23; PA29; PA67; PB00; PB07; PB12; PB33; PB77; PC11; PC52; PC60; PC71;

M[18P]-31: PA13; PA13; PA13; PA14; PA14; PA26; PA26; PA28; PA52; PA67; PB00; PB12; PB27; PB28; PB38; PB60; PC37; PC52;

M[18P]-33: PA11; PA11; PA13; PA14; PA14; PA26; PA26; PA28; PA52; PA67; PB00; PB12; PB27; PB28; PB38; PB60; PC37; PC52;

M[18P]-34: PA11; PA11; PA13; PA13; PA13; PA26; PA26; PA28; PA52; PA67; PB00; PB12; PB27; PB28; PB38; PB60; PC37; PC52;

M[18P]-34: PA11; PA11; PA13; PA13; PA13; PA14; PA14; PA28; PA52; PA67; PB00; PB12; PB27; PB28; PB38; PB60; PC37; PC52;

M[18P]-35: PC49; PC37; PA13; PA13; PA13; PA11; PA29; PA21; PB12; PC33; PA39; PA22; PA20; PC26; PC20; PA12; PA14; PA14;

M[18P]-36: PA11; PC37; PC33; PA39; PB60; PC26; PB12; PA13; PA13; PA13; PA21; PA29; PC20; PC49; PA14; PA14; PA22; PA20;

M[18P]-37: PA13; PA13; PA13; PC49; PC37; PA11; PA20; PA22; PA12; PC26; PB60; PA39; PC33; PC20; PA14; PA14; PA21; PA29;

M[19P]-1: PA13; PA14; PA20; PA21; PA25; PA26; PA28; PA29; PA67; PA75; PB02; PB12; PB27; PB33; PB60; PB88; PC20; PC49; PC60;

M[19P]-2: PA11; PA14; PA20; PA21; PA25; PA26; PA28; PA29; PA67; PA75; PB02; PB12; PB27; PB33; PB60; PB88; PC20; PC49; PC60;

M[19P]-3: PA11; PA13; PA20; PA21; PA25; PA26; PA28; PA29; PA67; PA75; PB02; PB12; PB27; PB33; PB60; PB88; PC20; PC49; PC60;

M[19P]-4: PA11; PA13; PA14; PA21; PA25; PA26; PA28; PA29; PA67; PA75; PB02; PB12; PB27; PB33; PB60; PB88; PC20; PC49; PC60;

M[19P]-5: PA11; PA13; PA14; PA20; PA25; PA26; PA28; PA29; PA67; PA75; PB02; PB12; PB27; PB33; PB60; PB88; PC20; PC49; PC60;

M[19P]-6: PA11; PA13; PA14; PA20; PA21; PA26; PA28; PA29; PA67; PA75; PB02; PB12; PB27; PB33; PB60; PB88; PC20; PC49; PC60;

M[19P]-7: PA11; PA13; PA14; PA20; PA21; PA25; PA28; PA29; PA67; PA75; PB02; PB12; PB27; PB33; PB60; PB88; PC20; PC49; PC60;

M[19P]-8: PA11; PA13; PA14; PA20; PA21; PA25; PA26; PA29; PA67; PA75; PB02; PB12; PB27; PB33; PB60; PB88; PC20; PC49; PC60;

M[19P]-9: PA11; PA13; PA14; PA20; PA21; PA25; PA26; PA28; PA67; PA75; PB02; PB12; PB27; PB33; PB60; PB88; PC20; PC49; PC60;

M[19P]-10: PA11; PA13; PA14; PA20; PA21; PA25; PA26; PA28; PA29; PA75; PB02; PB12; PB27; PB33; PB60; PB88; PC20; PC49; PC60;

M[19P]-11: PA11; PA13; PA14; PA20; PA21; PA25; PA26; PA28; PA29; PA67; PB02; PB12; PB27; PB33; PB60; PB88; PC20; PC49; PC60;

M[19P]-12: PA11; PA13; PA14; PA20; PA21; PA25; PA26; PA28; PA29; PA67; PA75; PB12; PB27; PB33; PB60; PB88; PC20; PC49; PC60;

M[19P]-13: PA11; PA13; PA14; PA20; PA21; PA25; PA26; PA28; PA29; PA67; PA75; PB02; PB27; PB33; PB60; PB88; PC20; PC49; PC60;

M[19P]-14: PA11; PA13; PA14; PA20; PA21; PA25; PA26; PA28; PA29; PA67; PA75; PB02; PB12; PB33; PB60; PB88; PC20; PC49; PC60;

M[19P]-15: PA11; PA13; PA14; PA20; PA21; PA25; PA26; PA28; PA29; PA67; PA75; PB02; PB12; PB27; PB60; PB88; PC20; PC49; PC60;

M[19P]-16: PA11; PA13; PA14; PA20; PA21; PA25; PA26; PA28; PA29; PA67; PA75; PB02; PB12; PB27; PB33; PB88; PC20; PC49; PC60;

M[19P]-17: PA11; PA13; PA14; PA20; PA21; PA25; PA26; PA28; PA29; PA67; PA75; PB02; PB12; PB27; PB33; PB60; PC20; PC49; PC60;

M[19P]-18: PA11; PA13; PA14; PA20; PA21; PA25; PA26; PA28; PA29; PA67; PA75; PB02; PB12; PB27; PB33; PB60; PB88; PC49; PC60;

M[19P]-19: PA11; PA13; PA14; PA20; PA21; PA25; PA26; PA28; PA29; PA67; PA75; PB02; PB12; PB27; PB33; PB60; PB88; PC20; PC60;
M[19P]-20: PA11; PA13; PA14; PA20; PA21; PA25; PA26; PA28; PA29; PA67; PA75; PB02; PB12; PB27; PB33; PB60; PB88; PC20; PC49;
M[19P]-21: PA00; PA10; PA20; PA21; PA23; PA24; PA29; PA57; PB07; PB12; PB12; PB12; PB12; PC11; PC12; PC20; PC51; PC55; PC67;
M[19P]-22: PA10; PA11; PA13; PA13; PA14; PA18; PA21; PA23; PA29; PA67; PB00; PB07; PB12; PB33; PB77; PC11; PC52; PC60; PC71;
M[19P]-23: PA11; PA12; PA13; PA13; PA13; PA14; PA14; PA20; PA21; PA22; PA29; PA39; PB12; PB60; PC20; PC26; PC33; PC37; PC49;
M[19P]-24: PA11; PA11; PA12; PA13; PA13; PA13; PA14; PA20; PA21; PA22; PA29; PA39; PB12; PB60; PC20; PC26; PC33; PC37; PC49;
M[19P]-25: PA10; PA11; PA13; PA15; PA20; PA20; PA21; PA23; PA26; PA26; PA26; PA33; PB08; PB12; PB12; PB60; PB88; PC12; PC20;
M[19P]-26: PA10; PA10; PA13; PA15; PA20; PA20; PA21; PA23; PA26; PA26; PA26; PA33; PB08; PB12; PB12; PB60; PB88; PC12; PC20;
M[19P]-27: PA10; PA10; PA11; PA15; PA20; PA20; PA21; PA23; PA26; PA26; PA26; PA33; PB08; PB12; PB12; PB60; PB88; PC12; PC20;
M[19P]-28: PA10; PA10; PA11; PA13; PA20; PA20; PA21; PA23; PA26; PA26; PA26; PA33; PB08; PB12; PB12; PB60; PB88; PC12; PC20;
M[19P]-29: PA10; PA10; PA11; PA13; PA15; PA20; PA21; PA23; PA26; PA26; PA26; PA33; PB08; PB12; PB12; PB60; PB88; PC12; PC20;
M[19P]-30: PA10; PA10; PA11; PA13; PA15; PA20; PA20; PA23; PA26; PA26; PA26; PA33; PB08; PB12; PB12; PB60; PB88; PC12; PC20;
M[19P]-31: PA10; PA10; PA11; PA13; PA15; PA20; PA20; PA21; PA26; PA26; PA26; PA33; PB08; PB12; PB12; PB60; PB88; PC12; PC20;
M[19P]-32: PA10; PA10; PA11; PA13; PA15; PA20; PA20; PA21; PA23; PA26; PA26; PA33; PB08; PB12; PB12; PB60; PB88; PC12; PC20;
M[19P]-33: PA10; PA10; PA11; PA13; PA15; PA20; PA20; PA21; PA23; PA26; PA26; PA26; PB08; PB12; PB12; PB60; PB88; PC12; PC20;
M[19P]-34: PA10; PA10; PA11; PA13; PA15; PA20; PA20; PA21; PA23; PA26; PA26; PA26; PA33; PB12; PB12; PB60; PB88; PC12; PC20;
M[19P]-35: PA10; PA10; PA11; PA13; PA15; PA20; PA20; PA21; PA23; PA26; PA26; PA26; PA33; PB08; PB12; PB60; PB88; PC12; PC20;
M[19P]-36: PA10; PA10; PA11; PA13; PA15; PA20; PA20; PA21; PA23; PA26; PA26; PA26; PA33; PB08; PB12; PB12; PB88; PC12; PC20;
M[19P]-37: PA10; PA10; PA11; PA13; PA15; PA20; PA20; PA21; PA23; PA26; PA26; PA26; PA33; PB08; PB12; PB12; PB60; PC12; PC20;
M[19P]-38: PA10; PA10; PA11; PA13; PA15; PA20; PA20; PA21; PA23; PA26; PA26; PA26; PA33; PB08; PB12; PB12; PB60; PB88; PC20;
M[19P]-39: PA10; PA10; PA11; PA13; PA15; PA20; PA20; PA21; PA23; PA26; PA26; PA26; PA33; PB08; PB12; PB12; PB60; PB88; PC12;
M[19P]-40: PA10; PA20; PA21; PA23; PA24; PA29; PA57; PB07; PB12; PB12; PB12; PB12; PC11; PC11; PC12; PC20; PC51; PC55; PC67;
M[19P]-41: PA00; PA20; PA21; PA23; PA24; PA29; PA57; PB07; PB12; PB12; PB12; PB12; PC11; PC11; PC12; PC20; PC51; PC55; PC67;
M[19P]-42: PA00; PA10; PA21; PA23; PA24; PA29; PA57; PB07; PB12; PB12; PB12; PB12; PC11; PC11; PC12; PC20; PC51; PC55; PC67;
M[19P]-44: PA00; PA10; PA20; PA21; PA24; PA29; PA57; PB07; PB12; PB12; PB12; PB12; PC11; PC11; PC12; PC20; PC51; PC55; PC67;
M[19P]-45: PA00; PA10; PA20; PA21; PA23; PA29; PA57; PB07; PB12; PB12; PB12; PB12; PC11; PC11; PC12; PC20; PC51; PC55; PC67;
M[19P]-46: PA00; PA10; PA20; PA21; PA23; PA24; PA57; PB07; PB12; PB12; PB12; PB12; PC11; PC11; PC12; PC20; PC51; PC55; PC67;
M[19P]-47: PA00; PA10; PA20; PA21; PA23; PA24; PA29; PB07; PB12; PB12; PB12; PB12; PC11; PC11; PC12; PC20; PC51; PC55; PC67;
M[19P]-48: PA00; PA10; PA20; PA21; PA23; PA24; PA29; PA57; PB12; PB12; PB12; PB12; PC11; PC11; PC12; PC20; PC51; PC55; PC67;
M[19P]-49: PA00; PA10; PA20; PA21; PA23; PA24; PA29; PA57; PB07; PB12; PB12; PB12; PC11; PC11; PC12; PC20; PC51; PC55; PC67;
M[19P]-50: PA00; PA10; PA20; PA21; PA23; PA24; PA29; PA57; PB07; PB12; PB12; PB12; PB12; PC11; PC12; PC20; PC51; PC55; PC67;
M[19P]-51: PA00; PA10; PA20; PA21; PA23; PA24; PA29; PA57; PB07; PB12; PB12; PB12; PB12; PC11; PC11; PC20; PC51; PC55; PC67;
M[19P]-52: PA00; PA10; PA20; PA21; PA23; PA24; PA29; PA57; PB07; PB12; PB12; PB12; PB12; PC11; PC11; PC12; PC51; PC55; PC67;
M[19P]-53: PA00; PA10; PA20; PA21; PA23; PA24; PA29; PA57; PB07; PB12; PB12; PB12; PB12; PC11; PC11; PC12; PC20; PC55; PC67;
M[19P]-54: PA00; PA10; PA20; PA21; PA23; PA24; PA29; PA57; PB07; PB12; PB12; PB12; PB12; PC11; PC11; PC12; PC20; PC51; PC67;
M[19P]-55: PA00; PA10; PA20; PA21; PA23; PA24; PA29; PA57; PB07; PB12; PB12; PB12; PB12; PC11; PC11; PC12; PC20; PC51; PC55;
M[19P]-56: PA11; PA13; PA13; PA13; PA14; PA18; PA21; PA23; PA29; PA67; PB00; PB07; PB12; PB33; PB77; PC11; PC52; PC60; PC71;
M[19P]-57: PA10; PA13; PA13; PA13; PA14; PA18; PA21; PA23; PA29; PA67; PB00; PB07; PB12; PB33; PB77; PC11; PC52; PC60; PC71;
M[19P]-58: PA10; PA11; PA13; PA13; PA14; PA18; PA21; PA23; PA29; PA67; PB00; PB07; PB12; PB33; PB77; PC11; PC52; PC60; PC71;
M[19P]-59: PA10; PA11; PA13; PA13; PA13; PA18; PA21; PA23; PA29; PA67; PB00; PB07; PB12; PB33; PB77; PC11; PC52; PC60; PC71;
M[19P]-60: PA10; PA11; PA13; PA13; PA13; PA14; PA21; PA23; PA29; PA67; PB00; PB07; PB12; PB33; PB77; PC11; PC52; PC60; PC71;
M[19P]-62: PA10; PA11; PA13; PA13; PA13; PA14; PA18; PA23; PA29; PA67; PB00; PB07; PB12; PB33; PB77; PC11; PC52; PC60; PC71;
M[19P]-62: PA10; PA11; PA13; PA13; PA13; PA14; PA18; PA21; PA29; PA67; PB00; PB07; PB12; PB33; PB77; PC11; PC52; PC60; PC71;
M[19P]-63: PA10; PA11; PA13; PA13; PA13; PA14; PA18; PA21; PA23; PA67; PB00; PB07; PB12; PB33; PB77; PC11; PC52; PC60; PC71;

M[19P]-64: PA10; PA11; PA13; PA13; PA13; PA14; PA18; PA21; PA23; PA29; PB00; PB07; PB12; PB33; PB77; PC11; PC52; PC60; PC71;

M[19P]-65: PA10; PA11; PA13; PA13; PA13; PA14; PA18; PA21; PA23; PA29; PA67; PB07; PB12; PB33; PB77; PC11; PC52; PC60; PC71;

M[19P]-66: PA10; PA11; PA13; PA13; PA13; PA14; PA18; PA21; PA23; PA29; PA67; PB00; PB12; PB33; PB77; PC11; PC52; PC60; PC71;

M[19P]-67: PA10; PA11; PA13; PA13; PA13; PA14; PA18; PA21; PA23; PA29; PA67; PB00; PB07; PB33; PB77; PC11; PC52; PC60; PC71;

M[19P]-68: PA10; PA11; PA13; PA13; PA13; PA14; PA18; PA21; PA23; PA29; PA67; PB00; PB07; PB12; PB77; PC11; PC52; PC60; PC71;

M[19P]-69: PA10; PA11; PA13; PA13; PA13; PA14; PA18; PA21; PA23; PA29; PA67; PB00; PB07; PB12; PB33; PC11; PC52; PC60; PC71;

M[19P]-70: PA10; PA11; PA13; PA13; PA13; PA14; PA18; PA21; PA23; PA29; PA67; PB00; PB07; PB12; PB33; PB77; PC52; PC60; PC71;

M[19P]-71: PA10; PA11; PA13; PA13; PA13; PA14; PA18; PA21; PA23; PA29; PA67; PB00; PB07; PB12; PB33; PB77; PC11; PC60; PC71;

M[19P]-72: PA10; PA11; PA13; PA13; PA13; PA14; PA18; PA21; PA23; PA29; PA67; PB00; PB07; PB12; PB33; PB77; PC11; PC52; PC71;

M[19P]-73: PA10; PA11; PA13; PA13; PA13; PA14; PA18; PA21; PA23; PA29; PA67; PB00; PB07; PB12; PB33; PB77; PC11; PC52; PC60;

M[19P]-89: PA11; PA13; PA13; PA13; PA14; PA14; PA26; PA26; PA28; PA52; PA67; PB00; PB12; PB27; PB28; PB38; PB60; PC37; PC52;

M[19P]-91: PA11; PA11; PA13; PA13; PA14; PA14; PA26; PA26; PA28; PA52; PA67; PB00; PB12; PB27; PB28; PB38; PB60; PC37; PC52;

M[19P]-92: PA11; PA11; PA13; PA13; PA13; PA14; PA26; PA26; PA28; PA52; PA67; PB00; PB12; PB27; PB28; PB38; PB60; PC37; PC52;

M[19P]-93: PA11; PA11; PA13; PA13; PA13; PA14; PA14; PA26; PA28; PA52; PA67; PB00; PB12; PB27; PB28; PB38; PB60; PC37; PC52;

M[19P]-93: PA11; PA11; PA13; PA13; PA13; PA14; PA14; PA26; PA26; PA52; PA67; PB00; PB12; PB27; PB28; PB38; PB60; PC37; PC52;

M[19P]-95: PA11; PA11; PA13; PA13; PA13; PA14; PA14; PA26; PA26; PA28; PA67; PB00; PB12; PB27; PB28; PB38; PB60; PC37; PC52;

M[19P]-96: PA11; PA11; PA13; PA13; PA13; PA14; PA14; PA26; PA26; PA28; PA52; PB00; PB12; PB27; PB28; PB38; PB60; PC37; PC52;

M[19P]-96: PA11; PA11; PA13; PA13; PA13; PA14; PA14; PA26; PA26; PA28; PA52; PA67; PB12; PB27; PB28; PB38; PB60; PC37; PC52;

M[19P]-98: PA11; PA11; PA13; PA13; PA13; PA14; PA14; PA26; PA26; PA28; PA52; PA67; PB00; PB12; PB28; PB38; PB60; PC37; PC52;

M[19P]-100: PA11; PA11; PA13; PA13; PA13; PA14; PA14; PA26; PA26; PA28; PA52; PA67; PB00; PB12; PB27; PB38; PB60; PC37; PC52;

M[19P]-100: PA11; PA11; PA13; PA13; PA13; PA14; PA14; PA26; PA26; PA28; PA52; PA67; PB00; PB12; PB27; PB28; PB60; PC37; PC52;

M[19P]-101: PA11; PA11; PA13; PA13; PA13; PA14; PA14; PA26; PA26; PA28; PA52; PA67; PB00; PB12; PB27; PB28; PB38; PC37; PC52;

M[19P]-102: PA11; PA11; PA13; PA13; PA13; PA14; PA14; PA26; PA26; PA28; PA52; PA67; PB00; PB12; PB27; PB28; PB38; PB60; PC52;

M[19P]-103: PA11; PA11; PA13; PA13; PA13; PA14; PA14; PA26; PA26; PA28; PA52; PA67; PB00; PB12; PB27; PB28; PB38; PB60; PC37;

M[19P]-104: PC49; PC37; PA13; PA13; PA13; PA11; PA29; PA21; PB12; PC33; PA39; PA22; PA20; PC26; PC20; PA12; PA14; PA14; PB60;

M[19P]-105: PA11; PC37; PC33; PA39; PB60; PC26; PB12; PA13; PA13; PA13; PA21; PA29; PC20; PC49; PA14; PA14; PA22; PA20; PA12;

M[19P]-106: PA13; PA13; PA13; PC49; PC37; PA11; PA20; PA22; PA12; PC26; PB60; PA39; PC33; PC20; PA14; PA14; PA21; PA29; PB12;

M[20P]-29: PA10; PA11; PA12; PA13; PA14; PA15; PA16; PA17; PA18; PA19; PA20; PA21; PA22; PA23; PA24; PA25; PA26; PA27; PA28; PA29;

M[20P]-240: PA21; PA24; PA26; PA33; PA37; PA39; PA67; PB00; PB10; PB12; PB26; PB28; PB33; PB82; PB88; PC20; PC21; PC52; PC60; PC97;

M[20P]-296: PA00; PA11; PA13; PA15; PA21; PA22; PA24; PA26; PA28; PA33; PA39; PA94; PB08; PB12; PB20; PB28; PB33; PB99; PC26; PC52;

M[20P]-297: PA10; PA11; PA13; PA14; PA20; PA21; PA25; PA26; PA29; PA33; PA57; PA67; PA69; PB07; PB12; PB60; PC20; PC37; PC49; PC98;

M[20P]-335: PA00; PA10; PA11; PA21; PA26; PA27; PA31; PA34; PA67; PA69; PA81; PA89; PB01; PB10; PB12; PB25; PB58; PC11; PC86; PC97;

M[20P]-340: PA11; PA13; PA15; PA18; PA21; PA26; PA34; PA36; PA69; PA79; PA95; PB00; PB05; PB07; PB25; PB48; PB60; PC35; PC74; PC84;

M[20P]-349: PA10; PA11; PA13; PA16; PA20; PA33; PA69; PA94; PB07; PB08; PB12; PC01; PC27; PC28; PC49; PC50; PC53; PC55; PC60; PC67;

M[20P]-371: PA05; PA14; PA15; PA21; PA22; PA23; PA25; PA27; PA32; PA34; PA35; PA57; PA72; PA89; PB12; PB39; PB88; PC20; PC55; PC74;

M[20P]-374: PA06; PA13; PA21; PA24; PA25; PA26; PA27; PA57; PB12; PB24; PB28; PB29; PB35; PB38; PB61; PC11; PC37; PC54; PC74; PC86;

M[20P]-375: PA11; PA15; PA19; PA20; PA21; PA22; PA28; PA29; PA67; PA81; PB10; PB12; PB26; PB28; PC23; PC52; PC58; PC60; PC73; PC98;

M[20P]-377: PA07; PA10; PA11; PA13; PA14; PA21; PA22; PA24; PA29; PA32; PA33; PA35; PA57; PB10; PB28; PB36; PB82; PC49; PC52; PC94;

M[20P]-380: PA13; PA15; PA16; PA21; PA24; PA28; PA33; PA38; PA40; PA72; PB12; PB26; PB27; PB82; PC14; PC33; PC55; PC57; PC58; PC98;

M[20P]-382: PA00; PA12; PA13; PA16; PA21; PA24; PA25; PA26; PA28; PA29; PA35; PA57; PA75; PB33; PB88; PC14; PC24; PC36; PC58; PC66;

M[20P]-383: PA10; PA21; PA22; PA23; PA25; PA27; PA81; PA85; PB12; PB26; PB28; PB39; PB77; PB82; PC01; PC17; PC37; PC50; PC52; PC67;

M[20P]-386: PA13; PA14; PA28; PA29; PA33; PA35; PA40; PA57; PA67; PA79; PA88; PB00; PB01; PB07; PB12; PB33; PB77; PB85; PC50; PC66;

M[20P]-387: PA00; PA05; PA10; PA21; PA23; PA24; PA29; PA40; PA94; PA99; PB12; PB82; PB88; PB99; PC11; PC20; PC24; PC34; PC37; PC61;

M[20P]-388: PA12; PA13; PA14; PA15; PA20; PA21; PA26; PA29; PA35; PA40; PA67; PA89; PA98; PB12; PB33; PC01; PC14; PC58; PC68; PC88;

M[20P]-392: PA11; PA14; PA21; PA23; PA26; PA29; PA30; PA57; PA81; PA85; PA94; PB03; PB07; PB12; PB29; PC33; PC51; PC53; PC71; PC73;

M[20P]-396: PA05; PA14; PA15; PA17; PA21; PA28; PA29; PA35; PA37; PA39; PA40; PA69; PA72; PA89; PB10; PB12; PC34; PC67; PC71; PC97;

M[20P]-401: PA13; PA15; PA16; PA23; PA26; PA29; PA33; PA34; PA85; PB12; PB26; PB33; PC21; PC50; PC52; PC53; PC55; PC58; PC67; PC71;

M[20P]-403: PA13; PA14; PA20; PA22; PA24; PA26; PA33; PA35; PB08; PB12; PB26; PB33; PB50; PB61; PC21; PC27; PC37; PC52; PC54; PC58;

M[20P]-407: PA20; PA21; PA22; PA25; PA29; PA48; PA51; PA57; PA67; PA75; PA94; PB07; PB12; PC21; PC34; PC41; PC51; PC53; PC55; PC97;

M[20P]-408: PA11; PA12; PA13; PA15; PA16; PA20; PA21; PA22; PA25; PA26; PA27; PA28; PA29; PB10; PB26; PC20; PC21; PC24; PC25; PC58;

M[20P]-409: PA10; PA15; PA21; PA28; PA35; PA69; PA89; PA94; PA98; PB07; PB12; PB28; PB35; PB36; PC11; PC23; PC49; PC52; PC73; PC98;

M[20P]-416: PA11; PA13; PA14; PA20; PA21; PA25; PA26; PA28; PA29; PA67; PA75; PB02; PB12; PB27; PB33; PB60; PB88; PC20; PC49; PC60;

M[20P]-418: PA10; PA11; PA12; PA13; PA21; PA22; PA23; PA24; PA26; PA39; PB07; PB12; PB38; PC11; PC12; PC20; PC23; PC24; PC49; PC55;

M[20P]-420: PA10; PA14; PA21; PA22; PA23; PA29; PA30; PA33; PA37; PB01; PB12; PB26; PB33; PB99; PC20; PC21; PC36; PC37; PC73; PC98;

M[20P]-421: PA13; PA15; PA21; PA25; PA26; PA29; PA39; PA40; PA75; PA94; PB20; PB55; PB82; PC06; PC20; PC24; PC49; PC71; PC74; PC99;

M[20P]-422: PA10; PA11; PA13; PA18; PA21; PA23; PA25; PA29; PA33; PA57; PA70; PB01; PB07; PB12; PB88; PC11; PC27; PC33; PC55; PC97;

M[20P]-427: PA06; PA13; PA15; PA21; PA24; PA25; PA27; PA29; PA33; PA75; PA98; PB00; PB28; PB60; PC11; PC20; PC26; PC50; PC55; PC74;

M[20P]-429: PA11; PA19; PA21; PA23; PA26; PA33; PA40; PA75; PB00; PB03; PB12; PB60; PC11; PC21; PC24; PC26; PC36; PC37; PC68; PC98;

M[20P]-430: PA00; PA07; PA13; PA23; PA26; PA27; PA34; PA40; PA75; PB07; PB12; PB18; PB28; PB88; PC20; PC41; PC66; PC67; PC71; PC97;

M[20P]-431: PA00; PA06; PA11; PA12; PA13; PA15; PA18; PA21; PA22; PA25; PA28; PA33; PA81; PB09; PB32; PB33; PB38; PC11; PC33; PC52;

M[20P]-432: PA12; PA14; PA19; PA21; PA24; PA26; PA33; PA67; PB05; PB09; PB12; PB28; PB32; PB46; PB60; PC20; PC49; PC58; PC71; PC73;

M[20P]-435: PA10; PA13; PA14; PA15; PA21; PA28; PA33; PA40; PA55; PA57; PB07; PB12; PB58; PB88; PB99; PC12; PC21; PC29; PC66; PC67;

M[20P]-439: PA10; PA13; PA16; PA21; PA24; PA27; PA29; PA34; PA40; PA60; PA75; PB12; PB27; PB35; PB38; PC25; PC26; PC36; PC51; PC55;

M[20P]-443: PA00; PA10; PA13; PA15; PA17; PA20; PA29; PA33; PA35; PA40; PB07; PB12; PB26; PB27; PB82; PC12; PC24; PC50; PC60; PD02;

M[20P]-444: PA11; PA13; PA14; PA18; PA21; PA24; PA28; PA39; PA40; PA57; PA60; PA67; PA88; PB20; PB85; PB88; PC06; PC52; PC57; PC58;

M[20P]-445: PA11; PA13; PA17; PA20; PA21; PA29; PA30; PA33; PA35; PA40; PA57; PB00; PB12; PB28; PB60; PC11; PC20; PC35; PC50; PC51;

M[20P]-446: PA13; PA15; PA16; PA21; PA22; PA23; PA25; PA26; PA27; PA29; PA39; PA67; PA75; PB12; PB26; PB27; PC36; PC49; PC60; PC98;

M[20P]-447: PA11; PA13; PA17; PA19; PA24; PA28; PA30; PA33; PA39; PA40; PA57; PA92; PB07; PB08; PB12; PB33; PB61; PB85; PC58; PC94;

M[20P]-449: PA10; PA11; PA13; PA14; PA15; PA20; PA21; PA24; PA28; PA40; PA67; PA75; PA95; PB12; PB20; PB35; PC14; PC20; PC52; PC60;

M[20P]-453: PA10; PA13; PA15; PA18; PA21; PA25; PA29; PA34; PA35; PA67; PA93; PB06; PB07; PB09; PB12; PB20; PB26; PB35; PB99; PC55;

M[20P]-455: PA00; PA00; PA11; PA11; PA13; PA14; PA18; PA20; PA25; PA28; PA33; PA70; PA75; PB00; PB12; PC20; PC23; PC26; PC67; PC67;

M[20P]-456: PA14; PA21; PA33; PA34; PA39; PB00; PB07; PB07; PB12; PB27; PB28; PB38; PB88; PC20; PC23; PC26; PC49; PC58; PC67; PC71;

M[20P]-457: PA00; PA10; PA11; PA12; PA13; PA13; PA14; PA29; PA29; PA57; PA67; PB02; PB07; PB09; PB12; PB38; PC11; PC60; PC97; PC98;

M[20P]-458: PA10; PA11; PA11; PA13; PA13; PA18; PA21; PA26; PA33; PA57; PA75; PA98; PB12; PB33; PB33; PB38; PB82; PC20; PC55; PC73;

M[20P]-459: PA00; PA06; PA21; PA26; PA26; PA29; PA33; PA75; PB10; PB10; PB12; PB18; PB32; PB85; PC20; PC24; PC49; PC55; PC66; PC98;

M[20P]-461: PA06; PA21; PA29; PA29; PA33; PA33; PA39; PA57; PA67; PB07; PB07; PB12; PB26; PB32; PB32; PB85; PC20; PC27; PC52; PC58;

M[20P]-465: PA11; PA11; PA13; PA16; PA21; PA22; PA27; PA29; PA33; PA69; PB07; PB26; PB28; PB32; PB77; PB88; PB88; PC23; PC60; PC73;

M[20P]-467: PA00; PA06; PA21; PA21; PA23; PA26; PA33; PA33; PA40; PA67; PB12; PB38; PB88; PC11; PC23; PC23; PC27; PC55; PC71; PC97;

M[20P]-469: PA00; PA12; PA13; PA13; PA13; PA21; PA29; PA33; PA33; PA34; PA57; PB07; PC11; PC11; PC20; PC23; PC23; PC55; PC74; PC97;

M[20P]-470: PA13; PA14; PA21; PA21; PA22; PA23; PA24; PA24; PA27; PA29; PA33; PA67; PA75; PB07; PB07; PB33; PB33; PB77; PC37; PC52;

M[20P]-472: PA10; PA10; PA11; PA13; PA21; PA25; PA25; PA28; PA33; PA39; PB07; PB12; PB88; PC12; PC12; PC20; PC20; PC24; PC55; PC71;

M[20P]-474: PA00; PA13; PA20; PA21; PA26; PA28; PA29; PA33; PA57; PA67; PA81; PA81; PA98; PB02; PB12; PB38; PB60; PB88; PC11; PC20;

M[20P]-475: PA11; PA12; PA12; PA13; PA28; PA28; PA29; PA29; PA32; PA52; PA52; PA75; PA81; PB12; PB20; PB33; PB60; PC21; PC49; PC51;

M[20P]-478: PA15; PA16; PA21; PA21; PA21; PA23; PA25; PA32; PA34; PA39; PB12; PB77; PB85; PB88; PB88; PB88; PB88; PC11; PC33; PC37;

M[20P]-479: PA10; PA11; PA13; PA13; PA18; PA20; PA21; PA28; PA32; PA40; PA67; PA69; PB07; PB07; PB10; PB12; PB20; PC55; PC60; PC98;

M[20P]-480: PA00; PA06; PA13; PA22; PA23; PA26; PA26; PA27; PA29; PA40; PA81; PB07; PB10; PB10; PB12; PB12; PB18; PB32; PC49; PC71;

M[20P]-481: PA11; PA13; PA26; PA29; PA29; PA35; PA69; PA75; PA75; PB02; PB12; PB33; PC20; PC23; PC23; PC37; PC41; PC50; PC52; PC98;

M[20P]-482: PA06; PA10; PA11; PA11; PA11; PA13; PA13; PA13; PA14; PA14; PA20; PA25; PA26; PA28; PA39; PA67; PB12; PC11; PC24; PC74;

M[20P]-484: PA11; PA13; PA23; PA28; PA29; PA29; PA35; PA39; PA40; PA60; PA75; PA98; PB02; PB12; PB38; PB38; PB82; PC20; PC35; PC50;
M[20P]-485: PA13; PA14; PA14; PA21; PA21; PA21; PA26; PA26; PA26; PA26; PA29; PA29; PA52; PA57; PB00; PC11; PC11; PC21; PC51; PC67;
M[20P]-486: PA11; PA13; PA23; PA24; PA35; PA35; PA35; PA69; PA69; PA75; PB07; PB12; PB27; PC20; PC20; PC21; PC23; PC50; PC55; PC73;
M[20P]-490: PA10; PA11; PA11; PA14; PA21; PA24; PA26; PA26; PA39; PA40; PA69; PA75; PB00; PB01; PB12; PB12; PB18; PB28; PB60; PC20;
M[20P]-493: PA06; PA14; PA20; PA21; PA21; PA28; PA29; PA33; PA69; PA81; PA98; PB12; PB38; PB60; PC11; PC12; PC49; PC55; PC71; PD02;
M[20P]-494: PA06; PA10; PA11; PA11; PA13; PA13; PA15; PA23; PA26; PA35; PB01; PB12; PB60; PC12; PC20; PC37; PC41; PC49; PC49; PC52;
M[20P]-495: PA10; PA10; PA13; PA14; PA18; PA20; PA21; PA26; PA29; PA29; PA57; PB02; PC11; PC11; PC20; PC20; PC24; PC33; PC49; PC49;
M[20P]-496: PA00; PA18; PA21; PA24; PA26; PA27; PA29; PA39; PA39; PA52; PA69; PA70; PA98; PB00; PB02; PB12; PC12; PC24; PC55; PC67;
M[20P]-497: PA11; PA11; PA13; PA13; PA15; PA21; PA23; PA24; PA25; PA26; PA28; PA39; PA52; PA67; PB00; PB12; PB27; PB28; PC12; PC37;
M[20P]-499: PA13; PA21; PA21; PA21; PA29; PA30; PA69; PA75; PB07; PB07; PB07; PB60; PC20; PC20; PC21; PC37; PC37; PC49; PC55; PD02;
M[20P]-503: PA06; PA06; PA10; PA10; PA13; PA13; PA20; PA21; PA25; PA26; PA29; PA33; PA39; PA70; PB28; PC11; PC20; PC23; PC49; PC97;
M[20P]-506: PA11; PA16; PA21; PA23; PA29; PA39; PA57; PB12; PB27; PB32; PB88; PB88; PB88; PC12; PC20; PC21; PC37; PC71; PD02; PD02;
M[20P]-510: PA13; PA21; PA25; PA26; PA27; PA33; PA39; PA40; PA69; PA81; PB01; PB28; PB60; PB85; PB88; PC27; PC41; PC41; PC50; PC55;
M[20P]-514: PA11; PA12; PA13; PA13; PA21; PA21; PA28; PA29; PA33; PA35; PA39; PA40; PA40; PA67; PA67; PB12; PC14; PC20; PC41; PC55;
M[20P]-516: PA07; PA10; PA13; PA14; PA17; PA21; PA28; PA29; PA39; PA40; PA40; PA69; PB07; PB12; PC21; PC21; PC27; PC37; PD02; PD02;
M[20P]-520: PA11; PA11; PA12; PA13; PA14; PA15; PA29; PA33; PA33; PA57; PA67; PA70; PA98; PB12; PC20; PC23; PC33; PC52; PC55; PD02;
M[20P]-523: PA10; PA11; PA18; PA20; PA21; PA33; PA39; PA67; PA67; PA69; PB07; PB12; PB28; PB88; PB88; PC21; PC33; PC35; PC49; PC50;
M[20P]-524: PA00; PA11; PA11; PA12; PA13; PA20; PA29; PA40; PB07; PB12; PB28; PB38; PB60; PB60; PB77; PC20; PC20; PC49; PC49; PC98;
M[20P]-525: PA11; PA11; PA13; PA15; PA21; PA26; PA26; PA27; PA28; PA29; PA29; PA30; PA40; PA52; PA75; PB07; PB07; PC11; PC33; PC37;
M[20P]-527: PA10; PA10; PA11; PA13; PA15; PA20; PA20; PA21; PA23; PA26; PA26; PA26; PA33; PB08; PB12; PB12; PB60; PB88; PC12; PC20;
M[20P]-532: PA14; PA20; PA20; PA21; PA22; PA25; PA26; PA27; PA28; PA29; PA33; PA40; PA75; PB00; PB12; PB12; PB60; PB85; PC12; PC51;
M[20P]-533: PA13; PA21; PA26; PA27; PA27; PA28; PA32; PA60; PA70; PA75; PB18; PB32; PB38; PC23; PC41; PC50; PC50; PC51; PC52; PC97;

M[20P]-535: PA11; PA21; PA26; PA28; PA29; PA29; PA29; PA34; PA57; PB07; PB12; PB12; PB12; PB33; PB60; PC20; PC20; PC51; PC55; PC67;
M[20P]-536: PA00; PA10; PA11; PA12; PA12; PA13; PA14; PA23; PA29; PA29; PA35; PA40; PA81; PB07; PB07; PB12; PB27; PB33; PB60; PC20;
M[20P]-538: PA21; PA23; PA25; PA26; PA27; PA28; PA75; PB07; PB12; PB27; PB32; PB88; PC11; PC11; PC12; PC20; PC33; PC49; PC55; PC97;
M[20P]-541: PA10; PA11; PA13; PA20; PA24; PA28; PA29; PA67; PA70; PB10; PB12; PB77; PC20; PC20; PC23; PC41; PC51; PC52; PC52; PC97;
M[20P]-548: PA10; PA13; PA14; PA14; PA22; PA27; PA27; PA28; PA29; PA29; PA33; PA39; PB10; PB12; PB60; PB88; PC20; PC37; PC50; PC55;
M[20P]-551: PA12; PA13; PA13; PA20; PA22; PA23; PA24; PA24; PA26; PA33; PA33; PA39; PA67; PB07; PB07; PB12; PB33; PC20; PC55; PC98;
M[20P]-552: PA06; PA11; PA11; PA13; PA14; PA14; PA20; PA21; PA21; PA21; PA24; PA35; PB00; PB02; PB12; PB60; PB60; PC12; PC21; PC98;
M[20P]-555: PA00; PA10; PA11; PA18; PA20; PA20; PA21; PA25; PA26; PA26; PA39; PA39; PA39; PA89; PB12; PB12; PC20; PC20; PC49; PC74;
M[20P]-557: PA00; PA10; PA20; PA21; PA23; PA24; PA29; PA57; PB07; PB12; PB12; PB12; PB12; PC11; PC11; PC12; PC20; PC51; PC55; PC67;
M[20P]-559: PA00; PA11; PA12; PA13; PA20; PA22; PA24; PA25; PA25; PA26; PA28; PA57; PA70; PA70; PB07; PB12; PB88; PB88; PC11; PC60;
M[20P]-560: PA10; PA10; PA11; PA12; PA13; PA14; PA20; PA25; PA28; PA28; PA29; PA67; PB12; PB38; PB60; PC24; PC35; PC41; PC51; PC97;
M[20P]-563: PA12; PA13; PA20; PA20; PA21; PA24; PA25; PA25; PA29; PA29; PA33; PA81; PB33; PB60; PB60; PB88; PB88; PB88; PC11; PC41;
M[20P]-564: PA07; PA13; PA13; PA21; PA26; PA37; PA39; PA67; PA67; PB02; PB07; PB07; PB12; PB12; PB28; PC12; PC37; PC97; PC97; PC97;
M[20P]-565: PA07; PA11; PA13; PA20; PA29; PA29; PA32; PA75; PA95; PA98; PB02; PB12; PB32; PB33; PB60; PB85; PC20; PC24; PC35; PC41;
M[20P]-567: PA10; PA13; PA14; PA16; PA21; PA26; PA28; PA75; PA81; PB07; PB07; PB12; PB88; PC23; PC24; PC24; PC33; PC52; PC55; PC67;
M[20P]-569: PA13; PA14; PA21; PA26; PA27; PA39; PA57; PA67; PB02; PB07; PB12; PB28; PC12; PC21; PC49; PC55; PC55; PC67; PC67; PC98;
M[20P]-572: PA13; PA14; PA21; PA27; PA29; PA33; PA67; PA69; PA79; PB00; PB01; PB12; PB33; PB38; PC37; PC41; PC49; PC51; PC55; PD02;
M[20P]-573: PA10; PA11; PA13; PA13; PA13; PA14; PA18; PA21; PA23; PA29; PA67; PB00; PB07; PB12; PB33; PB77; PC11; PC52; PC60; PC71;
M[20P]-574: PA13; PA21; PA22; PA23; PA25; PA29; PA35; PA67; PB01; PB12; PB12; PB35; PB88; PC24; PC37; PC37; PC51; PC52; PC52; PC66;
M[20P]-575: PA11; PA11; PA13; PA13; PA13; PA14; PA14; PA26; PA26; PA28; PA52; PA67; PB00; PB12; PB27; PB28; PB38; PB60; PC37; PC52;
M[20P]-576: PA11; PA11; PA12; PA13; PA13; PA13; PA14; PA14; PA20; PA21; PA22; PA29; PA39; PB12; PB60; PC20; PC26; PC33; PC37; PC49;
M[20P]-577: PA06; PA13; PA13; PA14; PA22; PA22; PA23; PA26; PA28; PA69; PA70; PB07; PB12; PB12; PB32; PC12; PC20; PC24; PC24; PC98;

M[20P]-579: PA12; PA13; PA13; PA13; PA14; PA26; PA26; PA28; PA57; PA81; PB02; PB07; PB12; PC11; PC12; PC20; PC51; PC55; PD02; PD02;

M[20P]-580: PA00; PA11; PA12; PA13; PA20; PA21; PA21; PA25; PA26; PA26; PA33; PA75; PA75; PA75; PB28; PB88; PC20; PC76; PC98; PC98;

M[20P]-581: PA10; PA11; PA13; PA21; PA22; PA25; PA29; PA67; PB07; PB60; PB88; PB88; PC20; PC21; PC24; PC37; PC41; PC55; PC66; PC98;

M[20P]-582: PA10; PA11; PA12; PA13; PA20; PA21; PA23; PA25; PA39; PA75; PB07; PB07; PB38; PB38; PB60; PB60; PC20; PC24; PC41; PC66;

M[20P]-583: PA11; PA13; PA14; PA23; PA25; PA25; PA26; PA26; PA28; PA67; PB12; PB18; PB88; PC24; PC24; PC37; PC41; PC49; PC55; PC60;

M[20P]-584: PA00; PA14; PA21; PA26; PA26; PA28; PA39; PA39; PA67; PA75; PB12; PB12; PB27; PB33; PB60; PC11; PC41; PC49; PC55; PC97;

M[20P]-588: PA07; PA13; PA14; PA21; PA26; PA26; PA26; PA26; PA32; PA67; PA67; PA75; PB12; PB27; PB33; PB60; PC20; PC20; PC23; PC24;

M[20P]-589: PA13; PA13; PA22; PA25; PA25; PA27; PA29; PA29; PA35; PA39; PA52; PA75; PB12; PB32; PB38; PB85; PB88; PC11; PC23; PC98;

M[20P]-590: PA11; PA13; PA13; PA14; PA25; PA29; PA33; PA35; PA35; PA35; PA39; PB02; PB12; PC11; PC20; PC20; PC21; PC27; PC55; PC55;

M[20P]-592: PA10; PA10; PA11; PA11; PA13; PA14; PA21; PA21; PA26; PA26; PA27; PA29; PA30; PA75; PB07; PB07; PB12; PB38; PC20; PC24;

M[20P]-594: PA13; PA21; PA21; PA21; PA23; PA27; PA28; PA39; PA60; PA69; PA70; PB02; PB09; PB12; PB12; PB88; PC24; PC49; PC97; PC98;

M[20P]-595: PA11; PA13; PA22; PA23; PA25; PA28; PA28; PA28; PA29; PA29; PA39; PA67; PA69; PB12; PB60; PC12; PC20; PC24; PC49; PC55;

M[20P]-596: PA11; PA11; PA13; PA13; PA14; PA21; PA22; PA23; PA26; PA26; PA67; PB12; PB60; PC11; PC20; PC20; PC37; PC50; PC55; PC60;

M[20P]-599: PA13; PA13; PA14; PA16; PA26; PA29; PA75; PA75; PB07; PB12; PB60; PB60; PB60; PB60; PC12; PC20; PC20; PC37; PC37; PC52;

M[20P]-601: PA11; PA11; PA13; PA13; PA13; PA23; PA26; PA29; PA29; PA35; PB02; PB10; PB12; PB33; PC20; PC21; PC41; PC49; PC60; PC67;

M[20P]-602: PA00; PA10; PA10; PA14; PA14; PA14; PA21; PA25; PA26; PA29; PA29; PB07; PB07; PB07; PB12; PB12; PC20; PC52; PC55; PD02;

M[20P]-603: PA11; PA13; PA16; PA20; PA21; PA23; PA23; PA26; PA26; PA28; PA33; PA39; PA39; PA67; PB60; PB60; PC20; PC23; PC49; PC55;

M[20P]-604: PA10; PA13; PA14; PA14; PA18; PA21; PA22; PA23; PA26; PA28; PA28; PA29; PB12; PB33; PC11; PC11; PC51; PC51; PC60; PC71;

M[20P]-605: PA11; PA11; PA11; PA11; PA13; PA13; PA13; PA20; PA25; PA29; PA39; PA39; PA69; PA81; PB07; PB12; PB88; PC20; PC41; PC55;

M[20P]-607: PA10; PA11; PA11; PA13; PA13; PA13; PA22; PA22; PA26; PA33; PA35; PA75; PA75; PA81; PB12; PB88; PC20; PC49; PC55; PC97;

M[20P]-608: PA00; PA13; PA13; PA13; PA18; PA26; PA27; PA29; PA35; PA57; PA69; PA75; PA98; PB12; PB60; PC11; PC20; PC20; PC55; PC60;

M[20P]-609: PA11; PA14; PA21; PA22; PA23; PA26; PA34; PA52; PA67; PA69; PA69; PB07; PB12; PB12; PB27; PB77; PC12; PC20; PC55; PC97;

M[20P]-612: PA11; PA13; PA14; PA14; PA14; PA21; PA22; PA23; PA52; PA81; PB00; PB07; PB12; PB33; PB38; PB60; PC12; PC24; PC33; PC37;

M[20P]-613: PA10; PA13; PA13; PA14; PA21; PA21; PA22; PA23; PA26; PA28; PA28; PA29; PB12; PB12; PB27; PB60; PC20; PC21; PC21; PC60;

M[20P]-616: PA13; PA26; PA28; PA29; PA39; PA57; PA67; PB07; PB12; PB38; PB60; PB77; PB77; PB88; PC33; PC49; PC52; PC52; PC98; PC98;

M[20P]-618: PA11; PA12; PA13; PA13; PA14; PA20; PA21; PA22; PA23; PA26; PA29; PA67; PA79; PB88; PC11; PC20; PC20; PC37; PC41; PC55;

M[20P]-620: PA12; PA13; PA20; PA22; PA22; PA23; PA26; PA26; PA28; PA39; PA69; PA95; PB12; PB60; PB77; PC20; PC21; PC52; PC60; PC98;

M[20P]-621: PA10; PA13; PA14; PA24; PA24; PA26; PA27; PA29; PA32; PA35; PA67; PB12; PB12; PB12; PB27; PB33; PB33; PB38; PB38; PB38;

M[20P]-622: PA10; PA12; PA14; PA14; PA15; PA20; PA21; PA26; PA27; PA32; PA40; PB10; PB12; PB12; PB88; PC20; PC20; PC21; PC52; PC60;

M[20P]-623: PA10; PA11; PA13; PA14; PA20; PA24; PA25; PA26; PA26; PA28; PA39; PA81; PB09; PB12; PB28; PB88; PC24; PC41; PC52; PC98;

M[20P]-626: PA11; PA11; PA13; PA13; PA20; PA21; PA21; PA25; PA27; PA27; PA28; PA39; PA39; PA40; PA57; PB12; PB60; PC20; PC37; PC41;

M[20P]-631: PA10; PA13; PA20; PA21; PA21; PA23; PA23; PA26; PA29; PA39; PA39; PA67; PB10; PB38; PB60; PC11; PC20; PC37; PC49; PC66;

M[20P]-632: PA10; PA11; PA18; PA21; PA22; PA23; PA28; PA29; PA33; PA34; PA69; PB07; PB12; PB60; PC20; PC20; PC20; PC37; PC41; PC55;

M[20P]-633: PA10; PA11; PA11; PA13; PA20; PA34; PA39; PB00; PB07; PB12; PB12; PB60; PB88; PB88; PC11; PC12; PC23; PC35; PC49; PC52;

M[20P]-634: PA13; PA13; PA13; PA21; PA22; PA22; PA25; PA25; PA28; PA28; PA29; PA67; PA81; PB00; PB12; PB12; PB27; PB33; PC11; PC98;

M[20P]-635: PA00; PA14; PA17; PA20; PA21; PA23; PA26; PA27; PA75; PA81; PB00; PB12; PB82; PC11; PC20; PC26; PC51; PC52; PC55; PC71;

M[20P]-638: PA00; PA14; PA17; PA21; PA22; PA24; PA28; PA33; PA52; PA57; PA75; PB00; PB07; PB12; PB28; PB88; PC20; PC37; PC41; PC97;

M[20P]-649: PA06; PA10; PA11; PA12; PA13; PA15; PA16; PA20; PA24; PA30; PA33; PA98; PB10; PB12; PB28; PB32; PB60; PC11; PC20; PC66;

M[20P]-654: PA00; PA11; PA15; PA20; PA21; PA26; PA32; PA34; PA35; PA39; PA57; PB10; PB12; PB18; PC11; PC20; PC21; PC50; PC55; PC66;

M[20P]-655: PA11; PA13; PA14; PA20; PA22; PA26; PA28; PA30; PA40; PA52; PA57; PA81; PB12; PB32; PB85; PC41; PC50; PC55; PC66; PC71;

M[20P]-658: PA10; PA11; PA12; PA13; PA14; PA15; PA17; PA20; PA21; PA28; PA29; PA52; PA67; PB10; PB12; PB18; PB60; PC20; PC41; PC66;

M[20P]-659: PA00; PA11; PA21; PA22; PA24; PA26; PA27; PA28; PA29; PA33; PA35; PA81; PB07; PB12; PB18; PB28; PB85; PC37; PC49; PC74;

M[20P]-663: PA06; PA13; PA20; PA25; PA26; PA27; PA28; PA40; PA67; PA81; PB00; PB12; PB18; PB33; PB61; PC20; PC24; PC37; PC41; PC52;

M[20P]-666: PA06; PA13; PA21; PA23; PA27; PA28; PA30; PA40; PA75; PB00; PB07; PB10; PB12; PB18; PB28; PB33; PC20; PC49; PC52; PC71;

M[20P]-668: PA10; PA16; PA17; PA21; PA24; PA27; PA28; PA33; PA40; PA57; PA75; PA79; PB07; PB08; PB12; PB33; PB88; PC20; PC35; PC97;

M[20P]-670: PA11; PA12; PA13; PA14; PA20; PA23; PA27; PA28; PA35; PA39; PA67; PA79; PA81; PA89; PB10; PB12; PB18; PC20; PC21; PC51;

M[20P]-678: PA06; PA11; PA12; PA13; PA21; PA23; PA29; PA35; PA39; PA40; PB00; PB07; PB10; PB12; PB33; PB60; PB77; PC11; PC67; PC76;

M[20P]-681: PA07; PA10; PA11; PA21; PA24; PA26; PA30; PA35; PA39; PA57; PA75; PB07; PB12; PB28; PB88; PC11; PC49; PC55; PC58; PC66;

M[20P]-686: PA00; PA10; PA13; PA22; PA24; PA27; PA28; PA33; PA39; PA40; PA69; PB12; PB32; PB38; PB85; PB88; PC20; PC55; PC60; PC66;

M[20P]-692: PA07; PA10; PA13; PA21; PA22; PA26; PA34; PA39; PA40; PA81; PB12; PB18; PB32; PB33; PB88; PC35; PC37; PC52; PC55; PC76;

M[20P]-694: PA07; PA11; PA13; PA14; PA15; PA16; PA21; PA27; PA28; PA29; PA35; PA39; PA40; PA75; PB12; PB33; PB88; PC50; PC51; PC52;

M[20P]-697: PA00; PA13; PA16; PA19; PA21; PA22; PA25; PA27; PA28; PA39; PA79; PA81; PB00; PB12; PB32; PB60; PB99; PC51; PC58; PC76;

M[20P]-703: PA00; PA13; PA14; PA15; PA24; PA26; PA33; PA35; PA52; PA75; PA81; PB07; PB12; PB28; PB85; PC20; PC21; PC35; PC41; PD02;

M[20P]-705: PA11; PA13; PA30; PA33; PA40; PA67; PA75; PB07; PB12; PB28; PB35; PB88; PC20; PC21; PC24; PC35; PC37; PC41; PC50; PC55;

M[20P]-708: PA07; PA13; PA23; PA25; PA27; PA29; PA30; PA33; PA52; PA57; PA75; PB00; PB08; PB12; PB38; PB60; PB77; PC50; PC76; PD02;

M[20P]-709: PA11; PA13; PA17; PA20; PA21; PA23; PA26; PA27; PA28; PA40; PA69; PA81; PA92; PB00; PB07; PB12; PC20; PC41; PC52; PC66;

M[20P]-712: PA12; PA13; PA15; PA20; PA22; PA26; PA27; PA29; PA35; PA52; PA81; PB07; PB10; PB12; PB33; PB88; PC11; PC20; PC41; PC52;

M[20P]-714: PA07; PA10; PA11; PA16; PA21; PA26; PA33; PA40; PA67; PA81; PA98; PB00; PB07; PB12; PB28; PC11; PC41; PC49; PC50; PC98;

M[20P]-716: PA11; PA13; PA15; PA19; PA22; PA26; PA33; PA37; PA39; PA57; PB07; PB12; PB28; PB33; PB88; PB99; PC14; PC23; PC35; PC67;

M[20P]-718: PA12; PA13; PA15; PA16; PA20; PA22; PA25; PA26; PA39; PA40; PA92; PB07; PB12; PB27; PB35; PB38; PB99; PC11; PC27; PC41;

M[20P]-721: PA19; PA20; PA21; PA24; PA25; PA27; PA29; PA30; PA55; PA57; PB12; PB32; PB58; PB60; PB88; PB99; PC41; PC50; PC60; PC67;

M[20P]-723: PA12; PA13; PA16; PA17; PA21; PA28; PA29; PA33; PA34; PA40; PA60; PA89; PB28; PB60; PB61; PC14; PC24; PC41; PC51; PC74;

M[20P]-724: PA13; PA23; PA25; PA35; PA57; PA67; PB07; PB12; PB32; PB33; PB88; PB99; PC12; PC20; PC23; PC49; PC50; PC66; PC67; PC94;

M[20P]-725: PA00; PA13; PA14; PA20; PA22; PA25; PA26; PA28; PA33; PA40; PA57; PA81; PB12; PB16; PB33; PB88; PC11; PC24; PC51; PC74;

M[20P]-733: PA11; PA13; PA15; PA21; PA28; PA30; PA33; PA40; PB12; PB32; PB33; PB99; PC11; PC12; PC20; PC60; PC73; PC74; PC94; PD02;

M[20P]-737: PA00; PA11; PA13; PA15; PA17; PA21; PA24; PA28; PA29; PA30; PA67; PB07; PB27; PB28; PB77; PC20; PC21; PC41; PC51; PC94;

M[20P]-740: PA11; PA13; PA14; PA15; PA22; PA23; PA28; PA33; PA39; PA57; PA75; PA89; PB02; PB12; PB28; PB33; PC12; PC21; PC24; PC55;

M[20P]-745: PA11; PA21; PA22; PA24; PA26; PA27; PA28; PA29; PA57; PA89; PB07; PB12; PB28; PB33; PC08; PC11; PC41; PC66; PC67; PC98;

M[20P]-746: PA20; PA21; PA25; PA26; PA28; PA33; PA39; PA40; PA81; PB06; PB07; PB12; PB32; PB60; PC20; PC21; PC24; PC37; PC50; PC55;

M[20P]-748: PA11; PA13; PA14; PA17; PA23; PA26; PA32; PA57; PA60; PA81; PB07; PB12; PB28; PB32; PB33; PB85; PB99; PC20; PC21; PC35;

M[20P]-752: PA11; PA13; PA18; PA26; PA28; PA29; PA33; PA35; PA39; PA67; PA75; PB07; PB12; PB32; PB88; PB99; PC12; PC50; PC54; PC62;

M[20P]-753: PA11; PA12; PA13; PA14; PA15; PA29; PA32; PA40; PA57; PA81; PB00; PB12; PB33; PB60; PC20; PC21; PC49; PC52; PC66; PD02;

M[20P]-757: PA11; PA13; PA21; PA22; PA23; PA27; PA34; PA35; PA40; PA57; PA67; PB10; PB12; PB22; PB58; PC11; PC14; PC23; PC55; PC98;

M[20P]-758: PA10; PA11; PA13; PA20; PA21; PA23; PA28; PA29; PA30; PA40; PA69; PA75; PA81; PB12; PC06; PC20; PC41; PC52; PC57; PC74;

M[20P]-764: PA11; PA13; PA22; PA29; PA35; PA40; PA57; PA73; PA75; PA81; PB08; PB12; PB33; PB82; PC11; PC20; PC21; PC29; PC41; PC52;

M[20P]-765: PA10; PA11; PA13; PA15; PA26; PA27; PA30; PA35; PA40; PA89; PB12; PB22; PB58; PB60; PC34; PC37; PC55; PC58; PC67; PD02;

M[20P]-766: PA11; PA13; PA17; PA22; PA24; PA25; PA29; PA30; PA33; PA34; PA35; PA81; PA92; PB00; PB12; PB82; PC24; PC50; PC74; PC97;

M[20P]-767: PA11; PA21; PA22; PA28; PA29; PA33; PA37; PB12; PB60; PB85; PB88; PB99; PC14; PC20; PC21; PC41; PC51; PC55; PC57; PC98;

M[20P]-771: PA10; PA11; PA13; PA14; PA22; PA26; PA27; PA28; PA29; PA35; PA86; PA89; PB07; PB12; PB28; PB88; PB99; PC12; PC21; PC50;

M[20P]-777: PA11; PA14; PA15; PA20; PA21; PA24; PA25; PA28; PA29; PA33; PA75; PB12; PB85; PB99; PC21; PC51; PC55; PC62; PC67; PD02;

M[20P]-779: PA15; PA19; PA20; PA21; PA22; PA23; PA24; PA25; PA29; PA30; PA57; PA67; PA75; PA89; PB07; PB12; PB32; PC20; PC51; PC74;

M[20P]-781: PA10; PA15; PA21; PA22; PA39; PA57; PA75; PB08; PB09; PB12; PB28; PB35; PB58; PB60; PC12; PC33; PC37; PC66; PC67; PC74;

M[20P]-782: PA10; PA11; PA12; PA13; PA14; PA20; PA26; PA30; PA75; PA89; PA92; PB05; PB07; PB12; PB32; PB82; PB99; PC51; PC58; PC73;

M[20P]-785: PA16; PA17; PA21; PA28; PA29; PA30; PA32; PA33; PA55; PB07; PB12; PB77; PB85; PB88; PB99; PC12; PC20; PC35; PC67; PC98;

M[20P]-786: PA11; PA13; PA14; PA18; PA19; PA21; PA22; PA27; PA28; PA29; PA33; PA40; PA52; PA57; PA81; PB28; PC11; PC20; PC21; PC50;

M[20P]-787: PA10; PA11; PA13; PA22; PA23; PA35; PB07; PB12; PB22; PB85; PB99; PC11; PC20; PC41; PC49; PC52; PC53; PC55; PC73; PD02;

M[20P]-789: PA10; PA11; PA13; PA22; PA23; PA27; PA40; PA57; PA75; PA81; PB07; PB12; PB27; PB60; PB88; PC11; PC20; PC23; PC35; PC41;

M[20P]-791: PA10; PA11; PA13; PA15; PA21; PA33; PA35; PA40; PA57; PA69; PA85; PA98; PA99; PB07; PB12; PB20; PB99; PC12; PC20; PC58;

M[20P]-793: PA11; PA13; PA14; PA15; PA19; PA26; PA29; PA55; PA67; PA89; PB12; PB33; PB88; PC14; PC20; PC21; PC34; PC37; PC67; PC97;

M[20P]-794: PA21; PA23; PA28; PA29; PA34; PA35; PA57; PA75; PA81; PB07; PB12; PB18; PB32; PB58; PC11; PC14; PC41; PC55; PC62; PC74;

M[20P]-795: PA10; PA13; PA20; PA23; PA27; PA29; PA57; PA60; PA69; PB00; PB07; PB12; PB18; PB32; PB85; PB88; PC20; PC66; PC74; PD02;

M[20P]-803: PA11; PA13; PA15; PA22; PA25; PA26; PA29; PA30; PA33; PA40; PA75; PB07; PB12; PB28; PC21; PC23; PC34; PC55; PC71; PC73;

M[20P]-804: PA11; PA12; PA13; PA20; PA22; PA23; PA30; PA33; PA34; PA79; PB12; PB18; PB58; PB60; PB85; PB88; PC20; PC50; PC67; PC68;

M[20P]-806: PA06; PA10; PA11; PA13; PA19; PA20; PA21; PA23; PA25; PA28; PA52; PA73; PA75; PA98; PB12; PB33; PB82; PB85; PB88; PC11;

M[20P]-816: PA11; PA13; PA19; PA25; PA28; PA29; PA33; PA57; PA81; PA89; PB00; PB10; PB12; PB26; PB28; PB99; PC11; PC12; PC76; PC97;

M[20P]-819: PA10; PA11; PA13; PA15; PA26; PA34; PA60; PA81; PA92; PB07; PB12; PB38; PB85; PC01; PC14; PC20; PC52; PC58; PC66; PC67;

M[20P]-823: PA00; PA11; PA12; PA13; PA14; PA17; PA27; PA29; PA40; PA60; PA75; PA79; PA89; PB07; PB12; PB99; PC20; PC52; PC66; PC71;

M[20P]-830: PA13; PA20; PA25; PA26; PA28; PA40; PA75; PA89; PB00; PB07; PB12; PB32; PB88; PC06; PC12; PC20; PC41; PC52; PC76; PC98;

M[20P]-831: PA11; PA15; PA21; PA25; PA33; PB12; PB28; PB32; PB33; PB38; PB60; PB77; PB88; PC20; PC23; PC35; PC37; PC49; PC58; PC66;

M[20P]-841: PA10; PA11; PA13; PA18; PA22; PA28; PA29; PA30; PA35; PA40; PA55; PA75; PB07; PB12; PB28; PB32; PB33; PC41; PC49; PC60;

M[20P]-844: PA11; PA15; PA21; PA24; PA26; PA29; PA33; PA40; PA69; PA81; PA98; PB12; PB28; PB61; PC49; PC67; PC71; PC73; PC74; PD02;

M[20P]-845: PA11; PA13; PA14; PA15; PA21; PA30; PA34; PA39; PA60; PA79; PA81; PA89; PB07; PB18; PC14; PC20; PC21; PC34; PC68; PC97;

M[20P]-846: PA11; PA13; PA25; PA27; PA29; PA32; PA33; PA35; PA37; PA39; PA40; PB08; PB12; PB33; PB88; PC24; PC41; PC52; PC58; PC62;

M[20P]-847: PA10; PA19; PA20; PA21; PA28; PA29; PA30; PA67; PA75; PA89; PB00; PB12; PB28; PB33; PB60; PC12; PC55; PC73; PC74; PD02;

M[20P]-848: PA07; PA11; PA13; PA15; PA20; PA22; PA26; PA27; PA30; PA40; PA69; PA75; PB12; PB32; PB85; PB88; PC34; PC37; PC66; PC68;

M[20P]-849: PA00; PA13; PA25; PA27; PA28; PA29; PA34; PA40; PA57; PA81; PB00; PB12; PB18; PB77; PC20; PC24; PC35; PC41; PC50; PC51;

M[20P]-852: PA00; PA11; PA13; PA15; PA19; PA22; PA26; PA35; PA89; PB00; PB12; PB58; PB77; PC12; PC20; PC29; PC62; PC71; PC94; PC98;

M[20P]-853: PA00; PA11; PA21; PA24; PA25; PA33; PA57; PA60; PB07; PB12; PB28; PB32; PB60; PB82; PB88; PC24; PC41; PC50; PC51; PC58;

M[20P]-857: PA00; PA11; PA13; PA26; PA28; PA75; PA76; PA79; PB12; PB28; PB60; PB88; PC11; PC12; PC20; PC37; PC50; PC52; PC67; PD02;

M[20P]-873: PA10; PA13; PA26; PA27; PA30; PA34; PA85; PA98; PB05; PB07; PB12; PB28; PB29; PB32; PB60; PC14; PC20; PC26; PC41; PC76;

M[20P]-880: PA11; PA13; PA17; PA20; PA22; PA24; PA26; PA27; PA29; PA38; PA57; PB07; PB12; PB20; PB29; PB97; PC24; PC37; PC51; PC71;

M[20P]-888: PA10; PA12; PA15; PA16; PA21; PA27; PA28; PA33; PA44; PB00; PB12; PB13; PB27; PC11; PC20; PC51; PC58; PC73; PC75; PD02;

M[20P]-890: PA00; PA11; PA13; PA15; PA16; PA25; PA34; PA75; PA82; PA86; PB00; PB12; PB16; PB27; PB33; PC20; PC49; PC50; PC57; PC98;

M[20P]-894: PA12; PA18; PA21; PA24; PA26; PA27; PA34; PA57; PA67; PA82; PB01; PB12; PB33; PB76; PB98; PB99; PC11; PC24; PC33; PC83;

M[20P]-902: PA12; PA13; PA21; PA26; PA29; PA39; PA40; PA57; PA96; PB00; PB07; PB12; PB27; PC20; PC50; PC53; PC61; PC62; PC75; PC94;

M[20P]-904: PA06; PA13; PA20; PA23; PA25; PA27; PA35; PA46; PA52; PA60; PA81; PA90; PA97; PB03; PB12; PB57; PB99; PC20; PC52; PC73;

M[20P]-907: PA00; PA07; PA14; PA21; PA24; PA25; PA45; PA75; PA83; PA97; PB12; PB26; PB32; PB60; PB92; PC06; PC20; PC35; PC37; PD02;

M[20P]-909: PA12; PA14; PA20; PA21; PA29; PA39; PA72; PA93; PB12; PB22; PB28; PB32; PC21; PC23; PC24; PC41; PC52; PC73; PC79; PD02.

Note: if in the previous and in the following analogous Lists a plant code occurs more than one time in the same herbal composition, it means that more than one calibrated spoon of the corresponding grinded dried plant was used.

Starting from the herbal compositions listed in List 6-3 corresponding water extracts (or processed samples) were prepared according to the previously described Method B using 40 mL of water containing 100 g/l of sucrose for water extraction and including the decantation step before filtration.

The biological activity of each processed sample was determined according to the previously described Method C by using the following *Staphylococcus aureus* strains: ATCC 25923, ATCC 49476, ATCC 6538, ATCC 51740, ATCC 29213 and ATCC 14775, with the following final dilutions of processed samples: 1:20, 1:63 and 1:200.

The bacteria planktonic growth inhibition percentage average and biofilm formation inhibition percentage average over all the tested strains of the processed samples obtained from herbal compositions including the 2 plants of Mix [2P]-1 at 1:20 dilution is given in Table 5-1.

TABLE 5-1 average of planktonic growth inhibition percentage and biofilm formation inhibition percentage efficacy on the 6 tested *Staphylococcus aureus* strains of the processed sample based on Mix[2P]-1 at 1:20 dilution. (A) Mixes extracts showing higher antimicrobial and antibiofilm activity. (B) Mixes extracts showing antibiofilm activity and equivalent or lower antimicrobial activity. (C) Mixes extracts showing antimicrobial activity and equivalent or lower antibiofilm activity

| | Planktonic growth inhibition | Biofilm formation inhibition |
|---|---|---|
| (A) | | |
| Mix[2P]-1 | 22% | 36% |
| M[20P]-563 | 26% | 40% |
| M[20P]-495 | 25% | 43% |
| M[20P]-631 | 27% | 42% |
| M[20P]-465 | 24% | 50% |
| M[20P]-408 | 26% | 50% |
| M[09P]-8 | 31% | 48% |
| M[19P]-13 | 31% | 50% |

TABLE 5-1-continued average of planktonic growth inhibition percentage and biofilm formation inhibition percentage efficacy on the 6 tested *Staphylococcus aureus* strains of the processed sample based on Mix[2P]-1 at 1:20 dilution. (A) Mixes extracts showing higher antimicrobial and antibiofilm activity. (B) Mixes extracts showing antibiofilm activity and equivalent or lower antimicrobial activity. (C) Mixes extracts showing antimicrobial activity and equivalent or lower antibiofilm activity

| | Planktonic growth inhibition | Biofilm formation inhibition |
|---|---|---|
| M[18P]-12 | 40% | 50% |
| M[20P]-581 | 40% | 50% |
| M[20P]-469 | 40% | 55% |
| M[20P]-485 | 43% | 52% |
| M[20P]-427 | 37% | 66% |
| M[20P]-582 | 51% | 54% |
| M[20P]-431 | 44% | 65% |
| M[20P]-618 | 54% | 57% |
| M[20P]-580 | 61% | 59% |
| M[20P]-421 | 53% | 70% |
| M[20P]-499 | 60% | 67% |
| M[20P]-525 | 86% | 77% |
| M[2OP]-29 | 105% | 93% |
| (B) | | |
| Mix[2P]-1 | 22% | 36% |
| M[20P]-723 | 11% | 40% |
| M[20P]-786 | 20% | 40% |
| M[20P]-737 | 22% | 40% |
| M[20P]-340 | 11% | 40% |
| M[20P]-382 | 13% | 41% |
| M[20P]-444 | 18% | 42% |
| M[20P]-603 | 12% | 42% |
| M[20P]-470 | 19% | 42% |
| M[20P]-503 | 12% | 46% |
| M[19P]-67 | 18% | 49% |
| M[20P]-533 | 21% | 50% |
| M[20P]-845 | 16% | 51% |
| M[20P]-377 | 21% | 51% |
| M[20P]-510 | 7% | 55% |
| (C) | | |
| Mix[2P]-l | 22% | 36% |
| M[17P]-9 | 27% | 29% |
| M[18P]-37 | 29% | 36% |

20 processed samples obtained from herbal compositions containing 9, 18, 19 or 20 plants were found to have higher antibiofilm and antimicrobial activity than the reference mix extract Mix[2P]-1 (Table 5-1 A). Fourteen 20 plant mixes extracts were found to have higher antibiofilm activity and equivalent or lower antimicrobial activity (Table 5-1 B). Two processed samples obtained from herbal compositions containing 17 and 18 plants were found to have higher antimicrobial activity and equivalent or lower antibiofilm activity (Table 5-1 C).

The bacteria planktonic growth inhibition percentage average and biofilm formation inhibition percentage average over all the tested strains of the processed samples obtained from herbal compositions including the 2 plants of Mix [2P]-2 at 1:20 dilution is given in Table 5-2.

TABLE 5-2 average of planktonic growth inhibition percentage and biofilm formation inhibition percentage efficacy on the 6 tested *Staphylococcus aureus* strains of the processed sample based on Mix[2P]-2 at 1:20 dilution. (A) Mixes extracts showing higher antimicrobial and antibiofilm activity. (B) Mixes extracts showing antimicrobial activity and equivalent or lower antibiofilm activity.

| | Planktonic growth inhibition | Biofilm formation inhibition |
|---|---|---|
| (A) | | |
| Mix[2P]-2 | 12% | −3% |
| M[17P]-5 | 17% | 17% |
| M[20P]-654 | 16% | 20% |
| M[16P]-1 | 14% | 22% |
| M[17P]-1 | 16% | 22% |
| M[20P]-779 | 14% | 29% |
| M[20P]-746 | 15% | 28% |
| M[20P]-635 | 17% | 26% |
| M[20P]-844 | 15% | 29% |
| M[20P]-831 | 17% | 31% |
| M[20P]-894 | 18% | 30% |
| M[20P]-888 | 23% | 25% |
| M[20P]-407 | 19% | 31% |
| M[20P]-907 | 21% | 31% |
| M[20P]-335 | 19% | 33% |
| M[20P]-714 | 17% | 35% |
| M[20P]-668 | 15% | 38% |
| M[20P]-584 | 14% | 39% |
| M[20P]-777 | 16% | 37% |
| M[20P]-853 | 20% | 34% |
| M[20P]-785 | 16% | 39% |
| M[20P]-622 | 21% | 34% |
| M[09P]-2 | 17% | 39% |
| M[19P]-46 | 18% | 37% |
| M[20P]-387 | 13% | 43% |
| M[20P]-767 | 18% | 39% |
| M[18P]-23 | 24% | 33% |
| M[20P]-745 | 20% | 37% |
| M[20P]-478 | 22% | 36% |
| M[19P]-45 | 16% | 42% |
| M[19P]-49 | 19% | 40% |
| M[20P]-467 | 17% | 42% |
| M[20P]-396 | 21% | 38% |
| M[20P]-392 | 17% | 42% |
| M[19P]-44 | 20% | 42% |
| M[19P]-41 | 23% | 40% |
| M[19P]-48 | 18% | 46% |
| M[19P]-47 | 17% | 46% |
| M[20P]-490 | 20% | 44% |
| M[19P]-21 | 29% | 35% |
| M[20P]-632 | 24% | 40% |
| M[19P]-54 | 19% | 45% |
| M[20P]-461 | 19% | 46% |
| M[19P]-42 | 24% | 41% |
| M[20P]-506 | 17% | 49% |
| M[19P]-55 | 21% | 46% |
| M[20P]-459 | 26% | 42% |
| M[20P]-375 | 19% | 52% |
| M[19P]-2 | 26% | 49% |
| M[19P]-40 | 28% | 48% |
| M[20P]-523 | 28% | 51% |
| M[20P]-420 | 34% | 56% |
| M[20P]-429 | 36% | 59% |
| M[20P]-535 | 45% | 55% |
| M[20P]-532 | 42% | 60% |
| M[20P]-432 | 54% | 72% |
| M[20P]-555 | 68% | 65% |
| M[20P]-240 | 67% | 78% |
| M[20P]-557 | 86% | 78% |
| (B) | | |
| Mix[2P]-2 | 12% | −3% |
| M[20P]-638 | 11% | 13% |
| M[20P]-794 | 6% | 16% |
| M[20P]-909 | 0% | 19% |
| M[20P]-538 | 8% | 22% |
| M[20P]-781 | 6% | 24% |

TABLE 5-2-continued average of planktonic growth inhibition percentage and biofilm formation inhibition percentage efficacy on the 6 tested *Staphylococcus aureus* strains of the processed sample based on Mix[2P]-2 at 1:20 dilution. (A) Mixes extracts showing higher antimicrobial and antibiofilm activity. (B) Mixes extracts showing antimicrobial activity and equivalent or lower antibiofilm activity.

| | Planktonic growth inhibition | Biofilm formation inhibition |
|---|---|---|
| M[19P]-27 | 7% | 26% |
| M[20P]-681 | 11% | 24% |
| M[16P]-3 | 8% | 28% |
| M[20P]-721 | 2% | 28% |
| M[20P]-493 | 7% | 28% |
| M[17P]-6 | 9% | 29% |
| M[20P]-659 | 10% | 30% |
| M[20P]-409 | 10% | 30% |
| M[20P]-602 | 4% | 31% |
| M[20P]-456 | 9% | 31% |
| M[20P]-383 | 5% | 32% |
| M[20P]-847 | 13% | 33% |
| M[20P]-496 | 6% | 34% |
| M[19P]-51 | 10% | 34% |
| M[20P]-371 | 7% | 36% |
| M[20P]-609 | 12% | 36% |
| M[19P]-52 | 9% | 36% |
| M[19P]-50 | 12% | 36% |
| M[18P]-24 | 11% | 36% |
| M[19P]-53 | 10% | 40% |

58 processed samples obtained from herbal compositions containing 9, 16, 17, 18, 19 or 20 plants were found to have higher antibiofilm and antimicrobial activity than the reference mix extract Mix[2P]-2 (Table 5-2 A). 25 processed samples obtained from herbal compositions containing 16, 17, 19 or 20 plants were found to have higher antibiofilm activity and equivalent or lower antimicrobial activity (Table 5-2 B).

The bacteria planktonic growth inhibition percentage average and biofilm formation inhibition percentage average over all the tested strains of the processed samples obtained from herbal compositions including the 2 plants of Mix [2P]-3 at 1:20 dilution is given in Table 5-3.

TABLE 5-3 average of planktonic growth inhibition percentage and biofilm formation inhibition percentage efficacy on the 6 tested *Staphylococcus aureus* strains of the processed sample based on Mix[2P]-3 at 1:20 dilution. (A) Mixes extracts showing higher antimicrobial and antibiofilm activity. (B) Mixes extracts showing antimicrobial activity and equivalent or lower antibiofilm activity.

| | Planktonic growth inhibition | Biofilm formation inhibition |
|---|---|---|
| (A) | | |
| Mix[2P]-3 | 12% | 28% |
| M[20P]-649 | 16% | 29% |
| M[20P]-857 | 15% | 32% |
| M[20P]-703 | 13% | 36% |
| M[20P]-486 | 15% | 35% |
| M[20P]-766 | 13% | 37% |
| M[20P]-789 | 14% | 36% |
| M[20P]-725 | 14% | 37% |
| M[20P]-536 | 20% | 32% |
| M[20P]-753 | 14% | 38% |
| M[20P]-401 | 14% | 38% |
| M[20P]-765 | 14% | 38% |
| M[20P]-848 | 14% | 39% |
| M[20P]-782 | 14% | 40% |

TABLE 5-3-continued average of planktonic growth inhibition percentage and biofilm formation inhibition percentage efficacy on the 6 tested *Staphylococcus aureus* strains of the processed sample based on Mix[2P]-3 at 1:20 dilution. (A) Mixes extracts showing higher antimicrobial and antibiofilm activity. (B) Mixes extracts showing antimicrobial activity and equivalent or lower antibiofilm activity.

| | Planktonic growth inhibition | Biofilm formation inhibition |
|---|---|---|
| M[20P]-589 | 15% | 39% |
| M[20P]-607 | 14% | 40% |
| M[20P]-541 | 20% | 34% |
| M[20P]-447 | 15% | 39% |
| M[20P]-601 | 17% | 38% |
| M[20P]-494 | 13% | 43% |
| M[20P]-787 | 15% | 40% |
| M[20P]-748 | 15% | 41% |
| M[09P]-6 | 15% | 41% |
| M[20P]-480 | 18% | 38% |
| M[20P]-633 | 15% | 41% |
| M[20P]-849 | 14% | 42% |
| M[20P]-793 | 16% | 42% |
| M[18P]-9 | 17% | 41% |
| M[20P]-852 | 13% | 45% |
| M[20P]-819 | 20% | 39% |
| M[20P]-655 | 15% | 44% |
| M[20P]-455 | 15% | 44% |
| M[20P]-846 | 16% | 44% |
| M[20P]-481 | 18% | 41% |
| M[20P]-484 | 17% | 42% |
| M[20P]-590 | 26% | 34% |
| M[20P]-890 | 19% | 42% |
| M[20P]-670 | 21% | 40% |
| M[20P]-705 | 23% | 39% |
| M[20P]-816 | 22% | 39% |
| M[19P]-91 | 15% | 48% |
| M[20P]-457 | 22% | 43% |
| M[20P]-551 | 24% | 41% |
| M[19P]-100 | 16% | 50% |
| M[20P]-583 | 23% | 43% |
| M[20P]-823 | 22% | 44% |
| M[19P]-100 | 16% | 50% |
| M[19P]-98 | 17% | 50% |
| M[19P]-101 | 14% | 54% |
| M[19P]-93 | 14% | 53% |
| M[19P]-102 | 13% | 54% |
| M[19P]-5 | 19% | 49% |
| M[19P]-89 | 17% | 51% |
| M[19P]-103 | 13% | 55% |
| M[19P]-96 | 18% | 52% |
| M[20P]-475 | 25% | 45% |
| M[20P]-548 | 30% | 42% |
| M[19P]-96 | 19% | 53% |
| M[20P]-605 | 22% | 50% |
| M[20P]-577 | 29% | 44% |
| M[20P]-482 | 27% | 46% |
| M[19P]-95 | 19% | 55% |
| M[20P]-904 | 21% | 55% |
| M[20P]-559 | 32% | 47% |
| M[20P]-430 | 29% | 71% |
| M[20P]-520 | 62% | 67% |
| M[20P]-579 | 75% | 66% |
| M[20P]-560 | 72% | 70% |
| M[20P]-565 | 73% | 73% |
| M[20P]-524 | 81% | 79% |
| M[20P]-575 | 85% | 76% |
| (B) | | |
| Mix[2P]-3 | 12% | 28% |
| M[20P]-599 | 11% | 32% |
| M[20P]-621 | 10% | 32% |
| M[20P]-740 | 12% | 33% |
| M[20P]-830 | 7% | 33% |
| M[20P]-623 | 12% | 34% |
| M[20P]-708 | 8% | 35% |
| M[20P]-880 | 12% | 35% |
| M[20P]-716 | 8% | 35% |
| M[20P]-803 | 4% | 36% |

TABLE 5-3-continued average of planktonic growth inhibition percentage and biofilm formation inhibition percentage efficacy on the 6 tested *Staphylococcus aureus* strains of the processed sample based on Mix[2P]-3 at 1:20 dilution. (A) Mixes extracts showing higher antimicrobial and antibiofilm activity. (B) Mixes extracts showing antimicrobial activity and equivalent or lower antibiofilm activity.

| | Planktonic growth inhibition | Biofilm formation inhibition |
|---|---|---|
| M[20P]-686 | 13% | 36% |
| M[20P]-663 | 5% | 36% |
| M[20P]-873 | 7% | 36% |
| M[20P]-608 | 10% | 37% |
| M[20P]-752 | 10% | 37% |
| M[20P]-443 | 8% | 37% |
| M[19P]-30 | 3% | 37% |
| M[20P]-712 | 12% | 37% |
| M[20P]-616 | 7% | 38% |
| M[20P]-724 | 4% | 38% |
| M[20P]-795 | 11% | 38% |
| M[20P]-403 | 13% | 38% |
| M[20P]-595 | 7% | 38% |
| M[20P]-771 | 9% | 39% |
| M[20P]-718 | 5% | 39% |
| M[20P]-620 | 12% | 39% |
| M[20P]-841 | 6% | 40% |
| M[20P]-804 | 8% | 40% |
| M[20P]-386 | 6% | 41% |
| M[20P]-764 | 11% | 42% |
| M[18P]-33 | 11% | 42% |
| M[20P]-349 | 9% | 43% |
| M[19P]-92 | 10% | 46% |
| M[18P]-34 | 11% | 47% |
| M[19P]-93 | 12% | 50% |
| M[18P]-31 | 12% | 51% |
| M[18P]-34 | 12% | 51% |
| M[19P]-62 | 10% | 56% |

70 processed samples obtained from herbal compositions containing 9, 19 or 20 plants were found to have higher antibiofilm and antimicrobial activity than the reference mix extract Mix[2P]-3 (Table 5-3 A). 37 processed samples containing 18 to 20 plants were found to have higher antibiofilm activity and equivalent or lower antimicrobial activity (Table 5-3 B).

The bacteria planktonic growth inhibition percentage average and biofilm formation inhibition percentage average over all the tested strains of the processed samples obtained from herbal compositions including the 3 plants of Mix [3P]-1 at 1:20 dilution is given in Table 5-4.

TABLE 5-4 average of planktonic growth inhibition percentage and biofilm formation inhibition percentage efficacy on the 6 tested *Staphylococcus aureus* strains of the processed sample based on Mix[3P]-1 at 1:20 dilution. (A) Mixes extracts showing higher antimicrobial and antibiofilm activity. (B) Mixes extracts showing antimicrobial activity and equivalent or lower antibiofilm activity.

| | Planktonic growth inhibition | Biofilm formation inhibition |
|---|---|---|
| (A) | | |
| Mix[3P]-1 | 31% | 15% |
| M[18P]-2 | 35% | 42% |
| M[16P]-5 | 36% | 41% |
| M[14P]-2 | 34% | 44% |
| M[16P]-6 | 35% | 44% |
| M[09P]-9 | 33% | 47% |
| M[09P]-1 | 34% | 45% |
| M[18P]-7 | 35% | 45% |

TABLE 5-4-continued average of planktonic growth inhibition percentage and biofilm formation inhibition percentage efficacy on the 6 tested *Staphylococcus aureus* strains of the processed sample based on Mix[3P]-1 at 1:20 dilution. (A) Mixes extracts showing higher antimicrobial and antibiofilm activity. (B) Mixes extracts showing antimicrobial activity and equivalent or lower antibiofilm activity.

| | Planktonic growth inhibition | Biofilm formation inhibition |
|---|---|---|
| M[17P]-3 | 36% | 44% |
| M[09P]-7 | 35% | 49% |
| M[20P]-594 | 40% | 46% |
| M[09P]-6 | 37% | 51% |
| M[20P]-658 | 45% | 43% |
| M[19P]-3 | 34% | 54% |
| M[18P]-11 | 40% | 49% |
| M[19P]-104 | 43% | 46% |
| M[09P]-3 | 46% | 44% |
| M[09P]-4 | 46% | 45% |
| M[19P]-19 | 34% | 57% |
| M[18P]-13 | 42% | 50% |
| M[18P]-10 | 43% | 49% |
| M[18P]-9 | 42% | 51% |
| M[18P]-17 | 45% | 51% |
| M[20P]-634 | 43% | 56% |
| M[20P]-596 | 44% | 55% |
| M[18P]-15 | 47% | 52% |
| M[20P]-449 | 47% | 56% |
| M[09P]-10 | 54% | 50% |
| M[20P]-588 | 48% | 56% |
| M[20P]-458 | 50% | 56% |
| M[19P]-105 | 49% | 56% |
| M[13P]-2 | 51% | 56% |
| M[19P]-11 | 43% | 67% |
| M[18P]-16 | 54% | 59% |
| M[20P]-569 | 55% | 60% |
| M[20P]-296 | 52% | 62% |
| M[18P]-18 | 56% | 61% |
| M[20P]-516 | 61% | 68% |
| M[20P]-592 | 70% | 71% |
| M[20P]-626 | 71% | 71% |
| M[19P]-23 | 72% | 72% |
| M[20P]-497 | 72% | 77% |
| M[20P]-572 | 74% | 78% |
| M[20P]-574 | 76% | 79% |
| M[20P]-527 | 76% | 80% |
| M[20P]-297 | 83% | 81% |
| M[20P]-422 | 81% | 83% |
| M[20P]-564 | 86% | 82% |
| M[20P]-418 | 98% | 87% |
| M[20P]-416 | 99% | 89% |
| M[20P]-576 | 104% | 86% |
| M[20P]-573 | 104% | 93% |
| (B) | | |
| Mix[3P]-1 | 31% | 15% |
| M[20P]-692 | 11% | 22% |
| M[20P]-612 | 6% | 25% |
| M[18P]-22 | 4% | 27% |
| M[20P]-388 | 9% | 27% |
| M[20P]-380 | 12% | 28% |
| M[11P]-12 | 22% | 29% |
| M[19P]-33 | 8% | 30% |
| M[19P]-35 | 6% | 30% |
| M[17P]-2 | 12% | 30% |
| M[20P]-678 | 10% | 31% |
| M[19P]-22 | 17% | 31% |
| M[20P]-552 | 16% | 32% |
| M[17P]-4 | 9% | 32% |
| M[20P]-806 | 12% | 32% |
| M[12P]-1 | 19% | 33% |
| M[14P]-1 | 18% | 33% |
| M[19P]-28 | 6% | 33% |
| M[12P]-2 | 22% | 34% |
| M[18P]-1 | 16% | 34% |
| M[19P]-36 | 6% | 34% |
| M[20P]-479 | 23% | 34% |
| M[15P]-1 | 23% | 34% |

TABLE 5-4-continued average of planktonic growth inhibition percentage and biofilm formation inhibition percentage efficacy on the 6 tested *Staphylococcus aureus* strains of the processed sample based on Mix[3P]-1 at 1:20 dilution. (A) Mixes extracts showing higher antimicrobial and antibiofilm activity. (B) Mixes extracts showing antimicrobial activity and equivalent or lower antibiofilm activity.

| | Planktonic growth inhibition | Biofilm formation inhibition |
|---|---|---|
| M[09P]-21 | 22% | 34% |
| M[20P]-446 | 10% | 34% |
| M[19P]-34 | 7% | 34% |
| M[19P]-106 | 29% | 35% |
| M[10P]-41 | 8% | 35% |
| M[13P]-1 | 22% | 35% |
| M[18P]-5 | 18% | 35% |
| M[19P]-39 | -1% | 35% |
| M[11P]-3 | 12% | 35% |
| M[20P]-439 | 19% | 36% |
| M[11P]-2 | 13% | 36% |
| M[18P]-20 | 6% | 36% |
| M[20P]-757 | 18% | 36% |
| M[10P]-303 | 25% | 36% |
| M[11P]-11 | 29% | 37% |
| M[11P]-6 | 9% | 37% |
| M[19P]-37 | 5% | 37% |
| M[18P]-19 | 10% | 37% |
| M[18P]-4 | 29% | 37% |
| M[18P]-35 | 27% | 37% |
| M[18P]-25 | 11% | 37% |
| M[11P]-5 | 10% | 38% |
| M[20P]-694 | 20% | 38% |
| M[11P]-8 | 10% | 38% |
| M[11P]-9 | 11% | 38% |
| M[20P]-733 | 12% | 38% |
| M[11P]-7 | 10% | 38% |
| M[19P]-31 | 6% | 38% |
| M[19P]-32 | 4% | 38% |
| M[19P]-29 | 6% | 38% |
| M[18P]-6 | 22% | 38% |
| M[20P]-374 | 2% | 38% |
| M[11P]-4 | 12% | 39% |
| M[20P]-791 | 13% | 39% |
| M[20P]-758 | 15% | 39% |
| M[19P]-26 | 6% | 39% |
| M[20P]-697 | 17% | 39% |
| M[19P]-38 | 4% | 40% |
| M[19P]-24 | 28% | 40% |
| M[16P]-2 | 24% | 40% |
| M[18P]-21 | 9% | 40% |
| M[15P]-5 | 29% | 40% |
| M[17P]-8 | 30% | 40% |
| M[20P]-613 | 8% | 41% |
| M[18P]-14 | 27% | 41% |
| M[20P]-604 | 14% | 41% |
| M[11P]-1 | 17% | 41% |
| M[18P]-36 | 29% | 41% |
| M[18P]-3 | 23% | 42% |
| M[20P]-453 | 5% | 42% |
| M[19P]-25 | 9% | 42% |
| M[20P]-709 | 18% | 42% |
| M[20P]-474 | 16% | 45% |
| M[20P]-666 | 22% | 45% |
| M[20P]-902 | 21% | 46% |
| M[20P]-435 | 15% | 46% |
| M[20P]-567 | 30% | 47% |
| M[19P]-4 | 24% | 47% |
| M[19P]-16 | 18% | 47% |
| M[19P]-59 | 10% | 48% |
| M[19P]-17 | 23% | 48% |
| M[19P]-58 | 20% | 49% |
| M[19P]-60 | 13% | 49% |
| M[19P]-15 | 27% | 50% |
| M[11P]-10 | 31% | 50% |
| M[19P]-14 | 27% | 50% |
| M[19P]-6 | 32% | 51% |
| M[20P]-445 | 21% | 51% |
| M[19P]-8 | 30% | 51% |
| M[19P]-18 | 21% | 52% |
| M[19P]-9 | 29% | 52% |
| M[19P]-7 | 30% | 52% |
| M[19P]-10 | 29% | 52% |
| M[19P]-68 | 23% | 53% |
| M[19P]-63 | 16% | 53% |
| M[19P]-69 | 22% | 53% |
| M[19P]-1 | 26% | 54% |
| M[19P]-66 | 24% | 54% |
| M[19P]-12 | 26% | 54% |
| M[20P]-472 | 27% | 54% |
| M[19P]-20 | 31% | 54% |
| M[19P]-70 | 19% | 55% |
| M[19P]-62 | 17% | 56% |
| M[19P]-57 | 21% | 56% |
| M[19P]-65 | 27% | 57% |
| M[19P]-73 | 18% | 57% |
| M[20P]-514 | 30% | 58% |
| M[19P]-56 | 24% | 58% |
| M[19P]-64 | 27% | 59% |
| M[19P]-72 | 20% | 60% |
| M[19P]-71 | 19% | 61% |

51 processed samples obtained from herbal compositions containing 9, 16, 17, 18, 19 or 20 plants were found to have higher antibiofilm and antimicrobial activity than the reference mix extract Mix[3P]-1 (Table 5-4 A). 113 processed samples containing 9 to 20 plants were found to have higher antibiofilm activity and equivalent or lower antimicrobial activity (Table 5-4 B).

Comparative Example 3

As a comparative Example, we report several 20 plant mixes extracts containing only one plant among the 3 plants of Example 1 (PA13, PA21, PB12), which have been found to have none or poor antimicrobial and antibiofilm activities against *Staphylococcus aureus*.

Ten herbal compositions having the content reported in List 5-8 were prepared according to the previously described Method A.

List 5-8: Herbal Compositions of Processed Samples

M[20P]-39: PB00; PB01; PB02; PB03; PB04; PB05; PB06; PB07; PB08; PB09; PB10; PB11; PB12; PB13; PB14; PB15; PB16; PB17; PB18; PB19;

M[20P]-239: PA00; PA05; PA21; PA23; PA26; PA33; PA39; PA60; PA85; PB00; PB06; PB32; PB79; PC02; PC26; PC34; PC38; PC62; PC78; PC84;

M[20P]-337: PA00; PA10; PA11; PA15; PA18; PA21; PA22; PA24; PA26; PA28; PA52; PA94; PA98; PB10; PB20; PB26; PB29; PB82; PC67; PC97;

M[20P]-362: PA21; PA23; PA25; PA33; PA37; PA57; PA69; PA81; PA92; PB16; PB25; PB26; PB28; PB29; PB78; PC20; PC21; PC71; PC83; PD02;

M[20P]-364: PA15; PA21; PA25; PA28; PA39; PA75; PA80; PA85; PA89; PA98; PB01; PB06; PB24; PB28; PB35; PC24; PC25; PC57; PC75; PC82;

M[20P]-540: PA06; PA10; PA12; PA14; PA20; PA21; PA26; PA27; PA27; PA57; PA57; PA57; PA69; PB07; PB82; PC11; PC20; PC23; PC55; PC98;

M[20P]-647: PA10; PA11; PA24; PA26; PA28; PA33; PA35; PA40; PA57; PA69; PB00; PB07; PB12; PB28; PB33; PB38; PB60; PC55; PC67; PC97;

M[20P]-652: PA00; PA07; PA13; PA15; PA16; PA23; PA26; PA28; PA33; PA39; PA57; PA92; PB28; PB38; PC20; PC21; PC52; PC55; PC74; PC97;

M[20P]-862: PA11; PA15; PA18; PA21; PA25; PA27; PA28; PA29; PA35; PA38; PA52; PA86; PA89; PA92; PB07; PB28; PB88; PC11; PC55; PC98;

M[20P]-872: PA13; PA14; PA16; PA28; PA29; PA30; PA33; PA35; PA39; PA81; PA90; PA92; PB00; PB32; PC12; PC34; PC37; PC67; PC97; PD02.

Ten water extracts (or processed samples) were prepared from the corresponding herbal compositions according to the previously described Method B using 40 mL of water containing 100 g/l of sucrose for water extraction and including the decantation step before filtration.

For each processed sample the biological activity was determined according to the previously described Method C, with the following final dilutions of processed samples: 1:20, 1:63 and 1:200.

The bacteria planktonic growth inhibition percentage average and biofilm formation inhibition percentage average over all the tested strains of the processed samples at 1:20 dilution is given in Table 5-5.

TABLE 5-5 average of planktonic growth inhibition percentage and biofilm formation inhibition percentage efficacy on the 6 tested *Staphylococcus aureus* strains of the processed samples at 1:20 dilution.

| | Planktonic growth inhibition | Biofilm formation inhibition |
|---|---|---|
| Mix[2P]-1 | 22% | 36% |
| Mix[2P]-2 | 12% | −3% |
| Mix[2P]-3 | 12% | 28% |
| M[20P]-362 | −1% | −6% |
| M[20P]-364 | −5% | 6% |
| M[20P]-039 | 1% | 6% |
| M[20P]-862 | 5% | 2% |
| M[20P]-337 | 0% | 9% |
| M[20P]-872 | 2% | 11% |
| M[20P]-540 | 5% | 10% |
| M[20P]-652 | 9% | 7% |
| M[20P]-239 | 9% | 7% |
| M[20P]-647 | 9% | 9% |

All tested processed samples obtained from herbal compositions containing 20 plants including only one plant among the 3 plants of Example 1 (PA13, PA21, PB12) showed lower antimicrobial activity than the three 2 plant mixes extracts of reference Mix[2P]-1 (obtained from PA13 and PA21), Mix[2P]-2 (obtained from PA21 and PB12) and Mix[2P]-3 (obtained from PA13 and PB12) and lower antibiofilm activity than Mix[2P]-1 and Mix[2P]-3.

Example 6

In this Example, we report the simultaneous antimicrobial and antibiofilm activities against *Staphylococcus aureus, Staphylococcus epidermidis* and *Staphylococcus pseudintermedius* of 2 processed samples chosen among the best mixes described in Example 4 and 5.

The dried plants of pharmaceutical grade were obtained from “Pharmacie Fontgiève” (Clermont-Ferrand, France) and “Pharmacie St Herem” (Clermont-Ferrand, France).

Two herbal preparations containing the dried plant powders reported in the Table 6-1 below, were prepared according to the previously described Method A.

TABLE 6-1

| Herbal compositions | M[20P]-576 | M[10P]-154 |
|---|---|---|
| Plant 1 | 2 spoons of PA11 | 1 spoon of PA11 |
| Plant 2 | 1 spoon of PA12 | 1 spoon of PA12 |
| Plant 3 | 3 spoons of PA13 | 1 spoon of PA13 |
| Plant 4 | 2 spoons of PA14 | 1 spoon of PA21 |
| Plant 5 | 1 spoon of PA20 | 1 spoon of PA22 |
| Plant 6 | 1 spoon of PA21 | 1 spoon of PA79 |
| Plant 7 | 1 spoon of PA22 | 1 spoon of PB12 |
| Plant 8 | 1 spoon of PA29 | 1 spoon of PB49 |
| Plant 9 | 1 spoon of PA39 | 1 spoon of PC29 |
| Plant 10 | 1 spoon of PB12 | 1 spoon of PC63 |
| Plant 11 | 1 spoon of PB60 | |
| Plant 12 | 1 spoon of PC20 | |
| Plant 13 | 1 spoon of PC26 | |
| Plant 14 | 1 spoon of PC33 | |
| Plant 15 | 1 spoon of PC37 | |
| Plant 16 | 1 spoon of PC49 | |

Starting from such herbal compositions 2 corresponding water extracts (or processed samples) were prepared according to the previously described Method B using 40 mL for M[20P]-576 and 20 mL for M[10P]-154 of water containing 100 g/l of sucrose for water extraction and including the centrifugation step before filtration.

The biological activity of the processed samples was determined according to the previously described Method C by using the following strains:

*Staphylococcus aureus* strains: ATCC 25923, ATCC 49476, ATCC 6538, ATCC 51740, ATCC 29213, ATCC 14775, NCTC 12493, ATCC 33591, ATCC 33592, ATCC 43300, ATCC 700698, ATCC 700699, ATCC 9144 and ATCC BAA-44

*Staphylococcus epidermidis* strains: ATCC 14990, ATCC 12228, ATCC 700296, ATCC 49134 and ATCC 49461

*Staphylococcus pseudintermedius* strain: ATCC 49444

The minimum inhibitory concentration (MIC) observed with the 2 processed samples is given in Table 6-2 in the form of HID, as well as the average efficacy over all the strains of *Staphylococcus aureus* and *Staphylococcus epidermidis*.

TABLE 6-2

HID of the 2 processed samples on 14 strains of *Staphylococcus aureus*, 5 strains of *Staphylococcus epidermidis* and 1 strain of *Staphylococcus pseudintermedius*

| | | M[10P]-154 | M[20P]-576 |
|---|---|---|---|
| *S. aureus* | ATCC 25923 | 20 | 20 |
| | ATCC 49476 | 40 | 40 |
| | ATCC 6538 | 10 | 10 |
| | ATCC 51740 | 20 | 40 |
| | ATCC 29213 | 20 | 20 |

TABLE 6-2-continued

| HID of the 2 processed samples on 14 strains of *Staphylococcus aureus*, 5 strains of *Staphylococcus epidermidis* and 1 strain of *Staphylococcus pseudintermedius* | | | |
|---|---|---|---|
| | | M[10P]-154 | M[20P]-576 |
| | ATCC 14775 | 20 | 20 |
| | NCTC 12493 | 40 | 40 |
| | ATCC 33591 | 20 | 40 |
| | ATCC 33592 | 20 | 40 |
| | ATCC 43300 | 20 | 40 |
| | ATCC 700698 | 20 | 20 |
| | ATCC 700699 | 40 | 20 |
| | ATCC 9144 | 20 | 20 |
| | ATCC BAA-44 | 40 | 20 |
| | Average | 25 | 28 |
| *S. epidermidis* | ATCC 14990 | 40 | 20 |
| | ATCC 12228 | 40 | 20 |
| | ATCC 700296 | 40 | 20 |
| | ATCC 49461 | 40 | 20 |
| | ATCC 49134 | 80 | 80 |
| | Average | 48 | 32 |
| *S. pseudintermedius* | ATCC 49444 | 40 | 40 |
| | Total average | 32 | 30 |

M[10P]-154 and M[20P]-576 showed full antimicrobial activity on all tested *Staphylococcus aureus* and *Staphylococcus epidermidis*. M[10P]-154 showed full antimicrobial activity at 1:80 on 1 *Staphylococcus epidermidis* strain, at 1:40 on 4 *Staphylococcus aureus* strains, 4 *Staphylococcus epidermidis* and the tested strain of *Staphylococcus pseudintermedius*, at 1:20 on 9 *Staphylococcus aureus* strains, and at 1:10 on 1 *Staphylococcus aureus* strain.

M[20P]-576 showed full antimicrobial activity at 1:80 on 1 *Staphylococcus epidermidis* strain, at 1:40 on 6 *Staphylococcus aureus* strains and the tested strain of *Staphylococcus pseudintermedius*, at 1:20 on 7 *Staphylococcus aureus* strains and 4 *Staphylococcus epidermidis* and at 1:10 on 1 *Staphylococcus aureus* strain.

The bacteria planktonic growth inhibition percentage and the biofilm formation inhibition (IBF) percentage of the 2 processed samples at 1:20 dilution is given in Table 6-3, as well as the average efficacy over all the strains of *Staphylococcus aureus* and *Staphylococcus epidermidis*.

TABLE 6-3

| planktonic growth inhibition and biofilm formation inhibition (IBF) of the 2 processed samples on 14 strains of *Staphylococcus aureus*, 5 strains of *Staphylococcus epidermidis* and 1 strain of *Staphylococcus pseudintermedius* at 1:20 dilution | | | | | |
|---|---|---|---|---|---|
| | | planktonic growth inhibition | | biofilm formation inhibition (IBF) | |
| | | M[10P]-154 | M[20P]-576 | M[10P]-154 | M[20P]-576 |
| *S. aureus* | ATCC 25923 | 96% | 99% | 90% | 88% |
| | ATCC 49476 | 93% | 109% | 93% | 95% |
| | ATCC 6538 | 49% | 56% | 45% | 60% |
| | ATCC 51740 | 91% | 106% | 89% | 96% |
| | ATCC 29213 | 94% | 105% | 91% | 92% |
| | ATCC 14775 | 90% | 105% | 88% | 90% |
| | NCTC 12493 | 99% | 113% | 93% | 92% |
| | ATCC 33591 | 95% | 113% | 91% | 93% |
| | ATCC 33592 | 97% | 107% | 91% | 93% |
| | ATCC 43300 | 94% | 110% | 90% | 92% |
| | ATCC 700698 | 92% | 113% | 89% | 91% |
| | ATCC 700699 | 88% | 95% | 98% | 96% |
| | ATCC 9144 | 82% | 91% | 88% | 84% |
| | ATCC BAA-44 | 90% | 101% | 93% | 94% |
| | Average | 89% | 102% | 88% | 90% |
| *S. epidermidis* | ATCC 14990 | 90% | 101% | 91% | 90% |
| | ATCC 12228 | 90% | 101% | 93% | 91% |
| | ATCC 700296 | 86% | 90% | 81% | 82% |
| | ATCC 49461 | 90% | 99% | 93% | 85% |
| | ATCC 49134 | 89% | 96% | 96% | 90% |
| | Average | 89% | 98% | 91% | 88% |
| *S. pseud-intermedius* | ATCC 49444 | 92% | 103% | 95% | 93% |
| | Total average | 89% | 101% | 89% | 89% |

At 1:20 dilution, M[10P]-154 showed an average of 88% of biofilm formation inhibition on all tested *Staphylococcus aureus* strains whereas M[20P]-576 showed an average of 90%. The two mixes showed lower antimicrobial activity on one strain: ATCC 6538 (45% for M[10P]-154, 60% for M[20P]-576). M[10P]-154 showed an average of 91% of planktonic growth inhibition on all tested *Staphylococcus epidermidis* strains whereas M[20P]-576 showed an average of 88%. (cf Table 6-3). The two mixes showed more respectively 95% (M[10P]-154) and 93% (M[20P]-576) of inhibition percentage on the *Staphylococcus pseudintermedius* tested. Thus, M[10P]-154 and M[20P]-576 have demonstrated antibiofilm activity on *Staphylococcus aureus, Staphylococcus epidermidis* and *Staphylococcus* pseudin term edius at 1:20 dilution.

Example 7

Solution of Mix[20C]-576 (described in Example 6) used for the following formulations was prepared according to the previously described Method A and B with the exception of the filtering step, which is in this Example performed by suction filtration with a Büchner funnel filled with 5 cm thick hydrophilic cotton layer. For clarity, this cotton filtered solution will be referred as SK576 in the following Example.

An ointment and two creams to be used for topical applications were prepared with an emulsification method as follows:

Phase A and Phase B were prepared by mixing with orbital shaking in two separate beakers the following ingredients:

| | Phase A | Phase B |
|---|---|---|
| Ointment | - 73.8 g of organic almond oil (Hyteck, “Aroma Zone ™”, France)<br>- 18.5 g of organic beeswax (Hyteck, “Aroma Zone ™”, France)<br>- 9.7 g of organic shea butter (Hyteck, “Aroma Zone ™”, France)<br>-1.0 mL of natural tocopherol (Hyteck, “Aroma Zone ™”, France) | - 29.6 g of SK576, prepared as disclosed in Example 6<br>- 13.5 g of organic glycerin (The Naissance Trading & Innovation, “Naissance ™”, UK)<br>- 2.7 g of Ascorbic acid (Hyteck “Aroma Zone ™”, France) |
| Cream 1 | - 30.4 g of organic almond oil (Hyteck, “Aroma Zone”, France):<br>- 8.3 g of organic Olivem ® 1000 (Hyteck, “Aroma Zone ™”, France)<br>- 3.1 g of menthol (Hyteck “Aroma Zone ™”, France)<br>- 1.0 mL of natural tocopherol (Hyteck, “Aroma Zone ™”, France) | - 51.5 g of SK576, prepared as disclosed in Example 6<br>- 14.9 g of organic glycerin (The Naissance Trading & Innovation “Naissance ™”, UK) |
| Cream 2 | - 14.9 g of organic almond oil (Hyteck “Aroma Zone ™”, France):<br>- 11.8 g of organic Olivem ® 1000 (Hyteck “Aroma Zone ™”, France)<br>- 5.1 g of organic shea butter (Hyteck “Aroma Zone ™”, France)<br>- 1.0 mL of natural tocopherol (Hyteck “Aroma Zone ™”, France) | - 160.0 g of SK576, prepared as disclosed in Example 6<br>- 10 g of organic glycerin (The Naissance Trading & Innovation, “Naissance ™”, UK) |

The two beakers were heated to 70° C. using a warm water bath and maintained at 70° C. during 10 min to avoid the crystallization of beeswax.

Phase B was then slowly poured into Phase A, keeping the beaker in the warm water bath and with constant stirring by a mechanical immersion blender (Moulinex “Infinyforce_hand blender”, France).

The beaker containing the mix of phase A and B was then removed from the warm bath and the ointment was formed by using an immersion “mayonnaise blender” (Moulinex “Infinyforce_hand blender”, France).

A gel to be used for topical applications was prepared by

Filtrating 20.6 g of SK576, on an hydrophilic syringe filter (0.22 μm).

Adding 0.75 g of Xanthan powder (Hyteck “Aroma Zone™”, France) and 0.25 g of ascorbic acid (Hyteck “Aroma Zone™”, France) to the filtered solution and mix with a spatula for 5-10 min such as to form.

A spray solution to be used for topical applications was prepared by:

Mixing 5.5 g of SK576 with 11.9 g of absolute ethanol (Sigma-Aldrich, France) in a 20 mL beaker which were stored in a 5° C. refrigerator for 3H.

Placing the beaker with the cold mixture in an ice-water bath and gently adding 0.7 g of Kolliphor® P-407 (Sigma-Aldrich, France) under agitation with a magnetic bar and stirrer.

Following 30 min agitation under ice-water bathing, the solution was filled into a reagent sprayer (CAMAG, Switzerland) for administration.

The protocol of each of these five preparations can be easily scaled to different volumes of preparation by keeping the same relative amount of each ingredient.

Example 8

Biological Activity of a Water Extract of the Invention in a Mouse Model of Lethal *Staphylococcus aureus* Infection

INTRODUCTION

*S. aureus* strain Newman was isolated in 1952 from a human infection and has been used extensively in animal models of staphylococcal infections due to its robust virulence phenotype.

Female OF1 mice have been extensively used to study the pathogenesis induced by *Staphylococcus aureus*. Early work on the pathogenesis of *Staphylococcus aureus* infections used the intraperitoneal route of challenge to infect and treat mice because of its technical ease.

The aim of this Example was to evaluate the antimicrobial activity of a water extract of the invention in female OF1 mice infected with lethal dose of Newman *Staphylococcus aureus*. The treatment was administered by oral route according to the schedule Q1Dx10, 2 days before infection to 7 days after infection. Monitoring of mortality was performed from D0 to D15.

Vehicle was used as negative control.

Material and Methods

Test Substance and Controls

Test Substance: water extract M[20C] 576 (obtained starting from 120 g/l of herbal composition, prepared as described in Example 6). It was provided in 11 vials containing 1,200 μl each of water extracts. It was stored at −20° C.

Vehicle: sucrose 10% water solution. It will be stored at −20° C.

Bacterial strain: Newman *Staphylococcus* strain (provided by Dr T. Foster, Trinity College, Dublin, Ireland, Batch No. 14156, LST4).

Animal Purchasing and Caging

Twenty (20) Crl:OF1 (outbred) female mice, 6 weeks old were purchased from Charles River (L'Arbresle, France).

The animal care unit was authorized by the French Ministries of Agriculture and Research (Agreement Number B35-288-1). Animal experiments were performed according to ethical guidelines of animal experimentations (Principes d'éthique de l'expérimentation animale, Directive n° 86/609 CEE du 24 Nov. 1986, Décrêt n° 87/848 du 19 Oct. 1987, Arrêté d'Application du 19 Avril 1988).

The animals were maintained in "A2" rooms under controlled conditions of temperature (22±3° C.), humidity (50±20%), photoperiod (12 h light/12 h dark), air exchange and low pressure. The air handling system is programmed for 14 air changes an hour, with no recirculation.

Food and water were provided ad libitum, being placed in the metal lid on top of the cage.

Treatment and Experimental Design

Preparation of Bacteria—Amplification of Bacteria for Challenge

One vial of bacteria was defrosted and 100 μl of inoculum was cultured in 50 ml of Tryptic Soy Broth (TSB, Ref. 43592 or 22902, Sigma). Bacteria were incubated at 37° C. during 20 h under 110 rpm agitation on horizontal shaker. Bacterial suspension will be diluted at 1/20 (100 μl+1.9 ml of TSB) and optical density will be read at 680 nm (O.D.680 nm).

Then, 10 ml of bacteria was centrifuged at 5,200 rpm (3400 g) during 10 min at 4° C. Supernatant was discarded and bacteria was solubilized in 10 ml of DPBS (Ref. BE17-512F, Lonza, France). Bacterial suspension (CO) was diluted at 1/20 (100 μl+1.9 ml of DPBS) and O.D.680 nm will be measured.

The O.D.680 nm measured before and after centrifugation must be similar.

The concentration of CFU/ml of the bacteria solution was calculated as follow:

CFU/ml=(O.D.680 nm×20(dilution factor)×6.5·108 (CFU/U.D.O)

Mucin Preparation

Mucin (Sigma, France) was prepared at 20% 14-16 days before treatment as described below:

DPBS (Dulbecco's Phosphate-Buffered Saline) was prewarmed at 56° C. and ¾ of the final volume was transferred in a mixer, then hog mucin will be added and mixed. The mixer was washed with the remaining volume of DPBS. Then, the 20% mucin solution was transferred in an Erlenmeyer Flask and was incubated at 37° C. under agitation during 1 hour and 30 minutes. The ¾ of 20% mucin solution was transferred in a sterile bottle. The remainder ¼ of solution was stocked separately. Then the ¾ and the ¼ solutions was sterilized by autoclaving. Sterile 20% hog mucin solution was stored at +4° C.

The day before the infection, the pH of ¾ of 20% mucin solution was adjusted at 7.4 by adding filtered NaOH 30%. If necessary, a part of the ¼ remaining solution was used to adjust pH.

Bacteria Preparation

According to O.D.680 nm results, bacteria (CO) were diluted in DPBS to reach the concentration of $6.8\times10^7$ CFU/ml. These suspensions were then diluted at % in 20% hog mucin to get the LD80 concentration of $3.4\times10^7$ CFU/ml in PBS-10% hog mucin. The suspension used for treatment was put in tube containing sterile glass beads (4 mm, Ref. 068502, Dutscher, France). Suspension were not vortexed, but mixed by inverting the tubes. Bacteria were placed on ice before treatments and kept on ice during treatment.

CFU Determination

To determine the exact concentration of the bacterial suspension before and after inoculated into the animals, the bacterial suspension was diluted in 10-fold serial dilutions in DPBS-0.5% Tween 20 (Sigma, France) as described in Table 8-1 in deep wells (50 μl of bacteria+450 μl of DPBS-0.5% Tween 20). Then, 6×50 μl of bacterial dilutions 3, 4, 5 and 6 were seeded on Tryptic Soy Agar plate (Tryptic Soy Agar, Sigma) and placed at 37° C. overnight. Colonies were counted to determine the real CFU (Colony-Forming Units) of inoculums.

The numeration was realized on the drop (50 μl) that contain between 20 and 100 colonies. The shaded boxes correspond to the dilutions seeded on plates.

TABLE 8-1

Dilutions of the bacterial suspension in order to determine the real CFU (viability) of inoculums. The shaded boxes correspond to the dilutions seeded on plates.

| Bacterial overnight | Dilutions | | | | | |
|---|---|---|---|---|---|---|
| suspension in PBS | 1<br>1/10 | 2<br>1/100 | 3<br>$1/10^3$ | 4<br>$1/10^4$ | 5<br>$1/10^5$ | 6<br>$1/10^6$ |
| For example, initial concentration: $3.4\times10^7$ CFU/ml | $3.4\times10^6$ | $3.4\times10^5$ | 34000 | 3400 | 340 | 34 |
| Number of colonies/50 μl (1 drop) | $1.7\times10^5$ | $1.7\times10^4$ | $1.7\times10^3$ | 170 | 17 | 1.7 |

Randomization

Before experiment (D-2), 20 healthy OFI female mice were randomized in 2 groups of 10 mice/group according to body weight criteria, so that the mean body weights of groups was not statistically different.

Treatments

Treatments were performed from D-2 to D7 (D0: day of bacteria inoculation) by oral (PO) administration. Bacterial inoculations were done by intraperitoneal injection (IP).

Inoculation

A D0, mice were inoculated with bacterial suspension. Each inoculation consisted in an intraperitoneal injection of 500 μl of the suspension at $3.4\times10^7$ CFU/ml ($1.7\times10^7$ CFU/mouse).

Experimental Design

Animals were treated with an oral administration of the Test Substance from D-2 to D7. At D0, treatments were performed 1 h after bacteria inoculation.

The experimental groups will be defined as described below and summarized in Table 8-2.

The 10 mice of the group 1 will be treated from D-2 to D7 with the Vehicle by oral administration according to the treatment schedule Q1DX10.

The 10 mice of the group 2 will be treated from D-2 to D7 with the Test Substance by oral administration according to the treatment schedule Q1DX10.

TABLE 8-2

| Experimental design | | | | | | |
|---|---|---|---|---|---|---|
| Groups | Number of mice | Test substance | Administration route | Administration volume | Treatment schedule | Bacterial model |
| 1<br>2 | 10 | Vehicule<br>Test Substance | PO | 10 mL/kg | Q1D × 10 (from D-2 to D7) | IP lethal Newman *Staphylococcus aureus* ($3.4 \times 10^7$ CFU/ml) 500 μl |

Monitoring of Animals

From D0 to D1, mice were observed twice a day for mortality.

From D2 to D15, mice were observed once a day for mortality.

The body weight of mice was recorded twice a week until the end of the experiment.

Detailed clinical observations (changes in skin, fur, eyes, mucous membranes, occurrence of secretions and excretions, respiratory function, changes in gait, posture) was monitored twice a week as described in Table 8-3 below for example. Description of this list is not exhaustive and was complemented by other observations, if necessary.

TABLE 8-3

| Clinical observations/parameters | | | | | |
|---|---|---|---|---|---|
| Para-meters | De-scription | Para-meters | De-scription | Para-meters | De-scription |
| Mobility/Gait | Stationary<br>Reduced<br>Normal<br>Excessive | Behavior | Fearful<br>Normal<br>Aggressive | Fur | Normal<br>Spiked<br>Loss<br>Colored<br>Not applicable |
| | | Breathing | Slow<br>Normal<br>Speed<br>Irregular | | |
| Carriage | Normal<br>Prostrate | | | | |
| Paralysis | No<br>Front right<br>Front left<br>Hind right<br>Hind left<br>Right<br>Left<br>Front<br>Hind | Eyes | Normal<br>Tearful<br>Closed | Mucous membranes | Normal<br>Abnormal (nose)<br>Abnormal (mouth)<br>Abnormal (nose/mouth) |
| | | Skin | Normal<br>Redness<br>Patch<br>Wound<br>Hematoma | Excretions | Few<br>Normal<br>Abundant<br>Dry |

Sacrifice of Mice

At D15, survived mice were sacrificed by exsanguinations, followed by cervical dislocation, if needed. No autopsy was performed.

Results

The analysis of mice survival showed the results reported in the following Tables 8-4 and 8-5.

TABLE 8-4

| Number of mice survived per day<br>Number of survived mice per day | | | | | | | | | |
|---|---|---|---|---|---|---|---|---|---|
| Groups | N D0 | N D1 | N D2 | N D3 | N D4 | N D5 | N D6 | N D7 | N D8 |
| Group 1 (Vehicle, PO, Q1D × 10, 10 ml/kg) | 10 | 6 | 6 | 5 | 5 | 3 | 2 | NA | 0 |

TABLE 8-4-continued

| Number of mice survived per day<br>Number of survived mice per day | | | | | | | | | |
|---|---|---|---|---|---|---|---|---|---|
| Groups | N D0 | N D1 | N D2 | N D3 | N D4 | N D5 | N D6 | N D7 | N D8 |
| Group 2 (TS pure, PO, Q1D × 10, 10 ml/kg) | 10 | 6 | 6 | 6 | 6 | 6 | 4 | NA | 3 |

TABLE 8-5

| Percentage of survived mice per day<br>Percentage of survival | | | | | | | | | |
|---|---|---|---|---|---|---|---|---|---|
| Groups | N D0 | N D1 | N D2 | N D3 | N D4 | N D5 | N D6 | N D7 | N D8 |
| Group 1 (Vehicle, PO, Q1D × 10, 10 ml/kg) | 100% | 60% | 60% | 50% | 50% | 30% | 20% | NA | 0% |
| Group 2 (TS pure, PO, Q1D × 10, 10 ml/kg) | 100% | 60% | 60% | 60% | 60% | 60% | 40% | NA | 30% |

NA = Not Available

The treatment allowed to reduce the mortality of mice from 100% to 70%. This animal study thus showed that the claimed antimicrobial and anti-biofilm activities observed in-vitro is translated into a therapeutic effect, when the water extract of the invention is administered via oral route to animals.

Example 9

In this Example we illustrate simultaneous antimicrobial and antibiofilm activities against *Staphylococcus aureus* of the disclosed composition of 2 plants among 3*: Filipendula ulmaria* PA13, *Camellia sinensis* PA21*, Arctostaphylos uva-ursi* PB12 and at least 1 plant among 3*: Eugenia caryophyllus* PC20, *Vitis vinifera* var. tinctorial PA22, *Desmodium adscendens* PB07. The dried plants of pharmaceutical grade were obtained from "Herboristerie Cailleau" (Chemillé, France).

Starting from such three different plant powders six herbal compositions were prepared according to the Method A reported before.

List 9-1: Herbal Compositions of Processed Samples

M[02P]-064: PA13; PA21;

M[03P]-050: PA13; PA21; PC20;

M[03P]-053: PA13; PA21; PB07;
M[03P]-056: PA13; PA21; PA22;
M[02P]-065: PA13; PB12;
M[03P]-051: PA13; PB12; PC20;
M[03P]-054: PA13; PB12; PB07;
M[03P]-057: PA13; PB12; PA22;
M[02P]-066: PA21; PB12;
M[03P]-052: PA21; PB12; PC20;
M[03P]-055: PA21; PB12; PB07;
M[03P]-058: PA21; PB12; PA22;
M[03P]-059: PA13; PB12; PA21;
M[04P]-025: PA13; PB12; PA21; PC20;
M[04P]-026: PA13; PB12; PA21; PB07;
M[04P]-027: PA13; PB12; PA21; PA22.

Starting from the herbal compositions listed in List 6-3 corresponding water extracts (or processed samples) were prepared according to the previously described Method B using 40 mL of water containing 100 g/l of sucrose for water extraction and including the decantation step before filtration.

The biological activity of each processed sample was determined according to the previously described Method C by using the following *Staphylococcus aureus* strains: ATCC 6538, with the following final dilutions of processed samples: 1:5 for the biofilm formation inhibition and 1:10 for the growth inhibition. Note that growth inhibition is close to 100% for each mix at 1:5 dilution, and biofilm formation inhibition is close to 0% for all mixes at 1:10 dilution.

The bacteria planktonic growth inhibition percentage and biofilm formation inhibition percentage over all the tested strain of the processed samples obtained from the different herbal compositions are reported in the following Table 9-1.

TABLE 9-1 average of planktonic growth inhibition percentage and biofilm formation inhibition percentage efficacy on the *Staphylococcus aureus* strain ATCC ® 6538 ™ of the processed sample based on the compositions given in List 9-1. The processed samples were used at a 1:10 dilution for the planktonic growth inhibition tests and at a dilution of 1:5 for the biofilm formation inhibition.

| (A) | Planktonic growth inhibition | Biofilm formation inhibition | (B) | Planktonic growth inhibition | Biofilm formation inhibition |
|---|---|---|---|---|---|
| M[02P]-064 | 47% | 34% | M[02P]-065 | 42% | 15% |
| M[03P]-050 | 70% | 56% | M[03P]-051 | 59% | 36% |
| M[03P]-053 | 55% | 35% | M[03P]-054 | 54% | 22% |
| M[03P]-056 | 56% | 38% | M[03P]-057 | 54% | 34% |
| (C) | Planktonic growth inhibition | Biofilm formation inhibition | (D) | Planktonic growth inhibition | Biofilm formation inhibition |
| M[02P]-066 | 40% | 23% | M[03P]-059 | 59% | 87% |
| M[03P]-052 | 53% | 28% | M[04P]-025 | 69% | 90% |
| M[03P]-055 | 59% | 27% | M[04P]-026 | 64% | 90% |
| M[03P]-058 | 60% | 33% | M[04P]-027 | 64% | 89% |

(A) lists extracts obtained from herbal compositions containing PA13 and PA21, in which the addition of one among PC20, PB07 and PA22 improves the activity; (B) lists extracts obtained from herbal compositions containing PA13 and PB12, in which the addition of one among PC20, PB07 and PA22 improves the activity; (C) lists extracts obtained from herbal compositions containing PA13, PA21 and PB12, in which the addition of one among PC20, PB07 and PA22 improves the activity; (D) lists extracts obtained from herbal compositions containing PA13 and PA21, in which the addition of one among PC20, PB07 and PA22 improves the activity.

Example 10

In this Example, we illustrate simultaneous antimicrobial and antibiofilm activities against *Staphylococcus aureus* of 324 mixtures extracts obtained from the disclosed herbal compositions comprising 2 plants among 3: *Filipendula ulmaria* (PA13), *Camellia sinensis* (PA21), *Arctostaphylos uva-ursi* (PB12) and at least 1 plant among 3: *Eugenia caryophyllus* (PC20), *Vitis vinifera* var. tinctorial (PA22), *Desmodium adscendens* (PB07).

For the mixes from M[20C]-2083 to M[20C]-20798, the dried plants of pharmaceutical grade were obtained from "Herboristerie Cailleau" (Chemillé, France). For the mixes from M[20C]-2805 to M[20C]-2957, the dried plants of pharmaceutical grade were obtained from "Pharmacie Fontgiève" (Clermont-Ferrand, France, plants PA00 to PB12) and "Pharmacie St Herem" (Clermont-Ferrand, France, plants PB13 to PD02).

Herbal compositions containing from 3 to 20 plant powders were prepared according to the previously described Method A.

Starting from the herbal compositions, corresponding water extracts (or processed samples) were prepared according to the previously described Method B using 40 mL of water containing 100 g/l of sucrose for water extraction and including the decantation step before filtration.

The biological activity of each processed sample was determined according to the previously described Method C by using the following *Staphylococcus aureus* strains: ATCC 25923, ATCC 49476, ATCC 6538, ATCC 51740, ATCC 29213 and ATCC 14775, with the 1:20 final dilutions of processed samples.

The bacteria planktonic growth inhibition percentage average and biofilm formation inhibition percentage average over all the tested strains of the processed samples obtained from the following herbal compositions of, respectively, List 10-1, List 10-2, List 10-3 and List 10-4 is given in, respectively, Table 10-1, Table 10-2, Table 10-3 and Table 10-4. In each set, the extracts obtained from herbal compositions containing more than 3 or 4 plants were found to exhibit planktonic growth inhibition or biofilm formation inhibition (or both inhibitions) greater than any of the mixes containing only 3 or 4 plants List 10-1: Extracts from herbal compositions containing 2 plants among 3: *Filipendula ulmaria* (PA13), *Camellia sinensis* (PA21) and at least one among 3: *Eugenia caryophyllus* (PC20), *Vitis vinifera* var. tinctorial (PA22), *Desmodium adscendens* (PB07):

M[03P]-050: PA13; PA21; PC20;
M[03P]-053: PA13; PA21; PB07;
M[03P]-056: PA13; PA21; PA22;
M[20C]-2808: PA11; PA12; PA13; PA13; PA18; PA21; PA23; PA24; PA28; PA69; PB07; PB88; PC23; PC24; PC49; PC52; PC55 (2 spoons); PC60; PC97;
M[20C]-2820: PA10; PA11 (2 spoons); PA12; PA13; PA14; PA18; PA20; PA21; PA25; PA29; PA33; PA35; PA67; PA75; PB07; PB60; PC33; PC35; PC55;
M[20C]-2821: PA11; PA13 (2 spoons); PA19; PA20; PA21; PA22; PA25; PA29; PA33; PA35; PA75; PB07; PB36; PC20; PC33 (2 spoons); PC49; PC55; PC97;
M[20C]-2826: PA11; PA13 (2 spoons); PA20; PA21; PA24; PA25; PA29; PA33; PA34; PA35; PA52; PA70; PA75; PB07; PC11; PC21; PC33; PC37; PC74;
M[20C]-2827: PA10; PA11; PA13 (2 spoons); PA20; PA21; PA25; PA26; PA29; PA33; PA35; PA57; PA75; PB02; PB07; PB28; PC11; PC23; PC33; PC49;
M[20C]-2830: PA10; PA11; PA12; PA13; PA14; PA18; PA21; PA22; PA25; PA29; PA32; PA34; PA67; PB07; PB60; PB88; PC33; PC35; PC55; PC98;
M[20C]-2831: PA13; PA13; PA19; PA21; PA22; PA22; PA25; PA29; PA32; PA34; PB07; PB36; PB88; PC20; PC33; PC33; PC49; PC55; PC97; PC98;
M[20C]-2833: PA10; PA11; PA13; PA14; PA21; PA22; PA24; PA25; PA26; PA29; PA32; PA34; PB33; PB88; PB88; PC12; PC23; PC27; PC33; PC98;
M[20C]-2836: PA13; PA13; PA21; PA22; PA24; PA25; PA29; PA32; PA34; PA34; PA52; PA70; PB07; PB88; PC11; PC21; PC33; PC37; PC74; PC98;
M[20C]-2837: PA10; PA13 (2 spoons); PA21; PA22; PA25; PA26; PA29; PA32; PA34; PA57; PB02; PB07; PB28; PB88; PC11; PC23; PC33; PC49; PC98;
M[20C]-2838: PA12; PA13 (2 spoons); PA18; PA21; PA21; PA22; PA24; PA25; PA29; PA32; PA34; PB88; PC23; PC33; PC49; PC52; PC55; PC97; PC98;
M[20C]-2839: PA13 (2 spoons); PA14; PA21; PA22; PA25; PA25; PA26; PA29; PA32; PA34; PA39; PA52; PA57; PB33; PB88; PC33; PC71; PC97; PC98;
M[20C]-2858: PA12; PA13; PA18; PA20; PA21; PA23; PA24; PA24; PA67; PB07; PB28; PB33; PC12; PC20; PC21; PC23; PC49; PC52; PC55; PC97;
M[20C]-2861: PA13; PA19; PA21; PA22 (2 spoons); PB07; PB28; PB36; PB60; PC11; PC20; PC20; PC23; PC33; PC49; PC55 (2 spoons); PC60; PC74; PC97;
M[20C]-2866: PA13; PA21; PA22; PA24; PA34; PA52; PA70; PB07; PB28; PB60; PC11 (2 spoons); PC20; PC21; PC23; PC37; PC55; PC60; PC74 (2 spoons);
M[20C]-2867: PA10; PA13; PA21; PA22; PA26; PA57; PB02; PB07; PB28; PB28; PB60; PC11 (2 spoons); PC20; PC23; PC23; PC49; PC55; PC60; PC74;
M[20C]-2868: PA12; PA13; PA18; PA21; PA21; PA22; PA24; PB28; PB60; PC11; PC20; PC23 (2 spoons); PC49; PC52; PC55 (2 spoons); PC60; PC74; PC97;
M[20C]-2869: PA13; PA14; PA21; PA22; PA25; PA26; PA39; PA52; PA57; PB28; PB33; PB60; PC11; PC20; PC23; PC55; PC60; PC71; PC74; PC97;
M[20C]-2871: PA10; PA11; PA13; PA19; PA21; PA22; PA35; PA57; PB07; PB07; PB36; PB77; PC20 (2 spoons); PC23; PC33; PC49; PC55; PC71; PC97;
M[20C]-2876: PA10; PA11; PA13; PA21; PA24; PA34; PA35; PA52; PA57; PA70; PB07 (2 spoons); PB77; PC11; PC20; PC21; PC23; PC37; PC71; PC74;
M[20C]-2877: PA10; PA10; PA11; PA13; PA21; PA26; PA35; PA57; PA57; PB02; PB07; PB28; PB77; PC11; PC20; PC23 (2 spoons); PC49; PC71;
M[20C]-2878: PA10; PA11; PA12; PA13; PA18; PA21; PA21; PA24; PA35; PA57; PB07; PB77; PC20; PC23; PC23; PC49; PC52; PC55; PC71; PC97;
M[20C]-2879: PA10; PA11; PA13; PA14; PA21; PA25; PA26; PA35; PA39; PA52; PA57 (2 spoons); PB07; PB33; PB77; PC20; PC23; PC71 (2 spoons); PC97;
M[20C]-2889: PA10; PA12; PA13; PA14; PA18; PA21; PA26; PA26; PA28; PA29; PA33; PA39; PA75; PB36; PC20; PC52; PC55 (2 spoons); PC60;
M[20C]-2894: PA11 (2 spoons); PA13; PA21; PA28; PA39; PA39; PA70; PB02; PB02; PB07; PB99 (2 spoons); PC14; PC20; PC49; PC71; PC97; PC98;
M[20C]-2944: PA10; PA11 (2 spoons); PA13; PA14; PA21; PA28; PA39; PA70; PB02; PB07; PB27; PB99; PC11; PC20; PC23; PC67; PC71; PC97; PC98;
M[20C]-2954: PA11; PA12; PA13; PA14; PA21; PA23; PA28; PA33; PA39; PA70; PB01; PB02; PB07; PB99; PC20; PC27; PC52; PC71; PC97; PC98.

TABLE 10-1 average of planktonic growth inhibition percentage and biofilm formation inhibition percentage efficacy on the 6 tested *Staphylococcus aureus* strains of the processed sample based on the extracts of List 10-1 at 1:20 dilution

| | Planktonic growth inhibition | Biofilm formation inhibition | | Planktonic growth inhibition | Biofilm formation inhibition |
|---|---|---|---|---|---|
| M[03C]-050 | 41% | 31% | M[20C]-2858 | 58% | 32% |
| M[03C]-053 | 37% | 23% | M[20C]-2861 | 58% | 31% |
| M[03C]-056 | 34% | 21% | M[20C]-2866 | 57% | 43% |
| M[20C]-2808 | 66% | 30% | M[20C]-2867 | 62% | 32% |
| M[20C]-2820 | 54% | 27% | M[20C]-2868 | 74% | 36% |
| M[20C]-2821 | 53% | 24% | M[20C]-2869 | 85% | 45% |
| M[20C]-2826 | 56% | 25% | M[20C]-2871 | 63% | 26% |
| M[20C]-2827 | 51% | 26% | M[20C]-2876 | 66% | 28% |
| M[20C]-2830 | 56% | 37% | M[20C]-2877 | 81% | 43% |

TABLE 10-1-continued average of planktonic growth inhibition percentage and biofilm formation inhibition percentage efficacy on the 6 tested *Staphylococcus aureus* strains of the processed sample based on the extracts of List 10-1 at 1:20 dilution

| | Planktonic growth inhibition | Biofilm formation inhibition | | Planktonic growth inhibition | Biofilm formation inhibition |
|---|---|---|---|---|---|
| M[20C]-2831 | 64% | 31% | M[20C]-2878 | 65% | 28% |
| M[20C]-2833 | 80% | 39% | M[20C]-2879 | 58% | 28% |
| M[20C]-2836 | 59% | 25% | M[20C]-2889 | 62% | 41% |
| M[20C]-2837 | 58% | 25% | M[20C]-2894 | 55% | 29% |
| M[20C]-2838 | 70% | 30% | M[20C]-2944 | 68% | 16% |
| M[20C]-2839 | 56% | 30% | M[20C]-2954 | 75% | 27% |

List 10-2: extracts from herbal compositions containing *Filipendula ulmaria* (PA13), *Arctostaphylos uva-ursi* (PB12) and at least one among 3*: Eugenia caryophyllus* (PC20), *Vitis vinifera* var. *tinctoria* (PA22), *Desmodium adscendens* (PB07):

M[03C]-051: PA13; PB12; PC20;
M[03C]-054: PA13; PB12; PB07;
M[03C]-057: PA13; PB12; PA22;
M[20C]-2083: PA02; PA13; PA28 (2 spoons); PA31; PA36; PA40; PA79; PA93; PB01; PB12; PB17; PB18; PB31; PB51; PB77; PC20; PC58; PC64; PC66;
M[20C]-2084: PA13; PA28; PA31; PA36; PA61; PA76; PA76; PA79; PA82; PB01; PB10; PB12; PB17; PB31; PB57; PC20; PC36; PC41; PC64; PC66;
M[20C]-2085: PA12; PA13; PA14; PA28; PA30; PA31; PA36; PA79; PA94; PB00; PB01; PB08; PB12; PB17; PB31; PCO2; PC14; PC20; PC64; PC66;
M[20C]-2090: PA08; PA13; PA20; PA23; PA26; PA32; PA46; PA52; PA57; PA79; PA95; PB10; PB12; PB33; PB76; PB82; PC08; PC20; PC21; PD00;
M[20C]-2091: PA08; PA13; PA26; PA52; PA57; PA72; PA79; PA88; PA92; PA95; PB12; PB60; PB76; PB83; PC08; PC11; PC20; PC26; PC68; PD00;
M[20C]-2092: PA08; PA13; PA17; PA26; PA52; PA53; PA57; PA79; PA95; PB06; PB12; PB50; PB76; PC08; PC20; PC20; PC27; PC97; PD00; PD02;
M[20C]-2100: PA13; PA20; PA23; PA32; PA41; PA46; PA53; PA79; PA80; PA90; PB08; PB10; PB12; PB33; PB82; PB85; PC20; PC21; PC28; PC75;
M[20C]-2102: PA13; PA17; PA41; PA53; PA53; PA79; PA80; PA90; PB06; PB08; PB12; PB50; PB85; PC20; PC20; PC27; PC28; PC75; PC97; PD02;
M[20C]-2104: PA13; PA41; PA53; PA61; PA76; PA76; PA79; PA80; PA82; PA90; PB08; PB10; PB12; PB57; PB85; PC20; PC28; PC36; PC41; PC75;
M[20C]-2105: PA12; PA13; PA14; PA30; PA41; PA53; PA79; PA80; PA90; PA94; PB00; PB08; PB08; PB12; PB85; PCO2; PC14; PC20; PC28; PC75;
M[20C]-2110: PA00; PA10; PA13; PA20; PA23; PA25; PA30; PA32; PA46; PA52; PA79; PB05; PB10; PB12; PB33; PB82; PC01; PC20; PC21; PD07;
M[20C]-2111: PA00; PA10; PA13; PA25; PA30; PA52; PA72; PA79; PA88; PA92; PB05; PB12; PB60; PB83; PC01; PC11; PC20; PC26; PC68; PD07;
M[20C]-2120: PA11; PA13; PA16; PA20; PA23; PA32; PA44; PA46; PA60; PA67; PA73; PA79; PB10; PB12; PB33; PB48; PB82; PC17; PC20; PC21;
M[20C]-2122: PA11; PA13; PA16; PA17; PA44; PA53; PA60; PA67; PA73; PA79; PB06; PB12; PB48; PB50; PC17; PC20; PC20; PC27; PC97; PD02;
M[20C]-2131: PA05; PA13; PA18; PA37; PA55; PA72; PA72; PA79; PA88; PA92; PA97; PB04; PB12; PB60; PB83; PC11; PC20; PC26; PC35; PC68;
M[20C]-2135: PA05; PA12; PA13; PA14; PA18; PA30; PA37; PA55; PA72; PA79; PA94; PA97; PB00; PB04; PB08; PB12; PCO2; PC14; PC20; PC35;
M[20C]-2137: PA05; PA13; PA18; PA27; PA37; PA46; PA55; PA72; PA79; PA82; PA97; PB00; PB04; PB11; PB12; PC20; PC35; PC45; PC52; PC67;
M[20C]-2140: PA13; PA14; PA20; PA23; PA32; PA37; PA46; PA79; PA85; PB10; PB12; PB33; PB49; PB82; PB98; PC20; PC21; PC55; PC62; PC98;
M[20C]-2141: PA13; PA14; PA37; PA72; PA79; PA85; PA88; PA92; PB12; PB49; PB60; PB83; PB98; PC11; PC20; PC26; PC55; PC62; PC68; PC98;
M[20C]-2142: PA13; PA14; PA17; PA37; PA53; PA79; PA85; PB06; PB12; PB49; PB50; PB98; PC20; PC20; PC27; PC55; PC62; PC97; PC98; PD02;
M[20C]-2143: PA02; PA13; PA14; PA28; PA37; PA40; PA79; PA85; PA93; PB12; PB18; PB49; PB51; PB77; PB98; PC20; PC55; PC58; PC62; PC98;
M[20C]-2144: PA13; PA14; PA37; PA61; PA76; PA76; PA79; PA82; PA85; PB10; PB12; PB49; PB57; PB98; PC20; PC36; PC41; PC55; PC62; PC98;
M[20C]-2150: PA13; PA20; PA23; PA31; PA32; PA46; PA60; PA74; PA79; PB03; PB10; PB12; PB33; PB82; PC20; PC21; PC29; PC37; PC60; PC86;
M[20C]-2151: PA13; PA31; PA60; PA72; PA74; PA79; PA88; PA92; PB03; PB12; PB60; PB83; PC11; PC20; PC26; PC29; PC37; PC60; PC68; PC86;
M[20C]-2152: PA13; PA17; PA31; PA53; PA60; PA74; PA79; PB03; PB06; PB12; PB50; PC20; PC20; PC27; PC29; PC37; PC60; PC86; PC97; PD02;
M[20C]-2153: PA02; PA13; PA28; PA31; PA40; PA60; PA74; PA79; PA93; PB03; PB12; PB18; PB51; PB77; PC20; PC29; PC37; PC58; PC60; PC86;
M[20C]-2154: PA13; PA31; PA60; PA61; PA74; PA76; PA76; PA79; PA82; PB03; PB10; PB12; PB57; PC20; PC29; PC36; PC37; PC41; PC60; PC86;
M[20C]-2155: PA12; PA13; PA14; PA30; PA31; PA60; PA74; PA79; PA94; PB00; PB03; PB08; PB12; PCO2; PC14; PC20; PC29; PC37; PC60; PC86;
M[20C]-2163: PA06; PA13; PA17; PA20; PA23; PA72; PA79; PA80; PA92; PB01; PB03; PB10; PB12; PB33; PB57; PB82; PC20; PC62; PC86; PC97;
M[20C]-2164: PA13; PA17; PA20; PA41; PA79; PA80; PA86; PA92; PB03; PB10; PB12; PC20; PC26; PC27; PC29; PC55; PC60; PC62; PC86; PC97;

M[20C]-2214: PA13; PA37; PA41; PA79; PA86; PB00; PB10; PB12; PB49; PB82; PC20; PC26; PC27; PC29; PC55; PC60; PC62; PC66; PC86;

M[20C]-2234: PA13; PA41; PA79; PA85; PA86; PB12; PB31; PB50; PB77; PC14; PC20; PC26; PC27; PC29; PC55; PC55; PC60; PC62; PC98;

M[20C]-2241: PA10; PA13; PA14; PA23; PA36; PA37; PA46; PA79; PB00; PB10; PB11; PB12; PB17; PB57; PC20; PC27; PC29; PC37; PC64; PC68;

M[20C]-2242: PA13; PA14; PA17; PA23; PA36; PA37; PA60; PA61; PA76; PA79; PA82; PB00; PB06; PB12; PB49; PC20; PC27; PC29; PC68; PC98;

M[20C]-2243: PA13; PA14; PA23; PA36; PA37; PA52; PA53; PA73; PA79; PA92; PB00; PB01; PB12; PB18; PB60; PC20; PC20; PC27; PC29; PC68;

M[20C]-2248: PA13; PA14 (2 spoons); PA23; PA25; PA36; PA36; PA37; PA46; PA79; PA85; PB00; PB12; PCO2; PC20; PC27; PC29; PC29; PC55; PC68;

M[20C]-2249: PA10; PA13; PA14; PA23; PA36; PA37; PA53; PA74; PA79; PA92; PB00; PB12; PC20; PC27; PC29; PC62; PC67; PC68; PC86; PC97;

M[20C]-2250: PA13; PA23; PA37; PA76; PA79; PB10; PB12; PB33; PB50; PB82; PB82; PB85; PB98; PC01; PC11; PC20; PC45; PC55; PC60; PD02;

M[20C]-2253: PA13; PA37; PA52; PA53; PA73; PA79; PA92; PB01; PB10; PB12; PB18; PB33; PB50; PB60; PB82; PB85; PC01; PC20; PC20; PC45;

M[20C]-2254: PA11; PA13; PA17; PA27; PA37; PA79; PB00; PB10; PB12; PB33; PB50; PB82; PB83; PB85; PB92; PB98; PC01; PC20; PC27; PC45;

M[20C]-2255: PA13; PA36; PA37; PA53; PA72; PA79; PA80; PB03; PB10; PB12; PB33; PB49; PB50; PB82; PB82; PB85; PC01; PC20; PC45; PC68;

M[20C]-2256: PA13; PA23; PA37; PA53; PA61; PA79; PA85; PB10; PB12; PB33; PB50; PB60; PB82; PB85; PC01; PC11; PC20; PC29; PC45; PD02;

M[20C]-2257: PA13; PA37; PA37; PA60; PA72; PA79; PB10; PB12; PB33; PB49; PB50; PB82; PB85; PC01; PC08; PC20; PC45; PC68; PC98; PD02;

M[20C]-2258: PA13; PA14; PA25; PA36; PA37; PA46; PA79; PA85; PB10; PB12; PB33; PB50; PB82; PB85; PC01; PCO2; PC20; PC29; PC45; PC55;

M[20C]-2259: PA10; PA13; PA37; PA53; PA74; PA79; PA92; PB10; PB12; PB33; PB50; PB82; PB85; PC01; PC20; PC45; PC62; PC67; PC86; PC97;

M[20C]-2261: PA10; PA13; PA23; PA36; PA37; PA46; PA53; PA73; PA79; PA97; PB10; PB11; PB12; PB17; PB57; PC20; PC26; PC29; PC37; PC64;

M[20C]-2278: PA10; PA13; PA14; PA25; PA28; PA30; PA36; PA37; PA41; PA46; PA79; PA85; PB12; PB50; PB60; PCO2; PC20; PC29; PC55; PC66;

M[20C]-2281: PA10; PA13; PA17; PA46; PA52; PA79; PA82; PA92; PA96; PB10; PB11; PB12; PB17; PB57; PB98; PC20; PC36; PC37; PC64; PC86;

M[20C]-2321: PA13; PA46; PA53; PA79; PA82; PA92; PB03; PB10; PB11; PB12; PB83; PB85; PC20; PC20; PC21; PC55; PC60; PC86; PC97; PD02;

M[20C]-2406: PA13; PA37; PA46; PA53; PA79; PA85; PB01; PB05; PB10; PB11; PB12; PB17; PB49; PB98; PC20; PC36; PC37; PC45; PC58; PC67;

M[20C]-2420: PA10; PA13; PA14; PA36; PA46; PA79; PB10; PB10; PB11; PB11; PB12; PB17; PB17; PB33; PB82; PC20; PC54; PC55; PC68; PC98;

M[20C]-2441: PA00; PA13; PA14; PA17; PA17; PA37; PA37; PA46; PA74; PA79; PB00; PB03; PB10; PB12; PB49; PC08; PC20; PC35; PC62; PC86;

M[20C]-2443: PA00; PA13; PA14; PA14; PA17; PA36; PA37; PA79; PB00; PB01; PB10; PB12; PCO2; PC08; PC11; PC20; PC29; PC62; PC67; PC86;

M[20C]-2449: PA00; PA13; PA14; PA17; PA36; PA37; PA60; PA79; PA85; PB00; PB10; PB12; PB82; PB98; PC08; PC20; PC29; PC62; PC86; PC98;

M[20C]-2451: PA10; PA13; PA17; PA23; PA37; PA46; PA74; PA76; PA79; PB00; PB03; PB08; PB10; PB12; PB49; PB49; PC20; PC35; PC97; PC98;

M[20C]-2460: PA08; PA13; PA14; PA36; PA36; PA46; PA79; PB10; PB11; PB12; PB17; PB17; PB98; PC20; PC36; PC54; PC62; PC68; PC68; PC86;

M[20C]-2488: PA10; PA13; PA37; PA46; PA53; PA74; PA79; PA82; PB00; PB00; PB12; PB49; PC20; PC29; PC37; PC45; PC54; PC74; PC86; PC98;

M[20C]-2545: PA00; PA08; PA10; PA13; PA46; PA73; PA76; PA79; PA90; PB01; PB08; PB10; PB12; PB17; PB33; PB33; PC20; PC55; PC68; PD02;

M[20C]-2551: PA13; PA14; PA16; PA27; PA36; PA79; PA82; PA92; PA95; PB10; PB12; PB57; PB85; PC11; PC20; PC29; PC29; PC54; PC64; PC98;

M[20C]-2553: PA13; PA16; PA23; PA60; PA79; PA82; PA95; PB00; PB10; PB10; PB12; PB33; PB49; PB50; PB85; PCO2; PC11; PC20; PC29; PC98;

M[20C]-2555: PA00; PA10; PA13; PA16; PA79; PA82; PA90; PA95; PB08; PB10; PB10; PB12; PB33; PB85; PC11; PC20; PC29; PC68; PC98; PD02;

M[20C]-2580: PA10; PA13; PA25; PA37; PA40; PA46; PA79; PB11; PB12; PB33; PB49; PB82; PB85; PB98; PC20; PC29; PC29; PC36; PC45; PC97;

M[20C]-2589: PA13; PA14; PA17; PA40; PA46; PA79; PA80; PB11; PB12; PB33; PB49; PB85; PB98; PC20; PC26; PC29; PC37; PC86; PC97; PD02;

M[20C]-2622: PA13; PA25; PA36; PA36; PA37; PA46; PA46; PA79; PA82; PB12; PB49; PB82; PC20; PC20; PC54; PC55; PC64; PC68; PC86; PC98;

M[20C]-2627: PA13; PA14; PA36; PA46; PA76; PA79; PA80; PA96; PB12; PB49; PB49; PC20; PC20; PC45; PC54; PC55; PC64; PC97; PC98; PC98;

M[20C]-2641: PA05; PA13; PA16; PA27; PA36; PA37; PA41; PA79; PA96; PB05; PB10; PB12; PB82; PB85; PB98; PC11; PC20; PC54; PC68; PD02;

M[20C]-2651: PA13; PA36; PA41; PA46; PA79; PA92; PB00; PB01; PB05; PB12; PB33; PB82; PB82; PB85; PB98; PC20; PC54; PC55; PC86; PD02;

M[20C]-2654: PA13; PA36; PA46; PA79; PA92; PB00; PB00; PB01; PB08; PB11; PB12; PB33; PB82; PC01; PC20; PC55; PC55; PC64; PC86; PC86;

M[20C]-2717: PA13; PA14; PA46; PA79; PB00; PB10; PB12; PB49; PB50; PB77; PB85; PB85; PCO2; PC20; PC29; PC64; PC64; PC68; PC98; PD02;

M[20C]-2728: PA05; PA13; PA16; PA30; PA46; PA60; PA61; PA79; PA85; PB04; PB10; PB12; PB49; PB82; PB82; PB85; PB98; PC11; PC20; PC37;

M[20C]-2730: PA13; PA36; PA37; PA46; PA61; PA79; PA82; PA85; PB00; PB12; PB17; PB33; PB82; PB85; PC01; PCO2; PC20; PC29; PC64; PC98;

M[20C]-2738: PA05; PA13; PA37; PA46; PA61; PA61; PA79; PA85; PB10; PB12; PB82; PB82; PB85; PB85; PB98; PCO2; PC20; PC29; PC37; PC64;

M[20C]-2788: PA00; PA05; PA13; PA27; PA46; PA61; PA79; PA82; PB00; PB10; PB12; PB82; PB85; PB85; PB98; PC20; PC37; PC37; PC58; PC97;

M[20C]-2805: PA11; PA13; PA13; PA14; PA22; PA23; PA28; PA33; PA35; PA69; PB07; PB12; PB38; PB88; PB88; PC20; PC24; PC55; PC55; PC60;

M[20C]-2812: PA11; PA11; PA13; PA20; PA23; PA29; PA30; PA83; PA98; PB02; PB12; PB27; PB38; PC11; PC11; PC20; PC23; PC37; PC51; PC60;

M[20C]-2815: PA11; PA13; PA14; PA22; PA23; PA29; PA33; PA35; PA98; PB02; PB12; PB27; PB38; PB38; PB88; PC11; PC20; PC23; PC37; PC55;

M[20C]-2840: PA10; PA11; PA12 (2 spoons); PA13; PA14; PA18; PA28; PA33; PA67; PA67; PB07 (2 spoons); PB12; PB60; PC23; PC35; PC37; PC55; PC67;

M[20C]-2841: PA12; PA13 (2 spoons); PA19; PA22; PA28; PA33; PA67; PB07 (2 spoons); PB12; PB36; PC20; PC23; PC33; PC37; PC49; PC55; PC67; PC97;

M[20C]-2842: PA11; PA12; PA13 (2 spoons); PA20; PA28; PA30; PA33; PA67; PA83; PB07; PB12 (2 spoons); PC11; PC20; PC23; PC37; PC51; PC60; PC67;

M[20C]-2843: PA10; PA11; PA12; PA13; PA14; PA24; PA26; PA28; PA33; PA67; PB07; PB12; PB33; PB88; PC12; PC23; PC23; PC27; PC37; PC67;

M[20C]-2844: PA12; PA13; PA13; PA15; PA18; PA20; PA28; PA32; PA33; PA67 (2 spoons); PB07; PB12; PB12; PC20; PC23; PC37; PC49; PC55; PC67;

M[20C]-2845: PA12; PA13 (2 spoons); PA14; PA22; PA28; PA33; PA33; PA35; PA67; PB07; PB12 (2 spoons); PB38; PB88; PC20; PC23; PC37; PC55; PC67;

M[20C]-2847: PA10; PA12; PA13 (2 spoons); PA26; PA28; PA33; PA57; PA67; PB02; PB07; PB07; PB12; PB28; PC11; PC23; PC23; PC37; PC49; PC67;

M[20C]-2849: PA12; PA13 (2 spoons); PA14; PA25; PA26; PA28; PA33; PA39; PA52; PA57; PA67; PB07; PB12; PB33; PC23; PC37; PC67; PC71; PC97;

M[20C]-2852: PA11; PA13; PA20 (2 spoons); PA23; PA24; PA30; PA67; PA83; PB07; PB12; PB28; PB33; PC11; PC12; PC20; PC20; PC21; PC51; PC60;

M[20C]-2854: PA13; PA15; PA18; PA20 (2 spoons); PA23; PA24; PA32; PA67 (2 spoons); PB07; PB12; PB28; PB33; PC12; PC20 (2 spoons); PC21; PC49; PC55;

M[20C]-2855: PA13; PA14; PA20; PA22; PA23; PA24; PA33; PA35; PA67; PB07; PB12; PB28; PB33; PB38; PB88; PC12; PC20; PC21; PC55;

M[20C]-2893: PA00; PA06; PA11; PA12; PA13; PA23; PA26; PA28; PA33; PA39; PB02; PB07 (2 spoons); PB12; PB99; PC14; PC20; PC49; PC98; PD02;

M[20C]-2897: PA11 (2 spoons); PA13; PA14; PA24; PA29; PA39; PA83; PB02; PB07; PB12; PB60; PB99; PC11; PC14; PC20; PC20; PC49; PC51; PC98;

M[20C]-2930: PA11; PA13; PA14; PA23; PA26; PA28; PA33; PA35; PA83; PB12; PB28; PB33; PB38; PB77; PB88; PC20; PC23; PC37; PC60; PC60;

M[20C]-2933: PA00; PA06; PA11; PA12; PA13; PA14; PA23; PA26; PA28 (2 spoons); PA33; PA33; PB07; PB12; PB12; PB28; PB38; PB77; PC60; PD02;

M[20C]-2935: PA10; PA11; PA13; PA14; PA28; PA29; PA33; PA57; PA67; PB07; PB12; PB28 (2 spoons); PB38; PB77; PB77; PC11; PC20; PC52; PC60;

M[20C]-2936: PA11 (2 spoons); PA13; PA14; PA18; PA28; PA33; PA57; PA67; PB02; PB12; PB28; PB38 (2 spoons); PC11; PC20; PC27; PC52; PC60;

M[20C]-2937: PA11; PA11; PA13; PA14 (3 spoons); PA28; PA29; PA33; PA83; PB12 (2 spoons); PB28; PB38; PB60; PB77; PC11; PC20; PC51; PC60;

M[20C]-2939: PA10; PA11; PA12; PA13 (2 spoons); PA14; PA18; PA26; PA28; PA33 (2 spoons); PA39; PB12; PB28; PB38; PB77; PC20; PC52; PC55; PC60;

M[20C]-2943: PA00; PA06; PA10; PA11; PA12; PA13; PA14; PA23; PA26; PA28; PA33; PB07 (2 spoons); PB12; PB27; PC11; PC20; PC23; PC67; PD02;

M[20C]-2947: PA10; PA11 (2 spoons); PA13; PA14 (2 spoons); PA24; PA29; PA83; PB07; PB12; PB27; PB60; PC11 (2 spoons); PC20 (2 spoons); PC23; PC51; PC67;

M[20C]-2953: PA00; PA06; PA12 (2 spoons); PA13; PA14; PA23 (2 spoons); PA26; PA28; PA33 (2 spoons); PB01; PB07 (2 spoons); PB12; PC20; PC27; PC52; PD02;

M[20C]-2957: PA11; PA12; PA13; PA14 (2 spoons); PA23; PA24; PA29; PA33; PA83; PB01; PB07; PB12; PB60; PC11; PC20 (2 spoons); PC27; PC51; PC52.

TABLE 10-2 average of planktonic growth inhibition percentage and biofilm formation inhibition percentage efficacy on the 6 tested *Staphylococcus aureus* strains of the processed sample based on the mixes of List 10-2 at 1:20 dilution

| | Planktonic growth inhibition | Biofilm formation inhibition | | Planktonic growth inhibition | Biofilm formation inhibition |
|---|---|---|---|---|---|
| M[03C]-051 | 37% | 24% | M[20C]-2321 | 55% | 30% |
| M[03C]-054 | 30% | 13% | M[20C]-2406 | 58% | 31% |
| M[03C]-057 | 27% | 22% | M[20C]-2420 | 55% | 34% |
| M[20C]-2083 | 84% | 55% | M[20C]-2441 | 52% | 36% |
| M[20C]-2084 | 72% | 40% | M[20C]-2443 | 58% | 33% |
| M[20C]-2085 | 70% | 45% | M[20C]-2449 | 55% | 32% |
| M[20C]-2090 | 57% | 46% | M[20C]-2451 | 53% | 28% |
| M[20C]-2091 | 66% | 35% | M[20C]-2460 | 54% | 37% |
| M[20C]-2092 | 71% | 43% | M[20C]-2488 | 54% | 27% |
| M[20C]-2100 | 56% | 40% | M[20C]-2545 | 52% | 29% |
| M[20C]-2102 | 53% | 41% | M[20C]-2551 | 52% | 29% |
| M[20C]-2104 | 60% | 43% | M[20C]-2553 | 52% | 27% |
| M[20C]-2105 | 81% | 55% | M[20C]-2555 | 58% | 39% |
| M[20C]-2110 | 59% | 43% | M[20C]-2580 | 58% | 44% |
| M[20C]-2111 | 63% | 46% | M[20C]-2589 | 56% | 35% |
| M[20C]-2120 | 66% | 28% | M[20C]-2622 | 57% | 40% |
| M[20C]-2122 | 72% | 37% | M[20C]-2627 | 58% | 39% |

TABLE 10-2-continued average of planktonic growth inhibition percentage and biofilm formation inhibition percentage efficacy on the 6 tested *Staphylococcus aureus* strains of the processed sample based on the mixes of List 10-2 at 1:20 dilution

| | Planktonic growth inhibition | Biofilm formation inhibition | | Planktonic growth inhibition | Biofilm formation inhibition |
|---|---|---|---|---|---|
| M[20C]-2131 | 54% | 37% | M[20C]-2641 | 53% | 36% |
| M[20C]-2135 | 59% | 40% | M[20C]-2651 | 53% | 33% |
| M[20C]-2137 | 78% | 50% | M[20C]-2654 | 53% | 35% |
| M[20C]-2140 | 60% | 35% | M[20C]-2717 | 55% | 30% |
| M[20C]-2141 | 56% | 40% | M[20C]-2728 | 56% | 24% |
| M[20C]-2142 | 61% | 34% | M[20C]-2730 | 55% | 27% |
| M[20C]-2143 | 77% | 37% | M[20C]-2738 | 52% | 26% |
| M[20C]-2144 | 74% | 39% | M[20C]-2788 | 56% | 25% |
| M[20C]-2150 | 65% | 27% | M[20C]-2805 | 71% | 25% |
| M[20C]-2151 | 61% | 34% | M[20C]-2812 | 54% | 31% |
| M[20C]-2152 | 66% | 32% | M[20C]-2815 | 52% | 29% |
| M[20C]-2153 | 82% | 50% | M[20C]-2840 | 55% | 31% |
| M[20C]-2154 | 67% | 26% | M[20C]-2841 | 51% | 31% |
| M[20C]-2155 | 63% | 32% | M[20C]-2842 | 53% | 35% |
| M[20C]-2163 | 61% | 40% | M[20C]-2843 | 58% | 34% |
| M[20C]-2164 | 70% | 35% | M[20C]-2844 | 76% | 42% |
| M[20C]-2214 | 76% | 37% | M[20C]-2845 | 46% | 33% |
| M[20C]-2234 | 56% | 31% | M[20C]-2847 | 61% | 41% |
| M[20C]-2241 | 60% | 40% | M[20C]-2849 | 76% | 32% |
| M[20C]-2242 | 59% | 33% | M[20C]-2852 | 77% | 32% |
| M[20C]-2243 | 63% | 38% | M[20C]-2854 | 57% | 27% |
| M[20C]-2248 | 84% | 49% | M[20C]-2855 | 66% | 35% |
| M[20C]-2249 | 63% | 36% | M[20C]-2893 | 61% | 37% |
| M[20C]-2250 | 58% | 36% | M[20C]-2897 | 66% | 36% |
| M[20C]-2253 | 76% | 37% | M[20C]-2930 | 81% | 52% |
| M[20C]-2254 | 55% | 25% | M[20C]-2933 | 60% | 32% |
| M[20C]-2255 | 60% | 29% | M[20C]-2935 | 65% | 34% |
| M[20C]-2256 | 58% | 30% | M[20C]-2936 | 68% | 41% |
| M[20C]-2257 | 59% | 25% | M[20C]-2937 | 78% | 41% |
| M[20C]-2258 | 81% | 39% | M[20C]-2939 | 77% | 44% |
| M[20C]-2259 | 60% | 29% | M[20C]-2943 | 67% | 29% |
| M[20C]-2261 | 52% | 25% | M[20C]-2947 | 71% | 40% |
| M[20C]-2278 | 53% | 25% | M[20C]-2953 | 66% | 38% |
| M[20C]-2281 | 56% | 26% | M[20C]-2957 | 71% | 45% |

List 10-3: herbal compositions of processed samples containing: *Camellia sinensis* (PA21), *Arctostaphylos uva-ursi* (PB12) and at least one among 3*: Eugenia caryophyllus* (PC20), *Vitis vinifera* var. tinctorial (PA22), *Desmodium adscendens* (PB07):

M[03C]-052: PA21; P1B12; PC20;

M[03C]-055: PA21; P1B12; P1B07;

M[03C]-058: PA21; PB12; PA22;

M[20C]-2888: PA14; PA15; PA18; PA21; PA21; PA23; PA26; PA28; PA28; PA29; PA39; PA57; PA75; PB07; PB12; PB36; PC11; PC55; PC55; PC60;

M[20C]-2913: PA00; PA06; PA12; PA21; PA23; PA26; PA26; PA27; PA28; PA33; PB07; PB07; PB12 (2 spoons); PB33; PC20; PC24; PC41; PC71; PD02;

M[20C]-2918: PA15; PA18; PA21 (2 spoons); PA23; PA26; PA27; PA28; PA57; PB07 (2 spoons); PB12 (2 spoons); PB33; PC11; PC20; PC24; PC41; PC55; PC71;

M[20C]-2920: PA20; PA21; PA23; PA26; PA28; PA35; PA35; PA67; PA83; PB12; PB33; PB88; PC12; PC20; PC23; PC37; PC37; PC60 (2 spoons); PC74;

M[20C]-2923: PA00; PA06; PA12; PA20; PA21; PA23; PA26; PA28 (2 spoons); PA33; PA35; PA67; PB07; PB12 (2 spoons); PC12; PC37; PC60; PC74; PD02;

M[20C]-2928: PA15; PA18; PA20; PA21 (2 spoons); PA23; PA28 (2 spoons); PA35; PA57; PA67; PB07; PB12 (2 spoons); PC11; PC12; PC37; PC55; PC60; PC74;

M[20C]-2887: PA11; PA14; PA14; PA21; PA24; PA26; PA28; PA29 (2 spoons); PA39; PA75; PA83; PB12; PB36; PB60; PC11; PC20; PC51; PC55; PC60;

M[20C]-2914: PA11; PA21 (2 spoons); PA26; PA27; PA28; PA39; PA70; PB02; PB07; PB12; PB33; PB99; PC20; PC24; PC41; PC71 (2 spoons); PC97; PC98;

M[20C]-2915: PA10; PA21; PA26; PA27; PA29; PA57; PA67; PB07 (2 spoons); PB12; PB28; PB33; PB77; PC11; PC20 (2 spoons); PC24; PC41; PC52; PC71;

M[20C]-2916: PA11; PA18; PA21; PA26; PA27; PA57; PA67; PB02; PB07; PB12; PB33; PB38; PC11; PC20; PC20; PC24; PC27; PC41; PC52; PC71;

M[20C]-2917: PA11; PA14; PA21; PA24; PA26; PA27; PA29; PA83; PB07; PB12 (2 spoons); PB33; PB60; PC11; PC20 (2 spoons); PC24; PC41; PC51; PC71;

M[20C]-2925: PA10; PA20; PA21; PA28; PA29; PA35; PA57; PA67 (2 spoons); PB07; PB12; PB28; PB77; PC11; PC12; PC20; PC37; PC52; PC60; PC74;

M[20C]-2926: PA11; PA18; PA20; PA21; PA28; PA35; PA57; PA67 (2 spoons); PB02; PB12; PB38; PC11; PC12; PC20; PC27; PC37; PC52; PC60; PC74;

M[20C]-2927: PA11; PA14; PA20; PA21; PA24; PA28; PA29; PA35; PA67; PA83; PB12; PB12; PB60; PC11; PC12; PC20; PC37; PC51; PC60; PC74;

M[20C]-2910: PA21; PA23; PA26 (2 spoons); PA27; PA35; PA83; PB07; PB12; PB33 (2 spoons); PB88; PC20 (2 spoons); PC23; PC24; PC37; PC41; PC60; PC71.

TABLE 10-3 average of planktonic growth inhibition percentage and biofilm formation inhibition percentage efficacy on the 6 tested *Staphylococcus aureus* strains of the processed sample based on the mixes of List 10-2 at 1:20 dilution

| | Planktonic growth inhibition | Biofilm formation inhibition | | Planktonic growth inhibition | Biofilm formation inhibition |
|---|---|---|---|---|---|
| M[03C]-052 | 31% | 13% | M[20C]-2887 | 46% | 8% |
| M[03C]-055 | 29% | 10% | M[20C]-2914 | 29% | 38% |
| M[03C]-058 | 31% | 18% | M[20C]-2915 | 30% | 35% |
| M[20C]-2888 | 48% | 27% | M[20C]-2916 | 39% | 40% |
| M[20C]-2913 | 46% | 37% | M[20C]-2917 | 40% | 41% |
| M[20C]-2918 | 46% | 32% | M[20C]-2925 | 41% | 36% |
| M[20C]-2920 | 54% | 30% | M[20C]-2926 | 47% | 36% |
| M[20C]-2923 | 51% | 28% | M[20C]-2927 | 41% | 41% |
| M[20C]-2928 | 46% | 32% | M[20C]-2910 | 46% | 39% |

List 10-4: extracts from herbal compositions containing: *Filipendula ulmaria* (PA13), *Camellia sinensis* (PA21), *Arctostaphylos uva-ursi* (PB12) and at least one among 3: *Eugenia caryophyllus* (PC20), *Vitis vinifera* var. tinctorial (PA22), *Desmodium adscendens* (PB07):

M[04C]-025: PA13; PA21; PB12; PC20;
M[04C]-026: PA13; PA21; PB12; PB07;
M[04C]-027: PA13; PA21; PB12; PA22;
M[20C]-2898: PA11; PA13; PA15; PA18; PA21; PA23; PA28; PA39; PA57; PB02; PB07 (2 spoons); PB07; PB12; PB99; PC11; PC14; PC20; PC49; PC55; PC98;
M[20C]-2900: PA10; PA11; PA13; PA21; PA23; PA25; PA26; PA35; PA69; PA83; PB12; PB32; PB33; PB88; PC20 (2 spoons); PC23; PC37; PC55; PC60;
M[20C]-2903: PA00; PA06; PA10; PA11; PA12; PA13; PA21; PA23; PA25; PA26; PA28; PA33; PA69; PB07; PB12 (2 spoons); PB32; PC20; PC55; PD02;
M[20C]-2908: PA10; PA11; PA13; PA15; PA18; PA21 (2 spoons); PA23; PA25; PA28; PA57; PA69; PB07; PB12 (2 spoons); PB32; PC11; PC20; PC55 (2 spoons);
M[20C]-2938: PA11; PA13; PA14; PA15; PA18; PA21; PA23; PA28 (2 spoons); PA33; PA57; PB07; PB12 (2 spoons); PB28; PB38; PB77; PC11; PC55; PC60;
M[20C]-2948: PA10; PA11; PA13; PA14; PA15; PA18; PA21; PA23; PA28; PA57; PB07 (2 spoons); PB12; PB27; PC11 (2 spoons); PC20; PC23; PC55; PC67;
M[20C]-2951: PA12; PA13 (2 spoons); PA14; PA21; PA23; PA24; PA33; PA39; PA67; PB01; PB07; PB12; PB77; PC20; PC27; PC33; PC49; PC52; PC60;
M[20C]-2952: PA12; PA13 (2 spoons); PA14; PA21; PA23; PA25; PA26; PA33; PA37; PA67; PB01; PB07 (2 spoons); PB12; PC20; PC27; PC49; PC52; PC71;
M[20C]-2958: PA12; PA13; PA14; PA15; PA18; PA21; PA23 (2 spoons); PA28; PA33; PA57; PB01; PB07 (2 spoons); PB12; PC11; PC20; PC27; PC52; PC55;
M[20C]-2822: PA11 (2 spoons); PA13 (2 spoons); PA20 (2 spoons); PA21; PA25; PA29; PA30; PA33; PA35; PA75; PA83; PB12; PC11; PC20; PC33; PC51; PC60;
M[20C]-2824: PA11; PA13 (2 spoons); PA15; PA18; PA20 (2 spoons); PA21; PA25; PA29; PA32; PA33; PA35; PA67; PA75; PB12; PC20; PC33; PC49; PC55;
M[20C]-2825: PA11; PA13 (2 spoons); PA14; PA20; PA21; PA22; PA25; PA29; PA33 (2 spoons); PA35 (2 spoons); PA75; PB12; PB38; PB88; PC20; PC33; PC55;
M[20C]-2834: PA13 (2 spoons); PA15; PA18; PA20; PA21; PA22; PA25; PA29; PA32 (2 spoons); PA34; PA67; PB12; PB88; PC20; PC33; PC49; PC55; PC98;
M[20C]-2835: PA13 (2 spoons); PA14; PA21; PA22 (2 spoons); PA25; PA29; PA32; PA33; PA34; PA35; PB12; PB38; PB88 (2 spoons); PC20; PC33; PC55; PC98;
M[20C]-2848: PA12 (2 spoons); PA13 (2 spoons); PA18; PA21; PA24; PA28; PA33; PA67; PB07; PB12; PC23 (2 spoons); PC37; PC49; PC52; PC55; PC67; PC97;
M[20C]-2862: PA11; PA13; PA20; PA21; PA22; PA30; PA83; PB12; PB28; PB60; PC11 (2 spoons); PC20 (2 spoons); PC23; PC51; PC55; PC60 (2 spoons); PC74;
M[20C]-2864: PA13; PA15; PA18; PA20; PA21; PA22; PA32; PA67; PB12; PB28; PB60; PC11; PC20 (2 spoons); PC23; PC49; PC55 (2 spoons); PC60; PC74;
M[20C]-2865: PA13; PA14; PA21; PA22 (2 spoons); PA33; PA35; PB12; PB28; PB38; PB60; PB88; PC11; PC20 (2 spoons); PC23; PC55 (2 spoons); PC60; PC74;
M[20C]-2872: PA10; PA11 (2 spoons); PA13; PA20; PA21; PA30; PA35; PA57; PA83; PB07; PB12; PB77; PC11; PC20 (2 spoons); PC23; PC51; PC60; PC71;
M[20C]-2874: PA10; PA11; PA13; PA15; PA18; PA20; PA21; PA32; PA35; PA57; PA67; PB07; PB12; PB77; PC20 (2 spoons); PC23; PC49; PC55; PC71;
M[20C]-2875: A10; A11; A13; A14; A21; A22; A33; A35; A35; A57; B07; B12; B38; B77; B88; C20 (2 spoons); C23; C55; C71;
M[20C]-2882: PA13; PA14; PA21 (2 spoons); PA25; PA26 (2 spoons); PA28; PA29; PA37; PA39; PA67; PA75; PB07; PB12; PB36; PC49; PC55; PC60; PC71;
M[20C]-2891: PA11; PA13 (2 spoons); PA21; PA24; PA39; PA39; PA67; PB02; PB07; PB12; PB77; PB99; PC14; PC20; PC33; PC49 (2 spoons); PC60; PC98;
M[20C]-2892: PA11; PA13 (2 spoons); PA21; PA25; PA26; PA37; PA39; PA67; PB02; PB07 (2 spoons); PB12; PB99; PC14; PC20; PC49 (2 spoons); PC71; PC98;
M[20C]-2901: PA10; PA11; PA13 (2 spoons); PA21 (2 spoons); PA24; PA25; PA39; PA67; PA69; PB12 (2 spoons); PB32; PB77; PC20; PC33; PC49; PC55; PC60;
M[20C]-2902: PA10; PA11; PA13 (2 spoons); PA21 (2 spoons); PA25 (2 spoons); PA26; PA37; PA67; PA69; PB07; PB12 (2 spoons); PB32; PC20; PC49; PC55; PC71;
M[20C]-2904: PA10; PA11 (2 spoons); PA13; PA21 (2 spoons); PA25; PA28; PA39; PA69; PA70; PB02; PB12; PB32; PB99; PC20; PC55; PC71; PC97; PC98;

M[20C]-2905: PA10 (2 spoons); PA11; PA13; PA21; PA25; PA29; PA57; PA67; PA69; PB07; PB12; PB28; PB32; PB77; PC11; PC20 (2 spoons); PC52; PC55;

M[20C]-2906: PA10; PA11 (2 spoons); PA13; PA18; PA21; PA25; PA57; PA67; PA69; PB02; PB12; PB32; PB38; PC11; PC20 (2 spoons); PC27; PC52; PC55;

M[20C]-2907: PA10; PA11 (2 spoons); PA13; PA14; PA21; PA24; PA25; PA29; PA69; PA83; PB12 (2 spoons); PB32; PB60; PC11; PC20 (2 spoons); PC51; PC55;

M[20C]-2909: A10 (2 spoons); A11; A12; A13 (2 spoons); A18; A21; A25; A26; A33; A39; A69; B12; B32; C20 (2 spoons); C52; C55 (2 spoons);

M[20C]-2911: PA13; PA21 (2 spoons); PA24; PA26; PA27; PA39; PA67; PB07; PB12 (2 spoons); PB33; PB77; PC20; PC24; PC33; PC41; PC49; PC60; PC71;

M[20C]-2912: PA13; A21 (2 spoons); PA25; PA26 (2 spoons); PA27; PA37; PA67; PB07 (2 spoons); PB12 (2 spoons); PB33; PC20; PC24; PC41; PC49; PC71 (2 spoons);

M[20C]-2919: PA10; PA12; PA13; PA18; PA21; PA26 (2 spoons); PA27; PA33; PA39; PB07; PB12; PB33; PC20 (2 spoons); PC24; PC41; PC52; PC55; PC71;

M[20C]-2922: PA13; PA20; PA21 (2 spoons); PA25; PA26; PA28; PA35; PA37; PA67 (2 spoons); PB07; PB12 (2 spoons); PC12; PC37; PC49; PC60; PC71; PC74;

M[20C]-2929: PA10; PA12; PA13; PA18; PA20; PA21; PA26; PA28; PA33; PA35; PA39; PA67; PB12; PC12; PC20; PC37; PC52; PC55; PC60; PC74;

M[20C]-2932: PA11; PA13 (2 spoons); PA14; PA21; PA25; PA26; PA28; PA33; PA37; PA67; PB07; PB12 (2 spoons); PB28; PB38; PB77; PC49; PC60; PC71;

M[20C]-2941: PA10; PA11; PA13 (2 spoons); PA14; PA21; PA24; PA39; PA67; PB07; PB12; PB27; PB77; PC11; PC20; PC23; PC33; PC49; PC60; PC67;

M[20C]-2942: PA10; PA11; PA13 (2 spoons); PA14; PA21; PA25; PA26; PA37; PA67; PB07 (2 spoons); PB12; PB27; PC11; PC20; PC23; PC49; PC67; PC71;

TABLE 10-4 average of planktonic growth inhibition percentage and biofilm formation inhibition percentage efficacy on the 6 tested *Staphylococcus aureus* strains of the processed sample based on the mixes of List 10-4 at 1:20 dilution

| | Planktonic growth inhibition | Biofilm formation inhibition | | Planktonic growth inhibition | Biofilm formation inhibition |
|---|---|---|---|---|---|
| M[04C]-025 | 57% | 18% | M[20C]-2872 | 59% | 36% |
| M[04C]-026 | 48% | 16% | M[20C]-2874 | 78% | 39% |
| M[04C]-027 | 49% | 18% | M[20C]-2875 | 83% | 47% |
| M[20C]-2898 | 60% | 21% | M[20C]-2882 | 61% | 28% |
| M[20C]-2900 | 78% | 32% | M[20C]-2891 | 70% | 27% |
| M[20C]-2903 | 48% | 28% | M[20C]-2892 | 76% | 39% |
| M[20C]-2908 | 54% | 15% | M[20C]-2901 | 59% | 29% |
| M[20C]-2938 | 70% | 26% | M[20C]-2902 | 51% | 30% |
| M[20C]-2948 | 56% | 22% | M[20C]-2904 | 62% | 24% |
| M[20C]-2951 | 47% | 17% | M[20C]-2905 | 55% | 37% |
| M[20C]-2952 | 60% | 19% | M[20C]-2906 | 59% | 37% |
| M[20C]-2958 | 53% | 31% | M[20C]-2907 | 75% | 41% |
| M[20C]-2822 | 46% | 38% | M[20C]-2909 | 82% | 49% |
| M[20C]-2824 | 60% | 32% | M[20C]-2911 | 55% | 30% |
| M[20C]-2825 | 76% | 38% | M[20C]-2912 | 59% | 29% |
| M[20C]-2834 | 55% | 27% | M[20C]-2919 | 75% | 48% |
| M[20C]-2835 | 64% | 29% | M[20C]-2922 | 63% | 32% |
| M[20C]-2848 | 52% | 29% | M[20C]-2929 | 54% | 30% |

TABLE 10-4-continued average of planktonic growth inhibition percentage and biofilm formation inhibition percentage efficacy on the 6 tested *Staphylococcus aureus* strains of the processed sample based on the mixes of List 10-4 at 1:20 dilution

| | Planktonic growth inhibition | Biofilm formation inhibition | | Planktonic growth inhibition | Biofilm formation inhibition |
|---|---|---|---|---|---|
| M[20C]-2862 | 46% | 31% | M[20C]-2932 | 73% | 39% |
| M[20C]-2864 | 51% | 29% | M[20C]-2941 | 63% | 48% |
| M[20C]-2865 | 56% | 43% | M[20C]-2942 | 56% | 34% |

Comparative Example 4

As a comparative Example, we report several extracts of herbal compositions containing only 1 plant among 3: *Filipendula ulmaria* (PA13), *Camellia sinensis* (PA21), *Arctostaphylos uva-ursi* (PB12) and only 1 among 3: *Eugenia caryophyllus* (PC20), *Vitis vinifera* var. *tinctoria* (PA22), *Desmodium adscendens* (PB07).

5 herbal compositions having the content reported in List 10-5 were prepared according to the previously described Method 1.

List 10-5 extracts from herbal compositions containing the following plants

M[20P]-318: PA15; PA21; PA34; PA35; PA82; PA83; PA85; PA92; PA96; PB03; PB07; PB26; PB30; PB36; PB79; PC11; PC49; PC91; PC92; PD10;

M[20P]-329: PA10; PA28; PA34; PA36; PASS; PA72; PA83; PA85; PA91; PB03; PB12; PB16; PB28; PB35; PB49; PB92; PC20; PC23; PC64; PC85;

M[20P]-333: PA04; PA05; PA13; PA16; PA22; PA39; PA51; PA55; PA57; PA72; PA82; PA92; PA98; PB05; PB20; PB36; PB43; PB74; PB77; PC37;

M[20P]-362: PA21; PA23; PA25; PA33; PA37; PA57; PA69; PA81; PA92; PB16; PB25; PB26; PB28; PB29; PB78; PC20; PC21; PC71; PC83; PD02;

M[20P]-513: PA12; PA14; PA14; PA20; PA20; PA21; PA22; PA33; PA35; PA52; PA57; PA69; PB00; PB32; PB38; PC24; PC37; PC52; PC55; PC67;

Herbal compositions containing 20 plant powders were prepared according to the previously described Method A.

Starting from the herbal compositions, corresponding water extracts (or processed samples) were prepared according to the previously described Method B using 40 mL of water containing 100 g/l of sucrose for water extraction and including the decantation step before filtration.

The biological activity of each processed sample was determined according to the previously described Method C by using the following *Staphylococcus aureus* strains: ATCC 25923, ATCC 49476, ATCC 6538, ATCC 51740, ATCC 29213 and ATCC 14775, with the 1:20 final dilutions of processed samples.

The bacteria planktonic growth inhibition percentage average and biofilm formation inhibition percentage average over all the tested strains of the processed samples obtained from the herbal compositions of List 10-4 is given in Table 10-5. Each percentage is the average of 2 measurements of the same condition in two different wells. Negative percentages reflect growth promotion and biofilm promotion, instead of the desired inhibition. It is appreciated that such extracts give very poor, if any inhibition as compared to the extracts of Example 10.

TABLE 10-5

| bacteria planktonic growth inhibition percentage average and biofilm formation inhibition percentage average over all the tested strains of the processed samples obtained from the herbal compositions of List 10-4 | | |
|---|---|---|
| | Planktonic growth inhibition | Biofilm formation inhibition |
| M[20C]-318 | −10% | 0% |
| M[20C]-329 | 12% | 9% |
| M[20C]-333 | 3% | 18% |
| M[20C]-362 | 22% | 3% |
| M[20C]-513 | −21% | 21% |

Example 11

In this Example, we illustrate antimicrobial activities against 14 different microbial species described in Table11-1 of 10 mixtures extracts obtained from the herbal compositions disclosed in List 11-1 comprising at least 2 plants among 3*: Filipendula ulmaria* (PA13), *Camellia sinensis* (PA21), *Arctostaphylos uva-ursi* (PB12) and at least 1 plant among 3*: Eugenia caryophyllus* (PC20), *Vitis vinifera* var. tinctorial (PA22), and *Desmodium adscendens* (PB07).

TABLE 11-1

| microbial species and strains used in Example 11 | | |
|---|---|---|
| Strain full name | Strain code | Innoculum concentration (bacteria/mL) |
| *Staphylococcus aureus* subsp. *aureus* (MRSA) ATCC ® 33592 ™ | B-A49 | $2.10^{5.5}$ |
| *Staphylococcus epidermidis* ATCC ® 14990 ™ | B-A08 | $2.10^{5}$ |
| *Staphylococcus pseudintermedius* ATCC ® 49444 ™ | B-A09 | $2.10^{5}$ |
| *Candida albicans* ATCC ® 60193 ™ | B-A61 | $2.10^{6.5}$ |
| *Escherichia coli* ATCC ® 11775 ™ | B-A67 | $2.10^{5.5}$ |
| *Klebsiella pneumoniae* ATCC ® 13883 ™ | B-A68 | $2.10^{5.5}$ |
| *Listeria innocua* ATCC ® 33090 ™ | B-A69 | $2.10^{5.5}$ |
| *Listeria monocytogenes* ATCC ® 19115 ™ | B-A70 | $2.10^{5.5}$ |
| *Pseudomonas aeruginosa* ATCC ® 27853 ™ | B-A71 | $2.10^{5.5}$ |
| *Salmonella enterica* subsp. *enterica serovar Enteritidis* ATCC ® 13076 ™ | B-A72 | $2.10^{5.5}$ |
| *Salmonella enterica* subsp. *enterica serovar Typhimurium* ATCC ® 13311 ™ | B-A73 | $2.10^{5.5}$ |
| *Streptococcus pneumoniae* ATCC ® 27336 ™ | B-A75 | $2.10^{5.5}$ |
| *Streptococcus egui* subsp. *zooepidemicus* ATCC ® 43079 ™ | B-A77 | $2.10^{5.5}$ |
| *Streptococcus pyogenes* ATCC ® BAA-1323 ™ | B-B26 | $2.10^{6.5}$ |

List 11-1: extracts from herbal compositions containing: *Filipendula ulmaria* (PA13), *Camellia sinensis* (PA21) and at least one among 3*: Eugenia caryophyllus* (PC20), *Vitis vinifera* var. *tinctoria* (PA22), *Desmodium adscendens* (PB07) used in Example—11:

M[20P]-297: PA10; PA11; PA13; PA14; PA20; PA21; PA25; PA26; PA29; PA33; PA57; PA67; PA69; PB07; PB12; PB60; PC20; PC37; PC49; PC98;

M[20P]-416: PA11; PA13; PA14; PA20; PA21; PA25; PA26; PA28; PA29; PA67; PA75; PB02; PB12; PB27; PB33; PB60; PB88; PC20; PC49; PC60;

M[20P]-418: PA10; PA11; PA12; PA13; PA21; PA22; PA23; PA24; PA26; PA39; PB07; PB12; PB38; PC11; PC12; PC20; PC23; PC24; PC49; PC55;

M[20P]-527: PA10; PA10; PA11; PA13; PA15; PA20; PA20; PA21; PA23; PA26 (3 spoons); PA33; PB08; PB12 (2 spoons); PB60; PB88; PC12; PC20;

M[20P]-557: PA00; PA10; PA20; PA21; PA23; PA24; PA29; PA57; PB07; PB12 (4 spoons); PC11 (2 spoons); PC12; PC20; PC51; PC55; PC67;

M[20P]-573: PA10; PA11; PA13 (3 spoons); PA14; PA18; PA21; PA23; PA29; PA67; PB00; PB07; PB12; PB33; PB77; PC11; PC52; PC60; PC71;

M[20P]-576: PA11 (2 spoons); PA12; PA13 (3 spoons); PA14 (2 spoons); PA20; PA21; PA22; PA29; PA39; PB12; PB60; PC20; PC26; PC33; PC37; PC49;

M[19P]-576: PA11 (2 spoons); PA12; PA13 (3 spoons); PA14 (2 spoons); PA20; PA21; PA22; PA29; PA39; PB12; PB60; PC20; PC26; PC33; PC37;

M[5P]-1: PA12; PA13; PA21; PA22; PB12;

M[5P]-2: PA11; PA13; PA21; PA22; PB12;

For the mixes M[5P]-1, M[5P]-2 and M[19P]-576, the dried plants of pharmaceutical grade were obtained from "Herboristerie Cailleau" (Chemillé, France). For the other mixes, the dried plants of pharmaceutical grade were obtained from "Pharmacie Fontgiève" (Clermont-Ferrand, France, plants PA00 to PB12) and "Pharmacie St Herem" (Clermont-Ferrand, France, plants PB13 to PD02).

All herbal compositions of 20 plants were prepared according to the previously described Method A.

Starting from the herbal compositions, corresponding water extracts (or processed samples) were prepared according to the previously described Method B using 40 mL of water containing 100 g/l of sucrose for water extraction and including the decantation step before filtration.

Herbal compositions M[19P]-576, M[5P]-1 and M[5P]-2 were prepared by weighting each dried herb as indicated in Table 11-2

TABLE 11-2

| weight of dried plant (mg) used in the herbal compositions of M[19P]-576, M[5P]-1 and M[5P]-2 used in Example-11 | | | | | | | | | | | | | | | |
|---|---|---|---|---|---|---|---|---|---|---|---|---|---|---|---|
| | PA11 | PA12 | PA13 | PA14 | PA20 | PA21 | PA22 | PA29 | PA39 | PB12 | PB60 | PC20 | PC26 | PC33 | PC37 |
| M[19P]-576 | 409 | 145 | 573 | 316 | 277 | 271 | 207 | 380 | 207 | 247 | 206 | 236 | 198 | 187 | 154 |
| M[5P]-1 | | 903 | 1574 | | | 2237 | 1263 | | | 2022 | | | | | |
| M[5P]-2 | 756 | | 720 | | | 1027 | 577 | | | 925 | | | | | |

Starting from the herbal compositions, corresponding water extracts (or processed samples) were prepared according to the previously described Method B using, using, respectively, 30 mL, 40 mL and 40 mL, of water without sucrose with, respectively, M[19P]-576, M[5P]-1 and M[5P] 2, for water extraction and including the decantation step before filtration.

The biological activity of each processed sample was determined according to the previously described Method C by using the following strains at the indicated final dilutions of processed samples is given in Table 11-3.

The microbial planktonic growth inhibition percentage average is given in Table 11-3.

TABLE 11-3 planktonic growth inhibition percentage on the 14 tested microbial strains of the processed sample of composition disclosed in List 11-1

| Dilution | M[20C]-297 1:10 | M[20C]-416 1:10 | M[20C]-418 1:10 | M[20C]-527 1:10 | M[20C]-557 1:10 | M[20C]-573 1:10 | M[20C]-576 1:10 | M[19C]-576 1:20 | M[5P]-1 1:20 | M[5P]-2 1:20 |
|---|---|---|---|---|---|---|---|---|---|---|
| B-A49 | 100% | 100% | 100% | 100% | 100% | 100% | 100% | 100% | 100% | 100% |
| B-A08 | 100% | 99% | 100% | 100% | 100% | 98% | 98% | 100% | 100% | 100% |
| B-A09 | 89% | 97% | 98% | 99% | 99% | 100% | 100% | 100% | 100% | 100% |
| B-A61 | 25% | 69% | 36% | 45% | 51% | 55% | 90% | ND | ND | ND |
| B-A67 | 45% | 52% | 59% | 66% | 62% | 52% | 39% | 34% | 55% | 38% |
| B-A68 | 100% | 97% | 100% | 100% | 100% | 94% | 92% | 100% | 100% | 100% |
| B-A69 | −1% | 21% | 21% | 38% | 30% | 30% | −1% | 38% | 100% | 38% |
| B-A70 | 39% | 52% | 53% | 74% | 54% | 57% | 32% | 34% | 100% | 40% |
| B-A71 | 63% | 71% | 69% | 75% | 75% | 82% | 71% | 42% | 100% | 55% |
| B-A72 | 47% | 53% | 59% | 63% | 58% | 58% | 32% | 39% | 62% | 42% |
| B-A73 | 59% | 59% | 59% | 71% | 72% | 58% | 32% | 42% | 100% | 45% |
| B-A75 | 51% | 52% | 63% | 71% | 63% | 57% | 31% | ND | ND | ND |
| B-A77 | 40% | 47% | 64% | 68% | 59% | 58% | 40% | 100% | 100% | 100% |
| B-B26 | 58% | 64% | 72% | 70% | 74% | 42% | 93% | ND | ND | ND |

Note:
"ND" stands for "not determined"

Example 12

In this Example, we illustrate antimicrobial activities of a plant mix where the extraction step was realized with the non-aqueous solvents acetone, ethyl-acetate, ethanol, used alone or as binary mixes as indicated in Table 12-1. A comparison with water is provided.

TABLE 12-1 composition of the binary mixes used in Example 12 for non-aqueous extraction

| A) | | B) | | C) | |
|---|---|---|---|---|---|
| Binary solvant name | Acetone to Ethanol ratio | Binary solvant name | Ethyl-acetate to Ethanol ratio | Binary solvant name | Ethyl-acetate to Acetone ratio |
| AC9ET1 | 90/10 | EA9ET1 | 90/10 | EA9AC1 | 90/10 |
| AC8ET2 | 80/20 | EA8ET2 | 80/20 | EA8AC2 | 80/20 |
| AC7ET3 | 70/30 | EA7ET3 | 70/30 | EA7AC3 | 70/30 |
| AC6ET4 | 60/40 | EA6ET4 | 60/40 | EA6AC4 | 60/40 |
| AC5ET5 | 50/50 | EA5ET5 | 50/50 | EA5AC5 | 50/50 |
| AC4ET6 | 40/60 | EA4ET6 | 40/60 | EA4AC6 | 40/60 |
| AC3ET7 | 30/70 | EA3ET7 | 30/70 | EA3AC7 | 30/70 |
| AC2ET8 | 20/80 | EA2ET8 | 20/80 | EA2AC8 | 20/80 |
| AC1ET9 | 10/90 | EA1ET9 | 10/90 | EA1AC9 | 10/90 |

The M[20P]-576 dried plant mix was composed of following Table 12-2 and placed in a 500 mL vial and thoroughly mixed by manual flipping and rolling. The dried herbs were obtained form "Herboristerie Cailleau" (Chemillé, France), except PC49 which was obtained from Siccarapam (Aubiat, France).

TABLE 12-2 list of dried plant composing the M[20P]-576 used in Example 12

| Dried plant | PA11 | PA12 | PA13 | PA14 | PA20 | PA21 | PA22 | PA29 | PA39 | PB12 | PB60 | PC20 | PC26 | PC33 | PC37 | PC49 |
|---|---|---|---|---|---|---|---|---|---|---|---|---|---|---|---|---|
| Weight (g) | 29.7 | 10.5 | 41.5 | 22.9 | 19.8 | 19.9 | 15.0 | 27.5 | 15.0 | 17.8 | 15.0 | 17.1 | 14.4 | 13.6 | 11.3 | 9.3 |

For each solvent tested, 5 g of dried plant mix were placed into a 100 ml coloured vial (Schott, Germany) with a magnetic bar and 50 ml solvent was added. The liquid suspension was stirred with a magnetic stirrer (RO 15P IKA, Germany) at maximum speed during 48 hours at room temperature. Each suspension/solution was filtered by gravity using a 250 mm folded filter (J025106, Prats Dumas, France) placed on a glass funnel (Schott, Germany) itself placed into an evaporation flask. The flask containing the liquid which crossed the filter is placed on a rotary vacuum evaporation device (Rotavapor® R205+V800 vacuum controller, Büchi, Switzerland) and evaporation is performed at 35° C. with vacuum adjusted to be below the solvent's ebullition point, until all solvent has evaporated. The remaining material is weighted and dissolved into DMSO (Acros organic, USA) qsp 10 g/L to form the extracted mix.

Two water extracts were prepared according to the previously described Method B, where the spoons of dried plants were replaced by 2 g of the M[20P]-576 dried plant mix of Example 12, using 40 mL of water for water extraction and including the decantation step before filtration. The dry residue content of one of the plant mix extract has been determined by weighting the lyophilisation residue obtained with a lyophilisation device (FreeZone™ 2.5, Labconco USA, with RZ6 Vacuubrand, Germany) of the frozen extract.

These dry residue contents were used to deduce the specific activities of the different extracts.

The biological activity of each extracted mix was determined according to the previously described Method C by using the strains indicted in Table 12-3, where the dilution of the extracted mix was: 1:20, 1:40, 1:80, 1:160. The minimal inhibiting concentration (MIC) was noted by visual observation of the wells as the lowest concentration where no growth is observed.

TABLE 12-3 list of the bacterial strains used in the Example 12

| *Staphylococcus aureus* | | *Staphylococcus epidermidis* | |
|---|---|---|---|
| NCTC 12493 ™ | B-A47 | ATCC ® 12228 ™ | B-A22 |
| ATCC ® 33591 ™ | B-A48 | ATCC ® 700296 ™ | B-A23 |
| ATCC ® 33592 ™ | B-A49 | ATCC ® 49461 ™ | B-A24 |
| NCTC 43300 ™ | B-A51 | ATCC ® 14990 ™ | B-A08 |

The results are compiled in tables 12-4 for the different solvents.

TABLE 12-4

CMI in mg/L of the extracted mixes using, A) acetone, ethanol-acetate, ethanol and water as a solvent, B), different proportions of acetone and ethanol as binary solvent as indicated in Table 12-2-A, C) different proportions of ethanol-acetate and ethanol as binary solvent as indicated in Table 12-2-B, and D) using different proportions of ethanol-acetate and acetone as binary solvent as indicated in Table 12-2-C.

| A) | Acetone | Ethanol-Acetate | Ethanol | Water |
|---|---|---|---|---|
| B-A47 | 500 | 500 | 500 | 725 |
| B-A48 | 500 | 500 | 500 | 725 |
| B-A49 | 500 | 500 | 500 | 725 |
| B-A51 | 500 | 500 | 500 | 725 |
| B-A22 | 250 | 250 | 250 | 363 |
| B-A23 | 250 | 250 | 250 | 363 |
| B-A24 | 250 | 250 | 250 | 363 |
| B-A08 | 250 | 250 | 250 | 725 |

| B) | AC9ET1 | AC8ET2 | AC7ET3 | AC6ET4 | AC5ET5 | AC4ET6 | AC3ET7 | AC2ET8 | AC1ET9 |
|---|---|---|---|---|---|---|---|---|---|
| B-A47 | 500 | 500 | 500 | 500 | 500 | 500 | 500 | 500 | 500 |
| B-A48 | 250 | 250 | 250 | 250 | 250 | 500 | 500 | 500 | 500 |
| B-A49 | 250 | 250 | 250 | 250 | 250 | 500 | 500 | 500 | 500 |
| B-A51 | 500 | 500 | 500 | 500 | 500 | 500 | 500 | 500 | 500 |
| B-A22 | 250 | 250 | 250 | 250 | 250 | 250 | 250 | 250 | 250 |
| B-A23 | 250 | 125 | 125 | 125 | 125 | 250 | 250 | 250 | 250 |
| B-A24 | 250 | 250 | 250 | 250 | 250 | 250 | 250 | 250 | 250 |
| B-A08 | 250 | 250 | 250 | 250 | 250 | 250 | 250 | 250 | 250 |

| C) | EA9ET1 | EA8ET2 | EA7ET3 | EA6ET4 | EA5ET5 | EA4ET6 | EA3ET7 | EA2ET8 | EA1ET9 |
|---|---|---|---|---|---|---|---|---|---|
| B-A47 | 500 | 500 | 500 | 500 | 500 | 500 | 500 | 500 | 500 |
| B-A48 | 250 | 250 | 250 | 250 | 250 | 500 | 500 | 500 | 500 |
| B-A49 | 250 | 250 | 250 | 250 | 250 | 500 | 500 | 500 | 500 |
| B-A51 | 250 | 500 | 500 | 500 | 500 | 500 | 500 | 500 | 500 |

TABLE 12-4-continued

CMI in mg/L of the extracted mixes using, A) acetone, ethanol-acetate, ethanol and water as a solvent, B), different proportions of acetone and ethanol as binary solvent as indicated in Table 12-2-A, C) different proportions of ethanol-acetate and ethanol as binary solvent as indicated in Table 12-2-B, and D) using different proportions of ethanol-acetate and acetone as binary solvent as indicated in Table 12-2-C.

| | | | | | | | | | |
|---|---|---|---|---|---|---|---|---|---|
| B-A22 | 250 | 250 | 250 | 250 | 250 | 250 | 250 | 250 | 250 |
| B-A23 | 250 | 250 | 250 | 250 | 250 | 250 | 250 | 250 | 250 |
| B-A24 | 250 | 250 | 250 | 250 | 250 | 250 | 250 | 250 | 250 |
| B-A08 | 250 | 250 | 250 | 250 | 250 | 250 | 250 | 250 | 250 |
| D) | EA9AC1 | EA8AC2 | EA7AC3 | EA6AC4 | EA5AC5 | EA4AC6 | EA3AC7 | EA2AC8 | EA1AC9 |
| B-A47 | 500 | 500 | 500 | 500 | 500 | 500 | 500 | 500 | 500 |
| B-A48 | 500 | 500 | 500 | 500 | 500 | 500 | 500 | 500 | 500 |
| B-A49 | 500 | 500 | 500 | 500 | 500 | 500 | 500 | 500 | 500 |
| B-A51 | 500 | 500 | 500 | 500 | 500 | 500 | 500 | 500 | 500 |
| B-A22 | 500 | 250 | 250 | 250 | 250 | 250 | 250 | 250 | 250 |
| B-A23 | 500 | 250 | 250 | 250 | 250 | 250 | 250 | 250 | 250 |
| B-A24 | 500 | 250 | 250 | 250 | 250 | 250 | 250 | 250 | 250 |
| B-A08 | 500 | 500 | 250 | 250 | 250 | 250 | 250 | 250 | 250 |

Example 13

In this Example, we illustrate antimicrobial activities of a plant mixes prepared according to the previously described Method B, where the added carbohydrate is chosen among sucrose, dextrose, maltose and galactose.

The M[19P]-576, M [5P]-1 and M[5P]-2 dried plant mix were composed following Table 13-1 and placed in a 500 mL vial and thoroughly mixed by manual flipping and rolling. The dried herbs were obtained form "Herboristerie Cailleau" (Chemillé, France), except PC49 which was obtained from Siccarapam (Aubiat, France).

TABLE 13-1 list of dried plant composing: A) the M[20P]-576 mix, B) the M[5P]-1 mix and C), the M[5P]-2 mix used in Example 13

A)

| Dried plant | PA11 | PA12 | PA13 | PA14 | PA20 | PA21 | PA22 | PA29 | PA39 | PB12 | PB60 | PC20 | PC26 | PC33 | PC37 | PC49 |
|---|---|---|---|---|---|---|---|---|---|---|---|---|---|---|---|---|
| Weight (g) | 29.7 | 10.5 | 41.5 | 22.9 | 19.8 | 19.9 | 15.0 | 27.5 | 15.0 | 17.8 | 15.0 | 17.1 | 14.4 | 13.6 | 11.3 | 9.3 |

B)

| Dried plant | PA12 | PA13 | PA21 | PA22 | PB12 |
|---|---|---|---|---|---|
| Weight (g) | 34.1 | 59.2 | 84.1 | 47.5 | 75.8 |

C)

| Dried plant | PA11 | PA13 | PA21 | PA22 | PB12 |
|---|---|---|---|---|---|
| Weight (g) | 56.9 | 54 | 76.9 | 43.4 | 69.4 |

For each dried plant mix, extracts were prepared according to the previously described Method B, where the spoons of dried plants were replaced by 2 g of the plant mix of Example 13, using 40 mL of water and the amounts of carbohydrate indicated in Table13-3 for water extraction and including the decantation step before filtration.

The dry residue content of the plant mixes without carbohydrate was determined separately, by weighting the lyophilisation residue obtained with a lyophilisation device (FreeZone™ 2.5, Labconco USA, with RZ6 Vacuubrand, Germany) of a frozen 40 mL extract prepared according to the previously described Method B, where the spoons of dried plants were replaced by 2 g of the plant mix of Example 13, using 40 mL of water for water extraction and including the decantation step before filtration. These dry residue contents were used to deduce the specific activities of the different extracts, where the carbohydrate is considered as an adjuvant and not accounted as part of the active ingredient.

The biological activity of each extracted mix was determined according to the previously described Method C by using the strains indicted in Table 13-2, where the dilution of the extracted mix was: 1:20, 1:40, 1:80, 1:160. The minimal inhibiting concentration (MIC) was noted by visual observation of the wells as the lowest concentration where no growth is observed.

TABLE 13-2 list of the bacterial strains used in the Example 13

| *Staphylococcus aureus* | | *Staphylococcus epidermidis* | |
|---|---|---|---|
| NCTC 12493 ™ | B-A47 | ATCC ® 12228 ™ | B-A22 |
| ATCC ® 33591 ™ | B-A48 | ATCC ® 700296 ™ | B-A23 |
| ATCC ® 33592 ™ | B-A49 | ATCC ® 49461 ™ | B-A24 |
| NCTC 43300 ™ | B-A51 | ATCC ® 14990 ™ | B-A08 |

The results are compiled in tables 13-4.

TABLE 13-3

MIC in mg/L of the extracted mixes using sucrose, lactose, dextrose, maltose or galactose for: A) the M[20P]-576 mix, B) the M[5P]-1 mix and C), the M[5P]-2 mix

| A) | Sucrose | Lactose | | | Dextrose | | | Maltose | | | Galactose | | |
|---|---|---|---|---|---|---|---|---|---|---|---|---|---|
| M[20P]-576 | 100 g/L | 100 g/L | 50 g/L | 25 g/L | 100 g/L | 50 g/L | 25 g/L | 100 g/L | 50 g/L | 25 g/L | 100 g/L | 50 g/L | 25 g/L |
| B-A47 | 725 | >725 | >725 | 725 | >725 | >725 | >725 | >725 | 725 | 725 | 725 | 725 | 725 |
| B-A48 | 725 | >725 | >725 | 725 | >725 | >725 | >725 | 725 | 725 | 725 | 725 | 725 | 725 |
| B-A49 | 725 | >725 | >725 | 725 | >725 | >725 | >725 | 725 | 725 | 725 | 725 | 725 | 725 |
| B-A51 | 725 | >725 | >725 | 725 | >725 | >725 | >725 | 725 | 725 | 725 | 725 | 725 | 725 |
| B-A22 | 363 | 725 | 725 | 725 | 725 | 725 | 363 | 363 | 363 | 363 | 363 | 363 | 363 |
| B-A23 | 363 | 725 | 725 | 363 | 725 | 725 | 363 | 363 | 363 | 363 | 363 | 363 | 363 |
| B-A24 | 363 | 725 | 725 | 725 | 725 | 725 | 363 | 363 | 363 | 363 | 363 | 363 | 363 |
| B-A08 | 725 | 725 | 725 | 725 | 725 | 725 | 725 | 363 | 363 | 363 | 363 | 363 | 363 |
| B) | Sucrose | Lactose | | | Dextrose | | | Maltose | | | Galactose | | |
| M[5P]-1 | 100 g/L | 100 g/L | 50 g/L | 25 g/L | 100 g/L | 50 g/L | 25 g/L | 100 g/L | 50 g/L | 25 g/L | 100 g/L | 50 g/L | 25 g/L |
| B-A47 | 327 | 327 | 327 | 327 | 327 | 327 | 327 | 327 | 327 | 327 | 327 | 327 | 327 |
| B-A48 | 327 | 327 | 327 | 327 | 327 | 327 | 327 | 327 | 327 | 327 | 327 | 327 | 327 |
| B-A49 | 327 | 327 | 327 | 327 | 327 | 327 | 327 | 327 | 327 | 327 | 327 | 327 | 653 |
| B-A47 | 327 | 327 | 327 | 327 | 327 | 327 | 327 | 327 | 327 | 327 | 327 | 327 | 327 |
| B-A22 | 327 | 327 | 327 | 327 | 327 | 327 | 327 | 163 | 163 | 163 | 163 | 327 | 327 |
| B-A23 | 163 | 163 | 327 | 163 | 163 | 163 | 327 | 163 | 163 | 163 | 163 | 327 | 163 |
| B-A24 | 327 | 327 | 327 | 327 | 327 | 327 | 327 | 163 | 163 | 163 | 163 | 327 | 163 |
| B-A08 | 327 | 327 | 327 | 327 | 327 | 327 | 327 | 163 | 327 | 327 | 163 | 327 | 327 |
| C) | Sucrose | Lactose | | | Dextrose | | | Maltose | | | Galactose | | |
| M[5P]-2 | 100 g/L | 100 g/L | 50 g/L | 25 g/L | 100 g/L | 50 g/L | 25 g/L | 100 g/L | 50 g/L | 25 g/L | 100 g/L | 50 g/L | 25 g/L |
| B-A47 | 344 | 344 | 344 | 344 | 344 | 344 | 344 | 344 | 344 | 344 | 344 | 344 | 688 |
| B-A48 | 344 | 344 | 344 | 344 | 344 | 344 | 344 | 344 | 344 | 344 | 344 | 344 | 344 |
| B-A49 | 344 | 344 | 344 | 344 | 344 | 344 | 344 | 344 | 344 | 344 | 344 | 344 | 688 |
| B-A51 | 344 | 344 | 344 | 344 | 344 | 344 | 344 | 688 | 344 | 688 | 344 | 344 | 688 |
| B-A22 | 344 | 344 | 344 | 344 | 344 | 344 | 344 | 344 | 344 | 344 | 344 | 344 | 344 |
| B-A23 | 344 | 344 | 344 | 344 | 344 | 344 | 344 | 344 | 344 | 344 | 344 | 344 | 344 |
| B-A24 | 344 | 344 | 344 | 344 | 344 | 344 | 344 | 344 | 344 | 344 | 344 | 344 | 344 |
| B-A08 | 344 | 344 | 344 | 344 | 344 | 344 | 344 | 344 | 344 | 344 | 344 | 344 | 344 |

Example 14

In this Example, we illustrate the antimicrobial activity enhancement of the M[20P]-576 herbal mix extract towards commonly used antibiotics.

TABLE 14-1 bacterial species and strains used in Example 14

| Strain full name | Strain code |
|---|---|
| *Staphylococcus aureus* subsp. *aureus* ATCC ® 25923 ™ | B-A17 |
| *Staphylococcus aureus* subsp. *aureus* ATCC ® 29213 ™ | B-A21 |

List 14-1: herbal compositions of processed sample used in Example 14:

M[19P]-576: PA11; PA12; PA13; PA14; PA20; PA21; PA22; PA29; PA39; PB12; PB60; PC20; PC26; PC33; PC37.

The dried plants of pharmaceutical grade were obtained from "Herboristerie Cailleau" (Chemillé, France).

Herbal compositions M[19P]-576 was prepared by weighting each dried herb as indicated in Table 14-2

TABLE 14-2 weight of dried plant (mg) used in the herbal compositions of M[19P]-576

| | PA11 | PA12 | PA13 | PA14 | PA20 | PA21 | PA22 | PA29 | PA39 | PB12 | PB60 | PC20 | PC26 | PC33 | PC37 |
|---|---|---|---|---|---|---|---|---|---|---|---|---|---|---|---|
| M[19P]-576 | 409 | 145 | 573 | 316 | 277 | 271 | 207 | 380 | 207 | 247 | 206 | 236 | 198 | 187 | 154 |

Starting from the herbal composition, the corresponding water extracts (or processed samples) was prepared according to the previously described Method B using 2.06 g of the above herbal composition with 40 mL water with 100 g/L sucrose for water extraction and including the decantation step before filtration. In an independent water extract preparation without sucrose, it has been measured that 2.06 g/40 mL of herbal composition corresponds to 14.5 g/L as deduced from the weight of the lyophilized dry herbal extract.

The biological activity of each processed sample was determined according to the previously described Method C by using the following strains at the indicated final dilutions of processed samples is given in Table 14-3. In Example 14 we calculate the growth of the bacteria in presence of antibiotic and/or herbal mix relative to the growth in the absence of both antibiotic and herbal mix extract.

The bacteria planktonic growth inhibition percentage average is given in Table 14-3.

It has to be noted that the presence of the herbal extract M[19P]-576 has three effects at the concentration used: 1) it reduces the growth of the bacteria at low concentration and absence of antibiotic, 2) it reduces the increase of bacterial growth induced by low antibiotic concentration relative to the growth in the absence of antibiotics, and 3) it reduces the minimal inhibitory concentration (MIC), of, respectively, vancomycin for B-A17 and of ampicillin and penicillin for B-A21, at M[20C]-576 concentration starting at, respectively, 90.6 μg/mL, 181.3 μg/mL, and 90.6 μg/mL.

TABLE 14-3 planktonic growth in the presence of different extract concentrations and anttibiotic concentrations relative to the grrowth of the bacteria in the absence of both extract and antibiotic, on two different strains

| | | M[20C]-576 | Antibiotic concentration (μg/mL) | | | | | | | | | | | |
|---|---|---|---|---|---|---|---|---|---|---|---|---|---|---|
| | Strain | (μg/mL) | 0 | 3.91 | 7.81 | 15.63 | 31.25 | 62.50 | 125 | 250 | 500 | 1000 | 2000 | 4000 |
| Ampicillin | B-A17 | 0 | 100% | 176% | 176% | 148% | 131% | 112% | 2% | 0% | 0% | 0% | 0% | −1% |
| | B-A21 | 90.6 | 57% | 64% | 76% | 75% | 58% | 18% | 1% | 0% | 0% | 0% | 0% | 0% |
| | | 181.3 | 54% | 52% | 53% | 52% | 31% | 7% | −4% | −4% | −4% | −4% | −5% | −1% |
| | | 0 | 100% | 153% | 132% | 131% | 132% | 116% | 150% | 113% | 112% | 106% | −1% | 0% |
| | | 90.6 | 64% | 108% | 83% | 82% | 82% | 74% | 83% | 75% | 83% | 0% | 0% | 0% |
| | | 181.3 | 42% | 44% | 63% | 70% | 69% | 70% | 62% | 62% | 61% | −2% | −3% | −2% |
| Penicillin | B-A17 | 0 | 100% | 137% | 138% | 3% | 1% | 0% | −1% | 0% | 0% | 0% | 0% | 0% |
| | B-A21 | 90.6 | 53% | 39% | 25% | 1% | 0% | 0% | 0% | 0% | 0% | 0% | 0% | 0% |
| | | 181.3 | 51% | 23% | 5% | −3% | −3% | −3% | −3% | −2% | −3% | −4% | −4% | −2% |
| | | 0 | 100% | 135% | 116% | 115% | 113% | 108% | 106% | 101% | 0% | 0% | 0% | 0% |
| | | 90.6 | 65% | 104% | 83% | 83% | 84% | 80% | 74% | 26% | 0% | 0% | 0% | 0% |
| | | 181.3 | 44% | 62% | 43% | 70% | 61% | 60% | 45% | −3% | −3% | −3% | −3% | −3% |
| Vancomycin | B-A17 | 0 | 100% | 135% | 118% | 114% | 117% | 115% | 116% | 118% | 128% | 117% | 0% | 0% |
| | B-A21 | 90.6 | 62% | 65% | 66% | 65% | 74% | 70% | 67% | 66% | 63% | 0% | 0% | 0% |
| | | 181.3 | 42% | 40% | 41% | 53% | 55% | 55% | 54% | 46% | 47% | −3% | −3% | −2% |
| | | 0 | 100% | 118% | 117% | 113% | 117% | 110% | 102% | 102% | 102% | 0% | 0% | 0% |
| | | 90.6 | 45% | 102% | 82% | 88% | 77% | 76% | 77% | 74% | 67% | 0% | 0% | 0% |
| | | 181.3 | 58% | 48% | 63% | 57% | 60% | 57% | 41% | 57% | 32% | −2% | −3% | 0% |

Example 15

In this Example, we illustrate how to adapt the temperature in Method B in order to cope with industrial constraints.

The dried plants of organic grade were obtained from "Herboristerie Cailleau" (Chemillé, France).

Herbal compositions M[5P]-1 was prepared by weighting each dried herb as indicated in Table 15-1

TABLE 15-1

| | weight of dried plant (mg) used in the herbal compositions of M[5P]-1 | | | | |
|---|---|---|---|---|---|
| | PA12 | PA13 | PA21 | PA22 | PB12 |
| M[5P]-1 | 395.2 | 688.8 | 978.9 | 552.5 | 884.6 |

A first extract M[5P]-1-A was prepared by incorporating 120 g of the herbal composition into 600 mL of water contained in a 2 L beaker (Schott, Germany). A second extract M[5P]-1-B was prepared by placing 120 g of the herbal composition into a 25×30 cm organic grade cotton bag (Ecobags, USA), and the filled bag was placed into 600 mL of water contained into a 2 L beaker (Schott, Germany). A third extract M[5P]-1-C was prepared by twice placing 60 g of the herbal composition into a 25×30 cm organic grade cotton bag (Ecobags, USA), and the two filled bags were placed into 600 mL of water contained into a single 2 L beaker (Schott, Germany). Each, respectively, M[5P]-1-A, M[5P]-1-B and M[5P]-1-C, preparation was left for maceration for 3 hours at room temperature and then placed in its beaker into an autoclave (VWR Vapour Line Eco 25, USA) for 30 minutes at, respectively, 121° C., 121° C. and 134° C. For each of M[5P]-1-B and M[5P]-1-C, the cotton bags were pressed using a manually operated 5 L fruit press (Brouwland, Belgium) and the recovered liquid was placed back into the 2 L beaker. Each beaker was left for decantation and the necessary amount of supernatant liquid was used to measure its biological activity.

TABLE 15-2

| bacterial species and strains used in Example 15 | |
|---|---|
| Strain full name | Strain code |
| *Staphylococcus aureus* subsp. *aureus* ATCC ® 25923 ™ | B-A17 |
| *Staphylococcus aureus* subsp. *aureus* ATCC ® 29213 ™ | B-A21 |
| *Staphylococcus aureus* subsp. *aureus* ATCC ® 33592 ™ | B-A49 |

The biological activity of each processed sample was determined according to the previously described Method C by using the strains listed in Table 15-2 at final dilutions of 1:40, 1:80, 1:160 and 1:320. The dilution corresponding to the minimal inhibiting concentration (MIC) was noted by visual observation of the wells as the lowest concentration where no growth is observed and is reported into Table 15-3

TABLE 15-3 dilution corresponding to the minimal inhibiting concentration (MIC) of the extracts realized with different industrial details and temperature

| | M[5P]-1-A at 121° | M[5P]-1-B at 121° | M[5P]-1-C at 134°C |
|---|---|---|---|
| B-A17 | 1/80 | 1/40 | 1/80 |
| B-A21 | 1/80 | 1/40 | 1/80 |
| B-A49 | 1/80 | 1/40 | 1/160 |

It is to be noted that introducing the cotton bag to ease the industrial process reduced slightly the activity of the extract as compared to the unsatisfactory process without bag. Increasing the temperature of the autoclave during the hot extraction phase allowed to recover the full activity.

Example 16

In the following example, the quantitative difference of antimicrobial activities between extracts of mix of plants versus mixing extracts of plants are illustrated.

The extract of the herbal compositions described hereinbelow were prepared according to Method B described on page 15, but without the addition of sucrose as disclosed on page 6.

Specifically, the hereinbelow specified amounts of dried plant powders were dissolved in 20 ml or 21.5 ml of alimentary grade spring water in falcon tubes. Each falcon tube was agitated using a vortex mixer for 10 seconds, incubated at room temperature for 10 minutes and placed in an autoclave for a 20 minutes sterilization cycle.

Extract Mix M[7P]-9 was prepared adding to a falcon tube the following amounts of dried powders in 21.5 ml of water: 273 mg of *Rheum palmatum* (PA11), 116 mg of *Rosmarinus officinalis* (PA12), 206 mg of *Filipendula ulmaria* (PA13), 282 mg of *Camellia sinensis* (PA21), 206 mg of *Vitis vinifera* var. *tinctoria* (PA22), 229 mg of *Arctostaphylos uva-ursi* (PB12) and 276 mg of *Eugenia caryophyllus* (PC20). Therefore, the w/w weight ratio between *Filipendula ulmaria* and *Rheum palmatum* was 0.7, the w/w weight ratio between *Filipendula ulmaria* and *Rosmarinus officinalis* was 1.8, the w/w weight ratio between *Filipendula ulmaria* and *Camellia sinensis* was 0.7, the w/w weight ratio between *Filipendula ulmaria* and *Vitis vinifera* var. *tinctoria* was 1, the w/w weight ratio between *Filipendula ulmaria* and *Arctostaphylos uva-ursi* was 0.9 and the w/w weight ratio between *Filipendula ulmaria* and *Eugenia caryophyllus* was 0.7.

The extraction was performed as described in Method B as discussed above.

The single plant extract EPA11 was prepared adding to a falcon tube the 1652 mg of *Rheum palmatum* (PA11) in 20 ml of water. The extraction was otherwise performed as described in Method B as discussed above.

The single plant extract EPA12 was prepared adding to a falcon tube the 976 mg of *Rosmarinus officinalis* (PA12) in 20 ml of water. The extraction was otherwise performed as described in Method B as discussed above.

The single plant extract EPA13 was prepared adding to a falcon tube the 1244 mg of *Filipendula ulmaria* (PA13) in 20 ml of water. The extraction was otherwise performed as described in Method B as discussed above.

The single plant extract EPA21 was prepared adding to a falcon tube the 1840 mg of *Camellia sinensis* (PA21) in 20 ml of water. The extraction was otherwise performed as described in Method B as discussed above.

The single plant extract EPA22 was prepared adding to a falcon tube the 1295 mg of *Vitis vinifera* var. *tinctoria* (PA22) in 20 ml of water. The extraction was otherwise performed as described in Method B as discussed above.

The single plant extract EPB12 was prepared adding to a falcon tube the 1506 mg of *Vitis vinifera* var. *tinctoria* (PB12) in 20 ml of water. The extraction was otherwise performed as described in Method B as discussed above.

The single plant extract EPC20 was prepared adding to a falcon tube the 1711 mg of *Eugenia caryophyllus* (PC20) in 20 ml of water. The extraction was otherwise performed as described in Method B as discussed above.

Mix M[7E]-9 was prepared by mixing extracts EPA11, EPA12, EPA13, EPA21, EPA22, EPB12 and EPC20 in such proportions as to obtain a mix nominally equivalent in its composition in dried plants to M[7P]-9. This condition is obtained by using for each botanical subscribed k (k among A11, A12, A13, A21, A22, B12 and C20) a volume $VEP_k$ such that $SVEP \times QMk/21.5\ mL = VEP_k \times QEPk/20\ mL$, where SVEP is the sum of all VEPk, QMk is the amount of dry plant k used to prepare Mix M[7E]-9 and QEk is the amount of dry plant k used to prepare EPk. Mix M[7E]-9 was thus prepared by mixing 157 µL of *Rheum palmatum* EPA11, 113 µL of *Rosmarinus officinalis* EPA12, 157 µL of *Filipendula ulmaria* EPA13, 146 µL of *Camellia sinensis* EPA21, 151 µL of *Vitis vinifera* var. *tinctoria* EPA22, 145 µL of *Arctostaphylos uva-ursi* EPB12 and 153 µL of *Eugenia caryophyllus* EPC20.

For each extract the biological activity was determined according to the previously described Method C, with the following final dilutions of processed samples: 1:10 (*Pseudomonas aeruginosa* ATCC® 27853™), and 1:40 (*Staphylococcus aureus* subsp. *aureus* ATCC® 29213™). Optical density measures are taken every hour and reported in the following graphs which show the growth kinetics of *Pseudomonas aeruginosa* (first and second graphs) and *Staphylococcus aureus* (third and fourth graphs) without and with mixes Mix M[7P]-9 and M[7E]-9.

Figure 2:
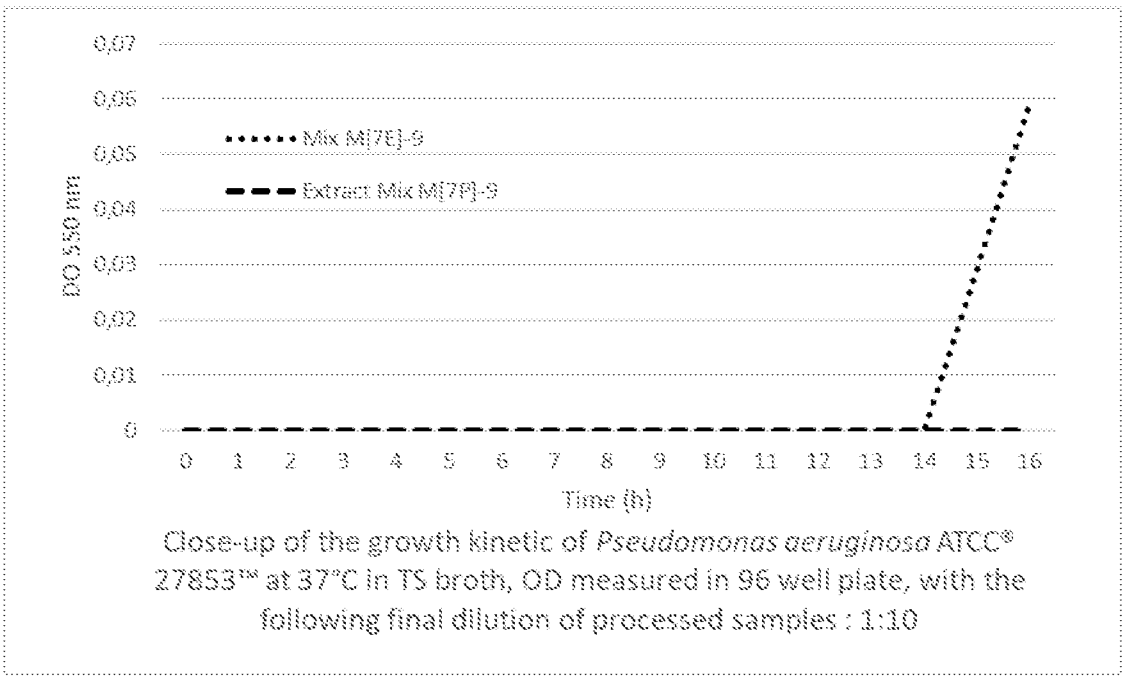
FIG. 2 shows the close-up growth kinetics of *Pseudomonas aeruginosa* ATCC® 27853™ at 37° C. in TS broth, OD measured in 96 well plate, with the following final dilution of processed sample: 1:10.
Figure 3:
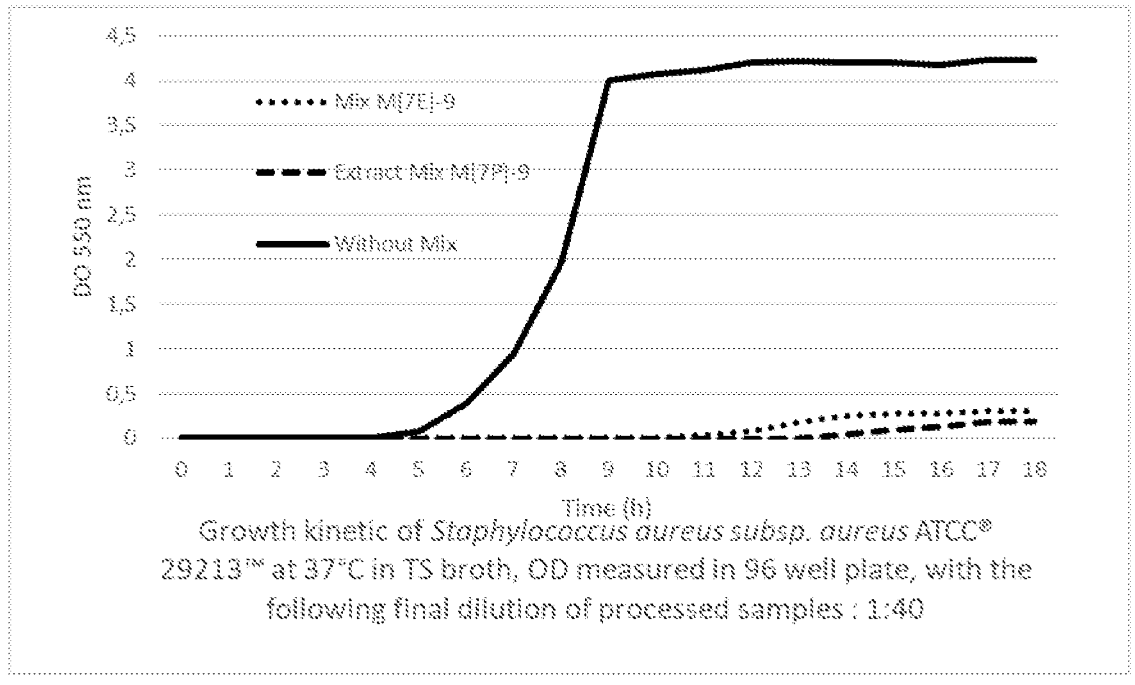
FIG. 3 shows the growth kinetics of *Staphylococcu aureus* subsp. *aureus* ATCC® 29213 at 37° C. in TS broth, OD measured in 96 well plate, with the following final dilution of processed sample: 1:40.
Figure 4:
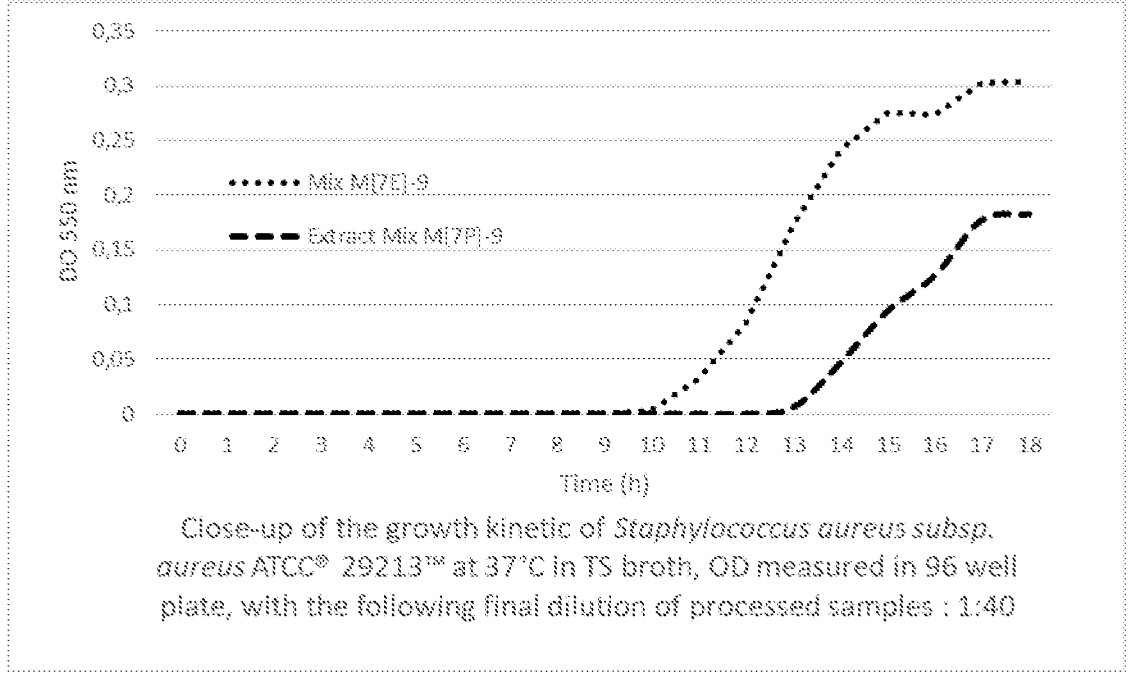
FIG. 4 shows the close-up growth kinetics of *Staphylococcu aureus* subsp. *aureus* ATCC® 29213 at 37° C. in TS broth, OD measured in 96 well plate, with the following final dilution of processed sample: 1:40.

From the results reported in FIGS. 1-4, it is evident that the biological activity of the growth kinetics of *Pseudomonas aeruginosa* (FIGS. 1 and 2) and *Staphylococcus aureus* (FIGS. 3 and 4) is significantly decreased in the presence of the extract of herbal compositions presently claimed (Mix M[7P]-9) compared to the growth achieved with M[7E]-9, i.e., the corresponding composition of extracts, or in the absence of any mix, i.e., the control. Thus, there are quantitative and qualitative differences between the herbal compositions presently claimed and the composition of the corresponding natural herbal extracts. That is, the effects obtainable with the claimed invention are markedly different from the effects obtainable from its closest naturally occurring counterparts.

Example 17

In the following example we report the composition in dry plants of some final products prepared according to the invention.

For each of the following final products we report in a corresponding table the amount of dry plant (in grams) used for 1 kg of ingredient and the amount of extract (in grams) in 1 kg of ingredient, where "ingredient" means the final extract.

To calculate the amount of extract of single plant, we started with a separate test experiment for each plant "i" taken individually to get Xi=E'i/D'i, where E' is extract and D' dry plant, both measured.

Then, for the extract from the MIX of plants, we calculated Ei=Xi, Di, Et/sum(Xi. Di), where Ei, is a calcualted amount and represents the "theoretical" extract and Di (the measured weight) is the dry plant and where Et is the experimentally measured extract obtained from sum(Di) amount of mix.

1. Ingredient of a Cosmetic Final Product A Having Antibacterial Activity:

TABLE 17.1.1

Composition in dry plants for product A

| Code | Botanical Name | Amount of dry plant (g) used for 1 kg of ingredient | Amount of extract (g) in 1 kg of ingredient | w/w weight ratio *Filipendula ulmaria*/other dry plant |
|---|---|---|---|---|
| PA12 | *Rosmarinus officinalis L.* | 30 g | 2.8 g | 1.8 |
| PA13 | *Filipendula ulmaria (L.) Maxim.* | 53 g | 3.9 g | 1 |
| PA21 | *Camellia sinensis (L.) Kuntze* | 75 g | 8.3 g | 0.7 |
| PA22 | *Vitis vinifera L.* | 42 g | 4.0 g | 1.3 |

TABLE 17.1.2

Ingredient used in final product A at recommended proportion of 5% to 20%.

| Code | Botanical Name | Range of amount of dry plant (g) used for 1 kg of final product | Range of amount of extract (g) in 1 kg of final product |
|---|---|---|---|
| PA12 | *Rosmarinus officinalis L.* | 1.5 g-6 g | 0.1 g-0.6 g |
| PA13 | *Filipendula ulmaria (L.) Maxim.* | 2.6 g-10.5 g | 0.2 g-0.8 g |
| PA21 | *Camellia sinensis (L.) Kuntze* | 3.7 g-15 g | 0.4 g-1.7 g |
| PA22 | *Vitis vinifera L.* | 2.1 g-8.5 g | 0.2 g-0.8 g |

TABLE 17.1.3

Final product A typically sold in packages having volumes in the range of 50 mL to 200 mL

| Code | Botanical Name | Range of amount of dry plant (g) used for 50 mL to 200 mL of final product | Range of amount of extract (g) in 50 mL to 200 mL of final product |
|---|---|---|---|
| PA12 | *Rosmarinus officinalis L.* | 0.1 g-1.2 g | 0.01 g-0.1 g |
| PA13 | *Filipendula ulmaria (L.) Maxim.* | 0.1 g -2.1 g | 0.01 g-0.2 g |
| PA21 | *Camellia sinensis (L.) Kuntze* | 0.2 g-3 g | 0.02 g-0.3 g |
| PA22 | *Vitis vinifera L.* | 0.1 g-1.7 g | 0.01 g-0.2 g |

2. Ingredient of a Cosmetic Final Product B Having Antibacterial Activity:

TABLE 17.2.1

Composition in dry plants for product B

| Code | Botanical Name | Amount of dry plant (g) used for 1 kg of ingredient | Amount of extract (g) in 1 kg of ingredient | w/w weight ratio *Filipendula ulmaria*/other dry plant |
|---|---|---|---|---|
| PA12 | *Rosmarinus officinalis L.* | 23 g | 3.2 g | 1.7 |
| PA13 | *Filipendula ulmaria (L.) Maxim.* | 39 g | 4.6 g | 1 |
| PA21 | *Camellia sinensis (L.) Kuntze* | 56 g | 9.7 g | 0.7 |
| PA22 | *Vitis vinifera L.* | 32 g | 4.7 g | 1.2 |
| PB12 | *Arctostaphylos uva-ursi(L.) Spreng.* | 51 g | 8.2 g | 0.8 |

TABLE 17.2.2

Ingredient used in final product B at recommended proportion of 5% to 20%.

| Code | Botanical Name | Range of amount of dry plant (g) used for 1 kg of final product | Range of amount of extract (g) in 1 kg of final product |
|---|---|---|---|
| PA12 | *Rosmarinus officinalis L.* | 1.1 g-4.5 g | 0.2 g-0.6 g |
| PA13 | *Filipendula ulmaria (L.) Maxim.* | 2 g-7.9 g | 0.2 g-0.9 g |
| PA21 | *Camellia sinensis (L.) Kuntze* | 2.8 g-11.2 g | 0.5 g-1.9 g |
| PA22 | *Vitis vinifera L.* | 1.6 g-6.3 g | 0.2 g-0.9 g |
| PB12 | *Arctostaphylos uva-ursi(L.) Spreng.* | 2.5 g-10.1 g | 0.4 g-1.6 g |

TABLE 17.2.3

| Final product B typically sold in packages having volumes in the range of 50 mL to 200 mL | | | |
|---|---|---|---|
| Code | Botanical Name | Range of amount of dry plant (g) used for 50 mL to 200 mL of final product | Range of amount of extract (g) in 50 mL to 200 mL of final product |
| PA12 | *Rosmarinus officinalis L.* | 0.1 g-0.9 g | 0.01 g-0.1 g |
| PA13 | *Filipendula ulmaria (L.) Maxim.* | 0.1 g-1.6 g | 0.01 g-0.2 g |
| PA21 | *Camellia sinensis (L.) Kuntze* | 0.1 g-2.2 g | 0.02 g-0.4 g |
| PA22 | *Vitis vinifera L.* | 0.1 g-1.3 g | 0.01 g-0.2 g |
| PB12 | *Arctostaphylos uva-ursi(L.) Spreng.* | 0.1 g-2 g | 0.02 g-0.3 g |

3. Ingredient of a Cosmetic Final Product C Having Antibacterial Activity:

TABLE 17.3.1

| Composition in dry plants for product C | | | | |
|---|---|---|---|---|
| Code | Botanical Name | Amount of dry plant (g) used for 1 kg of ingredient | Amount of extract (g) in 1 kg of ingredient | w/w weight ratio *Filipendula ulmaria*/other dry plant |
| PA11 | *Rheum palmatum L.* | 23 g | 2.9 g | 1.7 |
| PA13 | *Filipendula ulmaria (L.) Maxim.* | 39 g | 3 g | 1 |
| PA21 | *Camellia sinensis (L.) Kuntze* | 56 g | 6.4 g | 0.7 |
| PA22 | *Vitis vinifera* var. *tinctoria* | 32 g | 3.1 g | 1.2 |
| PB12 | *Arctostaphylos uva-ursi(L.) Spreng.* | 51 g | 5.4 g | 0.8 |

TABLE 17.3.2

| Ingredient used in final product C at recommended proportion of 5% to 20%. | | | |
|---|---|---|---|
| Code | Botanical Name | Range of amount of dry plant (g) used for 1 kg of final product | Range of amount of extract (g) in 1 kg of final product |
| PA11 | *Rheum palmatum L.* | 1.1 g-4.5 g | 0.1 g-0.6 g |
| PA13 | *Filipendula ulmaria (L.) Maxim.* | 2 g-7.9 g | 0.2 g-0.6 g |
| PA21 | *Camellia sinensis (L.) Kuntze* | 2.8 g-11.2 g | 0.3 g-1.3 g |
| PA22 | *Vitis vinifera* var. *tinctoria* | 1.6 g-6.3 g | 0.2 g-0.6 g |
| PB12 | *Arctostaphylos uva-ursi(L.) Spreng.* | 2.5 g-10.1 g | 0.3 g-1.1 g |

TABLE 17.3.3

| Final product C typically sold in packages having volumes in the range of 50 mL to 200 mL | | | |
|---|---|---|---|
| Code | Botanical Name | Range of amount of dry plant (g) used for 50 mL to 200 mL of final product | Range of amount of extract (g) in 50 mL to 200 mL of final product |
| PA11 | *Rheum palmatum L.* | 0.1 g-0.9 g | 0.01 g-0.1 g |
| PA13 | *Filipendula ulmaria (L.) Maxim.* | 0.1 g-1.6 g | 0.01 g-0.1 g |
| PA21 | *Camellia sinensis (L.) Kuntze* | 0.1 g-2.2 g | 0.02 g-0.3 g |
| PA22 | *Vitis vinifera* var. *tinctoria* | 0.1 g-1.3 g | 0.01 g-0.1 g |
| PB12 | *Arctostaphylos uva-ursi(L.) Spreng.* | 0.1 g-2 g | 0.01 g-0.2 g |

4. Ingredient of a Cosmetic Final Product D Having Antibacterial Activity:

Product D is commercialized as a 50 mL lotion, 150 mL lotion, 200 mL shampoo and 150 mL foam.

TABLE 17.4.1

| Composition in dry plants for product D-lotion | | | |
|---|---|---|---|
| Code | Botanical Name | Amount of dry plant used for 50 mL to 150 mL of lotion | Amount of dry extract used for 50 mL to 150 mL of lotion |
| PA11 | *Rheum palmatum L.* | 282 mg-847 mg | 89 mg-268 mg |
| PA12 | *Rosmarinus officinalis L.* | 100 mg-300 mg | 24 mg-71 mg |
| PA13 | *Filipendula ulmaria (L.) Maxim.* | 396 mg-1188 mg | 83 mg-248 mg |
| PA14 | *Satureja montana L.* | 150 mg-451 mg | 44 mg-133 mg |
| PA20 | *Valeriana officinalis L.* | 187 mg-562 mg | 80 mg-241 mg |
| PA21 | *Camellia sinensis (L.) Kuntze* | 151 mg-452 mg | 44 mg-133 mg |
| PA22 | *Vitis vinifera* var. *tinctoria* | 142 mg-425 mg | 33 mg-100 mg |
| PA29 | *Fucus vesiculosus L.* | 260 mg-780 mg | 80 mg-241 mg |
| PA39 | *Foeniculum vulgare* Mill. | 143 mg-428 mg | 36 mg-107 mg |
| PB12 | *Arctostaphylos uva-ursi (L.) Spreng.* | 170 mg-509 mg | 45 mg-134 mg |
| PB60 | *Arbutus unedo L.* | 144 mg-431 mg | 44 mg-132 mg |
| PC20 | *Syzygium aromaticum(L.)* Merr. & L. M. Perry | 150 mg-451 mg | 44 mg-133 mg |
| PC26 | *Juniperus communis L.* | 135 mg-405 mg | 16 mg-48 mg |
| PC33 | *Combretum micranthum* G. Don | 130 mg-389 mg | 33 mg-98 mg |
| PC37 | *Aloysia citriodora Palau* | 106 mg-318 mg | 29 mg-87 mg |
| PF38 | *Tanacetum parthenium(L.)* Sch. Bip. | 88 mg-263 mg | 26 mg-78 mg |

TABLE 17.4.2

| Composition in dry plants for product D-foam | | | | |
|---|---|---|---|---|
| Code | Botanical Name | Amount of dry plant used for 150 mL of foam | Amount of dry extract used for 150 mL of foam | w/w weight ratio *Filipendula ulmaria*/other dry plant |
| PA11 | *Rheum palmatum L.* | 85 mg | 27 mg | 1.4 |
| PA12 | *Rosmarinus officinalis L.* | 30 mg | 7 mg | 4 |
| PA13 | *Filipendula ulmaria (L.) Maxim.* | 119 mg | 25 mg | 1 |
| PA14 | *Satureja montana L.* | 45 mg | 13 mg | 2.7 |
| PA20 | *Valeriana officinalis L.* | 56 mg | 24 mg | 2.1 |
| PA21 | *Camellia sinensis (L.) Kuntze* | 45 mg | 13 mg | 2.7 |
| PA22 | *Vitis vinifera* var. *tinctoria* | 42 mg | 10 mg | 2.8 |
| PA29 | *Fucus vesiculosus L.* | 78 mg | 24 mg | 1.5 |
| PA39 | *Foeniculum vulgare* Mill. | 43 mg | 11 mg | 2.8 |
| PB12 | *Arctostaphylos uva-ursi (L.) Spreng.* | 51 mg | 13 mg | 2.3 |
| PB60 | *Arbutus unedo L.* | 43 mg | 13 mg | 2.8 |
| PC20 | *Syzygium aromaticum(L.)* Merr. & L. M. Perry | 45 mg | 13 mg | 2.6 |
| PC26 | *Juniperus communis L.* | 40 mg | 5 mg | 2.3 |
| PC33 | *Combretum micranthum* G. Don | 39 mg | 10 mg | 3 |
| PC37 | *Aloysia citriodora* Palau | 32 mg | 9 mg | 3.7 |
| PF38 | *Tanacetum parthenium(L.)* Sch. Bip. | 26 mg | 8 mg | 4.6 |

TABLE 17.4.3

| Composition in dry plants for product D-shampoo | | | | |
|---|---|---|---|---|
| Code | Botanical Name | Amount of dry plant used for 200 mL of shampoo | Amount of dry extract used for 200 mL of shampoo | w/w weight ratio *Filipendula ulmaria*/other dry plant |
| PA11 | *Rheum palmatum L.* | 23 mg | 7 mg | 1.4 |
| PA12 | *Rosmarinus officinalis L.* | 8 mg | 2 mg | 4 |
| PA13 | *Filipendula ulmaria (L.) Maxim.* | 32 mg | 7 mg | 1 |
| PA14 | *Satureja montana L.* | 12 mg | 4 mg | 2.7 |
| PA20 | *Valeriana officinalis L.* | 15 mg | 6 mg | 2.1 |
| PA21 | *Camellia sinensis (L.) Kuntze* | 12 mg | 4 mg | 2.7 |
| PA22 | *Vitis vinifera* var. *tinctoria* | 11 mg | 3 mg | 2.9 |
| PA29 | *Fucus vesiculosus L.* | 21 mg | 6 mg | 1.5 |
| PA39 | *Foeniculum vulgare* Mill. | 11 mg | 3 mg | 2.9 |
| PB12 | *Arctostaphylos uva-ursi (L.) Spreng.* | 14 mg | 4 mg | 2.3 |
| PB60 | *Arbutus unedo L.* | 11 mg | 4 mg | 2.9 |
| PC20 | *Syzygium aromaticum(L.)* Merr. & L. M. Perry | 12 mg | 4 mg | 2.7 |
| PC26 | *Juniperus communis L.* | 11 mg | 1 mg | 2.9 |
| PC33 | *Combretum micranthum* G. Don | 10 mg | 3 mg | 3.2 |
| PC37 | *Aloysia citriodora* Palau | 8 mg | 2 mg | 4 |
| | *Tanacetum parthenium*(L.) Sch. Bip. | 7 mg | 2 mg | 4.6 |

Note:
PC37 is synonym of *Lippia citrodora*
PC20 is synonum of *Eugenia caryophyllus*

5. Ingredient of a Cosmetic Final Mroduct E Having Antibacterial Activity:

Product B is a cosmetic gel commercialized in two forms "basic" and "forte", 50 mL each. It is recommended for dry skin, and it has shown to have antibacterial properties in clinical evaluation.

TABLE 17.5.1

| Composition in dry plants for product E | | | |
|---|---|---|---|
| Code | Botanical Name | Amount of dry plant used for 50 mL of basic and forte | Amount of dry extract used for 50 mL of basic and forte |
| PA11 | *Rheum palmatum L.* | 111 mg-332 mg | 27 mg-80 mg |
| PA12 | *Rosmarinus officinalis L.* | 39 mg-118 mg | 7 mg-21 mg |
| PA13 | *Filipendula ulmaria* (L.) *Maxim.* | 155 mg-466 mg | 25 mg-74 mg |
| PA14 | *Satureja montana L.* | 59 mg-177 mg | 13 mg-40 mg |
| PA20 | *Valeriana officinalis L.* | 74 mg-221 mg | 24 mg-72 mg |
| PA21 | *Camellia sinensis* (L.) *Kuntze* | 59 mg-177 mg | 13 mg-40 mg |
| PA22 | *Vitis vinifera* var. *tinctoria* | 56 mg-167 mg | 10 mg-30 mg |
| PA29 | *Fucus vesiculosus L.* | 102 mg-306 mg | 24 mg-72 mg |
| PA39 | *Foeniculum vulgare* Mill. | 56 mg-168 mg | 11 mg-32 mg |
| PB12 | *Arctostaphylos uva-ursi* (L.) *Spreng.* | 67 mg-200 mg | 13 mg-40 mg |
| PB60 | *Arbutus unedo L.* | 56 mg-169 mg | 13 mg-39 mg |
| PC20 | *Syzygium aromaticum*(L.) Merr. & L. M. Perry | 59 mg-177 mg | 13 mg-40 mg |
| PC26 | *Juniperus communis L.* | 53 mg-159 mg | 5 mg-14 mg |
| PC33 | *Combretum micranthum* G. Don | 51 mg-153 mg | 10 mg-29 mg |
| PC37 | *Aloysia citriodora* Palau | 42 mg-125 mg | 9 mg-26 mg |
| | *Tanacetum parthenium*(L.) Sch. Bip. | 34 mg-103 mg | 8 mg-23 mg |
| | *Coffea canephora* Pierre Ex. Froehner | 108 mg-323 mg | 27 mg-80 mg |

Note:
PC37 is synonym of *Lippia citrodora*
PC20 is synonym of *Eugenia caryophyllus*

6. Ingredient of a Drug Final Product G Having Antibacterial Activity:

Product G is a drug for oral administration to adult human as an alternative to antibiotic, typically 5 g of extract per dose to be administrated 1 to 4 times daily. It has shown to have antibacterial properties.

TABLE 17.6.1

| Composition in dry plants for product G for human treatment | | | | |
|---|---|---|---|---|
| Code | Botanical Name | Amount of dry plant (g) used for one dose | Amount of extract (g) in 1 one dose | w/w weight ratio *Filipendula ulmaria*/other dry plant |
| PA12 | *Rosmarinus officinalis L.* | 2.3 g | 0.5 g | 1.7 |
| PA13 | *Filipendula ulmaria (L.) Maxim.* | 3.9 g | 0.8 g | 1 |
| PA21 | *Camellia sinensis (L.) Kuntze* | 5.6 g | 1.6 g | 0.7 |
| PA22 | *Vitis vinifera* var. *tinctoria* | 3.2 g | 0.8 g | 1.2 |
| PB12 | *Arctostaphylos uva-ursi (L.) Spreng.* | 5.0 g | 1.4 g | 0.8 |

The invention claimed is:

1. A method of treating a human suffering from a *Staphylococcus* infection with a herbal composition consisting essentially of an aqueous extract of a mixture of powders of *Filipendula ulmaria, Camellia sinensis, Rosmarinus officinalis, Arctostaphylos uva-ursi* and *Vitis vinifera* var. *tinctoria*, wherein the w/w weight ratio between the *Filipendula ulmaria* and the powders of *Camellia sinensis* and *Vitis vinifera* var. *tinctoria* is between 0.2 and 5, wherein the w/w weight ratio between the *Filipendula ulmaria* and the powders of *Camellia sinensis* and *Vitis vinifera* var. *tinctoria* is between 0.3 and 3, wherein the w/w weight ratio between the *Filipendula ulmaria* and the powders of *Camellia sinensis* and *Vitis vinifera* var. *tinctoria* is between 0.5 and 2.5 and wherein the composition further consists essentially of the powders of a plant selected from the group consisting of *Achillea millefolium, Acorus calamus, Agrimonia eupatoria, Agropyrum repens, Agropyrum repens, Alchemilla vulgaris, Alkanna tinctoria, Althaea officinalis, Anethum graveolens, Angelica archangelica, Arbutus unedo, Arnica montana, Artemisia pontica, Artemisia vulgaris, Asparagus officinalis, Asparagus officinalis, Asperula odorata, Betula pendula, Borrago officinalis, Buxus sempervirens, Calamintha officinalis, Calendula officinalis, Calluna vulgaris, Carum carvi, Cassia angustifolia, Centaurea cyanus, Centaurium* erythraea, *Centella asiatica, Cetraria islandica, Chamaemelum nobile, Chamomilla recutita, Chrysanthellum americanum, Cichorium endivia, Cichorium intybus, Cinnamomum* zeylanicum, *Citrus aurantium, Combretum micranthum, Crataegus oxyacantha, Cuminum cyminum, Cupressus sempervirens, Curcuma zedoaria, Cynara scolymus, Cytisus scoparius, Desmodium adscendens, Elettaria cardamomum, Eleutherococcus senticosus, Epilobium parviflorum, Erysimum officinale, Eucalyptus globulus, Eugenia caryophyllus, Eupatorium cannabinum, Foeniculum vulgare, Fraxinus excelsior, Fucus vesiculosus, Fumaria officinalis, Galium odoratum, Gentiana lutea, Geranium robertianum, Ginkgo biloba, Glechoma hederacea, Glycyrrhiza glabra, Handroanthus impetiginosus, Harpagophytum procumbens, Hieracium pilosella, Humulus lupulus, Hypericum perforatum, Hyssopus officinalis, Illicium verum, Inula helenium, Juglans regia, Juniperus communis, Lamium album, Lavandula angustifolia, Levisticum officinale, Lippia citriodora, Lotus corniculatus, Lythrum salicaria, Malva sylvestris, Marrubium vulgare, Medicago sativa, Melissa officinalis, Mentha* X *piperita, Morus nigra, Myrtus communis, Olea europaea, Origanum majorana, Panax ginseng, Papaver rhoeas, Parietaria officinalis, Passiflora incarnata, Petroselinum crispum, Peumus boldus, Phaseolus vulgaris, Pimpinella anisum, Plantago lanceolata, Plantago ovata, Potentilla anserina, Quercus robur, Rhamnus frangula*, *Rheum palmatum, Rosa centifolia, Rubia tinctorum, Rubus idaeus, Salix alba, Salvia officinalis, Sambucus nigra, Satureja montana, Silybum marianum, Solanum dulcamara, Tabebuia impetiginosa, Tanacetum vulgare, Taraxacum officinalis, Thymus serpyllum, Thymus vulgaris, Tilia tomentosa, Tilia cordata, Trigonella foenum-graecum, Tussilago farfara, Vaccinium myrtillus, Valeriana officinalis, Verbascum thapsus, Verbena officinalis, Viscum album, Zea mays, Zingiber officinale* and combinations thereof, wherein said method consists essentially of administering to said human in need thereof a pharmaceutical effective amount of said composition.

2. The method according to claim 1, wherein the infections are caused by *Staphylococcus aureus, Staphylococcus epidermidis* or *Staphylococcus pseudintermedius*.

* * * * *